United States Patent
Canne Bannen et al.

(10) Patent No.: US 8,013,156 B2
(45) Date of Patent: Sep. 6, 2011

(54) TIE-2 MODULATORS AND METHODS OF USE

(75) Inventors: Lynne Canne Bannen, Pacifica, CA (US); S. David Brown, San Carlos, CA (US); Wei Cheng, South San Francisco, CA (US); Vasu Jammalamadaka, Pleasanton, CA (US); John M. Nuss, Danville, CA (US); Morrison B. Mac, San Francisco, CA (US); Jason Jevious Parks, Sacramento, CA (US); Matthew A. Williams, San Mateo, CA (US); Wei Xu, Danville, CA (US); Atwood Kim Cheung, Cambridge, MA (US); Lisa Esther Dalrymple, San Francisco, CA (US); Sergey Epshteyn, Fremont, CA (US); Mohamed Abdulkader Ibrahim, Mountain View, CA (US); James William Leahy, San Leandro, CA (US); Gary Lee Lewis, San Francisco, CA (US); Robin Tammie Noguchi, San Bruno, CA (US); Larry Wayne Mann, Richland, MI (US); Brian Hugh Ridgway, Belmont, CA (US); Joan C. Sangalang, Mountain View, CA (US); Kevin Luke Schnepp, Elk Grove, CA (US); Xian Shi, San Bruno, CA (US); Richard George Khoury, Redwood City, CA (US)

(73) Assignee: Exelixis, Inc., South San Francisco, CA (US)

( * ) Notice: Subject to any disclaimer, the term of this patent is extended or adjusted under 35 U.S.C. 154(b) by 1076 days.

(21) Appl. No.: 10/549,300

(22) PCT Filed: Mar. 19, 2004

(86) PCT No.: PCT/US2004/008579
§ 371 (c)(1),
(2), (4) Date: Jan. 31, 2007

(87) PCT Pub. No.: WO2004/083235
PCT Pub. Date: Sep. 30, 2004

(65) Prior Publication Data
US 2007/0275952 A1 Nov. 29, 2007

Related U.S. Application Data

(60) Provisional application No. 60/456,565, filed on Mar. 19, 2003.

(51) Int. Cl.
*C07D 401/14* (2006.01)
*C07D 403/14* (2006.01)
*A61K 31/4425* (2006.01)
*A61K 31/495* (2006.01)
*A61K 31/506* (2006.01)
*A61P 19/02* (2006.01)
*A61P 35/00* (2006.01)

(52) U.S. Cl. ........ 544/359; 544/360; 544/361; 544/324; 544/295; 546/193; 540/597; 540/598; 514/252.13; 514/252.14; 514/253.01; 514/275; 514/318; 514/211.01

(58) Field of Classification Search .................. 544/324, 544/295, 360, 359, 361; 546/193; 514/252.13, 514/252.14, 275, 318, 211.01, 253.01; 540/597, 540/598
See application file for complete search history.

(56) References Cited

U.S. PATENT DOCUMENTS

| | | | |
|---|---|---|---|
| 4,547,505 A | 10/1985 | Oepen et al. | |
| 4,849,422 A | 7/1989 | Giani et al. | |
| 4,994,476 A | 2/1991 | Poindexter | |
| 5,563,268 A * | 10/1996 | Linz et al. | 544/238 |
| 5,571,811 A * | 11/1996 | Heeres et al. | 514/252.02 |
| 5,637,592 A * | 6/1997 | Heeres et al. | 514/252.02 |
| 5,650,411 A * | 7/1997 | Heeres et al. | 514/63 |
| 5,728,700 A * | 3/1998 | Heeres et al. | 514/253.09 |
| 5,780,472 A * | 7/1998 | Cho et al. | 514/253.12 |
| 5,811,426 A * | 9/1998 | Heeres et al. | 514/252.02 |
| 6,391,874 B1 | 5/2002 | Cockerill et al. | |
| 7,320,979 B2 * | 1/2008 | Braje et al. | 514/252.14 |
| 7,449,576 B1 * | 11/2008 | Pennell et al. | 544/238 |
| 2002/0132853 A1 | 9/2002 | Bakthavatchalam et al. | |

FOREIGN PATENT DOCUMENTS

| | | |
|---|---|---|
| DE | 24 28 030 A1 | 1/1976 |
| EP | 0 096 006 A2 | 12/1983 |
| EP | 0 345 808 A1 | 12/1989 |
| GB | 1440722 | 6/1976 |
| JP | 2-134368 | 5/1990 |
| JP | 11-80119 | 3/1999 |
| WO | 94/03430 A1 | 2/1994 |

(Continued)

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, p. 596.*
West, Anthony R., Solid State Chemistry and its Applications, Wiley, New York, 1988, pp. 358 & 365.*

(Continued)

*Primary Examiner* — Venkataraman Balasubramanian
(74) *Attorney, Agent, or Firm* — McDonnell Boehnen Hulbert & Berghoff LLP

(57) ABSTRACT

The present invention provides compounds for modulating protein kinase enzymatic activity for modulating cellular activities such as proliferation, differentiation, programmed cell death, migration and chemoinvasion. Compounds of the invention inhibit, regulate and/or modulate kinases, particularly Tie-2. Methods of using the compounds and pharmaceutical compositions thereof to treat kinase-dependent diseases and conditions are also an aspect of the invention.

26 Claims, No Drawings

FOREIGN PATENT DOCUMENTS

| | | |
|---|---|---|
| WO | 98/58926 A1 | 12/1998 |
| WO | 00/51999 A1 | 9/2000 |
| WO | 00/76984 A2 | 12/2000 |
| WO | 01/23378 A1 | 4/2001 |
| WO | 01/87846 A2 | 11/2001 |
| WO | 02/059117 A1 | 8/2002 |
| WO | 02/060492 A1 | 8/2002 |
| WO | 02/080926 A1 | 10/2002 |
| WO | 02/080928 A1 | 10/2002 |
| WO | 03/004488 A1 | 1/2003 |

OTHER PUBLICATIONS

Vippagunta et al., Advanced Drug Delivery Reviews 48: 3-26, 2001.*
Rubland, T. et al., "Iron-Assisted Nucleophilic Aromatic Substitution on Solid Phase", Journal of Organic Chemistry, 2002, 67(15), 5257-5268.

* cited by examiner

TIE-2 MODULATORS AND METHODS OF USE

This application is a the National Stage of International Application PCT/US2004/008579, filed Mar. 19, 2004, which claims the benefit of U.S. Provisional Application No. 60/456,565, filed Mar. 19, 2003.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to compounds that inhibit, regulate and/or modulate kinases, particularly Tie-2. Kinase receptor signal transduction pathways related to the changes in cellular activities as mentioned above are modulated using compounds of the invention. Methods of using the compounds to treat kinase-dependent diseases and conditions are also an aspect of the invention.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation, with respect to antiangiogenic and antiproliferative activity is Tie-2. Tie-2 (also called TEK) is a member of the receptor tyrosine kinase (RTK) family, which is expressed primarily in endothelial cells and early hemopoietic cells, and plays a critical role in the processes of vasculogenesis and angiogenesis. As such, Tie-2 has been shown to participate in endothelial cell migration, sprouting, survival and periendothelial cell recruitment during angiogenesis.

The angiopoietin family of growth factors regulates Tie-2 activity through a combination of agonistic and antagonistic extracellular ligands. Binding of the ligands, Angiopoietin-1 (Ang-1) or Ang-4 by Tie-2 induces autophosphorylation resulting in an increase of receptor dependent signaling, while binding to Ang-2 and Ang-3 results in down regulation of receptor activity. Ang-1 signaling through Tie-2 facilitates later stages of vascular development by modulating cell-cell, and cell-matrix interactions, resulting in the survival and stabilization of newly formed blood vessels.

Tumor growth progression requires the recruitment of new blood vessels into the tumor from preexisting vessels. Accordingly, Tie-2 expression has been demonstrated on a wide variety of tumor types including ovarian, breast, renal, prostate, lung, thyroid, myeloid leukemia, hemangiomas, melanomas, astrocytomas, and glioblastomas. Tie-2 activation has also been linked to venous malformations (VM), the most common form of vascular morphogenesis in humans. As well, an activating mutation in the kinase domain of Tie-2 occurs in multiple families who exhibit a dominantly inherited form of VM. Tie-2 has been linked to multiple cancer types, including ovarian, breast, renal, prostate, lung, thyroid, myeloid leukemia, hemangiomas, melanomas, astrocytomas, and glioblastomas (See: Shirkawa et al Int J Cancer 2002 Jun. 20; 99(6):821-8; Tanka et al Clin Cancer Res 2002 May; 8(5):1125-31; Mitsutake et al Thyroid 2002 February; 12(2): 95-9; Muller et al Leuk Res 2002 February; 26(2): 163-8; Yu et al Am J Pathol 2001 December; 159(6):2271-80; Pomyje et al Melanoma Res 2001 December; 11(6):639-43; Harris et al Clin Cancer Res 2001 July; 7(7):1992-7; Wrumback et al Anticancer Res 2000 November-December; 20(6D):5217-20; Ding et al Deuro-oncol 2001 January; 3(1):1-10; Takahama et al Clin Cancer Res 1999 September; 5(9):2506-10; Stratmann et al Am J Pathol 1998 November; 153(5):1549-66; and, Kukk et al Br J Haematol 1997 July; 98(1):195-203). Additionally, activation of Tie-2 has been linked to the vascular dysmorphogenesis syndrome, venous malformation (See: Vikkula et al Cell 1996 December; 87(1):1181-1190). Thus modulation of Tie-2 is desirable as a means to treat cancer and cancer-related disease.

Accordingly, the identification of small-molecule compounds that specifically inhibit, regulate and/or modulate the signal transduction of kinases, particularly Tie-2, is desirable as a means to treat or prevent disease states associated with abnormal cell proliferation and angiogenesis, and is an object of this invention.

SUMMARY OF THE INVENTION

The present invention provides compounds for modulating kinase activity and methods of treating diseases mediated by kinase activity, in particular Tie-2, utilizing the compounds and pharmaceutical compositions thereof. Diseases mediated by kinase activity are from herein referred to as "kinase-dependent diseases or conditions" (see definition in detailed description of invention below). Inhibitors that are selective for a Tie-2 are included in this invention.

In another aspect, the invention provides methods of screening for modulators of kinase activity. The methods comprise combining a composition of the invention, a kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more kinase enzyme activity modulators as described herein. Such kits can also include, for example, other compounds and/or compositions (e.g., diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as atherosclerosis, myocardioinfarction, ischemia, pulmonary hypertension, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally," but proliferation and migration enhancement may be desired. Alternatively, reduction in "normal" cell proliferation and/or migration rate may be desired.

The present invention comprises a compound for modulating kinase activity, particularly Tie-2, of Formula I,

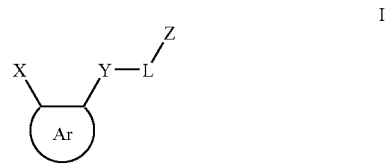

or a pharmaceutically acceptable salt, hydrate, or prodrug thereof, wherein,

Ar is a five- to six-membered aromatic ring system containing between one and three heteroatoms, said five- to six-membered aromatic ring system substituted with —X and —Y-L-Z, in an ortho relationship to each other, and said five- to six-membered aromatic ring system optionally substituted with up to four $R^1$;

each $R^1$ is independently selected from —H, halogen, —CN, —NO$_2$, —OR$^3$, —N(R$^3$)R$^3$, —S(O)$_{0\text{-}2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted lower alkyl, optionally substituted aryl, optionally substituted lower arylalkyl, optionally substituted heterocyclyl, and optionally substituted lower heterocyclylalkyl;

optionally two of $R^1$, together with the atoms to which they are attached, form a first ring system fused with Ar, said first ring system substituted with zero to three additional of $R^1$;

X is selected from the following six formulae:

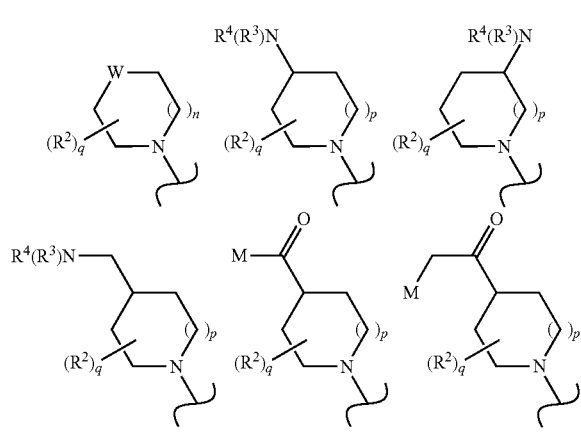

wherein,
W is selected from —C(R²)(R²)—, —N(R⁴)—, —S(O)$_{0-2}$—, and —O—;
n=1 or 2;
p=0 or 1;
q is 1 to 3;
M is —OR³ or —N(R³)R⁴;
each R² is independently selected from —H, halogen, oxo, —CN, —NH₂, —NO₂, —OR³, —N(R³)R³, —N(R³)R⁵, —S(O)$_{0-2}$R³, —SO₂N(R³)R³, —CO₂R³, —C(O)N(R³)R³, —N(R³)SO₂R³, —N(R³)C(O)R³, —N(R³)CO₂R³, —N(R³)C(O)N(R³)R³, —C(O)R³, —OC(O)R³, optionally substituted lower alkyl, optionally substituted aryl, optionally substituted lower arylalkyl, optionally substituted heterocyclyl, and optionally substituted lower heterocyclylalkyl;
two of R², together with the atoms to which they are attached, can form an optionally substituted three- to seven-membered ring system;
each R³ is independently selected from —H, optionally substituted lower alkyl, optionally substituted aryl, optionally substituted lower arylalkyl, optionally substituted heterocyclyl, and optionally substituted lower heterocyclylalkyl; or
two of R³, when taken together with a common nitrogen to which they are attached, form an optionally substituted five- to seven-membered heterocyclyl ring, said optionally substituted five- to seven-membered heterocyclyl ring optionally containing at least one additional heteroatom selected from N, O, S, and P;
each R⁴ is independently selected from R³, —SO₂R³, —SO₂N(R³)R³, —CO₂R³, —C(O)N(R³)R³, and —C(O)R³;
Y is selected from —CH₂—, —O—, —S(O)$_{0-2}$—, —N(R³)—, and absent;
L is selected from —(CH₂)$_{1-3}$—, —(CH₂)$_{1-3}$N(R³)—, —(CH₂)$_{1-3}$O—, —(CH₂)$_{1-3}$S(O)$_{0-2}$— and absent; each of the aforementioned methylenes optionally substituted;
Z is a five- to seven-membered ring system or —R³, said five- to seven-membered ring system optionally substituted with zero to four of R⁵; and
R⁵ is selected from —H, halogen, —CN, oxo, —NO₂, —OR³, —N(R³)R⁴, —S(O)$_{0-2}$R³, —SO₂N(R³)R³, —CO₂R³, —C(O)N(R³)R, —N(R³)SO₂R³, —N(R³)C(O)R³, —N(R³)CO₂R³, —C(O)R³, optionally substituted lower alkyl, optionally substituted aryl, optionally substituted lower arylalkyl, optionally substituted heterocyclyl, and optionally substituted lower heterocyclylalkyl; and
optionally two of R⁵, together with the atoms to which they are attached, form a second ring system fused with said five- to seven-membered ring system, said second ring system substituted with zero to four of R⁵, hereinafter embodiment [0021].

In one example, the compound is according to embodiment [0021], having formula II,

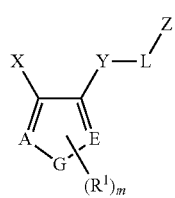

II wherein, A and E are each independently N or —C(R¹)—; and G is selected from —S(O)$_{0-2}$—, and —C(R¹)=C(R¹)—, hereinafter embodiment [0022].

In another example, the compound is according to embodiment [0022], wherein Ar is selected from the following formulae:

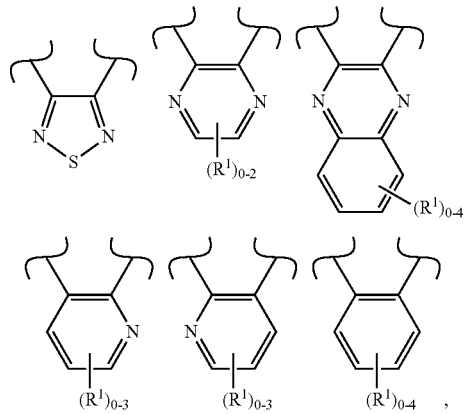

hereinafter embodiment [0023].

In another example, the compound is according to embodiment [0023], wherein —Y-L-Z is selected from the following formulae,

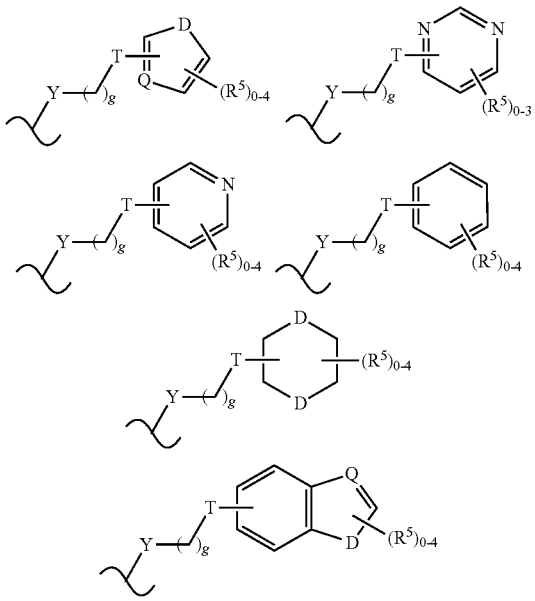

wherein g is zero to two; D is selected from —C(R⁵)(R⁵)—, —O—, —S(O)$_{0-2}$—, and —N(R⁴)—; Q is =N— or —C(R⁵)—, T is selected from absent, —N(R³)—, —S— and —O—; and each methylene between Y and T is optionally substituted; provided that when both Y and T are heteroatoms then g must be two, hereinafter embodiment [0024].

In another example, the compound is according to embodiment [0024], wherein Y is —O— or optionally substituted —CH₂—, hereinafter embodiment [0025].

In another example, the compound is according to embodiment [0025], wherein X is selected from the following formulae:

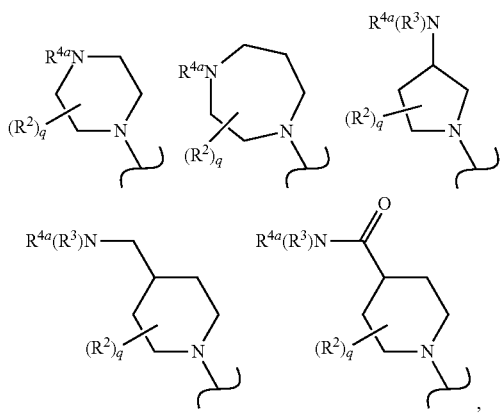

hereinafter embodiment [0026]

In another example, the compound is according to embodiment [0026], wherein $R^{4a}$ is selected from —$SO_2R^3$, —$SO_2N(R^3)R^4$, —$CO_2R^3$, —$C(O)N(R^3)R^4$, and —$C(O)R^3$, hereinafter embodiment [0027].

In another example, the compound is according to embodiment [0027], wherein each $R^2$ is independently selected from —H or optionally substituted lower alkyl, hereinafter embodiment [0028].

In another example, the compound is according to embodiment [0028], wherein each $R^2$ is independently selected from —H, haloalkyl, —$C_{1-6}$alkyl-$N(R^3)R^3$, —$C_{1-6}$alkyl-$OR^3$, —$C_{1-6}$alkyl-$CO_2R^3$, and —$C_{1-6}$alkyl-$C(O)N(R^3)R^3$, hereinafter embodiment [0029].

In another example, the compound is according to embodiment [0029], wherein $R^{4a}$ is —$C(O)N(R^3)R^3$ or —$C(O)R^3$, hereinafter embodiment [0030].

In another example, the compound is according to embodiment [0030], wherein —Y-L-Z is selected from the following formulae,

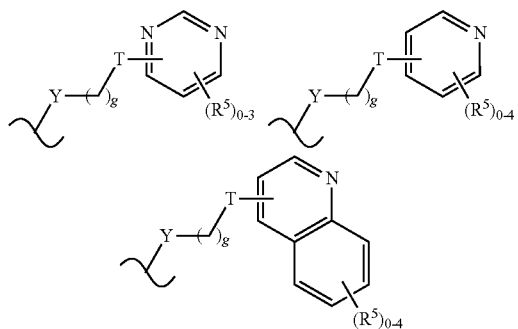

wherein Y, T, and g are as described above, hereinafter embodiment [0031].

In another example, the compound is according to embodiment [0031], wherein g is one or two, hereinafter embodiment [0032].

In another example, the compound is according to embodiment [0032], wherein each $R^5$ is independently selected from —H, halogen, —CN, —$NH_2$, —$NO_2$, —$OR^3$, —$N(R^3)R^4$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, and optionally substituted lower alkyl, hereinafter embodiment [0033].

In another example, the compound is according to embodiment [0033], wherein —Y-L-Z is selected from the following formulae:

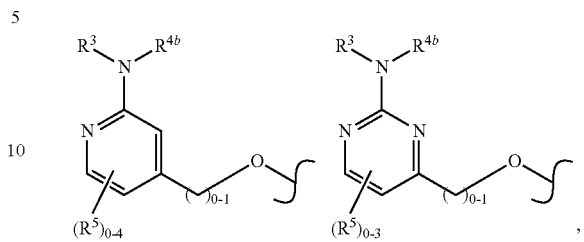

hereinafter embodiment [0034]

In another example, the compound is according to embodiment [0034], having formula III,

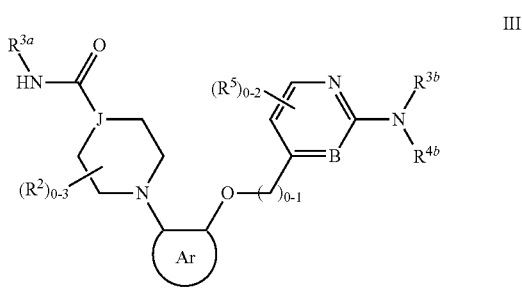

wherein J is N or CH, and B is =N— or =$C(R^5)$—, hereinafter embodiment [0035].

In another example, the compound is according to embodiment [0035], wherein $R^{3a}$ is selected from optionally substituted aryl, optionally substituted lower arylalkyl, optionally substituted heterocyclyl, and optionally substituted lower heterocyclylalkyl, hereinafter embodiment [0036].

In another example, the compound is according to embodiment [0036], wherein $R^{3a}$ is selected from optionally substituted aryl and optionally substituted heteroaryl, hereinafter embodiment [0037].

In another example, the compound is according to embodiment [0037], wherein $R^{3a}$ is optionally substituted phenyl, hereinafter embodiment [0038].

In another example, the compound is according to embodiment [0038], wherein said optionally substituted phenyl is substituted with at least one of halogen, —CN, —$CF_3$, —$NH_2$, —$NO_2$, —$OR^3$, —$N(R^3)R^3$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, optionally substituted lower alkyl, and optionally substituted aryl, hereinafter embodiment [0039].

In another example, the compound is according to embodiment [0039], wherein said optionally substituted phenyl group is substituted with at least one trifluoromethyl group, hereinafter embodiment [0040].

In another example, the compound is according to embodiment [0040], wherein said optionally substituted phenyl group is substituted with at least two trifluoromethyl groups, hereinafter embodiment [0041].

In another example, the compound is according to embodiment [0039], wherein said optionally substituted phenyl group is substituted with at least one lower alkyl group, hereinafter embodiment [0042].

In another example, the compound is according to embodiment [0039], wherein $R^{3b}$ is —H, hereinafter embodiment [0043].

In another example, the compound is according to embodiment [0043], wherein $R^{3b}$ is selected from $R^3$, —H, —$CO_2R^3$, —$C(O)N(R^3)R^4$, and —$C(O)R^3$, hereinafter embodiment [0044].

In another example, the compound is according to embodiment [0044], wherein Ar is according to the formula below, hereinafter embodiment [0045].

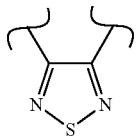

In another example, the compound is according to embodiment [0044], wherein Ar is according to the formula below, hereinafter embodiment [0046].

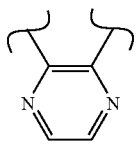

In another example, the compound is according to embodiment [0044], wherein Ar is according to the formula below, hereinafter embodiment [0047].

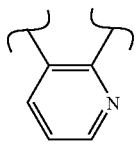

In another example, the compound is according to embodiment [0044], wherein Ar is according to the formula below, hereinafter embodiment [0048].

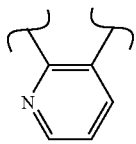

In another example, the compound is according to embodiment [0044], wherein Ar is according to the formula below, hereinafter embodiment [0049]

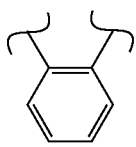

In another example, the present invention comprises a compound for modulating kinase activity, particularly Tie-2, of Formula IV,

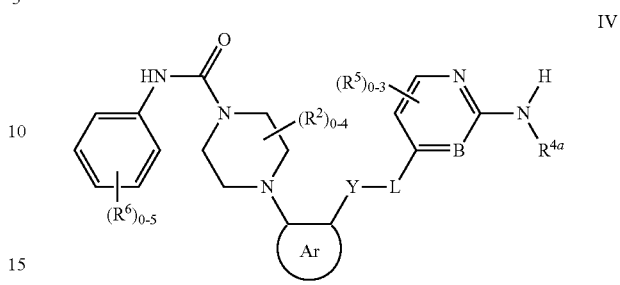

or a pharmaceutically acceptable salt, hydrate, or prodrug thereof, wherein, Ar is selected from the following formulae:

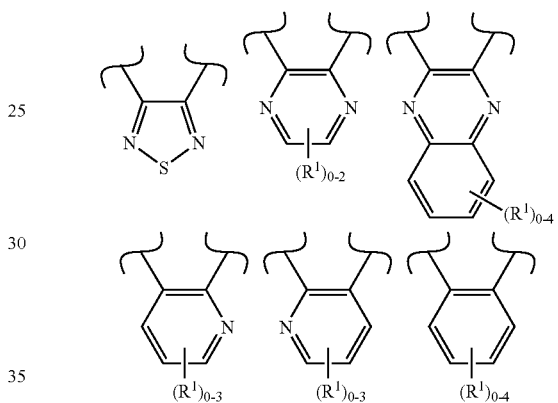

each $R^1$ is independently selected from —H, halogen, —CN, —$NO_2$, —$OR^3$, —$N(R^3)R^3$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$C(O)R^3$, optionally substituted lower alkyl, optionally substituted aryl, optionally substituted lower arylalkyl, optionally substituted heterocyclyl, and optionally substituted lower heterocyclylalkyl;

optionally two of $R^1$, together with the atoms to which they are attached, form a first ring system fused with Ar, said first ring system substituted with zero to three additional of $R^1$;

each $R^2$ is independently selected from —H, halogen, oxo, —CN, —$NH_2$, —$NO_2$, —$OR^3$, —$N(R^3)R^3$, —$N(R^3)R^5$, —$S(O)_{0-2}R^3$, —$SO_2N(R^3)R^3$, —$CO_2R^3$, —$C(O)N(R^3)R^3$, —$N(R^3)SO_2R^3$, —$N(R^3)C(O)R^3$, —$N(R^3)CO_2R^3$, —$N(R^3)C(O)N(R^3)R^3$, —$C(O)R^3$, optionally substituted lower alkyl, optionally substituted aryl, optionally substituted lower arylalkyl, optionally substituted heterocyclyl, and optionally substituted lower heterocyclylalkyl;

two of $R^2$, together with the atoms to which they are attached, can form an optionally substituted three- to seven-membered ring system;

each $R^3$ is independently selected from —H, optionally substituted lower alkyl, optionally substituted aryl, optionally substituted lower arylalkyl, optionally substituted heterocyclyl, and optionally substituted lower heterocyclylalkyl; or two of $R^3$, when taken together with a common nitrogen to which they are attached, form an optionally substituted five- to seven-membered heterocyclyl ring, said optionally substituted five- to seven-membered heterocyclyl ring optionally containing at least one additional heteroatom selected from N, O, S, and P;

each $R^4$ is independently selected from $R^3$, —SO$_2$R$^3$, —SO$_2$N(R$^3$)R$^3$, —CO$_2$R$^3$, —C(O)N(R$^3$)R$^3$, and —C(O)R$^3$;
Y is selected from optionally substituted —CH$_2$—, —O—, —S—, and —N(R$^3$)—;
L is selected from optionally substituted —CH$_2$—, —O—, —S—, —N(R$^3$)— and absent;
provided that Y and L are not both heteroatoms;
B is =N— or =C(H)—;
at each instance, $R^5$ and $R^6$ are independently selected from —H, halogen, —CN, —NO$_2$, —OR$^3$, —N(R$^3$)R$^4$, —S(O)$_{0-2}$R$^3$, —SO$_2$N(R$^3$)R$^3$, —CO$_2$R$^3$, —C(O)N(R$^3$)R, —N(R$^3$)SO$_2$R$^3$, —N(R$^3$)C(O)R$^3$, —N(R$^3$)CO$_2$R$^3$, —C(O)R$^3$, optionally substituted lower alkyl, optionally substituted aryl, optionally substituted lower arylalkyl, optionally substituted heterocyclyl, and optionally substituted lower heterocyclylalkyl; and
optionally two of $R^5$, together with the atoms to which they are attached, form a ring system fused with the ring containing B according to formula IV, said ring system substituted with zero to two additional of $R^5$, hereinafter embodiment [0050].

In another example, the compound is according to embodiment [0050], wherein Y is —O— and L is optionally substituted —CH$_2$—, hereinafter embodiment [0051].

In another example, the compound is according to embodiment [0051], wherein at least one of $R^6$ is optionally substituted lower alkyl, hereinafter embodiment [0052].

In another example, the compound is according to embodiment [0052], wherein said at least one optionally substituted lower alkyl is meta- to the piperazine urea function as depicted in formula IV, hereinafter embodiment [0053].

In another example, the compound is according to embodiment [0053], wherein $R^{4a}$ is selected from $R^3$, —H, —CO$_2$R$^3$, —C(O)N(R$^3$)R$^4$, and —C(O)R$^3$, hereinafter embodiment [0054].

In another example, the compound is according to embodiment [0054], wherein $R^{4a}$ is selected from —H, —CO$_2$R$^3$, —C(O)N(R$^3$)R$^4$, and —C(O)R$^3$, hereinafter embodiment [0055].

In another example, the compound is according to embodiment [0055], wherein —Y-L- is —OCH$_2$—, hereinafter embodiment [0056].

In another example, the compound is according to embodiment [0056], wherein Ar is according to the formula below, hereinafter embodiment [0057].

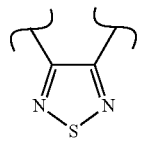

In another example, the compound is according to embodiment [0056], wherein Ar is according to the formula below, hereinafter embodiment [0058].

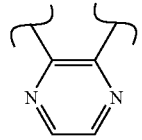

In another example, the compound is according to embodiment [0056], wherein Ar is according to the formula below, hereinafter embodiment [0059].

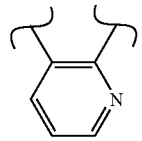

In another example, the compound is according to embodiment [0056], wherein Ar is according to the formula below, hereinafter embodiment [0060].

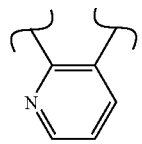

In another example, the compound is according to embodiment [0056], wherein Ar is according to the formula below, hereinafter embodiment [0061].

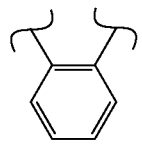

In another example, the compound is according to embodiment [0021], selected from Table 1, hereinafter embodiment [0062].

TABLE 1

| | | |
|---|---|---|
| 1 | N-[(1R,2S)-2-phenylcyclopropyl]-4-{4-[(pyridin-4-ylmethyl)oxy]-1,2,5-thiadiazol-3-yl}piperazine-1-carboxamide | 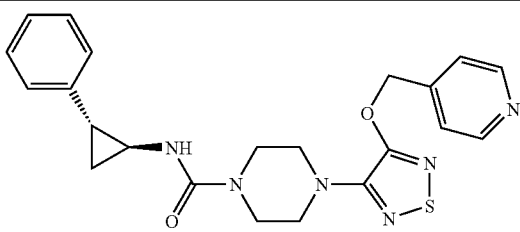 |

TABLE 1-continued

| | | |
|---|---|---|
| 2 | N-[3,5-bis(trifluoromethyl)phenyl]-4-{4-[(pyridin-4-ylmethyl)oxy]-1,2,5-thiadiazol-3-yl}piperazine-1-carboxamide | 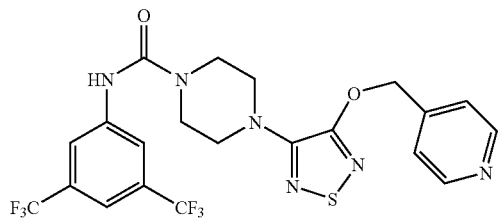 |
| 3 | N-[4-chloro-3-(trifluoromethyl)phenyl]-4-{4-[(pyridin-4-ylmethyl)oxy]-1,2,5-thiadiazol-3-yl}piperazine-1-carboxamide | 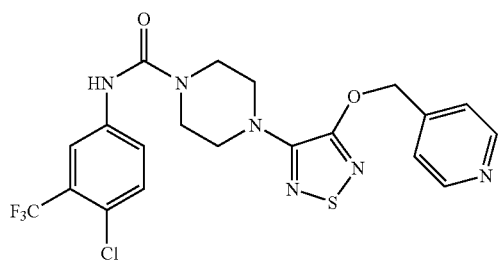 |
| 4 | N-[4-(1-methylethyl)phenyl]-4-{4-[(pyridin-4-ylmethyl)oxy]-1,2,5-thiadiazol-3-yl}piperazine-1-carboxamide | 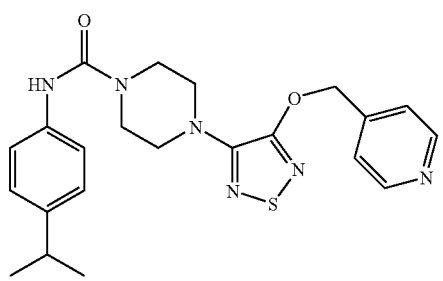 |
| 5 | N-(3-bromophenyl)-4-{4-[(pyridin-4-ylmethyl)oxy]-1,2,5-thiadiazol-3-yl}piperazine-1-carboxamide | 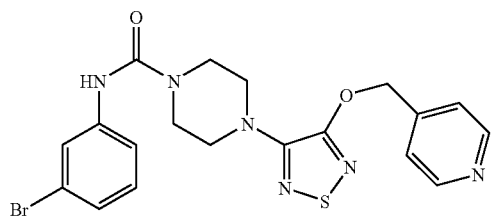 |
| 6 | N-[3-(methylthio)phenyl]-4-{4-[(pyridin-4-ylmethyl)oxy]-1,2,5-thiadiazol-3-yl}piperazine-1-carboxamide | 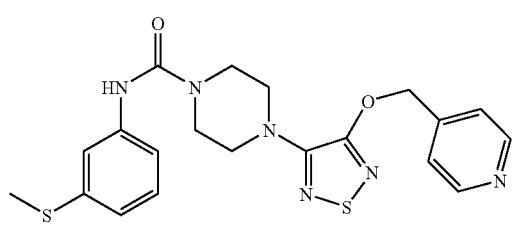 |
| 7 | N-(3-ethylphenyl)-4-{4-[(pyridin-4-ylmethyl)oxy]-1,2,5-thiadiazol-3-yl}piperazine-1-carboxamide | 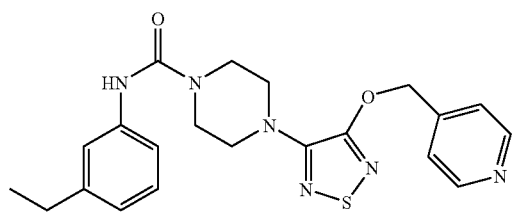 |
| 8 | N-(3,5-dimethylphenyl)-4-{4-[(pyridin-4-ylmethyl)oxy]-1,2,5-thiadiazol-3-yl}piperazine-1-carboxamide | 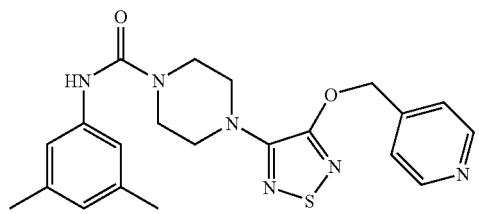 |

TABLE 1-continued

| | | |
|---|---|---|
| 9 | N-[3-trifluoromethylphenyl]-4-{4-[(pyridin-4-ylmethyl)oxy]-1,2,5-thiadiazol-3-yl}piperazine-1-carboxamide | 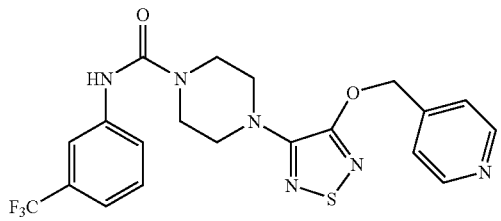 |
| 10 | N-[3,5-bis(trifluoromethyl)phenyl]-4-(4-{[(2-methylquinolin-4-yl)methyl]oxy}-1,2,5-thiadiazol-3-yl)piperazine-1-carboxamide | 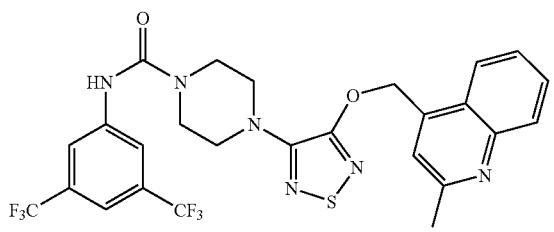 |
| 11 | N-[3,5-bis(trifluoromethyl)phenyl]-4-[4-({[3-(dimethylamino)phenyl]methyl}oxy)-1,2,5-thiadiazol-3-yl]piperazine-1-carboxamide | 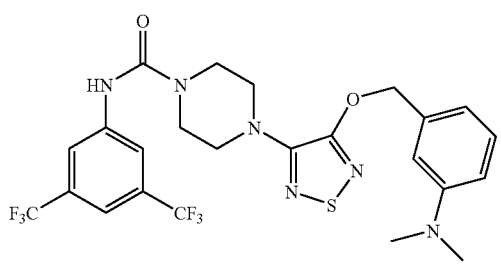 |
| 12 | N-[3,5-bis(trifluoromethyl)phenyl]-4-[4-(1H-indol-5-yloxy)-1,2,5-thiadiazol-3-yl]piperazine-1-carboxamide | 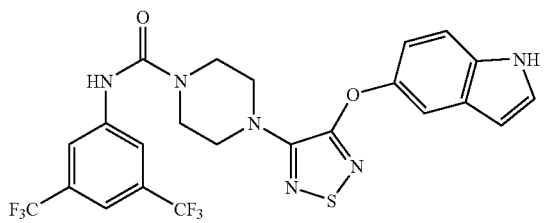 |
| 13 | N-[3,5-bis(trifluoromethyl)phenyl]-4-{4-[(3-thienylmethyl)oxy]-1,2,5-thiadiazol-3-yl}piperazine-1-carboxamide | 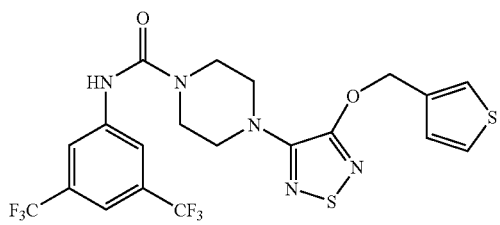 |
| 14 | N-[3,5-bis(trifluoromethyl)phenyl]-4-{4-[(2-morpholin-4-ylethyl)oxy]-1,2,5-thiadiazol-3-yl}piperazine-1-carboxamide | 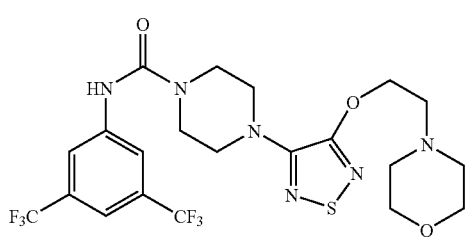 |

TABLE 1-continued

| | | |
|---|---|---|
| 15 | N-[3,5-bis(trifluoromethyl)phenyl]-4-(4-{[2-(1H-imidazol-1-yl)ethyl]oxy}-1,2,5-thiadiazol-3-yl)piperazine-1-carboxamide | 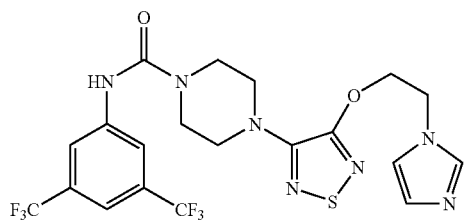 |
| 16 | N-[3,5-bis(trifluoromethyl)phenyl]-4-{4-[(1-methylpiperidin-4-yl)oxy]-1,2,5-thiadiazol-3-yl}piperazine-1-carboxamide | 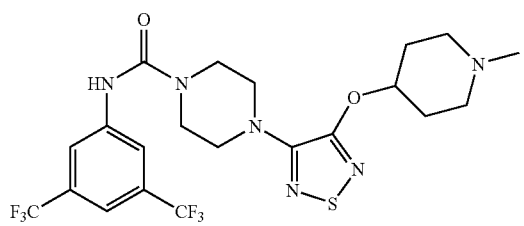 |
| 17 | N-[3,5-bis(trifluoromethyl)phenyl]-4-[4-({[4-(methyloxy)phenyl]methyl}oxy)-1,2,5-thiadiazol-3-yl]piperazine-1-carboxamide | 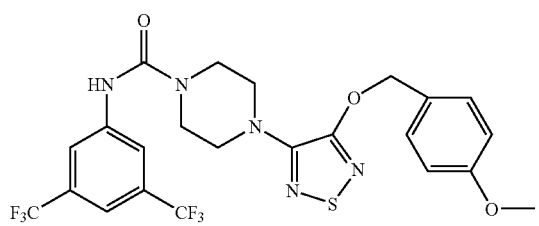 |
| 18 | 4-[4-({[3,4-bis(methyloxy)phenyl]methyl}oxy)-1,2,5-thiadiazol-3-yl]-N-[3,5-bis(trifluoromethyl)phenyl]piperazine-1-carboxamide | 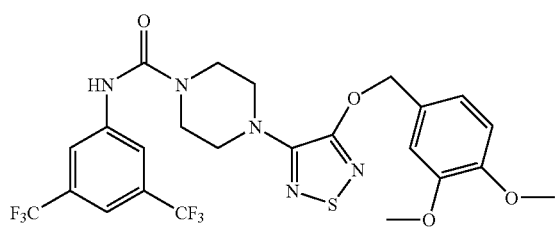 |
| 19 | 4-{4-[(1,3-benzodioxol-5-ylmethyl)oxy]-1,2,5-thiadiazol-3-yl}-N-[3,5-bis(trifluoromethyl)phenyl]piperazine-1-carboxamide | 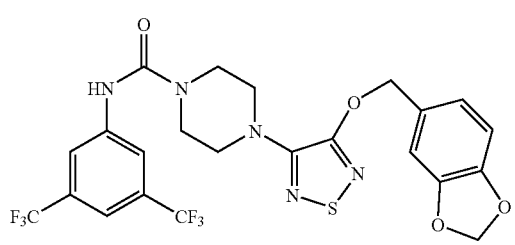 |
| 20 | N-[3,5-bis(trifluoromethyl)phenyl]-4-{4-[(furan-3-ylmethyl)oxy]-1,2,5-thiadiazol-3-yl}piperazine-1-carboxamide | 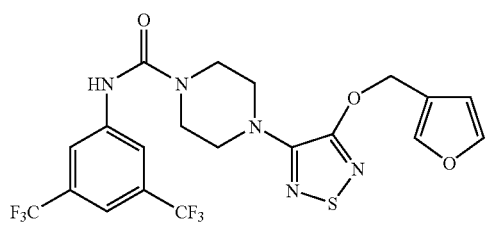 |
| 21 | N-[3,5-bis(trifluoromethyl)phenyl]-4-{4-[(tetrahydrofuran-3-ylmethyl)oxy]-1,2,5-thiadiazol-3-yl}piperazine-1-carboxamide | 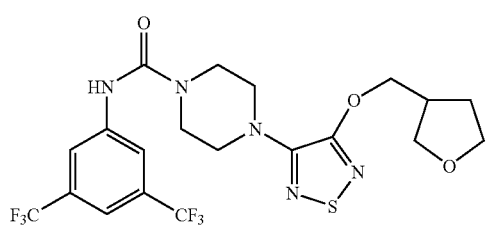 |

TABLE 1-continued

| | | |
|---|---|---|
| 22 | N-[3,5-bis(trifluoromethyl)phenyl]-2-methyl-4-{4-[(pyridin-4-ylmethyl)oxy]-1,2,5-thiadiazol-3-yl}piperazine-1-carboxamide | 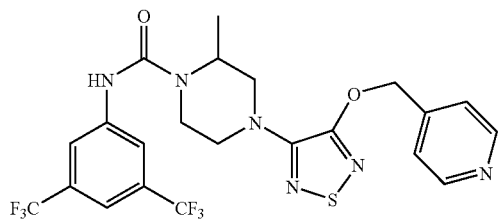 |
| 23 | N-[3,5-bis(trifluoromethyl)phenyl]-4-{4-[(pyridin-4-ylmethyl)oxy]-1,2,5-thiadiazol-3-yl}-1,4-diazepane-1-carboxamide | 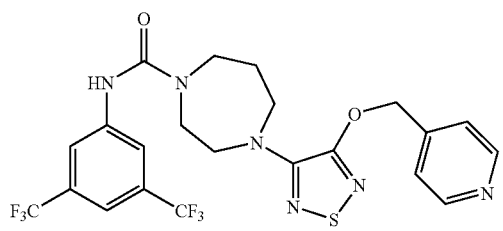 |
| 24 | 1-({[(1S,2R,5S)-5-methyl-2-(1-methylethyl)cyclohexyl]oxy}acetyl)-4-{4-[(pyridin-4-ylmethyl)oxy]-1,2,5-thiadiazol-3-yl}piperazine | 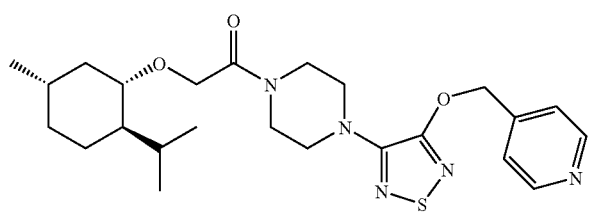 |
| 25 | 5-phenyl-N-(1-{4-[(pyridin-4-ylmethyl)oxy]-1,2,5-thiadiazol-3-yl}pyrrolidin-3-yl)-1,3-oxazole-4-carboxamide | 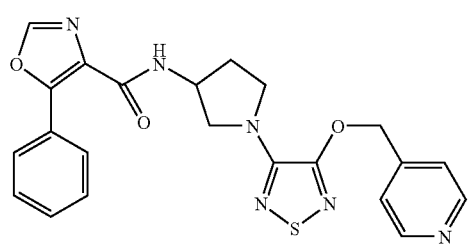 |
| 26 | 1-{4-[(pyridin-4-ylmethyl)oxy]-1,2,5-thiadiazol-3-yl}-4-{[3-(trifluoromethyl)phenyl]acetyl}piperazine | 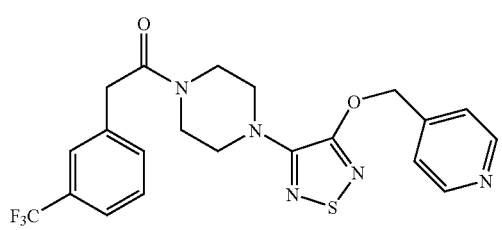 |
| 27 | N-[3,5-bis(trifluoromethyl)phenyl]-4-{4-[(piperidin-4-ylmethyl)oxy]-1,2,5-thiadiazol-3-yl}piperazine-1-carboxamide | 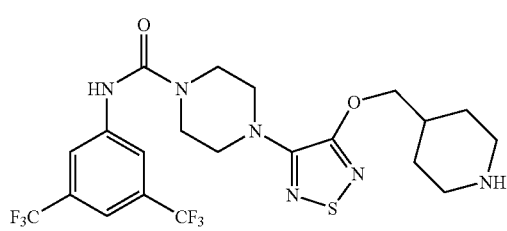 |
| 28 | N-[3,5-bis(trifluoromethyl)phenyl]-N'-[(4-{4-[(pyridin-4-ylmethyl)oxy]-1,2,5-thiadiazol-3-yl}piperidin-4-yl)methyl]urea | 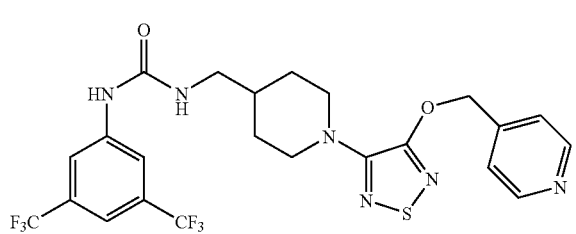 |

TABLE 1-continued

| 29 | N-[3,5-bis(trifluoromethyl)phenyl]-4-{4-[(3-pyridin-3-ylpropyl)oxy]-1,2,5-thiadiazol-3-yl}piperazine-1-carboxamide | 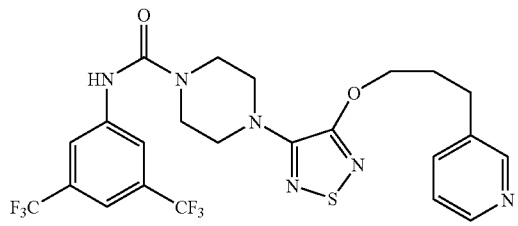 |
| 30 | N-[3,5-bis(trifluoromethyl)phenyl]-4-{1,1,-dioxido-4-[(pyridin-4-ylmethyl)oxy]-1,2,5-thiadiazol-3-yl}piperazine-1-carboxamide | 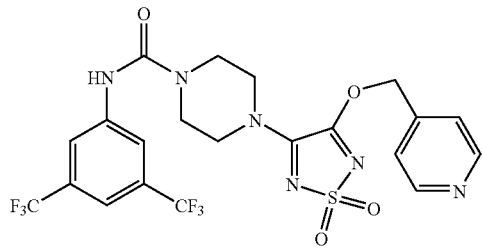 |
| 31 | 4-[4-(1-azabicyclo[2.2.2]oct-3-yloxy)-1,2,5-thiadiazol-3-yl]-N-[3,5-bis(trifluoromethyl)phenyl]piperazine-1-carboxamide | 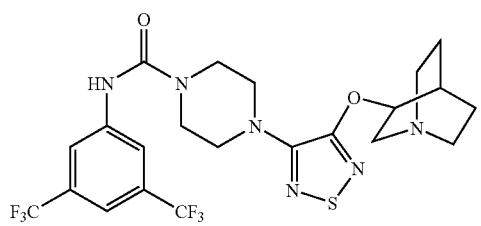 |
| 32 | 4-[({4-[4-({[3,5-bis(trifluoromethyl)phenyl]amino}carbonyl)piperazin-1-yl]-1,2,5-thiadiazol-3-yl}oxy)methyl]benzoic acid | 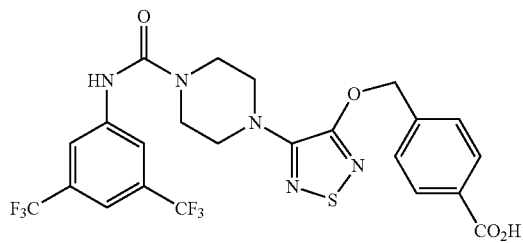 |
| 33 | N-[3,5-bis(trifluoromethyl)phenyl]-4-{4-[(piperidin-3-ylmethyl)oxy]-1,2,5-thiadiazol-3-yl}piperazine-1-carboxamide | 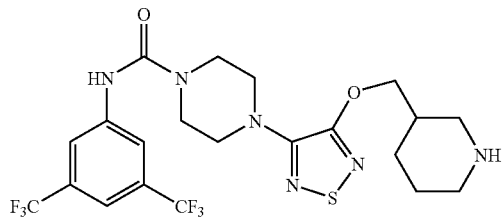 |
| 34 | N-[3,5-bis(trifluoromethyl)phenyl]-4-{4-[(2-pyrrolidin-1-ylethyl)oxy]-1,2,5-thiadiazol-3-yl}piperazine-1-carboxamide | 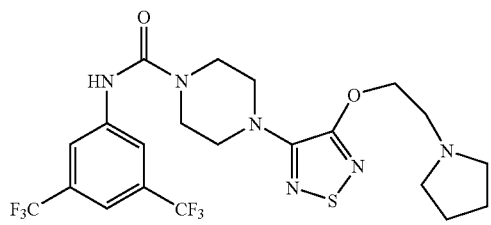 |

TABLE 1-continued

| | | |
|---|---|---|
| 35 | 4-{4-[(2-amino-2-methylpropyl)oxy]-1,2,5-thiadiazol-3-yl}-N-[3,5-bis(trifluoromethyl)phenyl]piperazine-1-carboxamide | 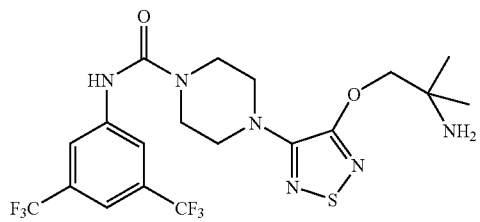 |
| 36 | N-[3,5-bis(trifluoromethyl)phenyl]-1-{4-[(pyridin-4-ylmethyl)oxy]-1,2,5-thiadiazol-3-yl}piperidine-4-carboxamide | 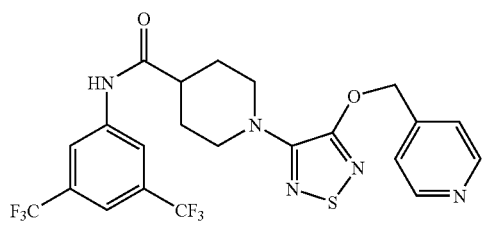 |
| 37 | 1-{4-[(pyridin-4-ylmethyl)oxy]-1,2,5-thiadiazol-3-yl}-N-[3-(trifluoromethyl)phenyl]piperidine-4-carboxamide | 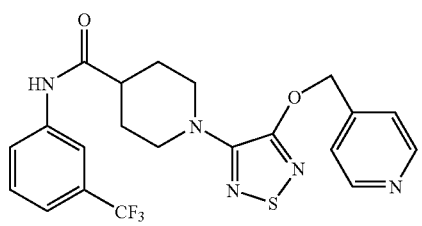 |
| 38 | N-[3,5-bis(trifluoromethyl)phenyl]-4-{3-[(pyridin-4-ylmethyl)oxy]pyrazin-2-yl}piperazine-1-carboxamide | 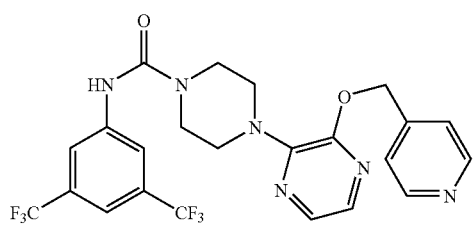 |
| 39 | 4-{3-[(pyridin-4-ylmethyl)oxy]pyrazin-2-yl}-N-[3-(trifluoromethyl)phenyl]piperazine-1-carboxamide | 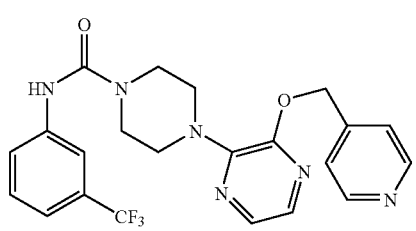 |
| 40 | N-[3,5-bis(trifluoromethyl)phenyl]-4-{4-[(2-piperidin-4-ylethyl)oxy]-1,2,5-thiadiazol-3-yl}piperazine-1-carboxamide | 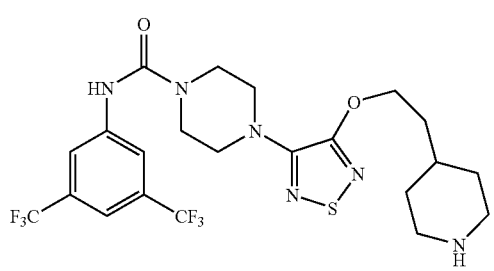 |
| 41 | 2-methyl-4-{4-[(pyridin-4-ylmethyl)oxy]-1,2,5-thiadiazol-3-yl}-N-[3-(trifluoromethyl)phenyl]piperazine-1-carboxamide | 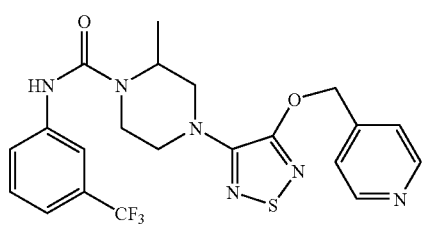 |

TABLE 1-continued

| | | |
|---|---|---|
| 42 | 1-phenyl-4-{4-[(pyridin-4-ylmethyl)oxy]-1,2,5-thiadiazol-3-yl}piperazine | 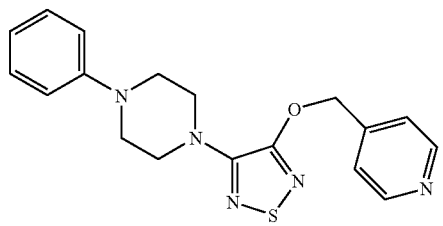 |
| 43 | 1-[(4-methylphenyl)methyl]-4-{4-[(pyridin-4-ylmethyl)oxy]-1,2,5-thiadiazol-3-yl}piperazine | 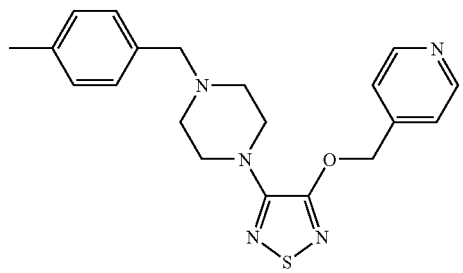 |
| 44 | N-[3,5-bis(trifluoromethyl)phenyl]-4-{4-[(pyridin-4-ylmethyl)amino]-1,2,5-thiadiazol-3-yl}piperazine-1-carboxamide | 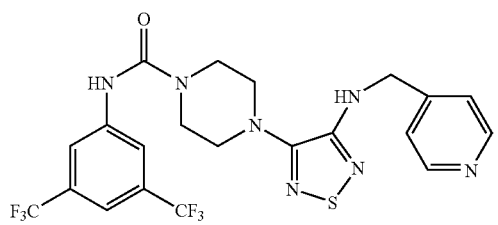 |
| 45 | 4-{4-[(pyridin-4-ylmethyl)oxy]-1,2,5-thiadiazol-3-yl}-N-[3-(trifluoromethyl)phenyl]-1,4-diazepane-1-carboxamide | 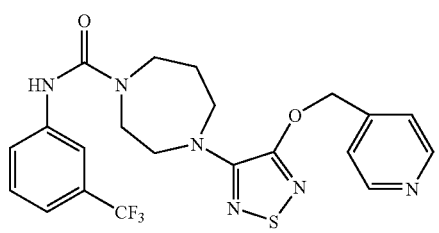 |
| 46 | 2-methyl-1-{[2-(methyloxy)phenyl]carbonyl}-4-{4-[(pyridin-4-ylmethyl)oxy]-1,2,5-thiadiazol-3-yl}piperazine | 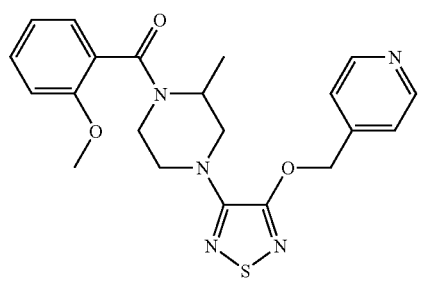 |
| 47 | N-[5-chloro-2-(methyloxy)phenyl]-N'-(1-{4-[(pyridin-4-ylmethyl)oxy]-1,2,5-thiadiazol-3-yl}pyrrolidin-3-yl)urea | 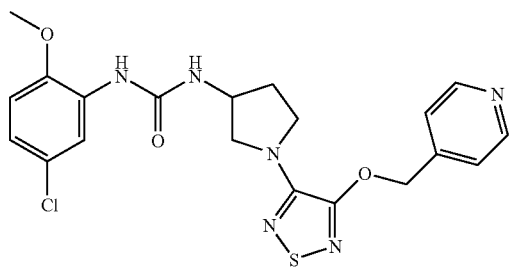 |

TABLE 1-continued

| | | |
|---|---|---|
| 48 | N-[5-methyl-2-(methyloxy)phenyl]-N'-(1-{4-[(pyridin-4-ylmethyl)oxy]-1,2,5-thiadiazol-3-yl}pyrrolidin-3-yl)urea | 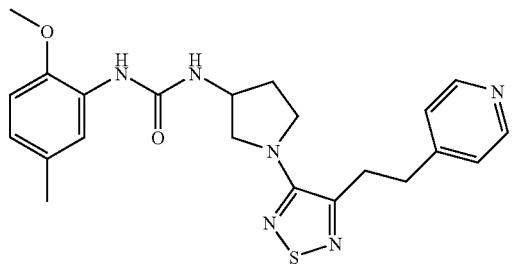 |
| 49 | N-(1-{4-[(pyridin-4-ylmethyl)oxy]-1,2,5-thiadiazol-3-yl}pyrrolidin-3-yl)-N'-[3-(trifluoromethyl)phenyl]urea | 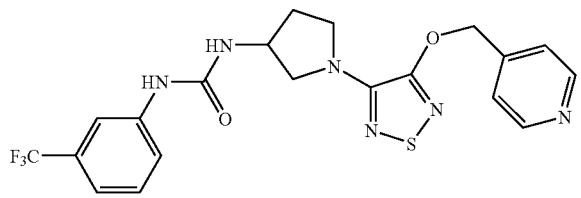 |
| 50 | 2-methyl-N-[4-(1-methylethyl)phenyl]-4-{4-[(pyridin-4-ylmethyl)oxy]-1,2,5-thiadiazol-3-yl}piperazine-1-carboxamide | 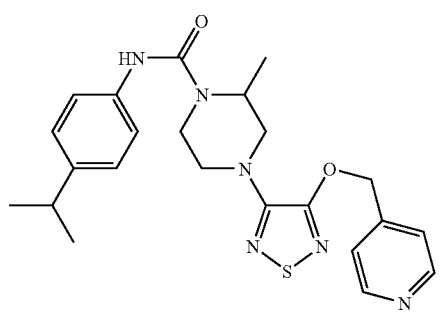 |
| 51 | 2-methyl-N-[3-(methylthio)phenyl]-4-{4-[(pyridin-4-ylmethyl)oxy]-1,2,5-thiadiazol-3-yl}piperazine-1-carboxamide | 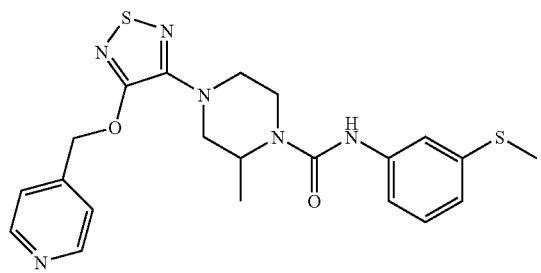 |
| 52 | (2R)-N-[3,5-bis(trifluoromethyl)phenyl]-2-methyl-4-{4-[(pyridin-4-ylmethyl)oxy]-1,2,5-thiadiazol-3-yl}piperazine-1-carboxamide | 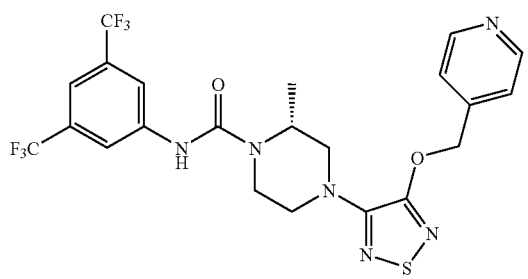 |
| 53 | (2R)-2-methyl-4-{4-[4-[(pyridin-4-ylmethyl)oxy]-1,2,5-thiadiazol-3-yl}-N-[3-(trifluoromethyl)phenyl]piperazine-1-carboxamide | 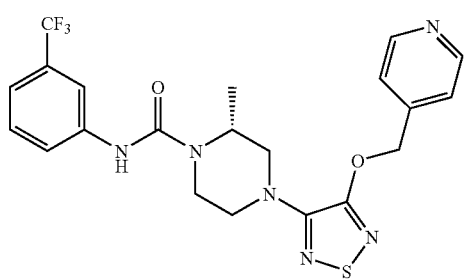 |

TABLE 1-continued

| | | |
|---|---|---|
| 54 | 1-[4-(4-{4-[(pyridin-4-ylmethyl)oxy]-1,2,5-thiadiazol-3-yl}piperazin-1-yl)phenyl]ethanone | 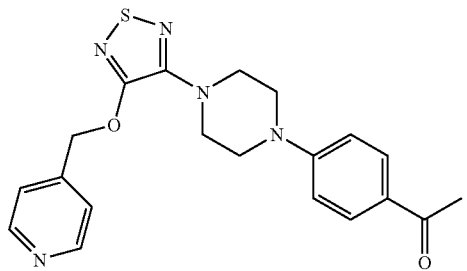 |
| 55 | 2-(4-{4-[(pyridin-4-ylmethyl)oxy]-1,2,5-thiadiazol-3-yl}piperazin-1-yl)pyrimidine | 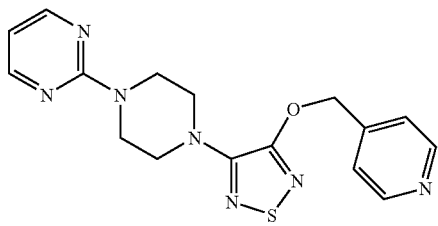 |
| 56 | 1-[2-nitro-4-(trifluoromethyl)phenyl]-4-{4-[(pyridin-4-ylmethyl)oxy]-1,2,5-thiadiazol-3-yl}piperazine | 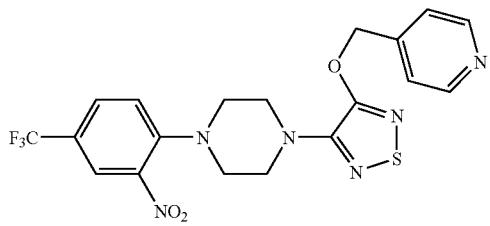 |
| 57 | (2S)-N-[3,5-bis(trifluoromethyl)phenyl]-2-methyl-4-{4-[(pyridin-4-ylmethyl)oxy]-1,2,5-thiadiazol-3-yl}piperazine-1-carboxamide | 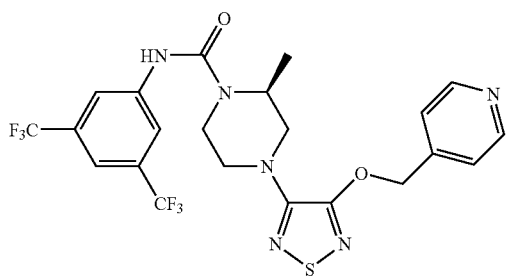 |
| 58 | (2S)-2-methyl-4-{4-[(pyridin-4-ylmethyl)oxy]-1,2,5-thiadiazol-3-yl}-N-[3-(trifluoromethyl)phenyl]piperazine-1-carboxamide | 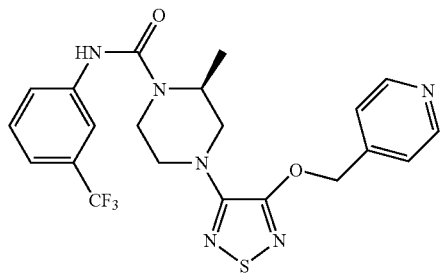 |
| 59 | N-[3,5-bis(trifluoromethyl)phenyl]-4-(3-hydroxypyrazin-2-yl)piperazine-1-carboxamide | 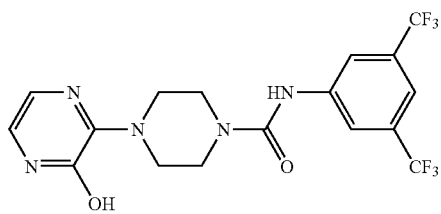 |

TABLE 1-continued

| 60 | 2-[2,5-bis(trifluoromethyl)phenyl]-N-(1-{4-[(pyridin-4-ylmethyl)oxy]-1,2,5-thiadiazol-3-yl}pyrrolidin-3-yl)acetamide | 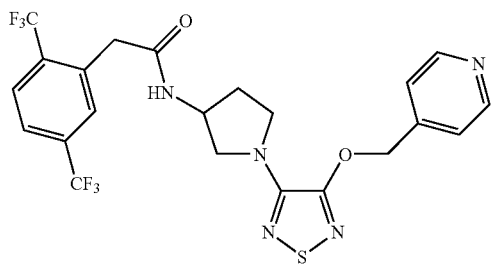 |
| --- | --- | --- |
| 61 | 1-{[2,5-bis(trifluoromethyl)phenyl]acetyl}-2-methyl-4-{4-[(pyridin-4-ylmethyl)oxy]-1,2,5-thiadiazol-3-yl}piperazine | 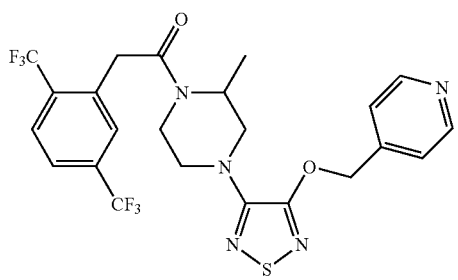 |
| 62 | N-[3,5-bis(trifluoromethyl)phenyl]-2-methyl-4-{3-[(pyridin-4-ylmethyl)oxy]pyrazin-2-yl}piperazine-1-carboxamide | 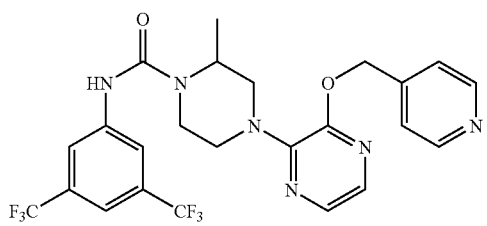 |
| 63 | 2-methyl-4-{3-[(pyridin-4-ylmethyl)oxy]pyrazin-2-yl}-N-[3-(trifluoromethyl)phenyl]piperazine-1-carboxamide | 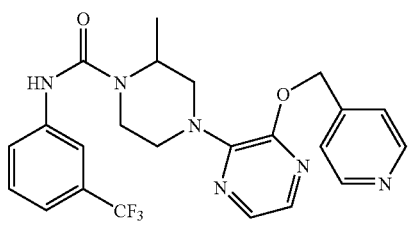 |
| 64 | N-[3,5-bis(trifluoromethyl)phenyl]-2,6-dimethyl-4-{3-[(pyridin-4-ylmethyl)oxy]pyrazin-2-yl}piperazine-1-carboxamide | 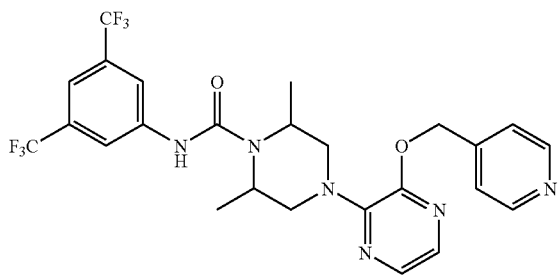 |
| 65 | 2,6-dimethyl-4-{3-[(pyridin-4-ylmethyl)oxy]pyrazin-2-yl}-N-[3-(trifluoromethyl)phenyl]piperazine-1-carboxamide | 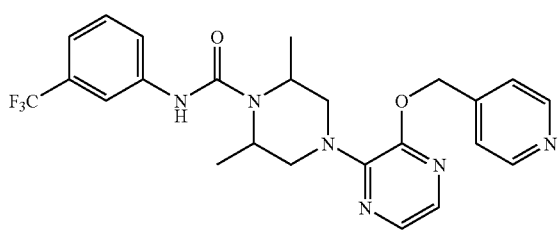 |

TABLE 1-continued

| | | |
|---|---|---|
| 66 | N-(1-{3-[(pyridin-4-ylmethyl)oxy]pyrazin-2-yl}pyrrolidin-3-yl)-N'-[3-(trifluoromethyl)phenyl]urea | 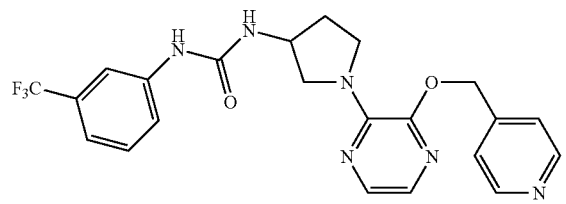 |
| 67 | N-[3,5-bis(trifluoromethyl)phenyl]-N'-(1-{3-[(pyridin-4-ylmethyl)oxy]pyrazin-2-yl}pyrrolidin-3-yl)urea | 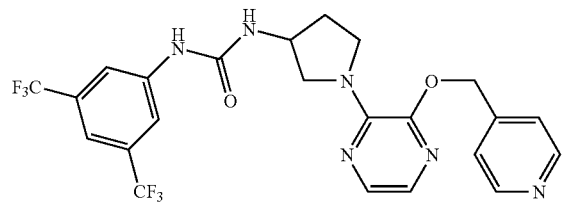 |
| 68 | N-[3,5-bis(trifluoromethyl)phenyl]-2,6-dimethyl-4-{4-[(pyridin-4-ylmethyl)oxy]-1,2,5-thiadiazol-3-yl}piperazine-1-carboxamide | 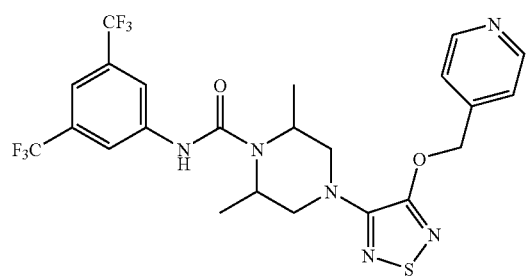 |
| 69 | 2,6-dimethyl-4-{4-[(pyridin-4-ylmethyl)oxy]-1,2,5-thiadiazol-3-yl}-N-[3-(trifluoromethyl)phenyl]piperazine-1-carboxamide | 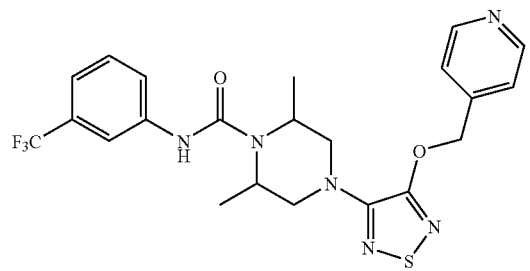 |
| 70 | N-[3,5-bis(trifluoromethyl)phenyl]-3-methyl-4-{3-[(pyridin-4-ylmethyl)oxy]pyrazin-2-yl}piperazine-1-carboxamide | 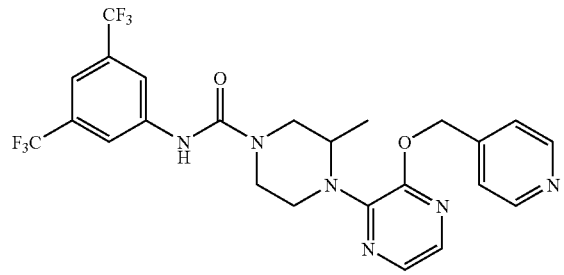 |
| 71 | 3-methyl-4-{3-[(pyridin-4-ylmethyl)oxy]pyrazin-2-yl}-N-[3-(trifluoromethyl)phenyl]piperazine-1-carboxamide | 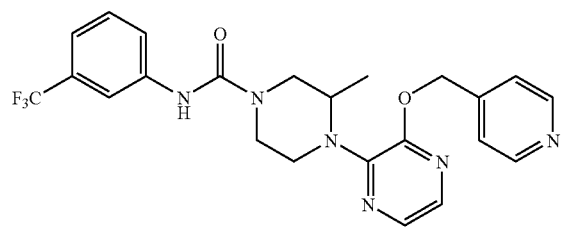 |

TABLE 1-continued

| | | |
|---|---|---|
| 72 | N-[3,5-bis(trifluoromethyl)phenyl]-4-{2-[(pyridin-4-ylmethyl)oxy]phenyl}piperazine-1-carboxamide | 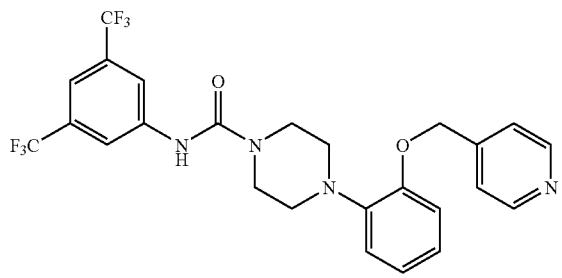 |
| 73 | 4-{2-[(pyridin-4-ylmethyl)oxy]phenyl}-N-[3-(trifluoromethyl)phenyl]piperazine-1-carboxamide | 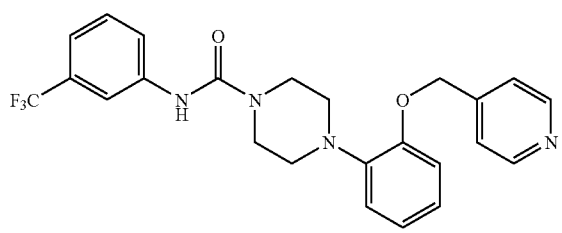 |
| 74 | N-[3,5-bis(trifluoromethyl)phenyl]-2-methyl-4-{3-[(pyridin-4-ylmethyl)oxy]quinoxalin-2-yl}piperazine-1-carboxamide | 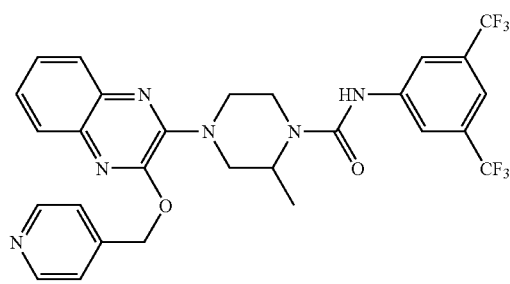 |
| 75 | N-[3,5-bis(trifluoromethyl)phenyl]-4-{3-[(pyridin-4-ylmethyl)oxy]pyrazin-2-yl}-1,4-diazepane-1-carboxamide | 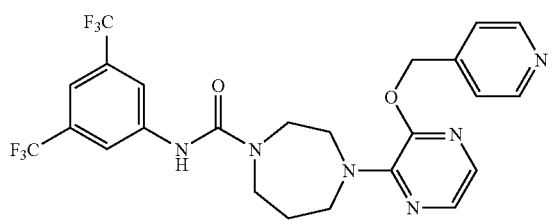 |
| 76 | 2-methyl-4-{3-[(pyridin-4-ylmethyl)oxy]quinoxalin-2-yl}-N-[3-(trifluoromethyl)phenyl]piperazine-1-carboxamide | 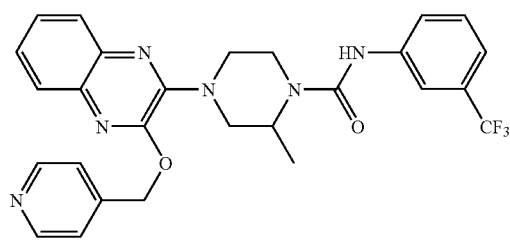 |
| 77 | 4-{3-[(pyridin-4-ylmethyl)oxy]pyrazin-2-yl}-N-[3-(trifluoromethyl)phenyl]-1,4-diazepane-1-carboxamide | 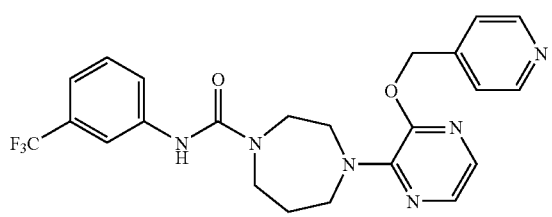 |

TABLE 1-continued

| 78 | N-[3,5-bis(trifluoromethyl)phenyl]-2,5-dimethyl-4-{3-[(pyridin-4-ylmethyl)oxy]pyrazin-2-yl}piperazine-1-carboxamide | 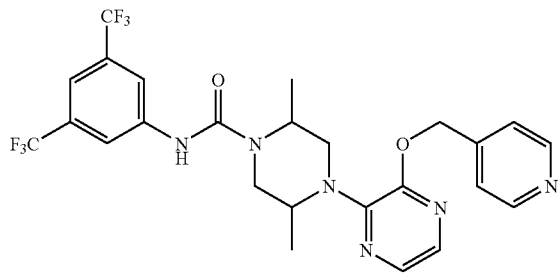 |
| --- | --- | --- |
| 79 | 2,5-dimethyl-4-{3-[(pyridin-4-ylmethyl)oxy]pyrazin-2-yl}-N-[3-(trifluoromethyl)phenyl]piperazine-1-carboxamide | 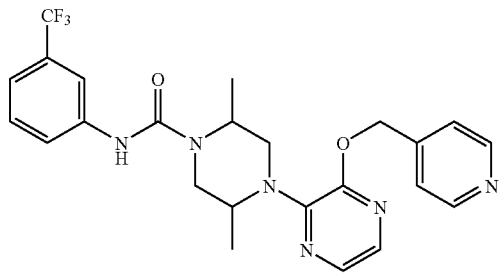 |
| 80 | (2S)-N-[3,5-bis(trifluoromethyl)phenyl]-2-methyl-4-{3-[(pyridin-4-ylmethyl)oxy]pyrazin-2-yl}piperazine-1-carboxamide | 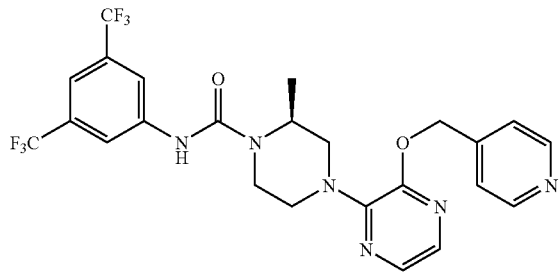 |
| 81 | (2S)-2-methyl-4-{3-[(pyridin-4-ylmethyl)oxy]pyrazin-2-yl}-N-[3-(trifluoromethyl)phenyl]piperazine-1-carboxamide | 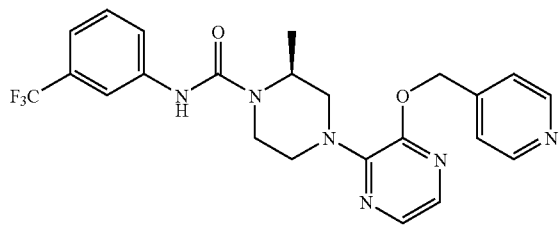 |
| 82 | N-[3,5-bis(trifluoromethyl)phenyl]-4-(4-{[(2-fluoropyridin-4-yl)methyl]oxy}-1,2,5-thiadiazol-3-yl)piperazine-1-carboxamide | 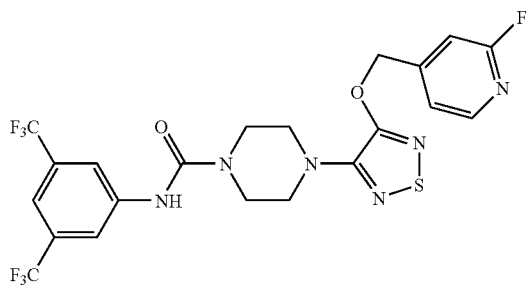 |

TABLE 1-continued

| | | |
|---|---|---|
| 83 | N-[3,5-bis(trifluoromethyl)phenyl]-4-(4-{[(2-chloropyridin-4-yl)methyl]oxy}-1,2,5-thiadiazol-3-yl)piperazine-1-carboxamide | 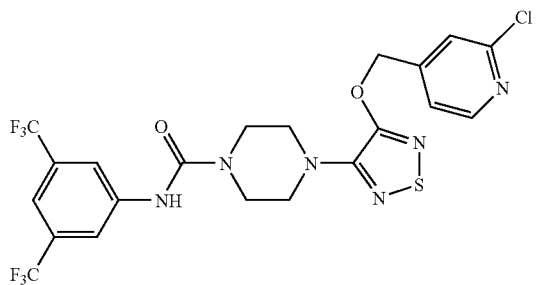 |
| 84 | N-[3,5-bis(trifluoromethyl)phenyl]-4-(3-{[(2-chloropyridin-4-yl)methyl]oxy}pyrazin-2-yl)piperazine-1-carboxamide | 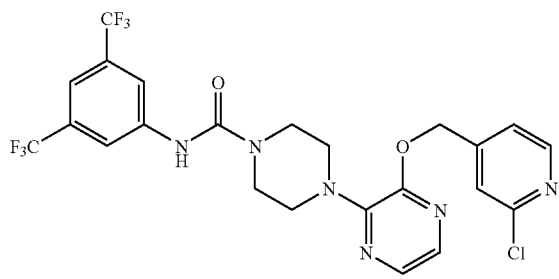 |
| 85 | N-[3,5-bis(trifluoromethyl)phenyl]-4-(2-{[(2,3,5,6-tetrafluoropyridin-4-yl)amino]methyl}phenyl)piperazine-1-carboxamide | 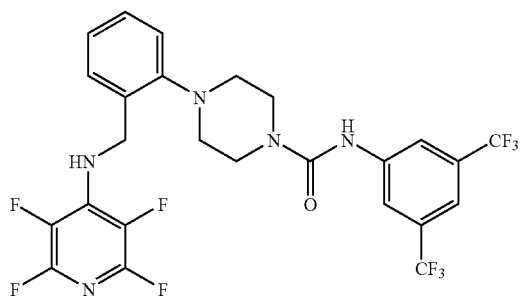 |
| 86 | N-[3,5-bis(trifluoromethyl)phenyl]-4-(2-{[(3-chloro-2,5,6-trifluoropyridin-4-yl)amino]methyl}phenyl)piperazine-1-carboxamide | 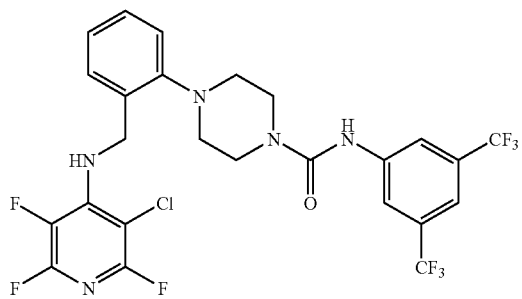 |
| 87 | N-[3,5-bis(trifluoromethyl)phenyl]-4-(4-{[(2-bromopyridin-4-yl)methyl]oxy}-1,2,5-thiadiazol-3-yl)piperazine-1-carboxamide | 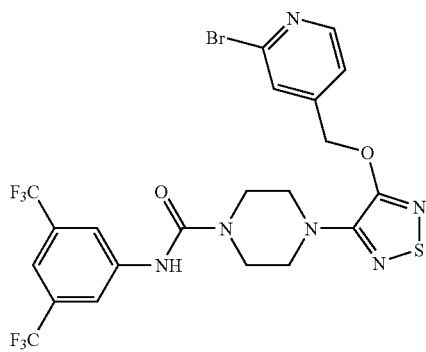 |

TABLE 1-continued

| | | |
|---|---|---|
| 88 | N-[3,5-bis(trifluoromethyl)phenyl]-4-(3-{[(2-bromopyridin-4-yl)methyl]oxy}pyrazin-2-yl)piperazine-1-carboxamide | 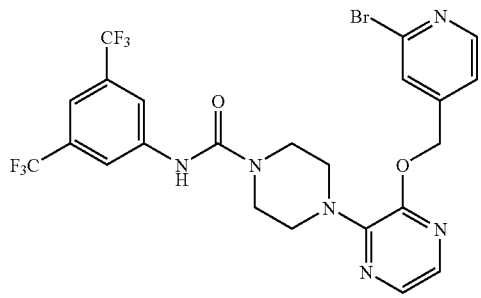 |
| 89 | N-[3,5-bis(trifluoromethyl)phenyl]-4-(3-{[(2-fluoropyridin-4-yl)methyl]oxy}pyrazin-2-yl)piperazine-1-carboxamide | 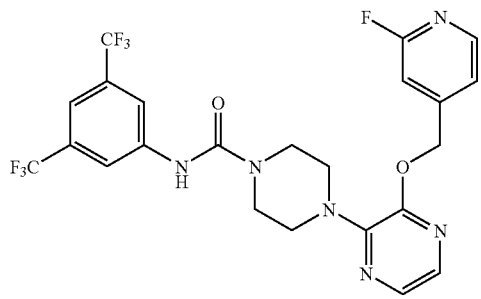 |
| 90 | N-[3,5-bis(trifluoromethyl)phenyl]-4-{5,6-dicyano-3-[(pyridin-4-ylmethyl)oxy]pyrazin-2-yl}piperazine-1-carboxamide | 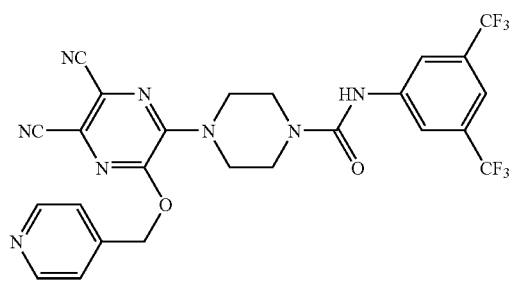 |
| 91 | 4-{5,6-dicyano-3-[(pyridin-4-ylmethyl)oxy]pyrazin-2-yl}-N-[3-(trifluoromethyl)phenyl]piperazine-1-carboxamide | 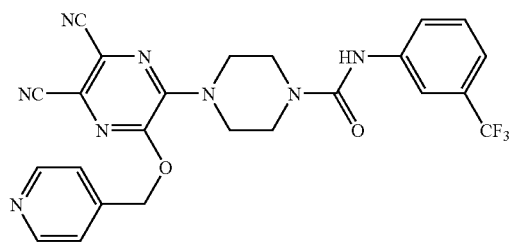 |
| 92 | N-(3-ethylphenyl)-4-{3-[(pyridin-4-ylmethyl)oxy]pyrazin-2-yl}piperazine-1-carboxamide | 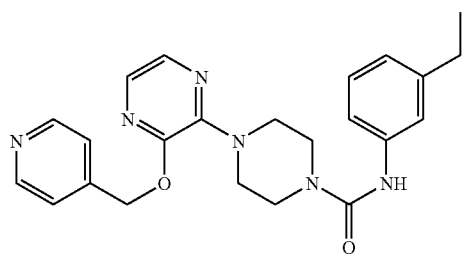 |
| 93 | N-(3-ethylphenyl)-2-methyl-4-{3-[(pyridin-4-ylmethyl)oxy]pyrazin-2-yl}piperazine-1-carboxamide | 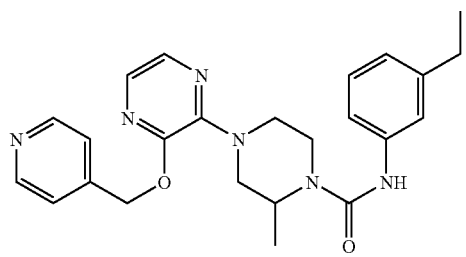 |

TABLE 1-continued

| | | |
|---|---|---|
| 94 | N-(3-ethylphenyl)-2,6-dimethyl-4-{3-[(pyridin-4-ylmethyl)oxy]pyrazin-2-yl}piperazine-1-carboxamide | 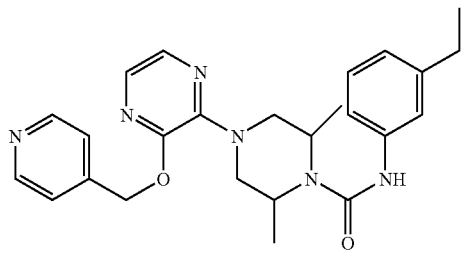 |
| 95 | N-(3-ethylphenyl)-2-methyl-4-{3-[(pyridin-4-ylmethyl)oxy]quinoxalin-2-yl}piperazine-1-carboxamide | 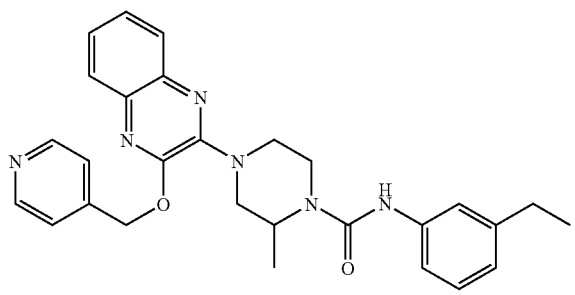 |
| 96 | N-[3,5-bis(trifluoromethyl)phenyl]-4-[3-(2-pyridin-4-ylethyl)pyrazin-2-yl]piperazine-1-carboxamide | 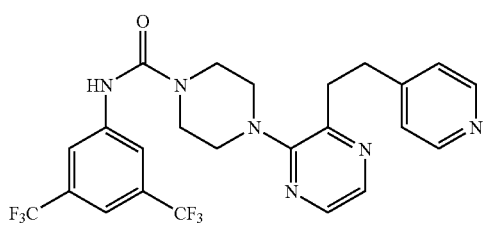 |
| 97 | N-[3,5-bis(trifluoromethyl)phenyl]-4-{3-[(pyridin-4-ylmethyl)oxy]pyridin-2-yl}piperazine-1-carboxamide | 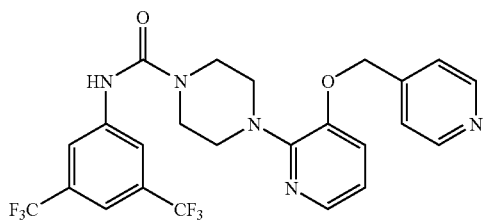 |
| 98 | N-[3,5-bis(trifluoromethyl)phenyl]-4-{2-[(pyridin-4-yloxy)methyl]phenyl}piperazine-1-carboxamide | 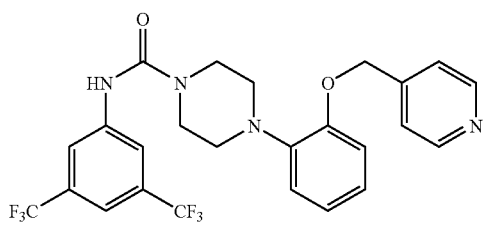 |
| 99 | 4-(4-{[(2-aminopyridin-4-yl)methyl]oxy}-1,2,5-thiadiazol-3-yl)-N-[3,5-bis(trifluoromethyl)phenyl]piperazine-1-carboxamide | 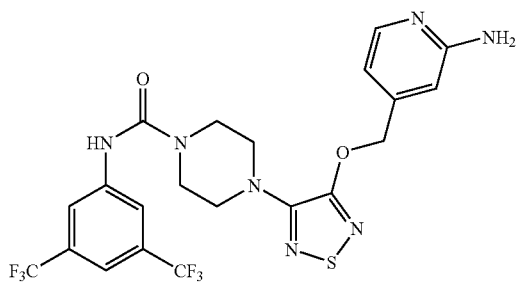 |

TABLE 1-continued

| | | |
|---|---|---|
| 100 | 1,1-dimethylethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | 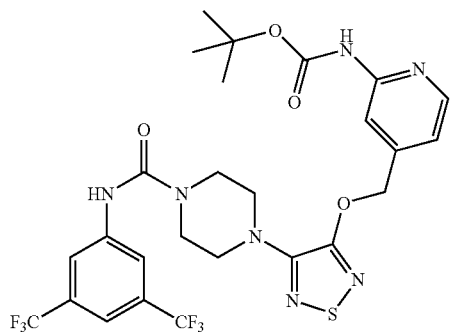 |
| 101 | methyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | 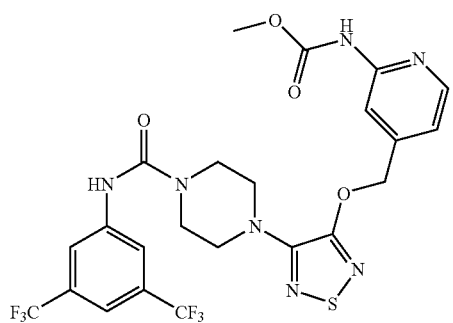 |
| 102 | 4-{[(4-piperazin-1-yl-1,2,5-thiadiazol-3-yl)oxy]methyl}pyridin-2-amine | 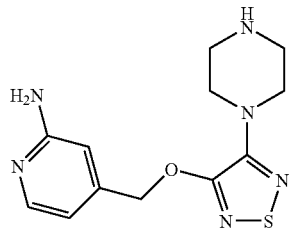 |
| 103 | N-(4-chlorophenyl)-4-{3-[(pyridin-4-ylmethyl)oxy]pyridin-2-yl}piperazine-1-carboxamide | 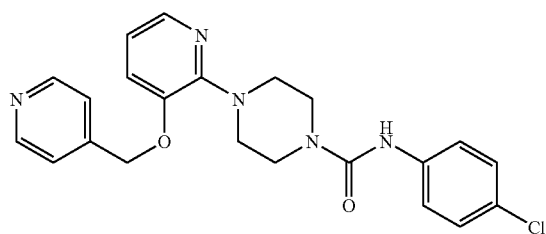 |
| 104 | 4-(4-{[(2-aminopyrimidin-4-yl)methyl]oxy}-1,2,5-thiadiazol-3-yl)-N-[3,5-bis(trifluoromethyl)phenyl]piperazine-1-carboxamide | 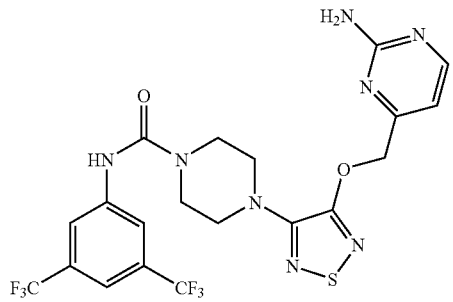 |

TABLE 1-continued

| | | |
|---|---|---|
| 105 | N-(3-chlorophenyl)-4-{3-[(pyridin-4-ylmethyl)oxy]pyridin-2-yl}piperazine-1-carboxamide | 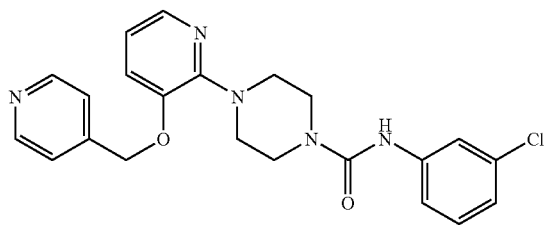 |
| 106 | 4-{[(4-piperazin-1-yl-1,2,5-thiadiazol-3-yl)oxy]methyl}-N-propylpyridin-2-amine | 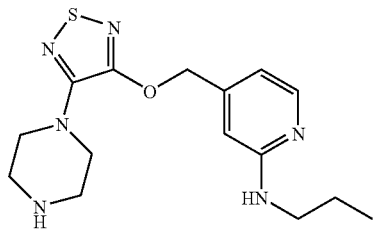 |
| 107 | N-[3,5-bis(trifluoromethyl)phenyl]-4-[4-({[2-(propylamino)pyridin-4-yl]methyl}oxy)-1,2,5-thiadiazol-3-yl]piperazine-1-carboxamide | 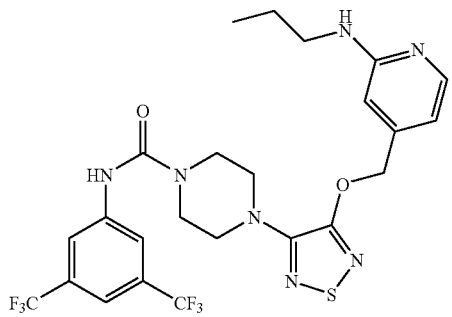 |
| 108 | N-[3,5-bis(trifluoromethyl)phenyl]-4-[4-({[2-(methylamino)pyrimidin-4-yl]methyl}oxy)-1,2,5-thiadiazol-3-yl]piperazine-1-carboxamide | 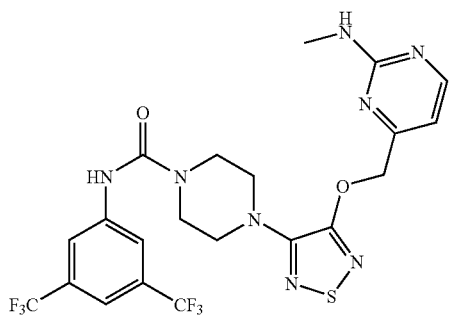 |
| 109 | N-methyl-4-{[(4-piperazin-1-yl-1,2,5-thiadiazol-3-yl)oxy]methyl}pyridin-2-amine | 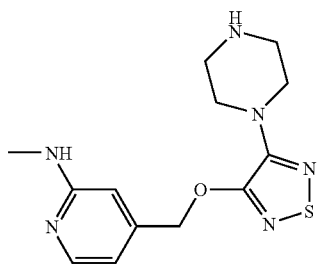 |
| 110 | N-ethyl-4-{[(4-piperazin-1-yl-1,2,5-thiadiazol-3-yl)oxy]methyl}pyridin-2-amine | 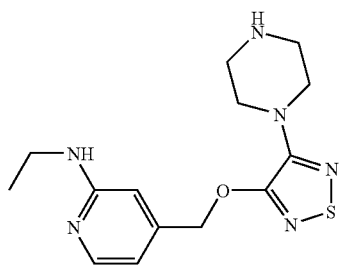 |

TABLE 1-continued

| 111 | N-butyl-4-{[(4-piperazin-1-yl-1,2,5-thiadiazol-3-yl)oxy]methyl}pyridin-2-amine | 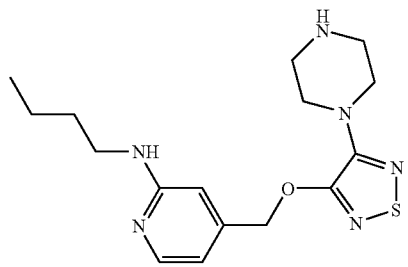 |
| 112 | N-[3,5-bis(trifluoromethyl)phenyl]-4-[4-({[2-(methylamino)pyridin-4-yl]methyl}oxy)-1,2,5-thiadiazol-3-yl]piperazine-1-carboxamide | 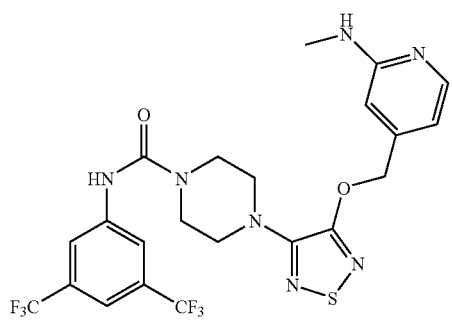 |
| 113 | N-[3,5-bis(trifluoromethyl)phenyl]-4-[4-({[2-(ethylamino)pyridin-4-yl]methyl}oxy)-1,2,5-thiadiazol-3-yl]piperazine-1-carboxamide | 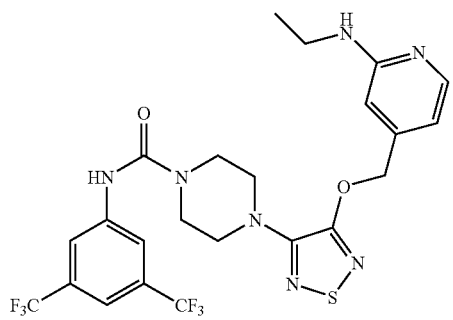 |
| 114 | N-[3,5-bis(trifluoromethyl)phenyl]-4-[4-({[2-(butylamino)pyridin-4-yl]methyl}oxy)-1,2,5-thiadiazol-3-yl]piperazine-1-carboxamide | 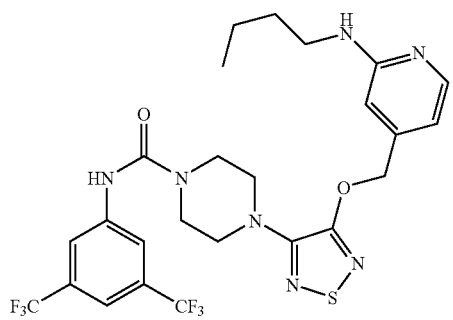 |
| 115 | N-[3,5-bis(trifluoromethyl)phenyl]-4-{4-[({2-[(phenylmethyl)amino]pyridin-4-yl}methyl)oxy]-1,2,5-thiadiazol-3-yl}piperazine-1-carboxamide | 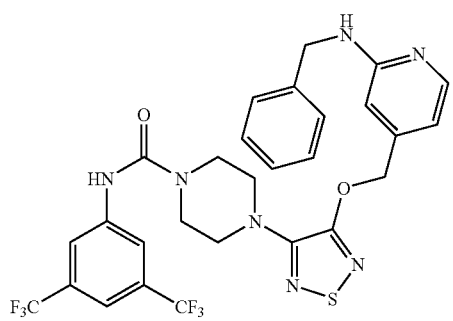 |

| | | |
|---|---|---|
| 116 | N-[3,5-bis(trifluoromethyl)phenyl]-4-{4-[({2-[(1-methylethyl)amino]pyrimidin-4-yl}methyl)oxy]-1,2,5-thiadiazol-3-yl}piperazine-1-carboxamide | 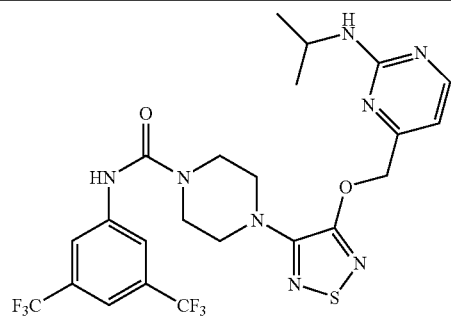 |
| 117 | N-[3,5-bis(trifluoromethyl)phenyl]-4-{4-[({2-[(phenylmethyl)amino]pyrimidin-4-yl}methyl)oxy]-1,2,5-thiadiazol-3-yl}piperazine-1-carboxamide | 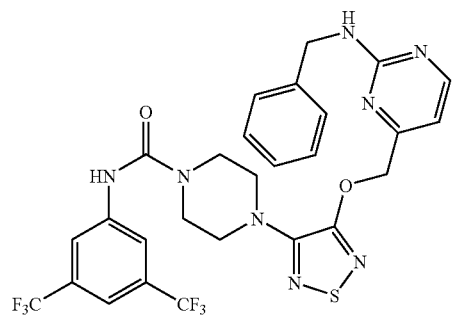 |
| 118 | N-[3,5-bis(trifluoromethyl)phenyl]-4-[4-({[2-(phenylamino)pyrimidin-4-yl]methyl}oxy)-1,2,5-thiadiazol-3-yl]piperazine-1-carboxamide | 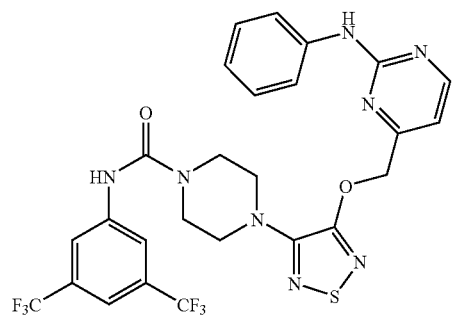 |
| 119 | N-[3,5-bis(trifluoromethyl)phenyl]-4-(4-{[2-{[2-(dimethylamino)ethyl]amino}pyrimidin-4-yl)methyl]oxy}-1,2,5-thiadiazol-3-yl)piperazine-1-carboxamide | 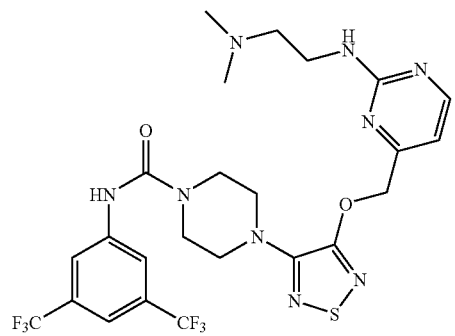 |
| 120 | N-[3,5-bis(trifluoromethyl)phenyl]-4-(4-{[(2-{[2-(dimethylamino)ethyl]amino}pyridin-4-yl)methyl]oxy}-1,2,5-thiadiazol-3-yl)piperazine-1-carboxamide | 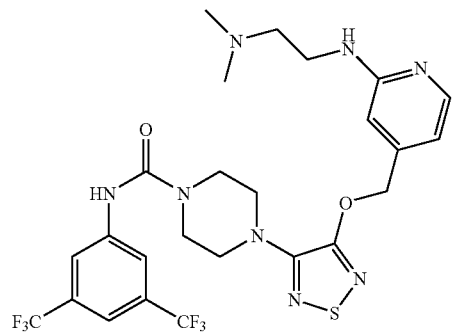 |

| | | |
|---|---|---|
| 121 | N-[3,5-bis(trifluoromethyl)phenyl]-4-[4-({[2-(ethylamino)pyrimidin-4-yl]methyl}oxy)-1,2,5-thiadiazol-3-yl]piperazine-1-carboxamide | 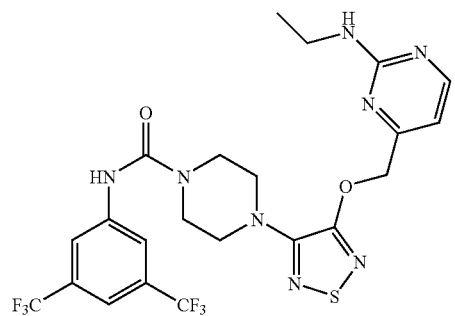 |
| 122 | N-[3,5-bis(trifluoromethyl)phenyl]-4-[4-({[2-(propylamino)pyrimidin-4-yl]methyl}oxy)-1,2,5-thiadiazol-3-yl]piperazine-1-carboxamide | 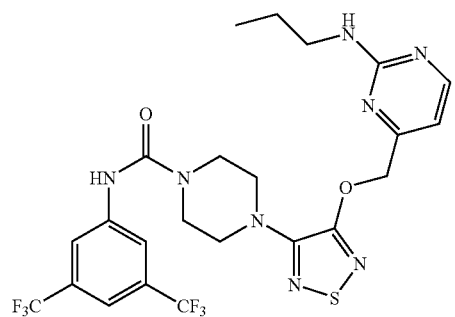 |
| 123 | N-[3,5-bis(triflouromethyl)phenyl]-4-[4-({[2-(cyclopropylamino)pyrimidin-4-yl]methyl}oxy)-1,2,5-thiadiazol-3-yl]piperazine-1-carboxamide | 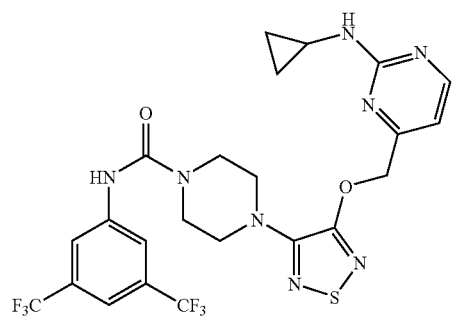 |
| 124 | 4-[4-({[2-(acetylamino)pyrimidin-4-yl]methyl}oxy)-1,2,5-thiadiazol-3-yl]-N-[3,5-bis(trifluoromethyl)phenyl]piperazine-1-carboxamide | 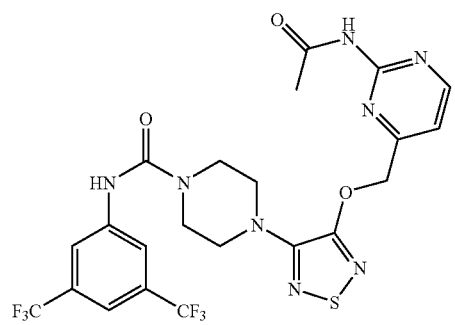 |
| 125 | N-[3,5-bis(trifluoromethyl)phenyl]-4-{4-[({2-[(phenylcarbonyl)amino]pyridin-4-yl}methyl)oxy]-1,2,5-thiadiazol-3-yl}piperazine-1-carboxamide | 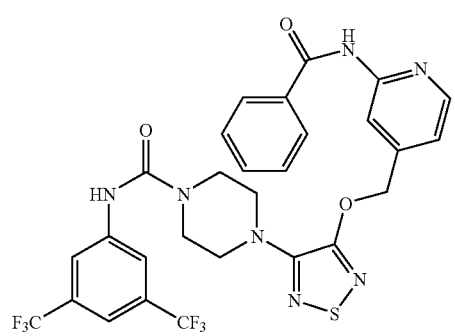 |

TABLE 1-continued

| 126 | N-[3,5-bis(trifluoromethyl)phenyl]-4-{4-[({2-[(phenylcarbonyl)amino]pyrimidin-4-yl}methyl)oxy]-1,2,5-thiadiazol-3-yl}piperazine-1-carboxamide | 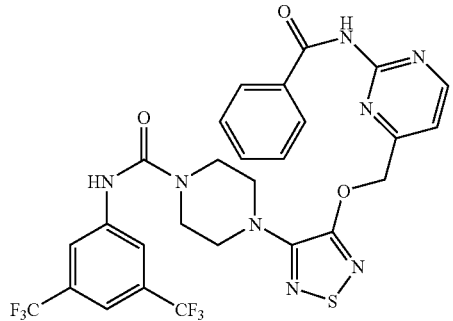 |

| 127 | 4-{4-[({2-[bis(phenylcarbonyl)amino]pyridin-4-yl}methyl)oxy]-1,2,5-thiadiazol-3-yl}-N-[3,5-bis(trifluoromethyl)phenyl]piperazine-1-carboxamide | 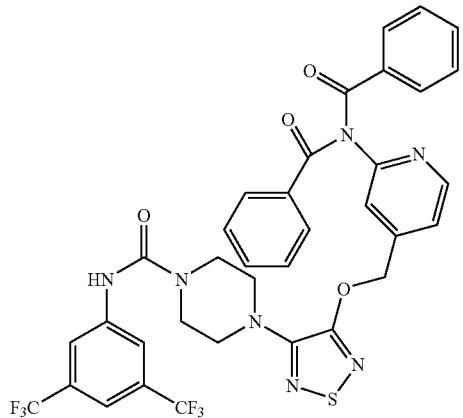 |

| 128 | N-[3,5-bis(trifluoromethyl)phenyl]-4-[4-({[2-(cyclopentylamino)pyrimidin-4-yl]methyl}oxy)-1,2,5-thiadiazol-3-yl]piperazine-1-carboxamide | 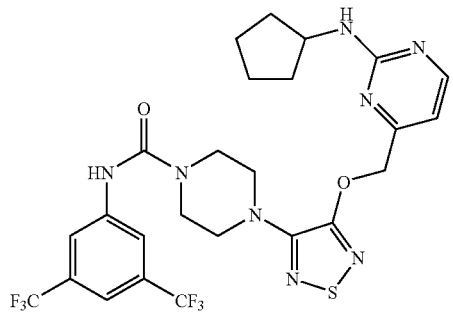 |

| 129 | 4-[4-({[2-(acetylamino)pyridin-4-yl]methyl}oxy)-1,2,5-thiadiazol-3-yl]-N-[3,5-bis(trifluoromethyl)phenyl]piperazine-1-carboxamide | 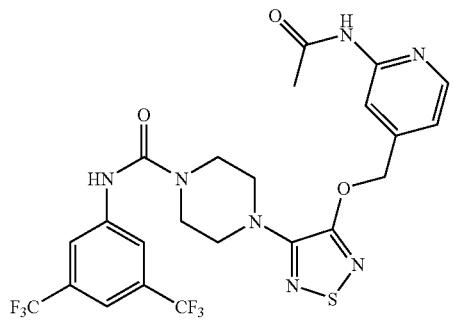 |

TABLE 1-continued

| 130 | N-[3,5-bis(trifluoromethyl)phenyl]-4-{4-[({2-[({[3,5-bis(trifluoromethyl)phenyl]amino}carbonyl)amino]pyridin-4-yl}methyl)oxy]-1,2,5-thiadiazol-3-yl}piperazine-1-carboxamide | 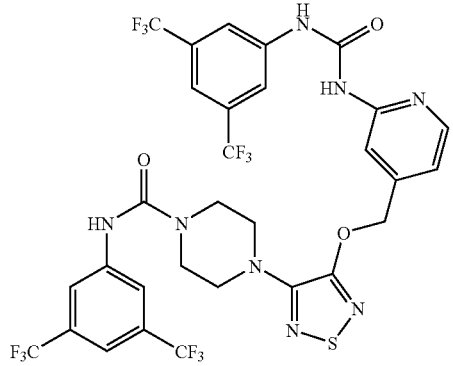 |
| --- | --- | --- |
| 131 | methyl {4-[({4-[4-({[3,5-bis(trifluoromethyl)phenyl]amino}carbonyl)piperazin-1-yl]-1,2,5-thiadiazol-3-yl}oxy)methyl]pyrimidin-2-yl}carbamate | 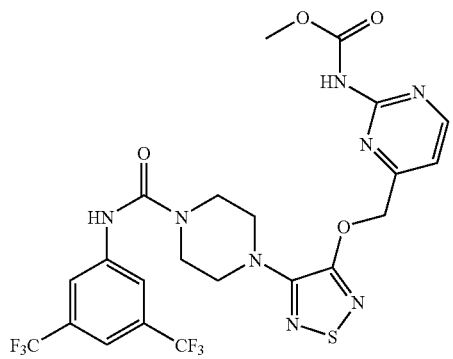 |
| 132 | 4-(4-{[(2-aminopyridin-4-yl)methyl]oxy}-1,2,5-thiadiazol-3-yl)-N-(3-ethylphenyl)piperazine-1-carboxamide | 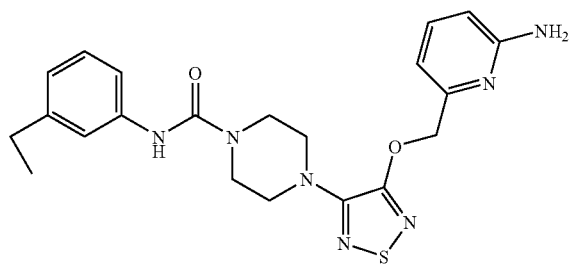 |
| 133 | methyl [4-({[4-(4-{[(3-ethylphenyl)amino]carbonyl}piperazin-1-yl)-1,2,5-thiadiazol-3-yl]oxy}methyl)pyridin-2-yl]carbamate | 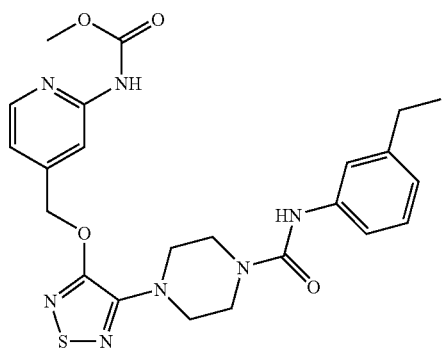 |

TABLE 1-continued

| | | |
|---|---|---|
| 134 | N-[3,5-bis(trifluoromethyl)phenyl]-4-(4-{[(2-cyanopyrimidin-4-yl)methyl]oxy}-1,2,5-thiadiazol-3-yl)piperazine-1-carboxamide | 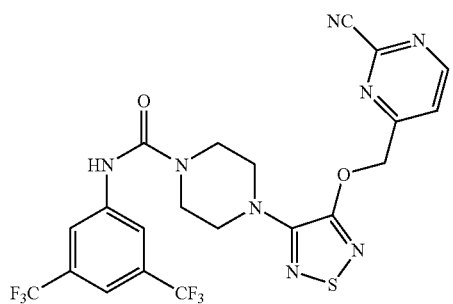 |
| 135 | 4-(3-{[(2-aminopyrimidin-4-yl)methyl]oxy}pyrazin-2-yl)-N-[3,5-bis(trifluoromethyl)phenyl]piperazine-1-carboxamide | 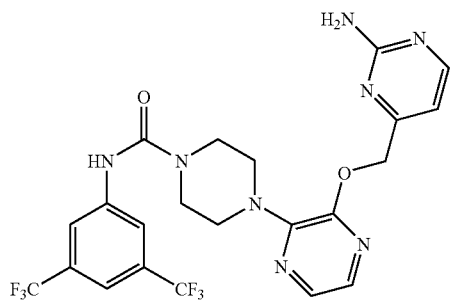 |
| 136 | 4-[({4-[4-({[3,5-bis(trifluoromethyl)phenyl]amino}carbonyl)piperazin-1-yl]-1,2,5-thiadiazol-3-yl}oxy)methyl]pyrimidine-2-carboxamide | 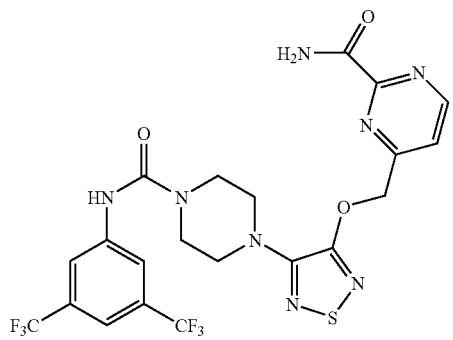 |
| 137 | N-[3,5-bis(trifluoromethyl)phenyl]-4-[4-({[2-(butyloxy)pyrimidin-4-yl]methyl}oxy)-1,2,5-thiadiazol-3-yl]piperazine-1-carboxamide | 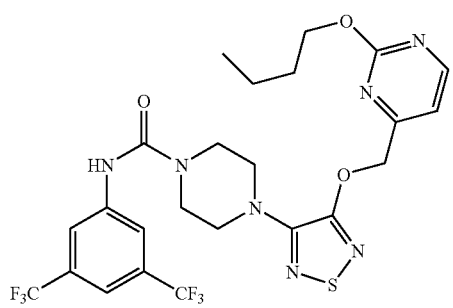 |
| 138 | N-[3,5-bis(trifluoromethyl)phenyl]-4-{4-[(pyrimidin-4-ylmethyl)oxy]-1,2,5-thiadiazol-3-yl}piperazine-1-carboxamide | 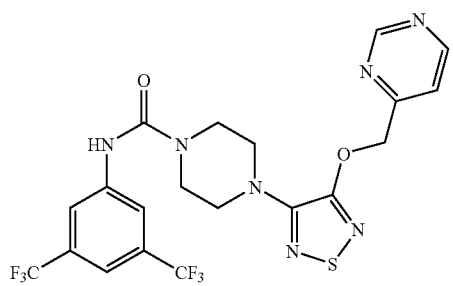 |

TABLE 1-continued

| 139 | 4-[({4-[4-({[3,5-bis(tirfluoromethyl)phenyl]amino}carbonyl)piperazin-1-yl]-1,2,5-thiadiazol-3-yl}oxy)methyl]pyridine-2-carboxylic acid | 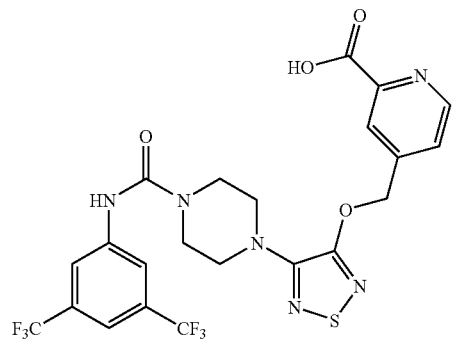 |

| 140 | 2-pyrrolidin-1-ylethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | 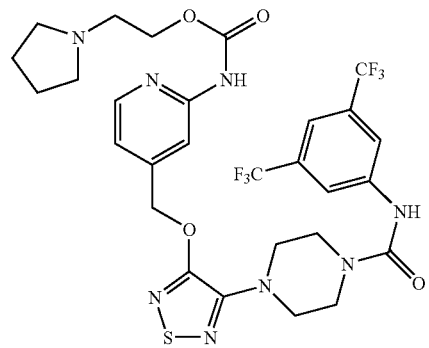 |

| 141 | 2-morpholin-4-ylethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | 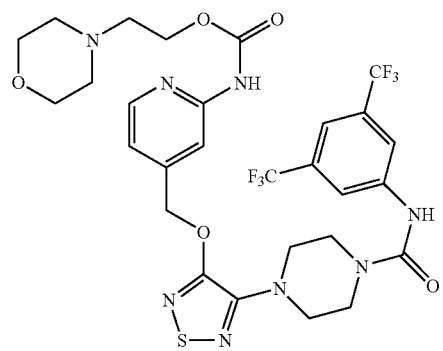 |

| 142 | 4-(3-{[(2-aminopyrimidin-4-yl)methyl]oxy}pyridin-2-yl)-N-[3,5-bis(trifluoromethyl)phenyl]piperazine-1-carboxamide | 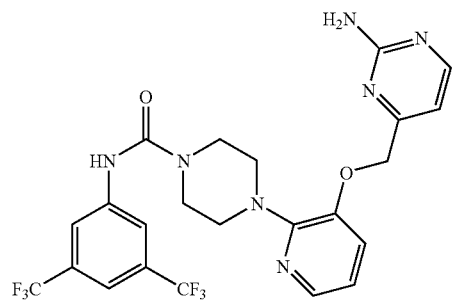 |

TABLE 1-continued

| 143 | N-[3,5-bis(trifluoromethyl)phenyl]-4-(4-{[(2-{[(1-methylpiperidin-3-yl)carbonyl]amino}pyridin-4-yl)methyl]oxy}-1,2,5-thiadiazol-3-yl)piperazine-1-carboxamide | 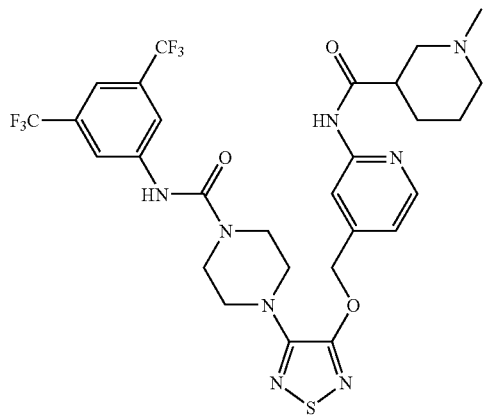 |
| --- | --- | --- |
| 144 | 4-(3-{[(2-aminopyrimidin-4-yl)methyl]oxy}pyridin-2-yl)-N-(3-ethylphenyl)piperazine-1-carboxamide | 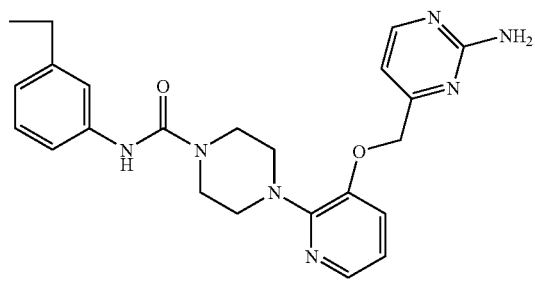 |
| 145 | 2-(4-methylpiperazin-1-yl)ethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | 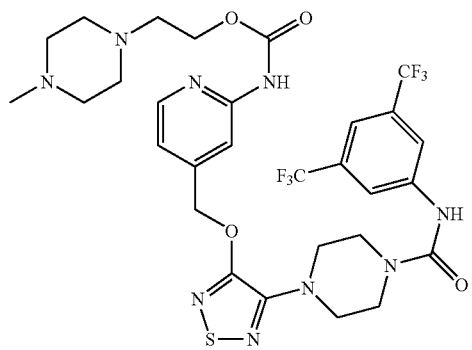 |
| 146 | N-[3,5-bis(trifluoromethyl)phenyl]-4-(4-{[(2-{[(1-ethylpiperidin-4-yl)carbonyl]amino}pyridin-4-yl)methyl]oxy}-1,2,5-thiadiazol-3-yl)piperazine-1-carboxamide | 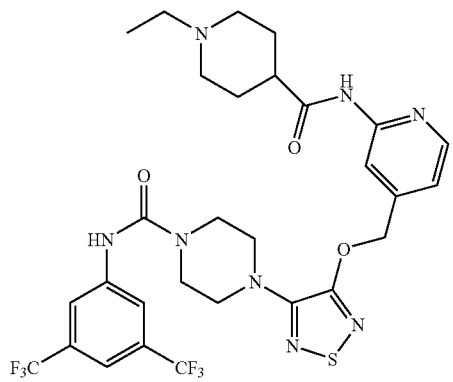 |

TABLE 1-continued

| 147 | 4-(4-{[(2-aminopyridin-4-yl)methyl]oxy}-1,2,5-thiadiazol-3-yl)-N-{3-[(trifluoromethyl)thio]phenyl}piperazine-1-carboxamide | 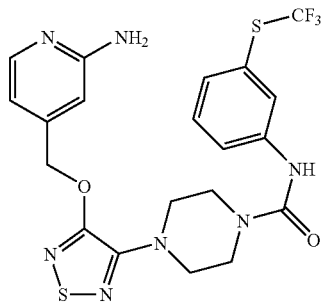 |
| 148 | 4-({[4-(4-{[3,5-bis(trifluoromethyl)phenyl]sulfonyl}piperazin-1-yl)-1,2,5-thiadiazol-3-yl]oxy}methyl)pyridin-2-amine | 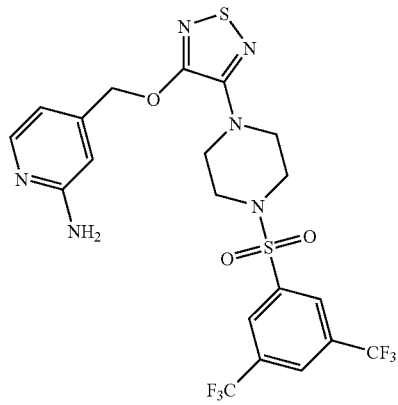 |
| 149 | 4-(4-{[(2-aminopyridin-4-yl)methyl]oxy}-1,2,5-thiadiazol-3-yl)-N-naphthalen-1-ylpiperazine-1-carboxamide | 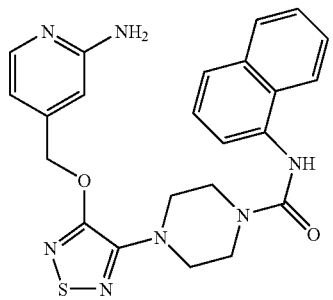 |
| 150 | N-[3,5-bis(trifluoromethyl)phenyl]-4-{4-[({2-[(N,N-dimethylglycyl)amino]pyridin-4-yl}methyl)oxy]-1,2,5-thiadiazol-3-yl}piperazine-1-carboxamide | 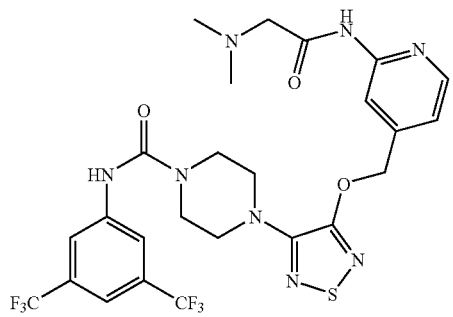 |
| 151 | N-[3,5-bis(trifluoromethyl)phenyl]-4-{4-[({2-[(morpholin-4-ylacetyl)amino]pyridin-4-yl}methyl)oxy]-1,2,5-thiadiazol-3-yl}piperazine-1-carboxamide | 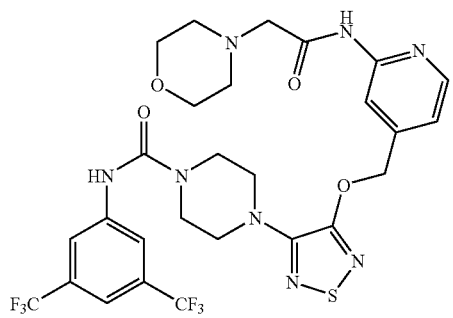 |

TABLE 1-continued

| | | |
|---|---|---|
| 152 | N-[3,5-bis(trifluoromethyl)phenyl]-4-{4-[({2-[(piperidin-1-ylacetyl)amino]pyridin-4-yl}methyl)oxy]-1,2,5-thiadiazol-3-yl}piperazine-1-carboxamide | 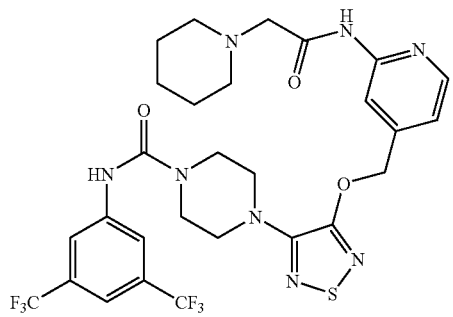 |
| 153 | ethyl {4-[({4-({[3,5-bis(trifluoromethyl)phenyl]amino}carbonyl)piperazin-1-yl]-1,2,5-thiadiazol-3-yl}oxy)methyl]pyridin-2-yl}carbamate | 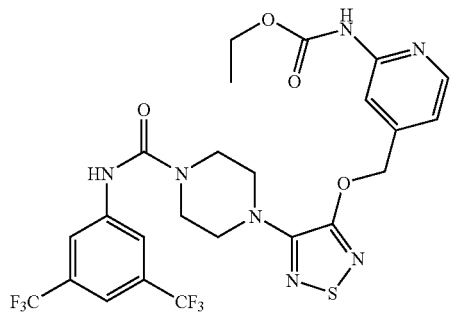 |
| 154 | N-[3,5-bis(trifluoromethyl)phenyl]-4-{4-[({2-[(pyrrolidin-1-ylacetyl)amino]pyridin-4-yl}methyl)oxy]-1,2,5-thiadiazol-3-yl}piperazine-1-carboxamide | 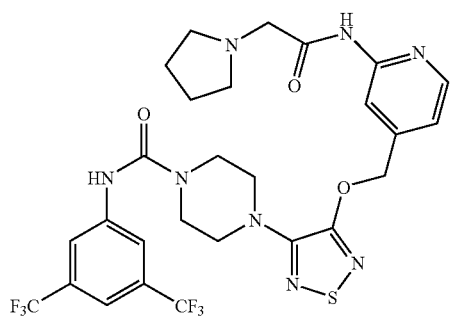 |
| 155 | N-[3,5-bis(trifluoromethyl)phenyl]-4-(4-{[(2-{[(4-methylpiperazin-1-yl)acetyl]amino}pyridin-4-yl)methyl]oxy}-1,2,5-thiadiazol-3-yl)piperazine-1-carboxamide | 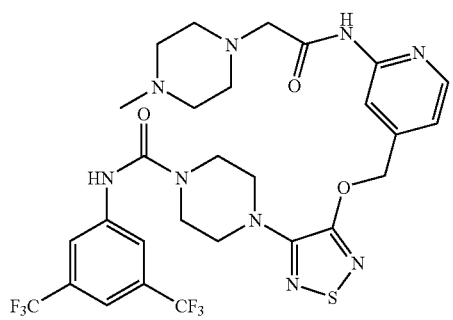 |
| 156 | N-[3,5-bis(trifluoromethyl)phenyl]-4-{4-[({2-[(N,N-diethylglycyl)amino]pyridin-4-yl}methyl)oxy]-1,2,5-thiadiazol-3-yl}piperazine-1-carboxamide | 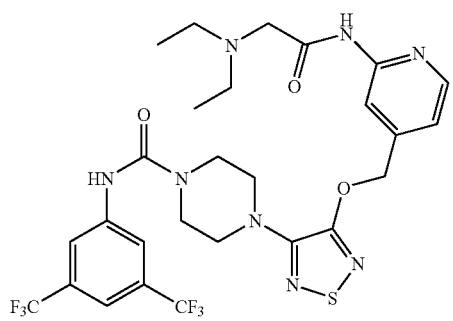 |

| | | |
|---|---|---|
| 157 | 1-ethylpiperidin-4-yl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | 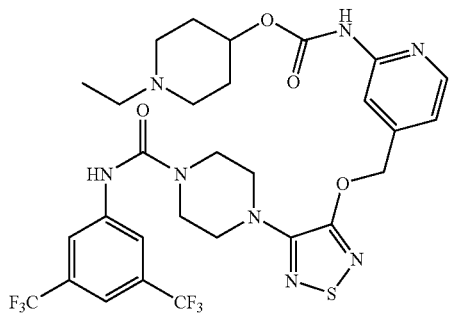 |
| 158 | 4-(4-{[(2-aminopyrimidin-4-yl)methyl]oxy}-1,2,5-thiadiazol-3-yl)-N-(3-ethylphenyl)piperazine-1-carboxamide | 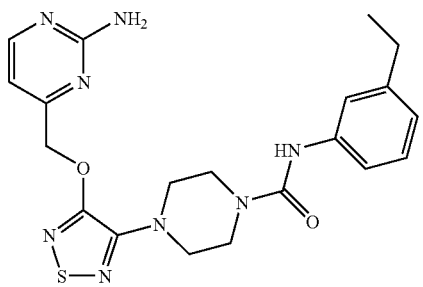 |
| 159 | N-[3,5-bis(trifluoromethyl)phenyl]-4-[4-({[2-(2-oxo-1,3-oxazolidin-3-yl)pyridin-4-yl]methyl}oxy)-1,2,5-thiadiazol-3-yl]piperazine-1-carboxamide | 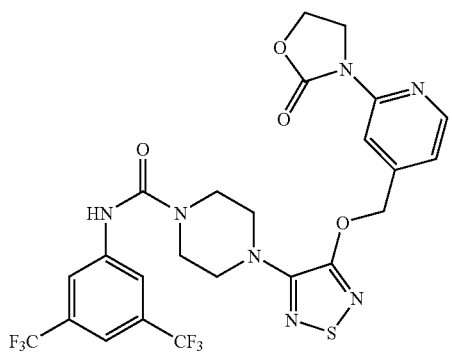 |
| 160 | 2-(diethylamino)ethyl {4-[({4-({[3,5-bis(trifluoromethyl)phenyl]amino}carbonyl)piperazin-1-yl]-1,2,5-thiadiazol-3-yl}oxy)methyl]pyridin-2-yl}carbamate | 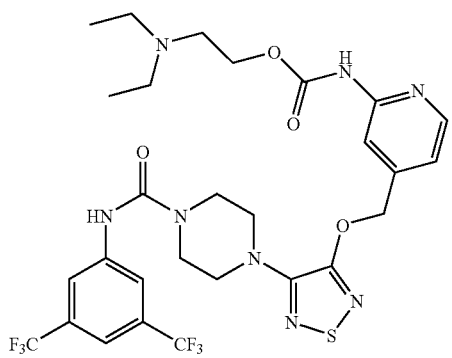 |
| 161 | methyl {4-({[2-(4-{[(3-ehtylphenyl)amino]carbonyl}piperazin-1-yl)pyridin-3-yl]oxy}methyl)pyridin-2-yl]carbamate | 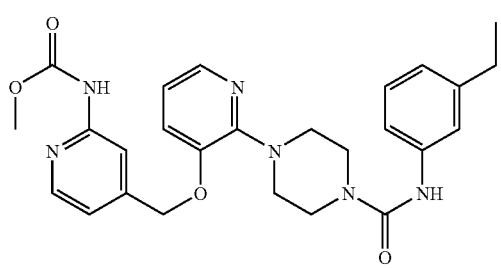 |

TABLE 1-continued

| | | |
|---|---|---|
| 162 | 2-pyrrolidin-1-ylethyl {4-[({4-[4-({[3,5-bis(trifluoromethyl)phenyl]amino}carbonyl)piperazin-1-yl]-1,2,5-thiadiazol-3-yl}oxy)methyl]pyrimidin-2-yl}carbamate | 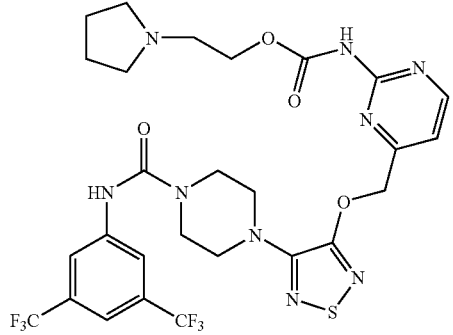 |
| 163 | 2-piperidin-1-ylethyl {4-[({4-[4-({[3,5-bis(trifluoromethyl)phenyl]amino}carbonyl)piperazin-1-yl]-1,2,5-thiadiazol-3-yl}oxy)methyl]pyrimidin-2-yl}carbamate | 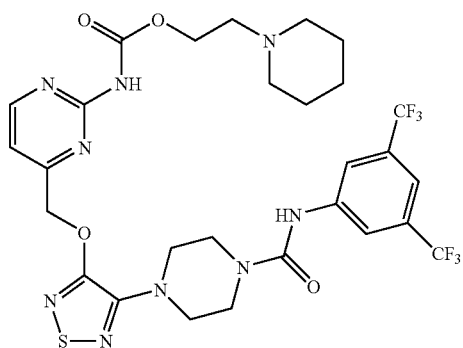 |
| 164 | methyl [4-({[2-(4-{[(3-bromophenyl)amino]carbonyl}piperazin-1-yl)pyridin-3-yl]oxy}methyl)pyridin-2-yl]carbamate | 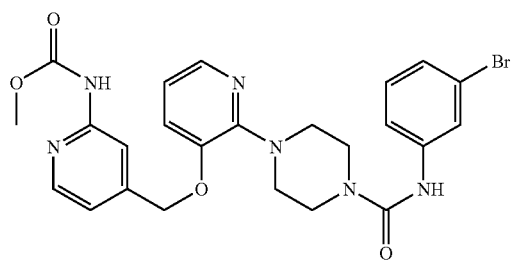 |
| 165 | methyl {4-[({2-[4-({[3-(methyloxy)phenyl]amino}carbonyl)piperazin-1-yl]pyridin-3-yl}oxy)methyl]pyridin-2-yl}carbamate | 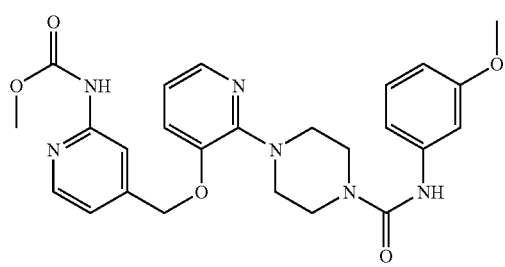 |
| 166 | 4-(3-{[(2-aminopyrimidin-4-yl)methyl]oxy}pyridin-2-yl)-N-[3-(methyloxy)phenyl]piperazine-1-carboxamide | 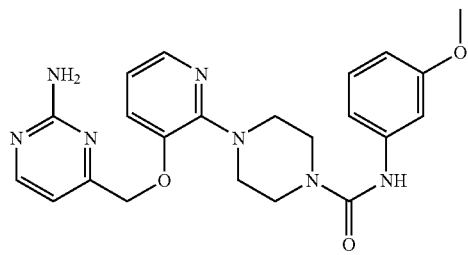 |

TABLE 1-continued

| 167 | 4-(3-{[(2-aminopyrimidin-4-yl)methyl]oxy}pyridin-2-yl)-N-[3-(1-methylethyl)phenyl]piperazine-1-carboxamide | 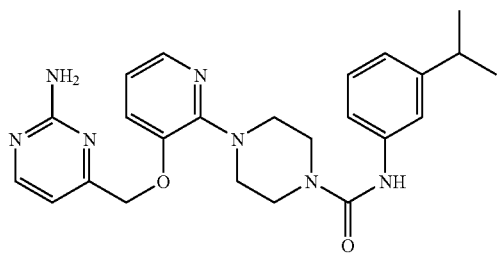 |
| 168 | 4-(3-{[(2-aminopyrimidin-4-yl)methyl]oxy}pyridin-2-yl)-N-{3-[(trifluoromethyl)oxy]phenyl}piperazine-1-carboxamide | 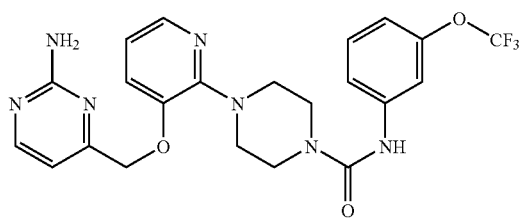 |
| 169 | 4-(3-{[(2-aminopyrimidin-4-yl)methyl]oxy}pyridin-2-yl)-N-[2-fluoro-5-(trifluoromethyl)phenyl]piperazine-1-carboxamide | 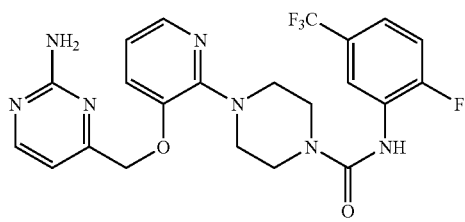 |
| 170 | N-(3-ethylphenyl)-4-[3-({[2-({[(3-ethylphenyl)amino]carbonyl}amino)pyridin-4-yl]methyl}oxy)pyridin-2-yl]piperazine-1-carboxamide | 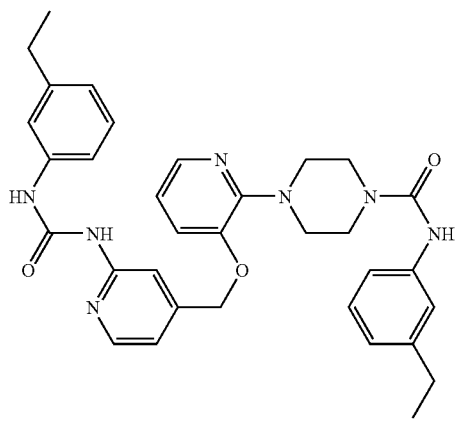 |
| 171 | N-(3-ethylphenyl)-4-(3-{[(2-{[(4-methylpiperazin-1-yl)acetyl]amino}pyridin-4-yl)methyl]oxy}pyridin-2-yl)piperazine-1-carboxamide | 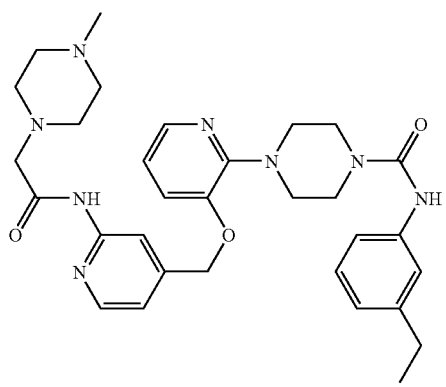 |

| | | |
|---|---|---|
| 172 | N-(3-ethylphenyl)-4-(4-{[(2-{[(4-methylpiperazin-1-yl)acetyl]amino}pyridin-4-yl)methyl]oxy}-1,2,5-thiadiazol-3-yl)piperazine-1-carboxamide | 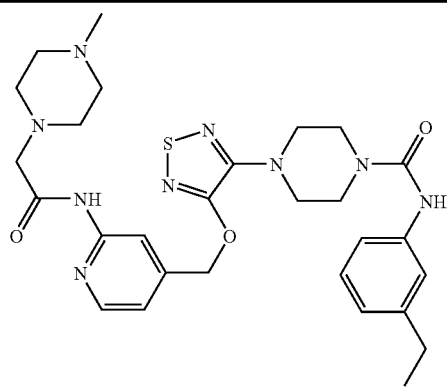 |
| 173 | N-[3,5-bis(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 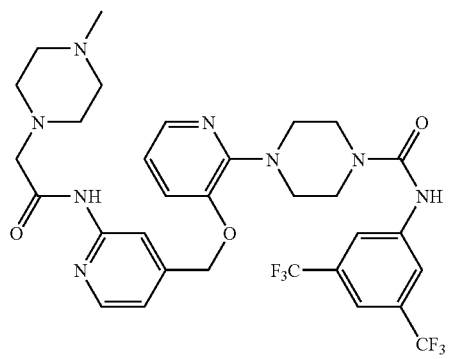 |
| 174 | 4-(3-{[(2-aminopyrimidin-4-yl)methyl]oxy}pyridin-2-yl)-N-[3-(trifluoromethyl)phenyl]piperazine-1-carboxamide | 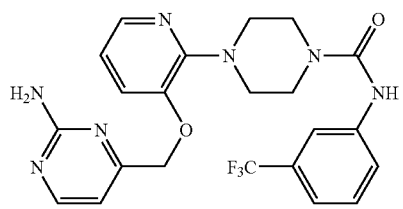 |
| 175 | 4-[3-({[2-(acetylamino)pyridin-4-yl]methyl}oxy)pyridin-2-yl]-N-(3-ethylphenyl)piperazine-1-carboxamide | 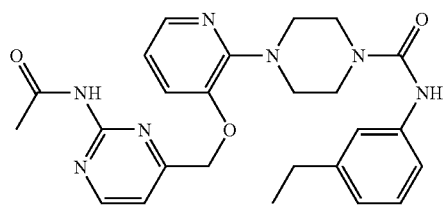 |
| 176 | 4-(3-{[(2-aminopyrimidin-4-yl)methyl]oxy}pyridin-2-yl)-N-(3-ethyl-4-fluorophenyl)piperazine-1-carboxamide | 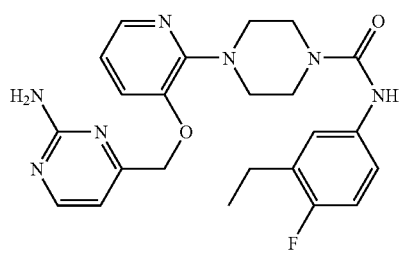 |

TABLE 1-continued

| | | |
|---|---|---|
| 177 | 2-[4-(3-{[(2-aminopyrimidin-4-yl)methyl]oxy}pyridin-2-yl)piperazin-1-yl]-N-[3,5-bis(trifluoromethyl)phenyl]acetamide | 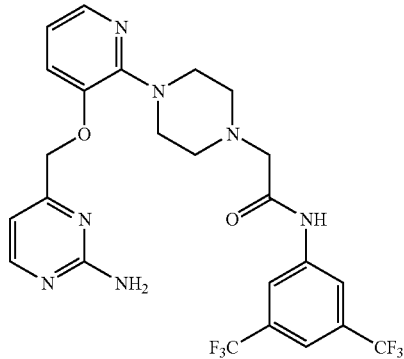 |
| 178 | 4-(3-{[(2-aminopyrimidin-4-yl)methyl]oxy}pyridin-2-yl)-N-phenylpiperazine-1-carboxamide | 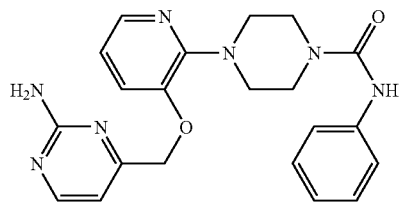 |
| 179 | 4-(3-{[(2-aminopyrimidin-4-yl)methyl]oxy}pyridin-2-yl)-N-(3-chloro-5-ethylphenyl)piperazine-1-carboxamide | 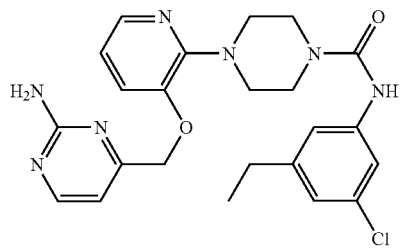 |
| 180 | 4-(3-{[(2-aminopyrimidin-4-yl)methyl]oxy}pyridin-2-yl)-N-(5-ethyl-2-fluorophenyl)piperazine-1-carboxamide | 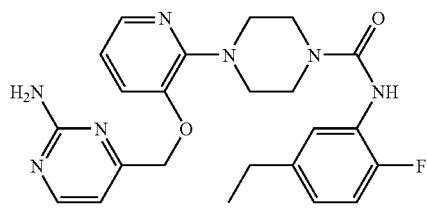 |
| 181 | 4-(3-{[(2-aminopyrimidin-4-yl)methyl]oxy}pyridin-2-yl)-N-(3-bromo-5-ethylphenyl)piperazine-1-carboxamide | 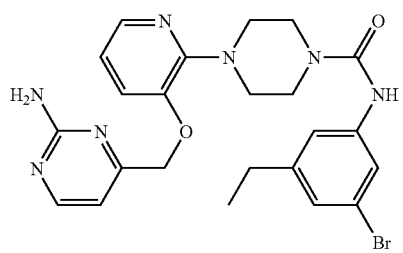 |

TABLE 1-continued

| 182 | 2-(4-methylpiperazin-1-yl)ethyl [4-({[2-(4-{[(3-ethylphenyl)amino]carbonyl}piperazin-1-yl)pyridin-3-yl]oxy}methyl)pyridin-2-yl]carbamate | 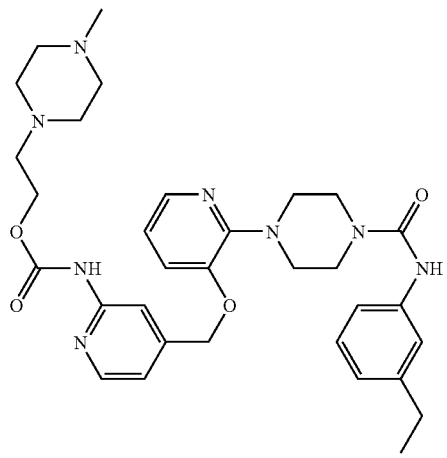 |
| --- | --- | --- |
| 183 | 4-(3-{[(2-aminopyrimidin-4-yl)methyl]oxy}pyridin-2-yl)-N-(3-chlorophenyl)piperazine-1-carboxamide | 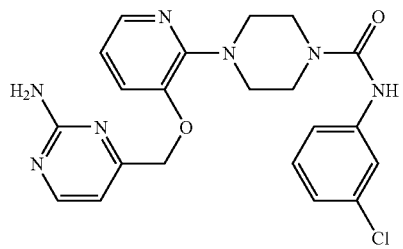 |
| 184 | 4-(3-{[(2-aminopyrimidin-4-yl)methyl]oxy}pyridin-2-yl)-N-(3-bromophenyl)piperazine-1-carboxamide | 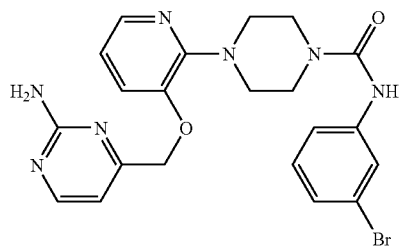 |
| 185 | N-[4-({[2-(4-acetylpiperazin-1-yl)pyridin-3-yl]oxy}methyl)pyridin-2-yl]-2-(4-methylpiperazin-1-yl)acetamide | 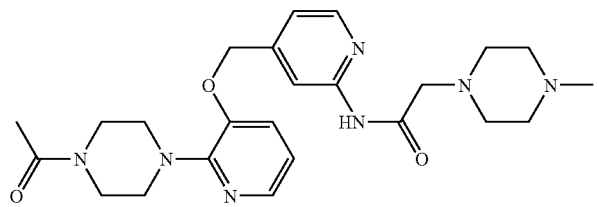 |
| 186 | 4-(3-{[(2-aminopyrimidin-4-yl)methyl]oxy}pyridin-2-yl)-N-(3-fluorophenyl)piperazine-1-carboxamide | 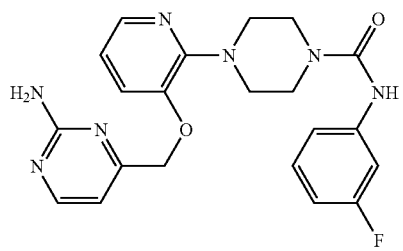 |

TABLE 1-continued

| | | |
|---|---|---|
| 187 | 4-(3-{[(2-aminopyrimidin-4-yl)methyl]oxy}pyridin-2-yl)-N-(4-fluorophenyl)piperazine-1-carboxamide | 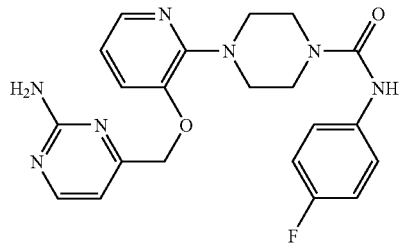 |
| 188 | 4-(3-{[(2-aminopyrimidin-4-yl)methyl]oxy}pyridin-2-yl)-N-(2-fluorophenyl)piperazine-1-carboxamide | 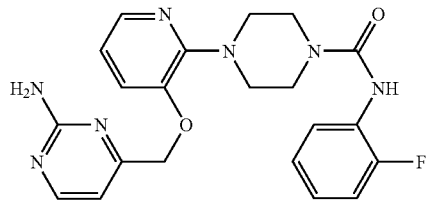 |
| 189 | 4-(3-{[(2-aminopyrimidin-4-yl)methyl]oxy}pyridin-2-yl)-N-(3,5-diethylphenyl)piperazine-1-carboxamide | 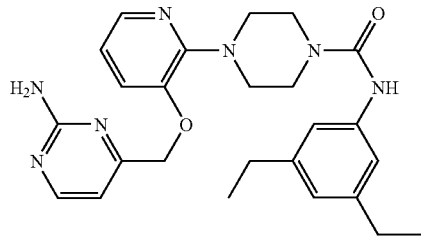 |
| 190 | 4-(3-{[(2-aminopyrimidin-4-yl)methyl]oxy}-5-bromopyridin-2-yl)-N-(3-ethylphenyl)piperazine-1-carboxamide | 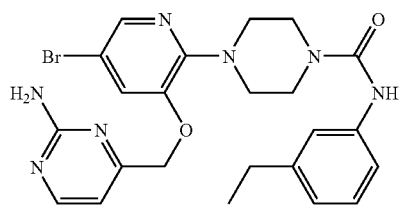 |
| 191 | N-methyl-4-(3-{[(2-{[(4-methylpiperazin-1-yl)acetyl]amino}pyridin-4-yl)methyl]oxy}pyridin-2-yl)piperazine-1-carboxamide | 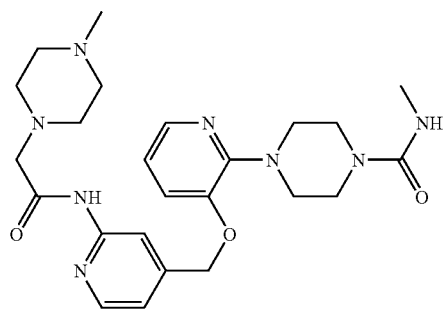 |
| 192 | 4-(3-{[(2-aminopyrimidin-4-yl)methyl]oxy}pyridin-2-yl)-N-[2-chloro-5-(trifluoromethyl)phenyl]piperazine-1-carboxamide | 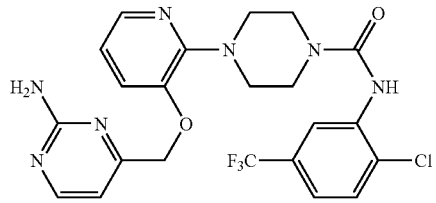 |

TABLE 1-continued

| 193 | 4-(3-{[(2-aminopyrimidin-4-yl)methyl]oxy}pyridin-2-yl)-N-(5-chloro-2-fluorophenyl)piperazine-1-carboxamide | 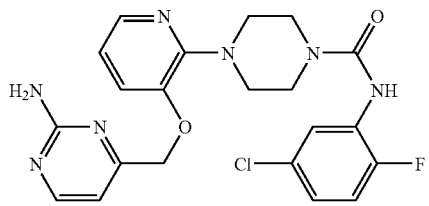 |
| 194 | 4-(3-{[(2-amino-5-bromopyrimidin-4-yl)methyl]oxy}-5-bromopyridin-2-yl)-N-(3-ethylphenyl)piperazine-1-carboxamide | 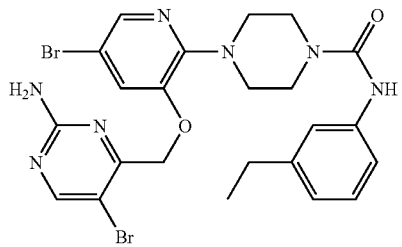 |
| 195 | 4-(3-{[(2-aminopyrimidin-4-yl)methyl]oxy}pyridin-2-yl)-N-[2-fluoro-3-(trifluoromethyl)phenyl]piperazine-1-carboxamide | 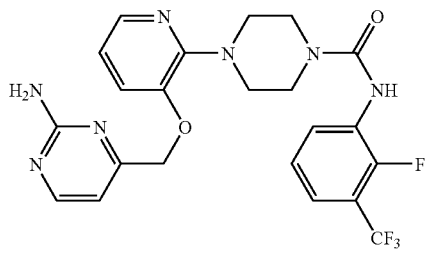 |
| 196 | 4-(3-{[(2-aminopyrimidin-4-yl)methyl]oxy}pyridin-2-yl)-N-[3-fluoro-5-(trifluoromethyl)phenyl]piperazine-1-carboxamide | 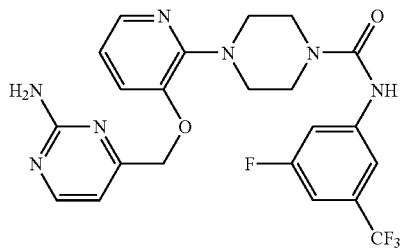 |
| 197 | 4-(3-{[(2-aminopyrimidin-4-yl)methyl]oxy}pyridin-2-yl)-N-(3,5-dichlorophenyl)piperazine-1-carboxamide | 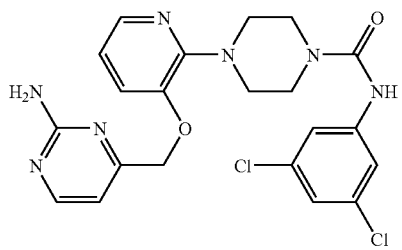 |
| 198 | N-(3-chloro-5-ethylphenyl)-4-(3-{[(2-{[(4-methylpiperazin-1-yl)acetyl]amino}pyridin-4-yl)methyl]oxy}pyridin-2-yl)piperazine-1-carboxamide | 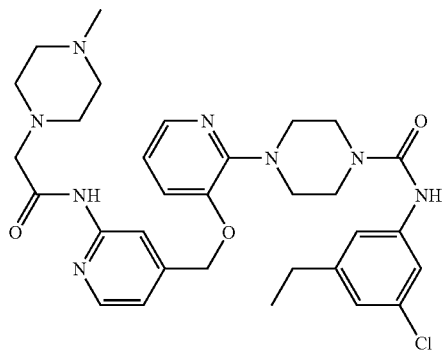 |

TABLE 1-continued

| | | |
|---|---|---|
| 199 | N-(5-ethyl-2-fluorophenyl)-4-(3-{[(2-{[(4-methylpiperazin-1-yl)acetyl]amino}pyridin-4-yl)methyl]oxy}pyridin-2-yl)piperazine-1-carboxamide | 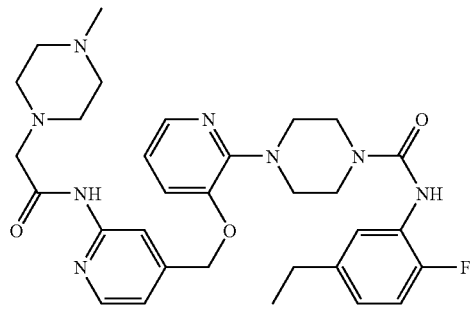 |
| 200 | 4-(3-{[(2-aminopyrimidin-4-yl)methyl]oxy}pyridin-2-yl)-N-[3-ethyl-5-(trifluoromethyl)phenyl]piperazine-1-carboxamide | 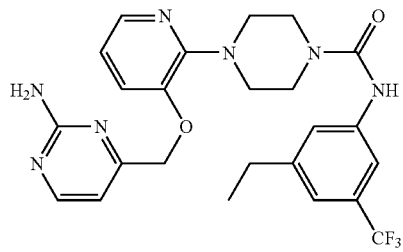 |
| 201 | 4-(3-{[(2-aminopyrimidin-4-yl)methyl]oxy}pyrazin-2-yl)-N-(3-ethylphenyl)piperazine-1-carboxamide | 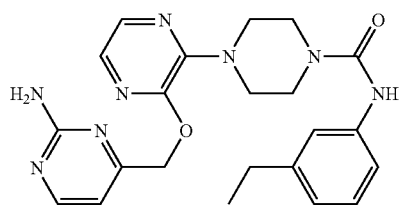 |
| 202 | 4-(3-{[(2-aminopyrimidin-4-yl)methyl]oxy}pyrazin-2-yl)-N-(3-chloro-5-ethylphenyl)piperazine-1-carboxamide | 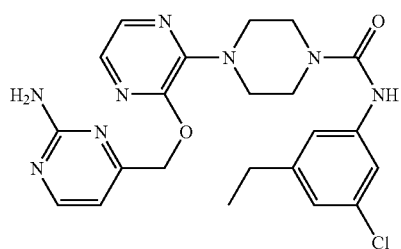 |
| 203 | 4-(3-{[(2-aminopyrimidin-4-yl)methyl]oxy}pyrazin-2-yl)-N-(5-ethyl-2-fluorophenyl)piperazine-1-carboxamide | 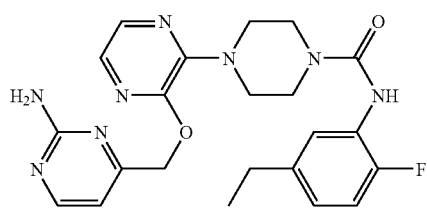 |
| 204 | 4-(3-{[(2-aminopyrimidin-4-yl)methyl]oxy}pyridin-2-yl)-N-methylpiperazine-1-carboxamide | 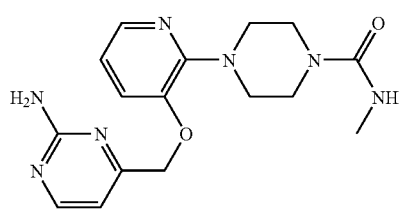 |

TABLE 1-continued

| | | |
|---|---|---|
| 205 | 4-(3-{[(2-aminopyrimidin-4-yl)methyl]oxy}pyridin-2-yl)-N-ethylpiperazine-1-carboxamide | 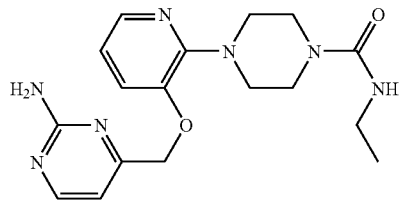 |
| 206 | 4-(3-{[(2-aminopyrimidin-4-yl)methyl]oxy}pyridin-2-yl)-N-cyclohexylpiperazine-1-carboxamide | 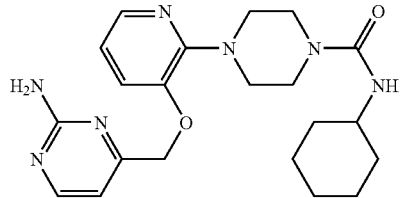 |
| 207 | 4-({[2-(4-acetylpiperazin-1-yl)pyridin-3-yl]oxy}methyl)pyrimidin-2-amine | 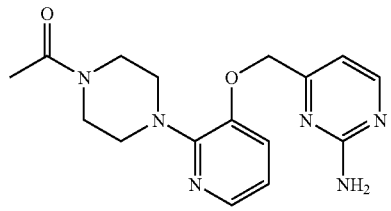 |
| 208 | 4-({[2-(4-propanoylpiperazin-1-yl)pyridin-3-yl]oxy}methyl)pyrimidin-2-amine | 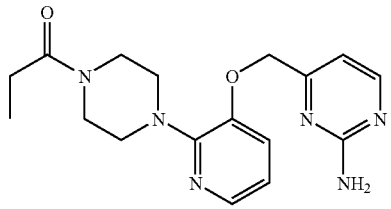 |
| 209 | N-(3-cyclopropylphenyl)-4-(3-{[(2-{[(4-methylpiperazin-1-yl)acetyl]amino}pyridin-4-yl)methyl]oxy}pyridin-2-yl)piperazine-1-carboxamide | 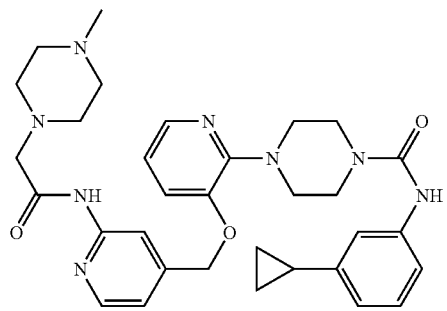 |
| 210 | 4-(3-{[(2-aminopyrimidin-4-yl)methyl]oxy}pyridin-2-yl)-N-(3-cyclopropylphenyl)piperazine-1-carboxamide | 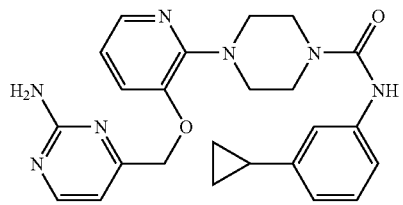 |

TABLE 1-continued

| | | |
|---|---|---|
| 211 | N-[2-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 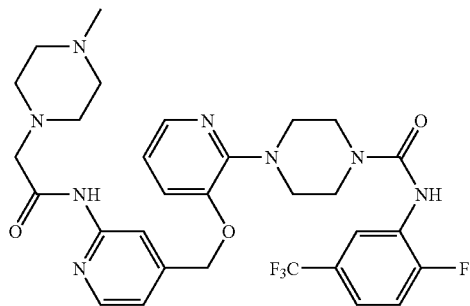 |
| 212 | N-[3-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 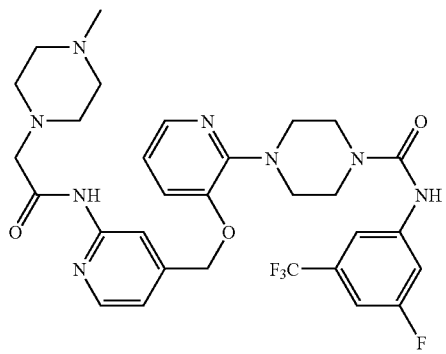 |
| 213 | N-(3,5-dichlorophenyl)-4-(3-{[(2-{[(4-methylpiperazin-1-yl)acetyl]amino}pyridin-4-yl)methyl]oxy}pyridin-2-yl)piperazine-1-carboxamide | 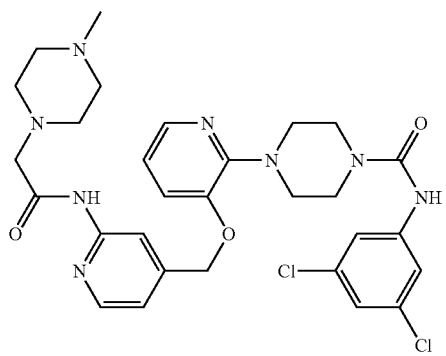 |
| 214 | 4-(3-{[(2-{[(4-methylpiperazin-1-yl)acetyl]amino}pyridin-4-yl)methyl]oxy}pyridin-2-yl)-N-[3-(trifluoromethyl)phenyl]piperazine-1-carboxamide | 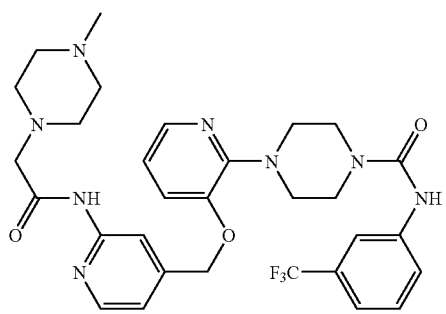 |
| 215 | 4-(3-{[(2-aminopyrimidin-4-yl)methyl]oxy}pyrazin-2-yl)-N-(3,5-diethylphenyl)piperazine-1-carboxamide | 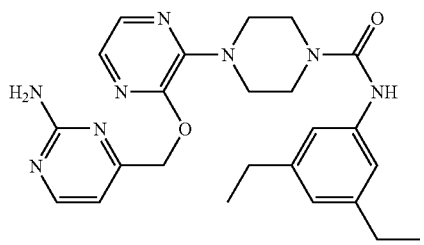 |

TABLE 1-continued

| | | |
|---|---|---|
| 216 | 4-(3-{[1-(2-aminopyrimidin-4-yl)ethyl]oxy}pyridin-2-yl)-N-[3,5-bis(trifluoromethyl)phenyl]piperazine-1-carboxamide | 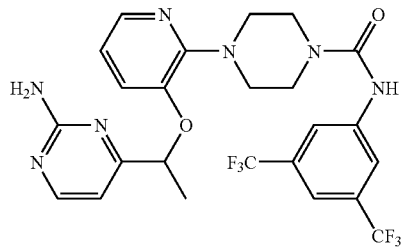 |
| 217 | 4-(3-{[(2-aminopyrimidin-4-yl)methyl]oxy}pyrazin-2-yl)-N-(3,5-dichlorophenyl)piperazine-1-carboxamide | 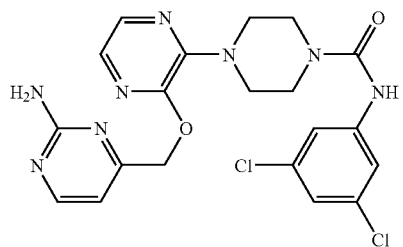 |
| 218 | 4-(3-{[(2-aminopyrimidin-4-yl)methyl]oxy}pyrazin-2-yl)-N-[3-fluoro-5-(trifluoromethyl)phenyl]piperazine-1-carboxamide | 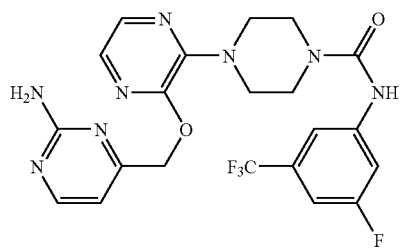 |
| 219 | 4-[({2-[4-(3,4-dihydroquinolin-1(2H)-ylcarbonyl)piperazin-1-yl]pyridin-3-yl}oxy)methyl]pyrimidin-2-amine | 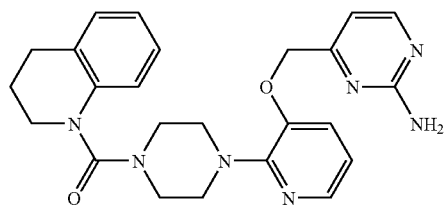 |
| 220 | 4-(3-{[(2-aminopyrimidin-4-yl)methyl]oxy}pyridin-2-yl)-N-(2-methylpropyl)piperazine-1-carboxamide | 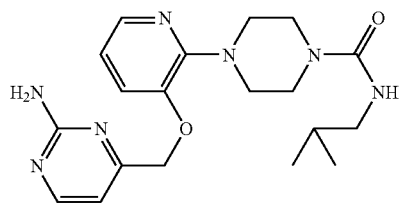 |
| 221 | 4-(4-{[(2-aminopyrimidin-4-yl)methyl]oxy}-1,2,5-thiadiazol-3-yl)-N-(3-chloro-5-ethylphenyl)piperazine-1-carboxamide | 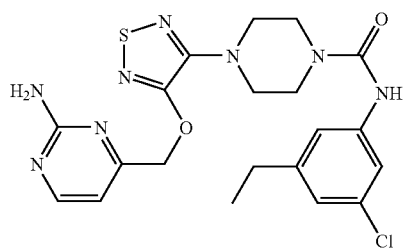 |

| | | |
|---|---|---|
| 222 | 4-(4-{[(2-aminopyrimidin-4-yl)methyl]oxy}-1,2,5-thiadiazol-3-yl)-N-(5-ethyl-2-fluorophenyl)piperazine-1-carboxamide | 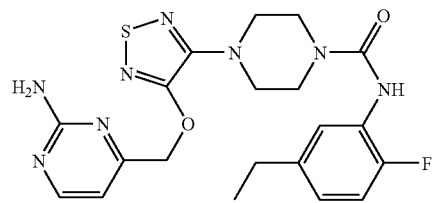 |
| 223 | 4-(4-{[(2-aminopyrimidin-4-yl)methyl]oxy}-1,2,5-thiadiazol-3-yl)-N-(3,5-dichlorophenyl)piperazine-1-carboxamide | 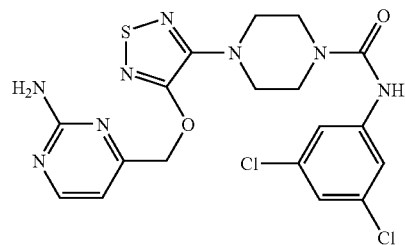 |
| 224 | 4-(3-{[(2-aminopyrimidin-4-yl)methyl]oxy}pyrazin-2-yl)-N-phenylpiperazine-1-carboxamide | 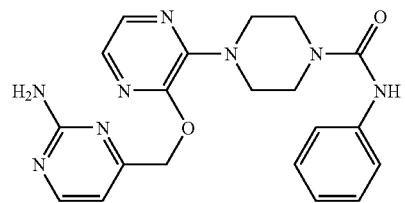 |
| 225 | 4-(3-{[(2-aminopyrimidin-4-yl)methyl]oxy}pyrazin-2-yl)-N-[2-fluoro-5-(trifluoromethyl)phenyl]piperazine-1-carboxamide | 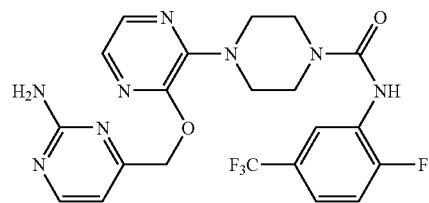 |
| 226 | N-(3,5-diethylphenyl)-4-(3-{[(2-{[(4-methylpiperazin-1-yl)acetyl]amino}pyridin-4-yl)oxy]methyl}pyridin-2-yl)piperazine-1-carboxamide | 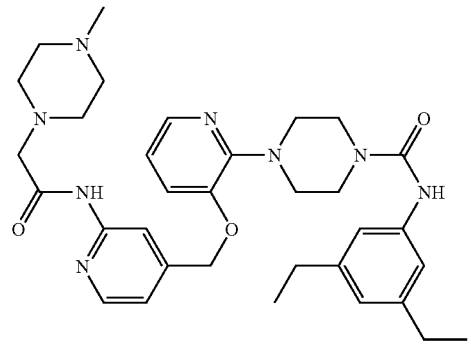 |
| 227 | 4-(3-{[(2-aminopyrimidin-4-yl)methyl]oxy}-6-methylpyridin-2-yl)-N-(3-ethylphenyl)piperazine-1-carboxamide | 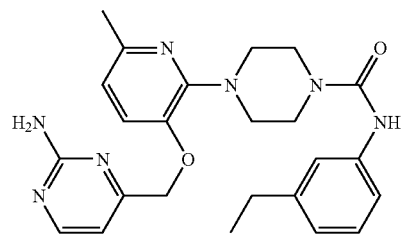 |

| | | |
|---|---|---|
| 228 | 4-(3-{[(2-aminopyrimidin-4-yl)methyl]oxy}-6-methylpyridin-2-yl)-N-[3,5-bis(trifluoromethyl)phenyl]piperazine-1-carboxamide | 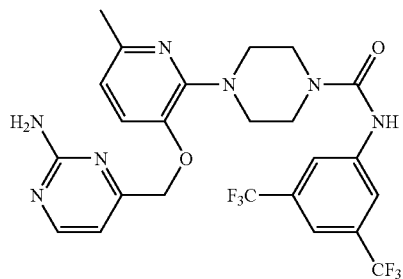 |
| 229 | 4-(3-{[(2-aminopyrimidin-4-yl)methyl]oxy}pyrazin-2-yl)-N-[3-(trifluoromethyl)phenyl]piperazine-1-carboxamide | 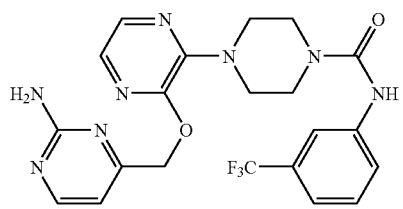 |
| 230 | 4-(4-{[(2-aminopyrimidin-4-yl)methyl]oxy}-1,2,5-thiadiazol-3-yl)-N-phenylpiperazine-1-carboxamide | 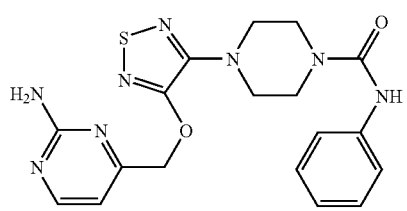 |
| 231 | 4-(4-{[(2-aminopyrimidin-4-yl)methyl]oxy}-1,2,5-thiadiazol-3-yl)-N-[3-(trifluoromethyl)phenyl]piperazine-1-carboxamide | 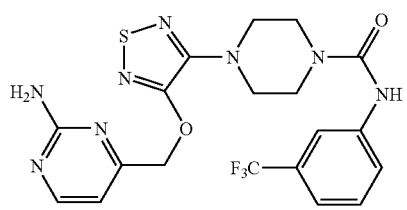 |
| 232 | 4-(4-{[(2-aminopyrimidin-4-yl)methyl]oxy}-1,2,5-thiadiazol-3-yl)-N-[2-fluoro-5-(trifluoromethyl)phenyl]piperazine-1-carboxamide | 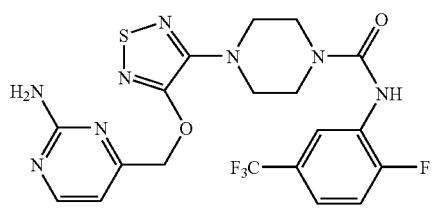 |
| 233 | N-[3-chloro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 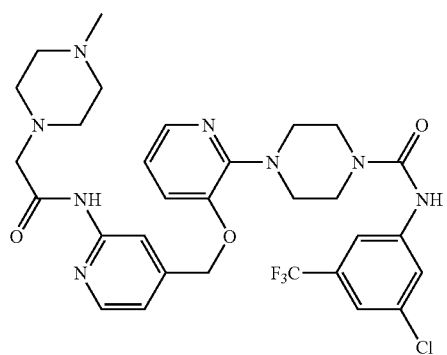 |

TABLE 1-continued

| | | |
|---|---|---|
| 234 | 4-(3-{[(2-aminopyrimidin-4-yl)methyl]oxy}pyrazin-2-yl)-N-[3-chloro-5-(trifluoromethyl)phenyl]piperazine-1-carboxamide | 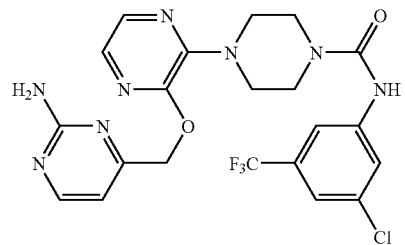 |
| 235 | 4-(3-{[(2-aminopyrimidin-4-yl)methyl]oxy}pyridin-2-yl)-N-[3-chloro-5-(trifluoromethyl)phenyl]piperazine-1-carboxamide | 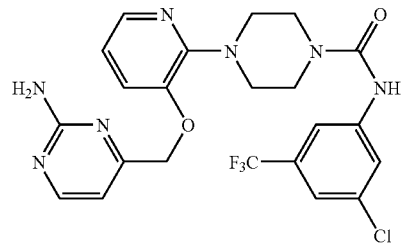 |
| 236 | 4-(3-{[(2-aminopyrimidin-4-yl)methyl]oxy}pyrazin-2-yl)-N-(3-bromo-5-ethylphenyl)piperazine-1-carboxamide | 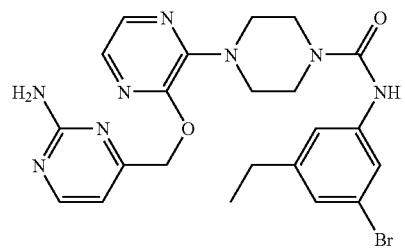 |
| 237 | 4-(3-{[(2-aminopyrimidin-4-yl)methyl]oxy}-6-chloropyridin-2-yl)-N-(3-ethylphenyl)piperazine-1-carboxamide | 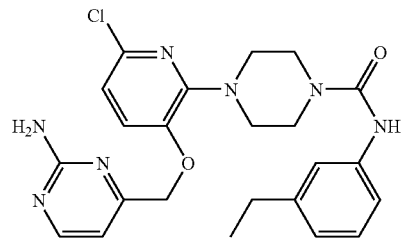 |
| 238 | 4-(4-{[(2-aminopyrimidin-4-yl)methyl]oxy}-1,2,5-thiadiazol-3-yl)-N-(3-bromo-5-ethylphenyl)piperazine-1-carboxamide | 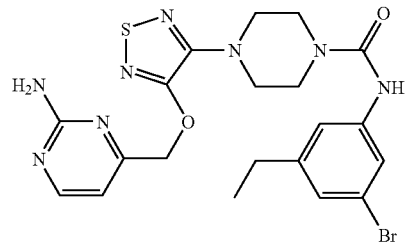 |
| 239 | 4-(4-{[(2-aminopyrimidin-4-yl)methyl]oxy}-1,2,5-thiadiazol-3-yl)-N-[3-fluoro-5-(trifluoromethyl)phenyl]piperazine-1-carboxamide | 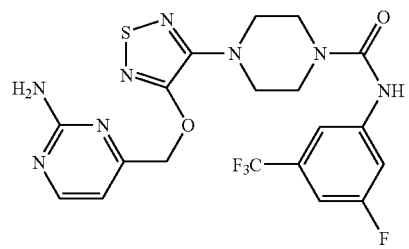 |

TABLE 1-continued

| | | |
|---|---|---|
| 240 | 4-(4-{[(2-aminopyrimidin-4-yl)methyl]oxy}-1,2,5-thiadiazol-3-yl)-N-[3-chloro-5-(trifluoromethyl)phenyl]piperazine-1-carboxamide | 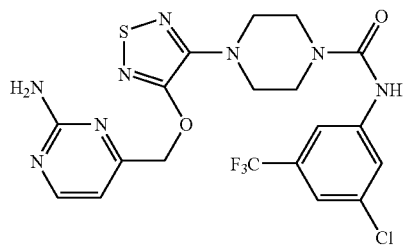 |
| 241 | 4-(3-{[(2-aminopyrimidin-4-yl)methyl]oxy}pyrazin-2-yl)-N-(3-ethyl-4-fluorophenyl)piperazine-1-carboxamide | 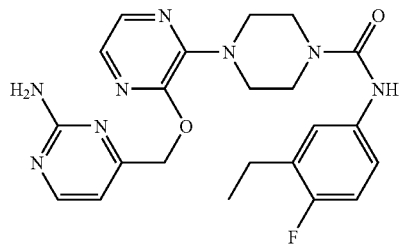 |
| 242 | 4-(4-{[(2-aminopyrimidin-4-yl)methyl]oxy}-1,2,5-thiadiazol-3-yl)-N-(3,5-diethylphenyl)piperazine-1-carboxamide | 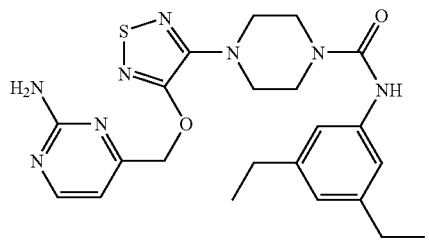 |
| 243 | N-[3-chloro-2-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 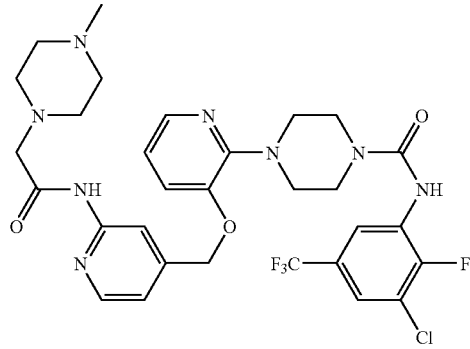 |
| 244 | 4-(3-{[(2-aminopyrimidin-4-yl)methyl]oxy}-6-chloropyridin-2-yl)-N-[3,5-bis(trifluoromethyl)phenyl]piperazine-1-carboxamide | 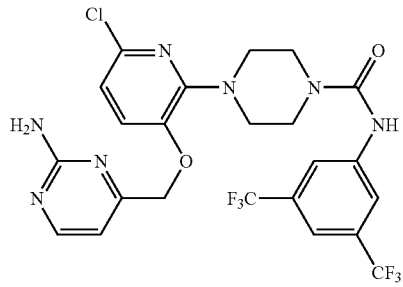 |
| 245 | 4-(3-{[1-(2-aminopyrimidin-4-yl)ethyl]oxy}pyridin-2-yl)-N-(3-ethylphenyl)piperazine-1-carboxamide | 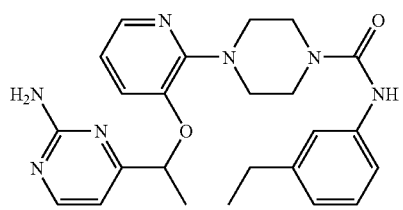 |

| | | |
|---|---|---|
| 246 | 4-(3-{[(2-aminopyrimidin-4-yl)methyl]oxy}-6-chloropyridin-2-yl)-N-(5-ethyl-2-fluorophenyl)piperazine-1-carboxamide | 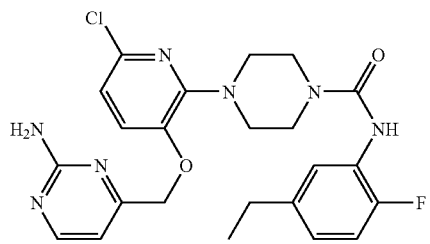 |
| 247 | 4-(3-{[(2-aminopyrimidin-4-yl)methyl]oxy}pyridin-2-yl)-N-(3-ethyl-5-fluorophenyl)piperazine-1-carboxamide | 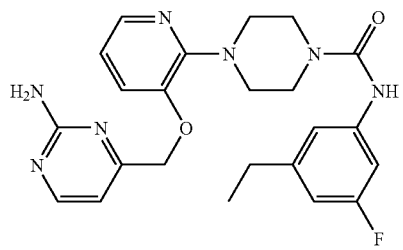 |
| 248 | 4-(4-{[(2-aminopyrimidin-4-yl)methyl]oxy}-1,2,5-thiadiazol-3-yl)-N-[3-chloro-2-fluoro-5-(trifluoromethyl)phenyl]piperazine-1-carboxamide | 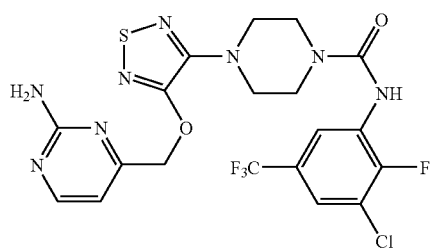 |
| 249 | 4-(3-{[(2-aminopyrimidin-4-yl)methyl]oxy}pyridin-2-yl)-N-[3-chloro-2-fluoro-5-(trifluoromethyl)phenyl]piperazine-1-carboxamide | 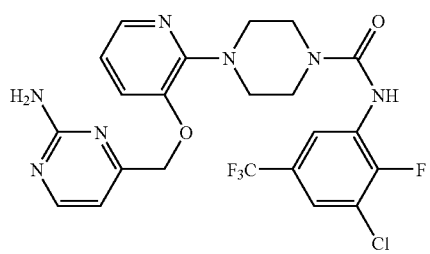 |
| 250 | 4-(3-{[(2-aminopyrimidin-4-yl)methyl]oxy}pyridin-2-yl)-N-[3,5-bis(trifluoromethyl)phenyl]-N-methylpiperazine-1-carboxamide | 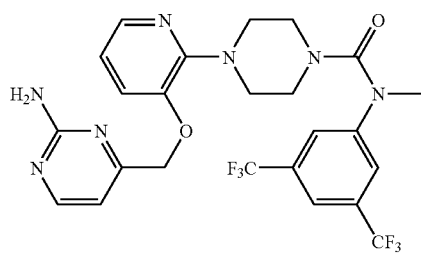 |
| 251 | 4-(3-{[(2-aminopyrimidin-4-yl)methyl]oxy}pyrazin-2-yl)-N-[3-(1-methylethyl)phenyl]piperazine-1-carboxamide | 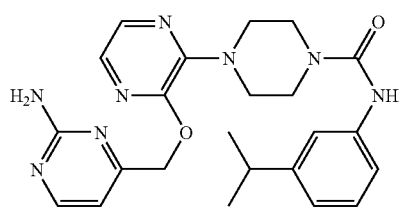 |

TABLE 1-continued

| | | |
|---|---|---|
| 252 | 4-(4-{[(2-aminopyrimidin-4-yl)methyl]oxy}-1,2,5-thiadiazol-3-yl)-N-(3-ethyl-4-fluorophenyl)piperazine-1-carboxamide | 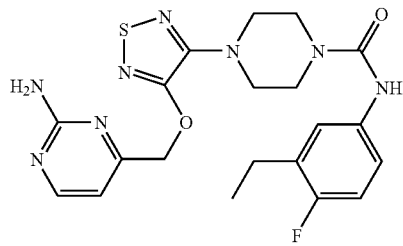 |
| 253 | 4-(4-{[(2-aminopyrimidin-4-yl)methyl]oxy}-1,2,5-thiadiazol-3-yl)-N-(3-chloro-4-fluorophenyl)piperazine-1-carboxamide | 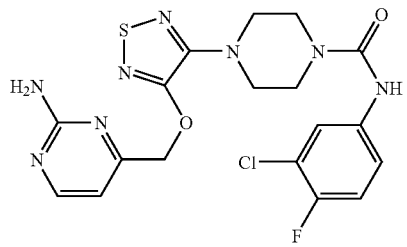 |
| 254 | 4-(4-{[(2-aminopyrimidin-4-yl)methyl]oxy}-1,2,5-thiadiazol-3-yl)-N-[2,5-bis(methyloxy)phenyl]piperazine-1-carboxamide | 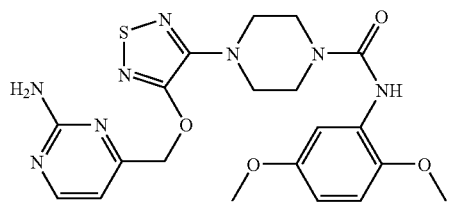 |
| 255 | 4-(2-{[(2-aminopyrimidin-4-yl)methyl]oxy}phenyl)-N-[3,5-bis(trifluoromethyl)phenyl]piperazine-1-carboxamide | 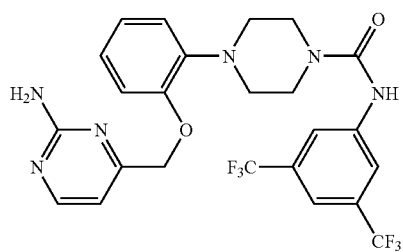 |
| 256 | 4-(2-{[(2-aminopyrimidin-4-yl)methyl]oxy}phenyl)-N-(3-ethylphenyl)piperazine-1-carboxamide | 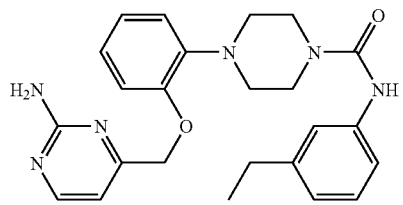 |
| 257 | 4-(4-{[(2-aminopyrimidin-4-yl)methyl]oxy}-1,2,5-thiadiazol-3-yl)-N-(5-chloro-2-fluorophenyl)piperazine-1-carboxamide | 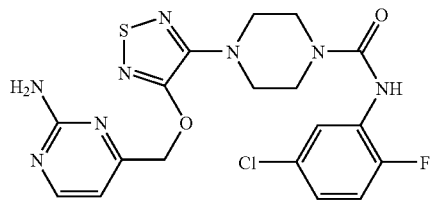 |
| 258 | 4-(4-{[(2-aminopyrimidin-4-yl)methyl]oxy}-1,2,5-thiadiazol-3-yl)-N-{3-[(trifluoromethyl)oxy]phenyl}piperazine-1-carboxamide | 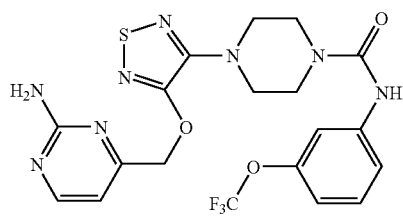 |

| | | |
|---|---|---|
| 259 | 4-(4-{[(2-aminopyrimidin-4-yl)methyl]oxy}-1,2,5-thiadiazol-3-yl)-N-[3-(methyloxy)phenyl]piperazine-1-carboxamide | 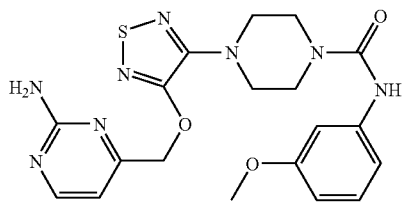 |
| 260 | 4-(4-{[(2-aminopyrimidin-4-yl)methyl]oxy}-1,2,5-thiadiazol-3-yl)-N-[3-ethyl-5-(trifluoromethyl)phenyl]piperazine-1-carboxamide | 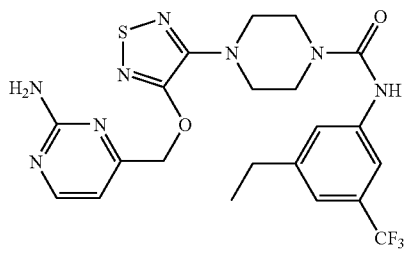 |
| 261 | 4-(4-{[(2-aminopyrimidin-4-yl)methyl]oxy}-1,2,5-thiadiazol-3-yl)-N-[3-(1-methylethyl)phenyl]piperazine-1-carboxamide | 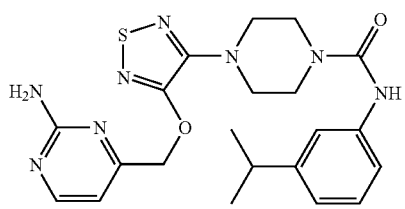 |
| 262 | 4-(4-{[(2-aminopyrimidin-4-yl)methyl]oxy}-1,2,5-thiadiazol-3-yl)-N-[2-chloro-5-(trifluoromethyl)phenyl]piperazine-1-carboxamide | 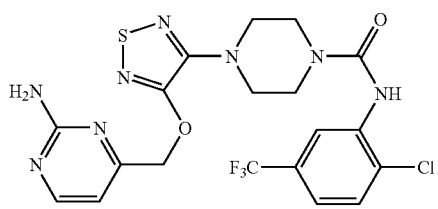 |
| 263 | 4-(4-{[(2-aminopyrimidin-4-yl)methyl]oxy}-1,2,5-thiadiazol-3-yl)-N-(3-fluorophenyl)piperazine-1-carboxamide | 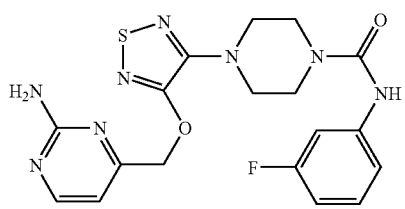 |
| 264 | 4-(4-{[(2-aminopyrimidin-4-yl)methyl]oxy}-1,2,5-thiadiazol-3-yl)-N-[2-(ethyloxy)phenyl]piperazine-1-carboxamide | 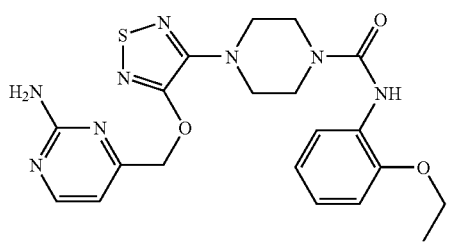 |
| 265 | 4-(4-{[(2-aminopyrimidin-4-yl)methyl]oxy}-1,2,5-thiadiazol-3-yl)-N-(3,4-difluorophenyl)piperazine-1-carboxamide | 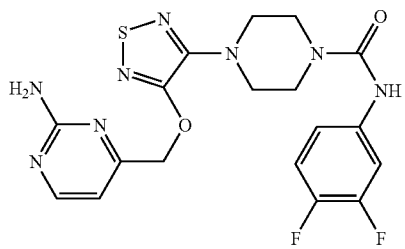 |

TABLE 1-continued

| 266 | 4-(4-{[(2-aminopyrimidin-4-yl)methyl]oxy}-1,2,5-thiadiazol-3-yl)-N-[3-(methylthio)phenyl]piperazine-1-carboxamide | 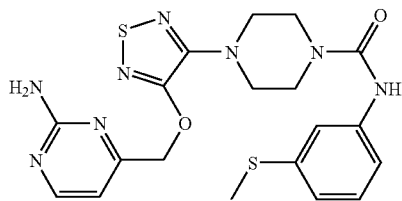 |
| 267 | N-(3-acetylphenyl)-4-(4-{[(2-aminopyrimidin-4-yl)methyl]oxy}-1,2,5-thiadiazol-3-yl)piperazine-1-carboxamide | 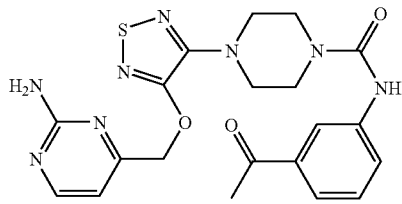 |
| 268 | 4-(2-{[(2-aminopyrimidin-4-yl)methyl]oxy}phenyl)-N-[2-fluoro-5-(trifluoromethyl)phenyl]piperazine-1-carboxamide | 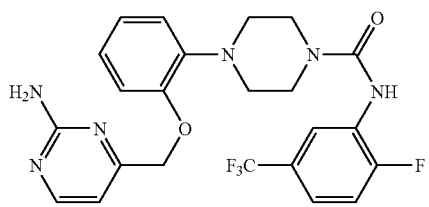 |
| 269 | 4-(2-{[(2-aminopyrimidin-4-yl)methyl]oxy}phenyl)-N-(3-fluorophenyl)piperazine-1-carboxamide | 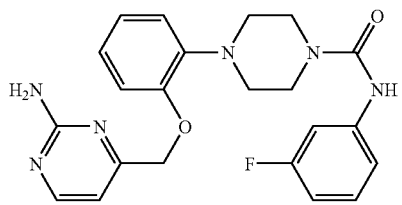 |
| 270 | 4-(2-{[(2-aminopyrimidin-4-yl)methyl]oxy}phenyl)-N-phenylpiperazine-1-carboxamide | 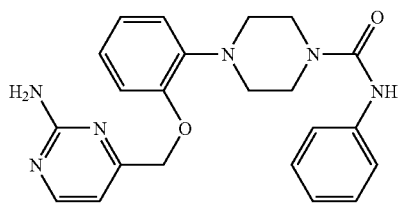 |
| 271 | 4-(2-{[(2-aminopyrimidin-4-yl)methyl]oxy}phenyl)-N-(3,5-dichlorophenyl)piperazine-1-carboxamide | 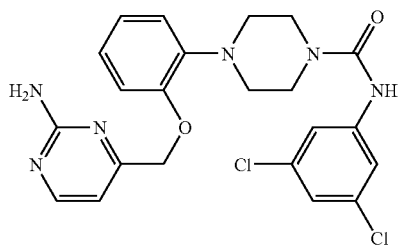 |
| 272 | 4-(2-{[(2-aminopyrimidin-4-yl)methyl]oxy}phenyl)-N-[3-fluoro-5-(trifluoromethyl)phenyl]piperazine-1-carboxamide | 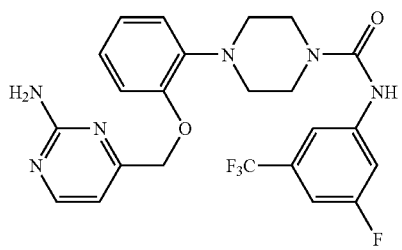 |

TABLE 1-continued

| 273 | 4-[4-({[6,7-bis(methyloxy)quinolin-4-yl]methyl}oxy)-1,2,5-thiadiazol-3-yl]-N-[3,5-bis(trifluoromethyl)phenyl]piperazine-1-carboxamide | 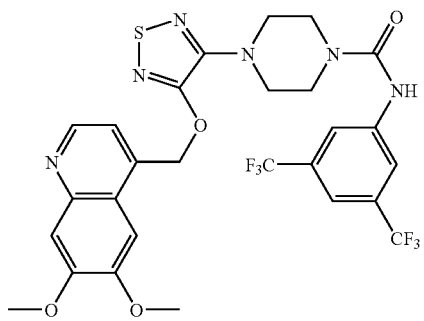 |
| 274 | 4-({[4-(4-{[3,5-bis(trifluoromethyl)phenyl]acetyl}piperazin-1-yl)-1,2,5-thiadiazol-3-yl]oxy}methyl)pyrimidin-2-amine | 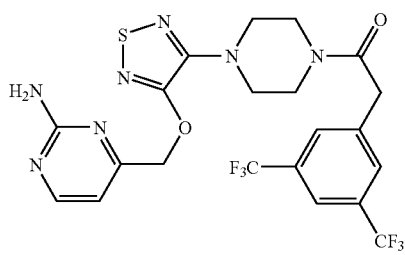 |
| 275 | 5-{[(2-aminopyrimidin-4-yl)methyl]oxy}-6-[4-({[3,5-bis(trifluoromethyl)phenyl]amino}carbonyl)piperazin-1-yl]pyrazine-2-carboxamide | 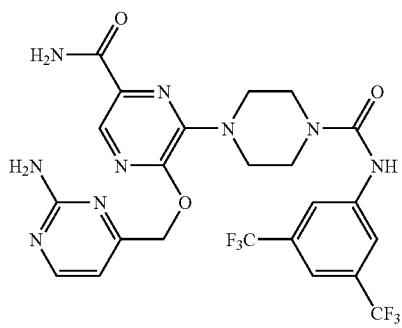 |
| 276 | 4-(4-{[6,7-bis(methyloxy)quinolin-4-yl]oxy}-1,2,5-thiadiazol-3-yl)-N-[3,5-bis(trifluoromethyl)phenyl]piperazine-1-carboxamide | 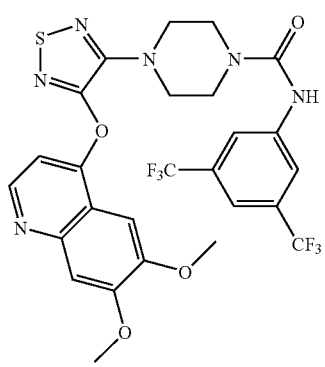 |
| 277 | 4-(2-{[(2-aminopyrimidin-4-yl)methyl]oxy}phenyl)-N-[3-ethyl-5-(trifluoromethyl)phenyl]piperazine-1-carboxamide | 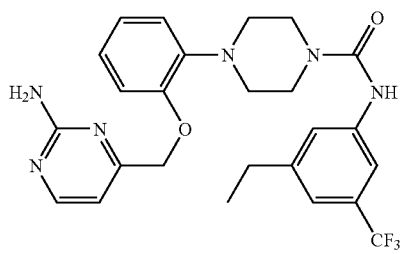 |

TABLE 1-continued

| | | |
|---|---|---|
| 278 | 4-(2-{[(2-aminopyrimidin-4-yl)methyl]oxy}phenyl)-N-(5-ethyl-2-fluorophenyl)piperazine-1-carboxamide | 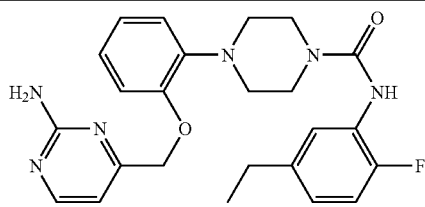 |
| 279 | 4-(2-{[(2-aminopyrimidin-4-yl)methyl]oxy}phenyl)-N-(3,5-diethylphenyl)piperazine-1-carboxamide | 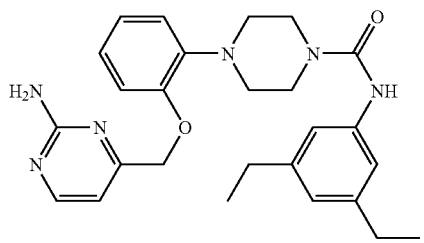 |
| 280 | 4-[({4-[4-(naphthalen-2-ylacetyl)piperazin-1-yl]-1,2,5-thiadiazol-3-yl}oxy)methyl]pyrimidin-2-amine | 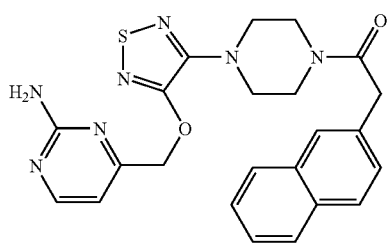 |
| 281 | 4-(2-{[(2-aminopyrimidin-4-yl)methyl]oxy}phenyl)-N-(3-chloro-5-ethylphenyl)piperazine-1-carboxamide | 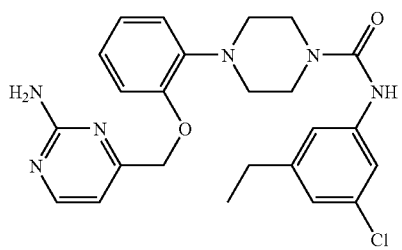 |

Another aspect of the invention is a pharmaceutical composition comprising the compound according to any one of embodiments [0021]-[0062] and a pharmaceutically acceptable carrier, hereinafter embodiment [0063].

Another aspect of the invention is a metabolite of the compound or the pharmaceutical composition according to any one of embodiments [0021]-[0063], hereinafter embodiment [0064].

Another aspect of the invention is a method of modulating the in vivo activity of a kinase, the method comprising administering to a subject an effective amount of a composition comprising at least one of the compound according to any of embodiments [0021]-[0062] and the pharmaceutical composition according to embodiment [0063], hereinafter embodiment [0065].

Another aspect of the invention is the method according to embodiment [0065], wherein the kinase is Tie-2, hereinafter embodiment [0066].

Another aspect of the invention is the method according to embodiment [0066], wherein modulating the in vivo activity of Tie-2 comprises inhibition of Tie-2.

Another aspect of the invention is a method of treating diseases or disorders associated with uncontrolled, abnormal, and/or unwanted cellular activities, the method comprising administering, to a mammal in need thereof, a therapeutically effective amount of a composition comprising at least one of the compound according to any of embodiments [0021]-[0062] and the pharmaceutical composition according to embodiment [0063].

Another aspect of the invention is a method of screening for modulator of a Tie-2 kinase, the method comprising combining either a composition comprising at least one of the compound according to any of embodiments [0021]-[0062] and the pharmaceutical composition according to embodiment [0063], and at least one candidate agent and determining the effect of the candidate agent on the activity of said kinase.

Another aspect of the invention is a method of inhibiting proliferative activity in a cell, the method comprising administering an effective amount of at least one of the compound according to any of embodiments [0021]-[0062] and the pharmaceutical composition according to embodiment [0063].

DEFINITIONS

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond. The symbol "⁓" refers to a group on a double-bond as occupying either position on the terminus of a double bond to which the symbol is attached; that is, the geometry, E- or Z—, of the double bond is ambiguous. When a group is depicted removed from its parent formula, the "~" symbol will be used at the end of the bond which was theoretically cleaved in order to separate the group from its parent structural formula.

Chemical formulae use descriptors such as "R¹" accompanied by a list of formulae or verbiage describing the scope of what is meant by the descriptor. A subsequent descriptor such as "R¹ᵃ" is used to describe some subset of the scope of R¹, and "R¹ᵇ" is used to describe another subset of the scope of R¹, and so on. In such subsequent cases, all other formulae containing simply "R¹" are meant to include the entire scope of the descriptor.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

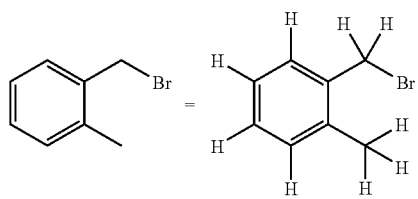

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

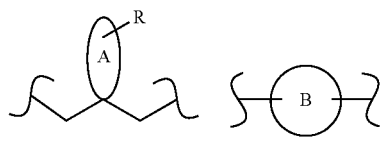

If a group "R" is depicted as "floating" on a ring system, as for example in the formula:

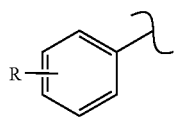

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

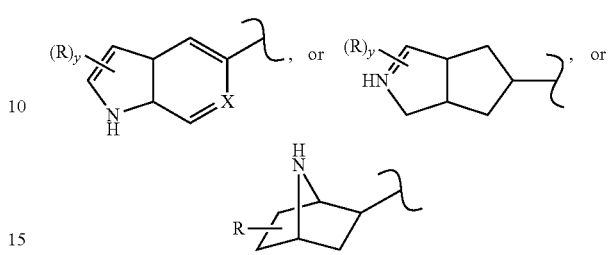

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

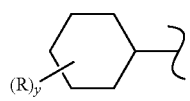

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

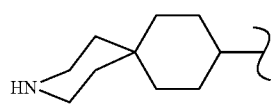

"Alkyl" is intended to include linear, branched, or cyclic hydrocarbon structures and combinations thereof, inclusively. For example, "C₈ alkyl" may refer to an n-octyl, isooctyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of C₂₀ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus, when an alkyl residue having a specific number of carbons is named, all geometric isomers having that number of carbons are intended to be encompassed; thus, for example, either "butyl" or "$C_4$alkyl" is meant to include n-butyl, sec-butyl, isobutyl, t-butyl, isobutenyl and but-2-yne radicals; and for example, "propyl" or "$C_3$alkyl" each include n-propyl, propenyl, and isopropyl. Otherwise, if alkenyl and/or alkynyl descriptors are used in a particular definition of a group, for example "$C_4$alkyl" along "$C_4$alkenyl," then $C_4$alkenyl geometric isomers are not meant to be included in "$C_4$alkyl," but other 4-carbon isomers are, for example $C_4$alkynyl. For example, a more general description, intending to encompass the invention as a whole may describe a particular group as "$C_{1-8}$alkyl" while a preferred species may describe the same group as including, "$C_{1-8}$alkyl," "$C_{1-6}$alkenyl" and "$C_{1-5}$alkynyl."

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, and furanyl-oxy-sulfonamino.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula below.

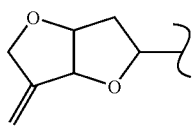

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl C$_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted arylC$_{1-8}$alkyl," optional substitution may occur on both the "C$_{1-8}$alkyl" portion and the "aryl" portion of the molecule; and for example, optionally substituted alkyl includes optionally substituted cycloalkyl groups, which in turn are defined as including optionally substituted alkyl groups, potentially ad infinitum. A list of exemplary optional substitutions is included below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

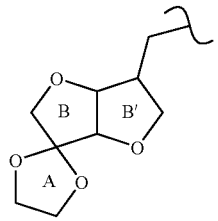

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from: optionally substituted alkyl (for example, fluoromethyl, hydroxypropyl, nitromethyl, aminoethyl and the like.), optionally substituted aryl (for example, 4-hydroxyphenyl, 2,3-difluorophenyl, and the like), optionally substituted arylalkyl (for example, 1-phenyl-ethyl, para-methoxyphenylethyl and the like), optionally substituted heterocyclylalkyl (for example, 1-pyridin-3-yl-ethyl, N-ethylmorphonlino and the like), optionally substituted heterocyclyl (for example, 5-chloro-pyridin-3-yl, 1-methyl-piperidin-4-yl and the like), optionally substituted alkoxy (for example methoxyethoxy, hydroxypropyloxy, methylenedioxy and the like), optionally substituted amino (for example, methylamino, diethylamino, trifluoroacetylamino and the like), optionally substituted amidino, optionally substituted aryloxy (for example, phenoxy, para-chlorophenoxy, meta-aminophenoxy, para-phenoxyphenoxy and the like), optionally substituted arylalkyloxy (for example, benzyloxy, 3-chlorobenzyloxy, meta-phenoxybenzyloxy and the like), carboxy (—CO₂H), optionally substituted carboalkoxy (that is, acyloxy or —OC(=O)R), optionally substituted carboxyalkyl (that is, esters or —CO₂R), optionally substituted carboxamido, optionally substituted benzyloxycarbonylamino (CBZ-amino), cyano, optionally substituted acyl, halogen, hydroxy, nitro, optionally substituted alkylsulfanyl, optionally substituted alkylsulfinyl, optionally substituted alkylsulfonyl, thiol, oxo, carbamyl, optionally substituted acylamino, optionally substituted hydrazino, optionally substituted hydroxylamino, and optionally substituted sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O₂)—H, —S(O₂)-(optionally substituted alkyl), —S(O₂)-optionally substituted aryl), —S(O₂)-(optionally substituted heterocyclyl), —S(O₂)-(optionally substituted alkoxy), —S(O₂)-optionally substituted aryloxy), and —S(O₂)-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —OCH₂—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—OCH₂—" is meant to mean not only "—OCH₂—" as drawn, but also "—CH₂O—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular c-Met, c-Kit, KDR, flt-3, or flt-4-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example Tie-2 receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, Tie-2 protein may be done in a number of ways. In one example, the candidate agent (the compound of the invention) is labeled, for example, with a fluorescent or radioactive moiety and binding determined directly. For example, thus may be done by attaching all or a portion of the Tie-2 protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, Tie-2 protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to Tie-2.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to Tie-2, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to Tie-2 protein for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to Tie-2 and thus is capable of binding to, and potentially modulating, the activity of the Tie-2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to Tie-2 with a higher affinity. Thus, if the candidate agent is labeled, the presence of the label on the support, coupled with a lack of competitor binding, may indicate the candidate agent is capable of binding to Tie-2.

It may be of value to identify the binding site of Tie-2. This can be done in a variety of ways. In one embodiment, once Tie-2 has been identified as binding to the candidate agent, the Tie-2 is fragmented or modified and the assays repeated to identify the necessary components for binding.

Modulation is tested by screening for candidate agents capable of modulating the activity of Tie-2 comprising the steps of combining a candidate agent with Tie-2, as above, and determining an alteration in the biological activity of the Tie-2. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native Tie-2, but cannot bind to modified Tie-2.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components can be added in any order that provides for the requisite binding.

One of ordinary skill in the art would understand that certain crystallized, protein-ligand complexes, in particular Tie-2-ligand complexes, and their corresponding x-ray structure coordinates can be used to reveal new structural information useful for understanding the biological activity of Tie-2 kinase's as described herein. As well, the key structural features of the aforementioned proteins, particularly, the shape of the ligand binding site, are useful in methods for designing or identifying selective modulators of Tie-2 kinase's and in solving the structures of other proteins with similar features. Ligands of such complexes may include compounds of the invention as described herein.

As well, one of ordinary skill in the art would appreciate that such suitable x-ray quality crystals can be used as part of a method of identifying a candidate agent capable of binding to and modulating the activity of Tie-2 kinases. Such methods may be characterized by the following aspects: a) introducing into a suitable computer program, information defining a ligand binding domain of a Tie-2 kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for Tie-2 kinase modulation, and determining whether said candidate agent modulates Tie-2 kinase activity in the assay. Such methods may also include administering the candidate agent, determined to modulate Tie-2 kinase activity, to a mammal suffering from a condition treatable by Tie-2 kinase modulation, such as those described above.

Also, one skilled in the art would appreciate that compounds of the invention can be used in a method of evaluating the ability of a test agent to associate with a molecule or molecular complex comprising a ligand binding domain of a Tie-2 kinase. Such a method may be characterized by the following aspects: a) creating a computer model of a Tie-2 kinase binding pocket using structure coordinates obtained from suitable x-ray quality crystals of the Tie-2 kinase, b) employing computational algorithms to perform a fitting operation between the test agent and the computer model of the binding pocket, and c) analyzing the results of the fitting operation to quantify the association between the test agent and the computer model of the binding pocket.

Abbreviations and their Definitions

The following abbreviations and terms have the indicated meanings throughout:

| Abbreviation | Meaning |
| --- | --- |
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ere |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-l-ethoxycarbonyl-1,2-dihydroquinoline |

| Abbreviation | Meaning |
|---|---|
| EI | Electron Impact ionization |
| Et | ethyl |
| Fmoc | 9-fluorenylmethoxycarbonyl |
| g | gram(s) |
| GC | gas chromatography |
| h or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| s- | secondary |
| t- | tertiary |
| t or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| μL | microliter(s) |
| μM | Micromole(s) or micromolar |

Synthesis of Compounds

Schemes 1 and 2 depict general synthetic routes for compounds of the invention and are not intended to be limiting. Specific examples are described subsequently to these general synthetic descriptions. In the generalizations below, specific reaction conditions, for example, added bases, acids, solvents, temperature, and the like were not described so as not to confuse the discussion. The general routes in conjunction with the specific examples contain sufficient information to allow one skilled in the art to synthesize compounds of the invention.

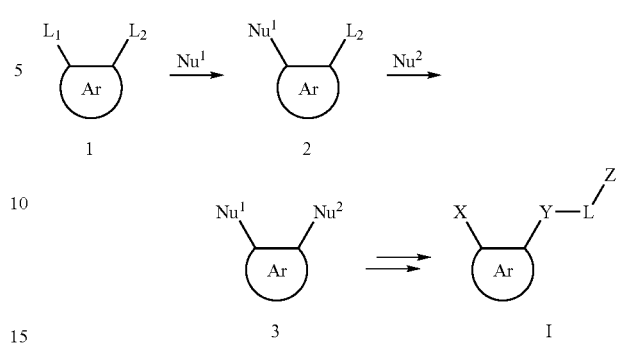

Scheme 1

Referring to Scheme 1, an aromatic starting material, 1, having ortho leaving groups $L_1$ and $L_2$ (and assuming there may be optional substituents on Ar), is combined with a first nucleophilic reagent $Nu^1$ to afford intermediate 2. Examples of starting material 1 include, but are not limited to, 3,4-dichloro-1,2,5-thiadiazole, 3,4-dichloro-pyrazine, 5,6-dichloro-2,3-dicyanopyrazine, and the like. Examples of first nucleophilic reagent $Nu^1$ include, but are not limited to, Boc-piperazine, t-butyl 1-homopiperazine carboxylate, 2,6-dimethyl-piperazine, 2,5-dimethyl-piperazine, and the like. Intermediates of type 2 may also be purchased, obviating the need for the aforementioned synthetic conversion 1→2.

Leaving groups and nucleophiles are chosen to effect desired regiochemical outcome of the particular synthesis, as is more fully exemplified below. $Nu^1$ may be a preformed intermediate corresponding to "—X" in formula I, or a precursor to "—X," in some instances as will be apparent from the examples below. Intermediate 2 is combined with a second nucleophilic reagent, $Nu^2$, to afford intermediate 3. Again, in some instances $Nu^2$ may be a preformed intermediate corresponding to "—Y-L-Z" in formula I, or a precursor to "—Y-L-Z." Examples of $Nu^2$ include, but are not limited to, pyridin-4-yl-methanol, 3-(dimethylamino-phenyl)-methanol, and the like. Therefore, there may be needed additional manipulation of $Nu^1$ and $Nu^2$ to synthesize compounds of formula I (as depicted), or intermediate 3 may itself be a compound according to formula I. As mentioned, intermediate 3 may be converted to compounds of formula I. Intermediate 3 may be purchased, made as depicted in Scheme 1, or a commercially available or other starting material is converted into 3, for example. This may entail, for example, a simple removal of a protecting group, reduction of an electrophilic moiety to make either of $Nu^1$ or $Nu^2$, or in some cases a more complex manipulation.

Scheme 2 shows one example of a conversion strategy 3→I to which any of the aforementioned scenarios would apply. Intermediate 3 (where $Nu^1$ has a nucleophilic group thereon) is combined with an electrophile, $E^1$ to afford intermediate 4. An example of this strategy is where $Nu^1$ is a piperazine (where in formation of 3 one of the piperazine nitrogens is attached to the aromatic ring) and in conversion to 4, a ring —NH— is "capped" with electrofile $E^1$. Conversion of 4→5 may proceed in much the same way, for example when $Nu^2$ has a free nucleophilic site, then an electrophile $E^2$ may be added as depicted. There may be needed additional manipulation of 5 to synthesize compounds of formula I (as depicted), or intermediate 5 may itself be a compound according to formula I.

Scheme 2

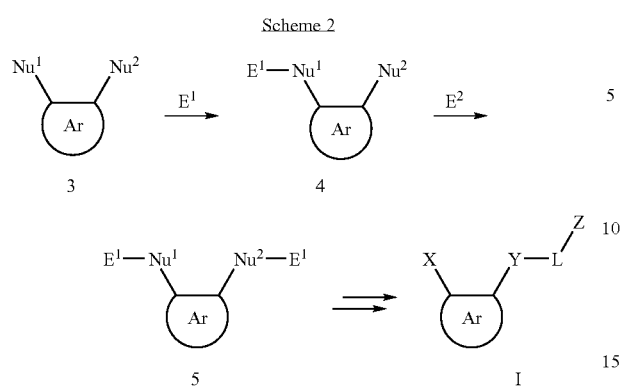

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, each example is set out below with a corresponding multi-step synthesis scheme. Following specific examples are lists of compounds that were made in a similar way.

Example 1

4-[4-(Pyridin-4-ylmethoxy)-[1,2,5]thiadiazol-3-yl]-piperazine-1-carboxylic acid (3,5-bis-trifluoromethyl-phenyl)-amide

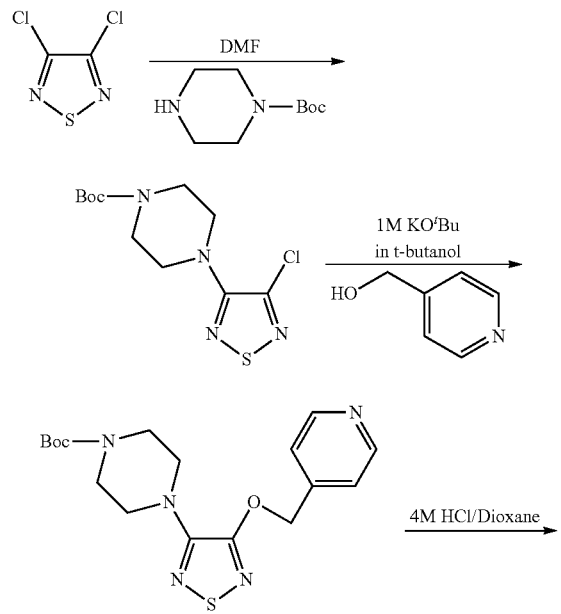

4-(4-Chloro-[1,2,5]thiadiazol-3-yl)-piperazine-1-carboxylic acid tert-butyl ester: 1-Boc-piperazine (30.2 g, 165 mmol) was dissolved in DMF (30.0 mL) and heated to 100° C. 3,4-Dichloro-1,2,5-thiadiazole (7.5 mL, 80 mmol) was added dropwise with stirring and the mixture heated at 100° C. for 5.5 h. The reaction mixture was diluted with H$_2$O and the pH adjusted to 2.0 with 1N HCl. The resulting solids were filtered, washed with H$_2$O and dried under vacuum to give 20.1 g (83%) of 4-(4-chloro-[1,2,5]thiadiazol-3-yl)-piperazine-1-carboxylic acid tert-butyl ester as a tan solid. $^1$H NMR (DMSO-d6) 3.48 (m, 4H), 3.36 (m, 4H), 1.42 (s, 9H) ppm. LC-MS (MH+)=205 (-Boc).

4-[4-(Pyridin-4-ylmethoxy)-[1,2,5]thiadiazol-3-yl]-piperazine-1-carboxylic acid tert-butyl ester. 4-(4-Chloro-[1,2,5]thiadiazol-3-yl)-piperazine-1-carboxylic acid tert-butyl ester (10.0 g, 33 mmol), pyridin-4-yl-methanol (6.9 g, 63 mmol) and a solution of 1M potassium tert-butyl butoxide in tert-butyl alcohol (60.0 mL, 60 mmol) were combined and stirred at room temperature overnight. The reaction mixture is diluted with EtOAc and washed with H$_2$O (3×), sat'd NaCl (1×), dried (Na$_2$SO$_4$), and concentrated in vacuo. The crude product is purified by column chromatography (4:1 hexanes:EtOAc, followed by 1:1 hexanes:EtOAc) to give 7.1 g (57%) of 4-[4-(pyridin-4-ylmethoxy)-[1,2,5]thiadiazol-3-yl]-piperazine-1-carboxylic acid tert-butyl ester. $^1$H NMR (CDCl$_3$) 8.65 (d, 2H), 7.32 (d, 2H), 5.49 (s, 2H), 3.55 (m, 8H) 1.48 (s, 9H) ppm. LC-MS (MH+)=378.

1-[4-(Pyridin-4-ylmethoxy)-[1,2,5]thiadiazol-3-yl]-piperazine, dihydrochloride salt. 4-[4-(pyridin-4-ylmethoxy)-[1,2,5]thiadiazol-3-yl]-piperazine-1-carboxylic acid tert-butyl ester (6.9 g, 18.3 mmol) was dissolved in 4M HCl in dioxane (200 mL) and stirred at room temperature for 2 h. The resulting suspension was diluted with EtOAc and the solids filtered, washed with EtOAc, and dried under high vacuum to give 6.15 g (96%) of 1-[4-(pyridin-4-ylmethoxy)-[1,2,5]thiadiazol-3-yl]-piperazine, dihydrochloride salt. $^1$H NMR (D$_2$O) 8.59 (d, 2H), 7.92 (d, 2H), 5.66 (s, 2H), 3.66 (m, 4H), 3.26 (m, 4H) ppm. LC-MS (MH+)=278.

4-[4-(Pyridin-4-ylmethoxy)-[1,2,5]thiadiazol-3-yl]-piperazine-1-carboxylic acid (3,5-bis-trifluoromethyl-phenyl)-amide. 1-[4-(pyridin-4-ylmethoxy)-[1,2,5]thiadiazol-3-yl]-piperazine, dihydrochloride salt (2.13 g, 6.1 mmol), dichloromethane (40 mL), and triethylamine (2.5 mL, 17.9 mmol) were combined and cooled in an icebath. 1-Isocyanato-3,5-bis-trifluoromethyl-benzene (1.89 g, 7.4 mmol) in dichloromethane (10 mL) was added dropwise and the resulting mixture stirred overnight at room temperature. The reaction mixture was diluted with EtOAc and washed with sat'd NaHCO$_3$ (3×), sat'd NaCl (1×), dried (Na$_2$SO$_4$), and concentrated in vacuo. The crude product was purified by column chromatography (1:1 hexanes:EtOAc, followed by 1:3 hexanes:EtOAc) to give 2.6 g (80%) of 4-[4-(pyridin-4-ylmethoxy)-[1,2,5]thiadiazol-3-yl]-piperazine-1-carboxylic acid (3,5-bis-trifluoromethyl-phenyl)-amide as a white solid after lyophilization from: H$_2$O—AcCN. $^1$H NMR (CDCl$_3$) 8.62 (d, 2H), 7.84 (s, 2H), 7.50 (s, 1H), 7.31 (d, 2H), 7.06 (s, 1H), 5.49 (s, 2H), 3.68-3.60 (m, 8H) ppm. LC-MS (MH+)=533.

Example 2

N-[3,5-bis(trifluoromethyl)phenyl]-4-{4-[(pyridin-4-ylmethyl)oxy]-1,2,5-thiadiazol-3-yl}-1,4-diazepane-1-carboxamide

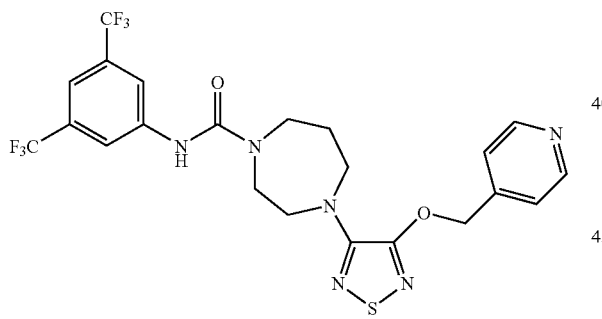

A mixture of t-butyl 1-homopiperazine carboxylate (45 mmol, 9 g) and DMF (50 ml) was heated to 100° C. 3,4-dichloro-1,2,5-thiadiazole (23 mmol, 2.2 ml) was added dropwise to the mixture with stirring. The resulting mixture was stirred at 100° C. for 2 days. Mixture was quenched with ice/water and extracted with ethyl acetate (3×). The combined organic layer was washed with water (2×) and Sat. sodium chloride, dried over sodium sulfate, filtered and concentrated. The crude was purified on a silica column using 20% ethyl acetate/hexanes to give 4-(4-chloro-[1,2,5]thiadiazol-3-yl)-[1,4]diazepane-1-carboxylic acid tert-butyl ester (5.8 g). The material thus obtained was converted into the title compound by following the same procedures as in Example 1. $^1$H NMR (CDCl3) 9.52 (s, 2H), 7.838 (s, 2H), 7.508 (s, 1H), 7.321-7.307 (d, 2H), 6.769 (br. s, 1H), 5.464 (s, 2H), 3.925-3.851 (m, 4H), 3.820-3.790 (t, 2H), 3.612-3.582 (t, 2H), 1.987-1.959 (m, 2H) ppm.

Example 3

2,6-Dimethyl-4-[4-(pyridin-4-ylmethoxy)-[1,2,5]thiadiazol-3-yl]-piperazine-1-carboxylic acid (3,5-bis-trifluoromethyl-phenyl)-amide

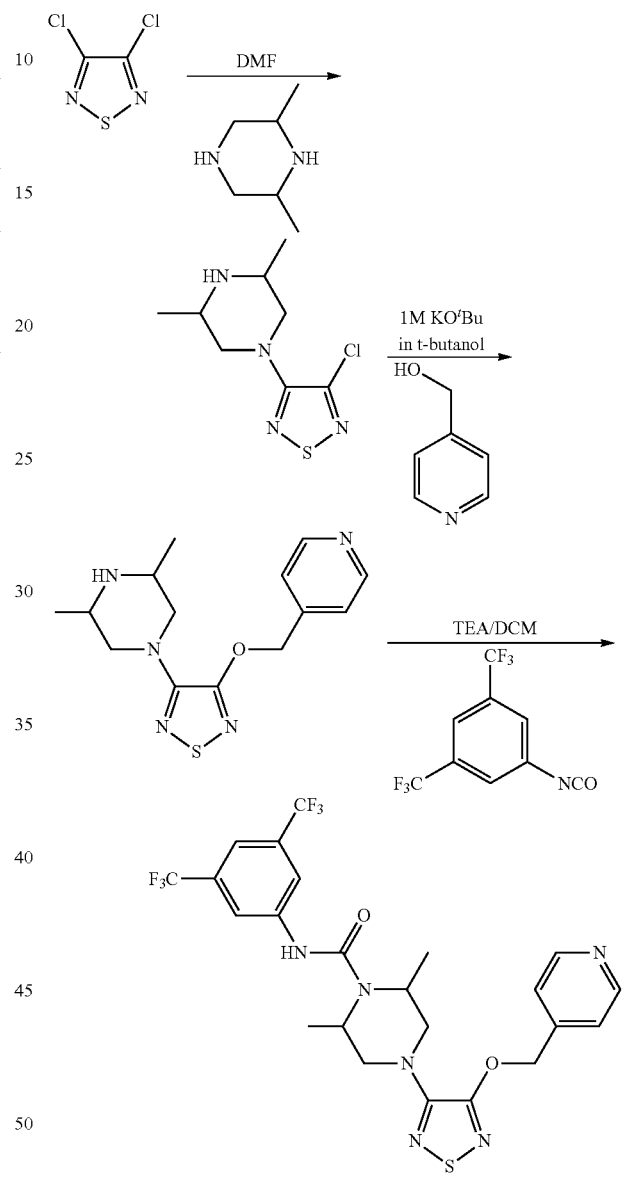

1-(4-Chloro-[1,2,5]thiadiazol-3-yl)-3,5-dimethyl-piperazine. 2,6-Dimethyl-piperazine (8.1 g, 71 mmol) was heated to 100° C. in DMF (8.0 ml). 3,4-Dichloro-1,2,5-thiadiazole (3.3 ml, 35 mmol) was added and the mixture stirred at 100° C. for 3-4 h. The reaction mixture was poured into H$_2$O and extracted with EtOAc (4×). The combined EtOAc extractions were washed with sat'd NaHCO$_3$ (1×), sat'd NaCl (1×), dried (Na$_2$SO$_4$), and concentrated in vacuo to give 7.9 g (97%) of 1-(4-chloro-[1,2,5]thiadiazol-3-yl)-3,5-dimethyl-piperazine which was used without further purification. $^1$H NMR (CDCl$_3$) 3.90-3.86 (m, 2H), 3.05 (m, 2H), 2.52 (m, 2H), 1.12 (d, 6H) ppm. LC-MS (MH+)=233.

3,5-Dimethyl-1-[4-(pyridin-4-ylmethoxy)-[1,2,5]thiadiazol-3-yl]-piperazine. 1-(4-Chloro-[1,2,5]thiadiazol-3-yl)-3, 5-dimethyl-piperazine (7.9 g, 34 mmol), pyridinyl-methanol (7.7 g, 70 mmol), potassium tert-butyl butoxide (11.4 g, 101 mmol) and tert-butyl alcohol (100 mL) were combined and stirred at room temperature overnight. The reaction mixture is diluted with $H_2O$ (3×) and extracted with EtOAc (3×). The combined EtOAc extractions are washed with sat'd $NaHCO_3$ (3×), sat'd NaCl (1×), dried ($Na_2SO_4$), and concentrated in vacuo. The crude product is purified by column chromatography (1:1 hexanes:EtOAc, followed by 49:1 EtOAc:triethylamine, followed by 18:1:1 EtOAc:MeOH:triethylamine) to give 4.15 g (40%) of 3,5-dimethyl-1-[4-(pyridin-4-yl-methoxy)-[1,2,5]thiadiazol-3-yl]-piperazine. $^1$H NMR ($CDCl_3$) 8.62 (d, 2H), 7.30 (d, 2H), 5.48 (s, 2H), 4.07 (m, 2H), 3.03 (m, 2H), 2.51 (m, 2H), 1.12 (d, 6H) ppm. LC-MS (MH+)=306.

2,6-Dimethyl-4-[4-(pyridin-4-ylmethoxy)-[1,2,5]thiadiazol-3-yl]-piperazine-1-carboxylic acid (3,5-bis-trifluoromethyl-phenyl)-amide. 3,5-dimethyl-1-[4-(pyridin-4-yl-methoxy)-[1,2,5]thiadiazol-3-yl]-piperazine (104 mg, 0.34 mmol), dichloromethane (1.0 mL), triethylamine (0.10 mL, 0.43 mmol), and 1-isocyanato-3,5-bis-trifluoromethyl-benzene (0.075 ml, 0.43 mmol) are combined and stirred at room temperature overnight. The reaction mixture was diluted with EtOAc and washed with $H_2O$ (1×), sat'd $NaHCO_3$ (2×), sat'd NaCl (1×), dried ($Na_2SO_4$), and concentrated in vacuo. The crude product was purified by column chromatography (1:1 hexanes:EtOAc, followed by 1:3 hexanes:EtOAc) to give 63 mg (33%) of 2,6-dimethyl-4-[(pyridin-4-ylmethoxy)-[1,2,5]thiadiazol-3-yl]-piperazine-1-carboxylic acid (3,5-bis-trifluoromethyl-phenyl)-amide as a white solid after lyophilization from $H_2O$—AcCN. $^1$H NMR ($CDCl_3$) 8.67 (d, 2H), 7.91 (s, 2H), 7.53 (s, 1H), 7.36 (d, 2H), 6.74 (s, 1H), 5.51 (s, 2H), 4.31 (m, 2H), 4.10 (d, 2H), 3.11 (dd, 2H), 1.47 (d, 6H) ppm. LC-MS (MH+)=561.

The following compound compounds were prepared using a procedure as in Example 3:

N-[3,5-bis(trifluoromethyl)phenyl]-2-methyl-4-{4-[(pyridin-4-ylmethyl)oxy]-1,2,5-thiadiazol-3-yl}piperazine-1-carboxamide was prepared by employing 3,4-dichloro-1,2,5-thiadiazole and 2-methyl-piperazine. $^1$H NMR (CDCl3) 8.80 (br., d, 2H), 7.93 (s, 2H), 7.66 (d, 2H), 7.53 (s, 1H), 6.90 (s, 1H), 5.64 (d, 2H), 4.43 (br., m, 1H), 4.17 (d, 1H), 4.07 (d, 1H), 3.98 (d, 1H), 3.46 (td, 1H), 3.20 (dd, 1H), 3.11 (td, 1H) 1.39 (d, 3H) ppm.

4-[4-(1-azabicyclo[2.2.2]oct-3-yloxy)-1,2,5-thiadiazol-3-yl]-N-[3,5-bis(trifluoro-methyl)phenyl]piperazine-1-carboxamide was prepared by employing 3,4-dichloro-1,2,5-thiadiazole and 1-aza-bicyclo[2.2.2]octan-3-ol. $^1$H NMR (DMSO-d6) 9.81 (s, 1H), 9.31 (s, 1H), 8.21 (s, 2H), 7.60 (s, 1H), 5.20 (m, 1H), 3.80-3.21 (m, 15H), 2.00-1.75 (m, 4H) ppm.

4-[({4-[4-({[3,5-bis(trifluoromethyl)phenyl]amino}carbonyl)-piperazin-1-yl]-1,2,5-thiadiazol-3-yl}oxy)methyl]benzoic acid was prepared by employing 3,4-dichloro-1,2,5-thiadiazole and 4-hydroxymethyl-benzoic acid. $^1$H NMR (DMSO-d6) 9.24 (s, 1H), 8.19 (s, 2H), 7.96 (d, 2H), 7.59 (s, 2H), 7.57 (s, 1H), 5.54 (s, 2H), 3.62-3.52 (m, 8H) ppm.

N-[3,5-bis(trifluoromethyl)phenyl]-4-{4-[(piperidin-3-yl-methyl)oxy]-1,2,5-thiadiazol-3-yl}piperazine-1-carboxamide was prepared by employing 3,4-dichloro-1,2,5-thiadiazole and piperidin-3-yl-methanol. $^1$H NMR (DMSO-d6) 9.30 (s, 1H), 8.20 (s, 2H), 7.60 (s, 1H), 4.32 (m, 2H), 3.63-3.51 (m, 8H), 1.99 (m, 7H), 1.82 (m, 2H) ppm.

N-[3,5-bis(trifluoromethyl)phenyl]-4-{4-[(2-pyrrolidin-1-ylethyl)oxy]-1,2,5-thiadiazol-3-yl}piperazine-1-carboxamide was prepared by employing 3,4-dichloro-1,2,5-thiadiazole and 2-pyrrolidin-1-yl-ethanol. $^1$H NMR (DMSO-d6) 9.90 (br., s, 1H), 9.33 (s, 1H), 8.20 (s, 2H), 7.60 (s, 1H), 4.70 (t, 2H), 3.70-3.34 (br., m, 12H), 3.13 (br., m, 2H), 2.07-1.87 (br., m, 4H) ppm.

4-{4-[(2-amino-2-methylpropyl)oxy]-1,2,5-thiadiazol-3-yl}-N-[3,5-bis(trifluoro-methyl)phenyl]piperazine-1-carboxamide was prepared by employing 3,4-dichloro-1,2,5-thiadiazole and 2-amino-2-methyl-propan-1-ol. $^1$H NMR (DMSO-d6) 9.29 (s, 1H), 8.21 (d, 2H), 8.10 (br., s, 211, 7.60 (s, 1H), 4.42 (s, 2H), 3.65-3.53 (m, 8H), 1.37 (s, 6H) ppm.

Example 4

N-[3,5-bis(trifluoromethyl)phenyl]-2,6-dimethyl-4-{3-[(pyridin-4-ylmethyl)oxy]pyrazin-2-yl}piperazine-1-carboxamide

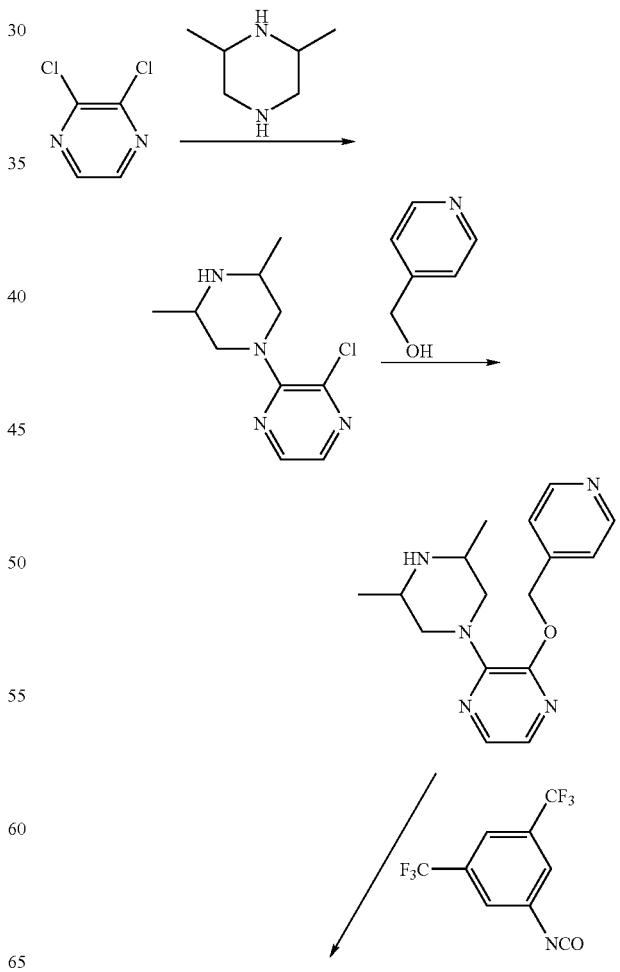

-continued

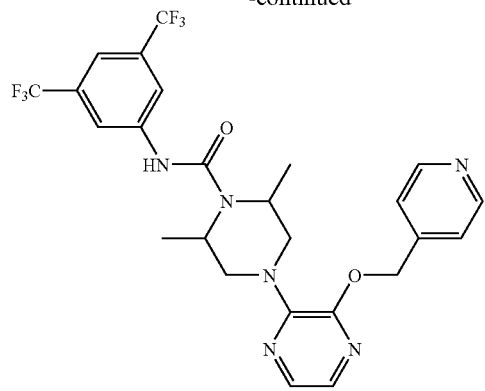

To a round bottom flask equipped with a magnetic stir bar was added 3,4-Dichloro-pyrazine (5 g, 33.8 mmol, 1.0 eq.), dry DMF (35 mL) 2,6-Dimethyl-piperazine (7.86 g, 68.9 mmol, 2 eq). The reaction mixture was heated to 100° C. and allowed to stir for 2 hours. After allowing the reaction to return to room temperature water (200 mL) was added and the product extracted with EtOAc (2×150 mL). The organic layer was washed 2× water, 5×LiCl, 1× brine and dried over $NaSO_4$. After removing the solvent in vacuo 3'-Chloro-3,5-dimethyl-3,4,5,6-tetrahydro-2H-[1,2']bipyrazinyl was obtained as a yellow oil (4.8 g, 63%). This intermediate was then converted to the title compound by following the similar procedures as in Examples 3b and 3c. $^1$H NMR (CDCl3) 8.87 (d, 2H), 7.92 (s, 2H), 7.83 (m, 4H), 7.51 (d, 2H), 5.69 (s, 2H), 4.37 (m, 2H), 4.17 (d, 2H), 3.15 (m, 2H), 1.48 (d, 5H) ppm.

The following compounds are prepared by using the procedure as in Example 4:

(2S)—N-[3,5-bis(trifluoromethyl)phenyl]-2-methyl-4-{3-[(pyridin-4-ylmethyl)oxy]pyrazin-2-yl}piperazine-1-carboxamide was prepared from 3,4-dichloro-pyrazine and 2-methyl-piperazine. $^1$H NMR (CDCl3) 8.62 (d, 2H), 7.88 (s, 2H), 7.77 (d, 1H), 7.57 (d, 1H), 7.51 (s, 1H), 7.33 (d, 2H), 6.64 (s, 1H), 5.44 (s, 2H), 4.32 (m, 1H), 4.21 (m, 2H), 3.95 (d, 1H), 3.46 (m, 1H), 3.15 (dd, 1H), 3.03 (m, 1H), 1.32 (m, 3H) ppm.

N-[3,5-bis(trifluoromethyl)phenyl]-2,5-dimethyl-4-(3-[(pyridin-4-ylmethyl)oxy]pyrazin-2-yl)piperazine-1-carboxamide was prepared from 3,4-dichloro-pyrazine and 2,5-Dimethyl-piperazine. $^1$H NMR (CDCl$_3$) 8.79 (d, 2H), 7.94-7.80 (s, 2H), 7.80 (d, 1H), 7.76 (s, 2H), 7.49-7.46 (m, 2H), 7.08 (s, 1H), 5.64 (s, 2H), 4.68 (m, 2H), 3.92 (d, 1H), 3.80 (d, 1H), 3.63-3.57 (m, 2H), 1.34 (d, 3H), 1.26 (d, 3H) ppm.

N-[3,5-bis(trifluoromethyl)phenyl]-2-methyl-4-{3-[(pyridin-4-ylmethyl)oxy]quinoxalin-2-yl}piperazine-1-carboxamide was prepared from 2,3-dichloro-quinoxaline and 2-methyl-piperazine. $^1$H NMR (CDCl3) 8.63 (d, 2H), 7.91 (s, 2H), 7.88 (m, 2H), 7.65 (m, 4H), 6.85 (s, 1H), 5.63 (s, 2H), 4.40 (m, 3H), 4.01 (d, 1H), 3.48 (m, 1H), 3.31 (dd, 1H), 3.08 (m, 1H), 1.38 (d, 3H) ppm.

Example 5

N-[3,5-Bis(trifluoromethyl)phenyl]-4-{3-[(pyridin-4-ylmethyl)-oxy]pyrazin-2-yl}piperazine-1-carboxamide

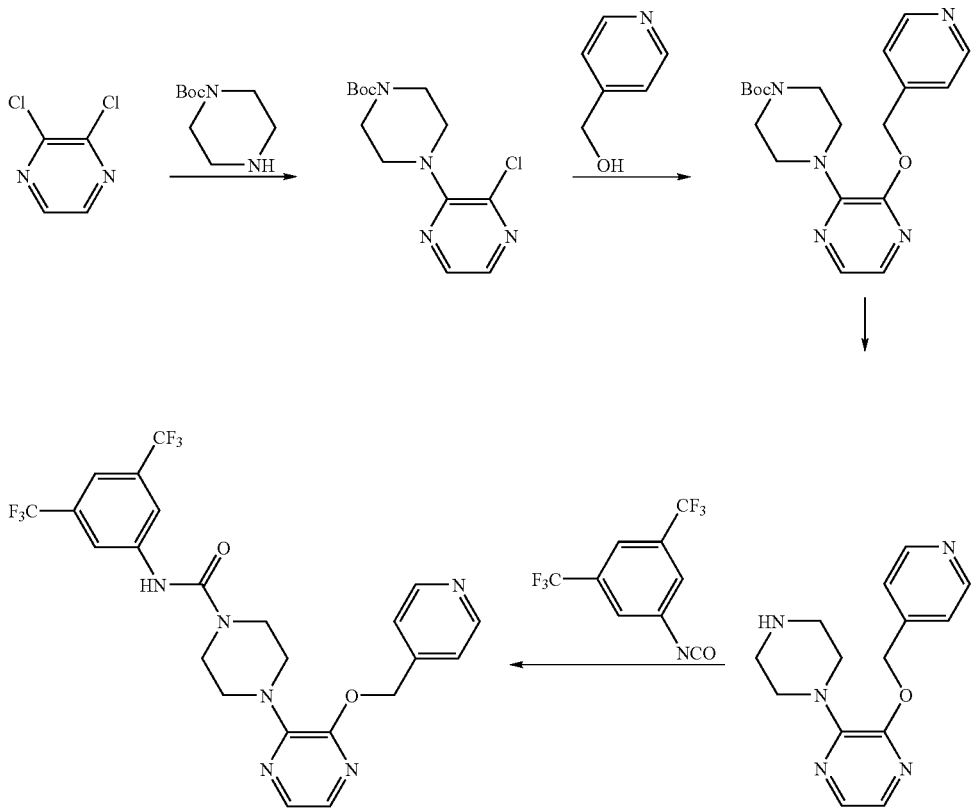

3'-Chloro-2,3,5,6-tetrahydro-[1,2']bipyrazinyl-4-carboxylic acid tert-butyl ester. To a round bottom flask equipped with a magnetic stir bar was added 3,4-Dichloro-pyrazine (3 g, 20.1 mmol, 1.0 eq.), dry DMF (20 mL) and piperazine-1-carboxylic acid tert-butyl ester (7.3 g, 40 mmol, 2 eq). The reaction mixture was heated to 90° C. and allowed to stir for 4 hours. After allowing the reaction to return to room temperature water (100 mL) was added and the product extracted with DCM (2×200 mL). The organic layer was washed 1 N HCl (2×) and brine (2×) and dried over $NaSO_4$. After removing the solvent the product was isolated as an orange oil (6 g, 80%).

3'-(Pyridin-4-ylmethoxy)-2,3,5,6-tetrahydro-[1,2']bipyrazinyl-4-carboxylic acid tert-butyl ester. To a round bottom flask equipped with a magnetic stir bar was added 3'-chloro-2,3,5,6-tetrahydro-[1,2']bipyrazinyl-4-carboxylic acid tert-butyl ester (7.89 g, 26.4 mmol, 1.0 eq.), pyridin-4-yl-methanol (3.74 g, 34.3 mmol, 1.3 eq) and 1M potassium tert-butyl butoxide in t-butanol (72 ml, 72 mmol, 2.7 eq). The reaction was then stirred overnight at room temperature after which the solvent was removed. The solid was then diluted with EtOAc, washed 3× with water, 2×$NaHCO_3$, 2× with brine, and dried over $NaSO_4$. Purification was then accomplished on column chromatography with the eluent being 1:2 ethyl acetate/hexane and 2% TEA. Removal of the solvent resulted in the title compound as a cream solid (6.98 g, 33% yield).

3'-(Pyridin-4-ylmethoxy)-3,4,5,6-tetrahydro-2H-[1,2']bipyrazinyl. To a round bottom flask equipped with a magnetic stir bar was added 4-(4-Chloro-[1,2,5]thiadiazol-3-yl)-piperazine-1-carboxylic acid tert-butyl ester (6.98 g, 18.8 mmol, 1.0 eq) and 4M HCl/Dioxane. The reaction was then allowed to stir for 1 hour at room temperature. The resulting precipitate was filtered, washed with hexane, and dried in vacuo to give the title compound as a white solid (5.12 g, 89% yield).

N-[3,5-bis(trifluoromethyl)phenyl]-4-{3-[(pyridin-4-ylmethyl)oxy]pyrazin-2-yl}piperazine-1-carboxamide. To a round bottom flask equipped with a magnetic stir bar was added 3'-(pyridin-4-ylmethoxy)-3,4,5,6-tetrahydro-2H-[1,2']bipyrazinyl (0.3 g, 0.97 mmol, 1.0 eq.), dry $CH_2Cl_2$ (3 mL), triethyl amine (TEA) (0.54 g, 0.4 mL, 5.1 mmol, 5 eq) and was then cooled in an ice bath. 1-Isocyanato-3,5-bis-trifluoromethyl-benzene (0.29 g, 0.2 ml, 1.2 mmol, 1.2 eq.) was then added drop wise to the reaction mixture. Total reaction time was 3 hours at which point the reaction was diluted with 3× the volume EtOAc. This solution was then washed 3× with $NaHCO_3$ and 2× with brine. The organic layer was dried with $Na_2SO_4$, concentrated, and the solid was columned with a Biotage system using a gradient. The initial eluent was 1:1 ethyl acetate/hexane followed by an eluent 3:1 ethyl acetate/hexane. The solvent was then removed and dried under high vacuum to yield the title compound (0.16 g, 32% yield) as a solid. $^1$H NMR (CDCl3) 8.63 (d, 2H), 7.90 (s, 2H), 7.81 (d, 1H), 7.62 (d, 1H), 7.54 (s, 1H), 7.34 (d, 2H), 7.26 (s, 2H), 6.78 (s, 1H), 5.48 (s, 2H), 3.67 (m, 8H) ppm.

N-[3,5-bis(trifluoromethyl)phenyl]-4-{3-[(pyridin-4-ylmethyl)oxy]pyrazin-2-yl}-1,4-diazepane-1-carboxamide was prepared as in example 5 starting from t-butyl 1-homopiperazine carboxylate (25 mmol, 5 g) and 2,3-dichloropyrazine. $^1$H NMR (CDCl3) 8.616-8.603 (d, 2H), 7.821 (s, 2H), 7.692-7.684 (d, 1H), 7.482 (s, 1H), 7.427-7.420 (d, 1H), 7.326-7.312 (d, 2H), 6.962 (s, 1H), 5.416 (s, 2H), 3.969-3.912 (m, 4H), 3.798-3.784 (t, 2H), 3.584-3.555 (t, 2H), 1.951-1.924 (t, 2H) ppm.

Example 6

2-Methyl-3'-(pyridin-4-ylmethoxy)-2,3,5,6-tetrahydro-[1,2']bipyrazinyl-4-carboxylic acid (3,5-bis-trifluoromethyl-phenyl)-amide

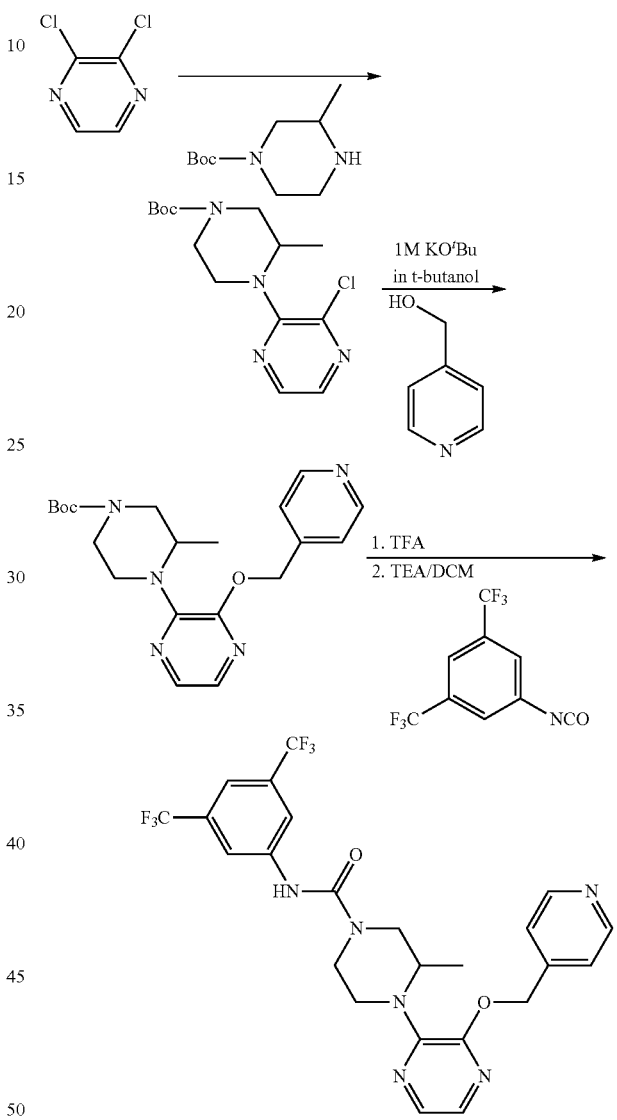

3'-Chloro-2-methyl-2,3,5,6-tetrahydro-[1,2']bipyrazinyl-4-carboxylic acid tert-butyl ester. 3-Methyl-piperazine-1-carboxylic acid tert-butyl ester (5.0 g, 25 mmol), 2,3-dichloropyrazine (1.3 mL, 12.5 mmol), and DMF (5.0 mL) were combined and heated to 100 C overnight with stirring. The reaction mixture was poured into $H_2O$ and extracted with EtOAc (3×). The combined EtOAc extractions were washed with sat'd $NaHCO_3$ (2×), sat's NaCl (1×), dried ($Na_2SO_4$), and concentrated in vacuo. The crude product was purified by column chromatography (4:1 hexanes:EtOAc) to give 1.76 g (45%) of 3'-chloro-2-methyl-2,3,5,6-tetrahydro-[1,2']bipyrazinyl-4-carboxylic acid tert-butyl ester. $^1$H NMR (CDCl$_3$) 8.08 (d, 1H), 7.86 (d, 1H), 4.22-3.76 (complex m, 3H), 3.48-3.17 (complex m, 4H), 1.48 (s, 9H), 1.19 (d, 3H) ppm. LC-MS (MH+)=257 (-t-butyl).

2-Methyl-3'-(pyridin-4-ylmethoxy)-2,3,5,6-tetrahydro-[1,2']bipyrazinyl-4-carboxylic acid tert-butyl ester. 3'-Chloro-2-methyl-2,3,5,6-tetrahydro-[1,2']bipyrazinyl-4-carboxylic acid tert-butyl ester (1.88 g, 6.0 mmol), pyridin-4-yl-methanol (1.35 g, 12.4 mmol) and a solution of 1M potassium tert-butyl butoxide in tert-butyl alcohol (14 mL, 14 mmol) were combined and stirred at room temperature overnight. The reaction mixture is diluted with H$_2$O and washed with EtOAc (3x). The combined EtOAc extractions were washed with 6% NaHCO$_3$ (2x), sat's NaCl (1x), dried (Na$_2$SO$_4$), and concentrated in vacuo. The crude product was purified by column chromatography (4:1 hexanes:EtOAc, followed by 1:1 hexanes:EtOAc) to give 1.89 g (81%) of 2-methyl-3'-(pyridin-4-ylmethoxy)-2,3,5,6-tetrahydro-[1,2']bipyrazinyl-4-carboxylic acid tert-butyl ester. $^1$H NMR (CDCl$_3$) 8.06 (d, 2H), 7.75 (d, 1H), 7.51 (d, 1H), 7.30 (d, 2H), 5.42 (s, 2H), 4.52 (m, 1H), 4.11-3.81 (complex m, 3H), 3.36-3.11 (complex m, 3H), 1.48 (s, 9H), 1.17 (d, 3H) ppm. LC-MS (MH+)=386.

2-Methyl-3'-(pyridin-4-ylmethoxy)-2,3,5,6-tetrahydro-[1,2']bipyrazinyl-4-carboxylic acid (3,5-bis-trifluoromethyl-phenyl)-amide. 2-Methyl-3'-(pyridin-4-ylmethoxy)-2,3,5,6-tetrahydro-[1,2']bipyrazinyl-4-carboxylic acid tert-butyl ester (103 mgs, 0.27 mmol) was dissolved in dichloromethane (1.5 mL) to which was added TFA (2.0 mL) and the mixture stirred at room temperature for 1 hr until Boc removal was complete. The reaction mixture was concentrated in vacuo and redissolved in dichloromethane (1.0 mL) to which was added triethylamine (0.2 mL, 1.43 mmol) and 1-isocyanato-3,5-bis-trifluoromethyl-benzene (0.055 ml, 0.32 mmol). The mixture was stirred at room temperature overnight. The reaction mixture was concentrated in vacuo and the resulting residue purified by column chromatography (1:1 hexanes:EtOAc, followed by 1:3 hexanes:EtOAc) to give 98.9 mgs (69%) of 2-methyl-3'-(pyridin-4-ylmethoxy)-2,3,5,6-tetrahydro-[1,2']bipyrazinyl-4-carboxylic acid (3,5-bis-trifluoromethyl-phenyl)-amide as a white solid after lyophilization from H$_2$O—AcCN. $^1$H NMR (CDCl$_3$) 8.77 (d, 2H), 7.94 (s, 2H), 7.82 (d, 1H), 7.71 (d, 2H), 7.52 (d, 1H), 7.49 (s, 1H), 7.23 (s, 1H), 5.62 (s, 2H), 4.60 (m, 1H), 4.01 (m, 1H), 3.97-3.86 (m, 2H), 3.52-3.45 (m, 2H), 3.34 (m, 1H), 1.26 (d, 3H) ppm. LC-MS (MH+)=541.

Example 7

1-[4-(Pyridin-4-ylmethoxy)-[1,2,5]thiadiazol-3-yl]-piperidine-4-carboxylic acid (3-trifluoromethyl-phenyl)-amide

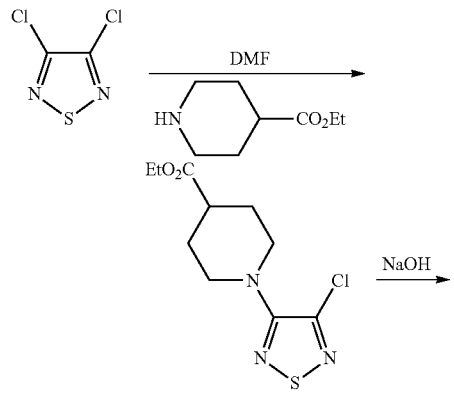

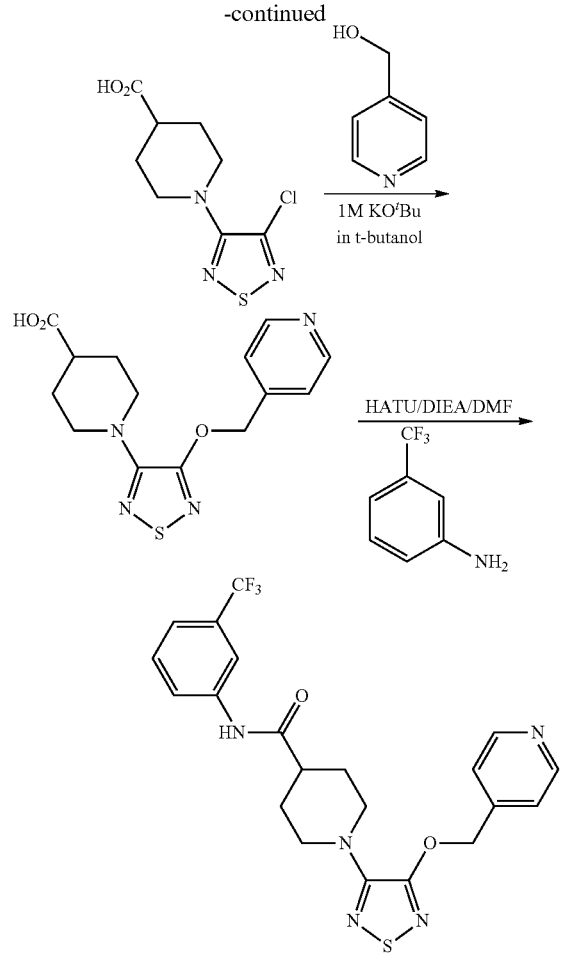

1-(4-Chloro-[1,2,5]thiadiazol-3-yl)-piperidine-4-carboxylic acid ethyl ester. Piperidine-4-carboxylic acid ethyl ester (14.0 mL, 91 mmol) was dissolved in DMF (15.0 mL) and heated to 100 C. 3,4-Dichloro-1,2,5-thiadiazole (4.0 mL, 42 mmol) was added and the mixture heated at 100 C. for 4 h. The reaction mixture was poured into 1N HCl and extracted with EtOAc (4x). The combined EtOAc extractions were washed with H$_2$O (1x), sat'd NaCl (1x), dried (Na$_2$SO$_4$), and concentrated in vacuo to give 12.3 g (105%) of 1-(4-chloro-[1,2,5]thiadiazol-3-yl)-piperidine-4-carboxylic acid ethyl ester which was used without further purification. $^1$H NMR (CDCl$_3$) 4.30-4.13 (m, 2H), 4.06-3.93 (m, 2H), 3.12-2.99 (m, 2H), 2.59 (m, 1H), 2.03 (m, 4H), 1.42-1.26 (m, (3H) ppm. LC-MS (MH+)=276.

1-(4-Chloro-[1,2,5]thiadiazol-3-yl)-piperidine-4-carboxylic acid. 1-(4-Chloro-[1,2,5]thiadiazol-3-yl)-piperidine-4-carboxylic acid ethyl ester (12.3 g, 45 mmol) was dissolved in EtOH (70 mL) to which was added 5N NaOH (15 mL). The mixture was stirred at room temperature for 2 h, then concentrated in vacuo. The resulting aqueous solution was further diluted with H$_2$O, washed with EtOAc (3x) and acidified to pH 2.0 with conc'd HCl. The resulting precipitate was filtered, washed with H$_2$O and dried under high vacuum to give 8.44 g (77%) of 1-(4-chloro-[1,2,5]thiadiazol-3-yl)-piperidine-4-carboxylic acid. $^1$H NMR (CDCl$_3$) 3.97-3.92 (m, 2H), 3.03 (m, 2H), 2.59 (m, 1H), 2.06 (m, 2H), 1.93 (m, 2H) ppm. LC-MS (M–)=246.

1-[4-(Pyridin-4-ylmethoxy)-[1,2,5]thiadiazol-3-yl]-piperidine-4-carboxylic acid. 1-(4-Chloro-[1,2,5]thiadiazol-3- yl)-piperidine-4-carboxylic acid (7.99 g, 32 mmol), pyridin-4-yl-methanol (7.39 g, 68 mmol) and a solution of 1M potassium tert-butyl butoxide in tert-butyl alcohol (100 mL, 100 mmol) were combined and stirred at room temperature overnight. The reaction mixture is diluted with H₂O (500 mL) and washed with EtOAc (3×). The aqueous phase is concentrated to ~250 mL and acidified to pH 5-6 with conc'd HCl. The resulting solids are filtered, washed with H₂O and dried under high vacuum to give 6.04 g (59%) of 1-[4-(pyridin-4-ylmethoxy)-[1,2,5]thiadiazol-3-yl]-piperidine-4-carboxylic acid. $^1$H NMR (DMSO-d6) 8.57 (d, 2H), 7.41 (d, 2H), 5.51 (s, 2H), 4.03 (m, 2H), 3.00 (m, 2H), 2.46 (m, 1H), 1.91 (m, 2H), 1.63 (m, 2H) ppm. LC-MS (M−)=319.

1-[4-(Pyridin-4-ylmethoxy)-[1,2,5]thiadiazol-3-yl]-piperidine-4-carboxylic acid (3-trifluoromethyl-phenyl)-amide. 1-[4-(Pyridin-4-ylmethoxy)-[1,2,5]thiadiazol-3-yl]-piperidine-4-carboxylic acid (280 mg, 0.87 mmol), HATU (328 mg, 0.86 mmol), DMF (1.5 mL) and DIEA (0.5 mL, 3.87 mmol) were combined and vortexed until a homogeneous mixture was obtained. 3-Trifluoromethyl-phenylamine (0.109 mL, 0.87 mmol) was added and the resulting mixture stirred at room temperature overnight. The reaction mixture was diluted with EtOAc and washed with sat'd NaHCO₃ (3×), sat'd NaCl (1×), dried (Na₂SO₄), and concentrated in vacuo. The crude product was purified by column chromatography (4:1 hexanes:EtOAc, followed by 1:1 hexanes:EtOAc) to give 100 mg (25%) of 1-[4-(Pyridin-4-ylmethoxy)-[1,2,5]thiadiazol-3-yl]-piperidine-4-carboxylic acid (3-trifluoromethyl-phenyl)-amide as a white solid after lyophilization from H₂O—AcCN. $^1$H NMR (CD₃OD) 8.54 (d, 2H), 8.02 (s, 1H), 7.74 (d, 1H), 7.51-7.46 (m, 3H), 7.36 (d, 1H), 5.57 (s, 2H), 4.32 (m, 2H), 3.00 (m, 2H), 2.64 (m, 1H), 1.96-1.90 (m, 4H) ppm. LC-MS (MH+)=464.

Example 8

1-(3,5-Bis-trifluoromethyl-phenyl)-3-{1-[4-(pyridin-4-ylmethoxy)-[1,2,5]thiadiazol-3-yl]-piperidin-4-ylmethyl}-urea

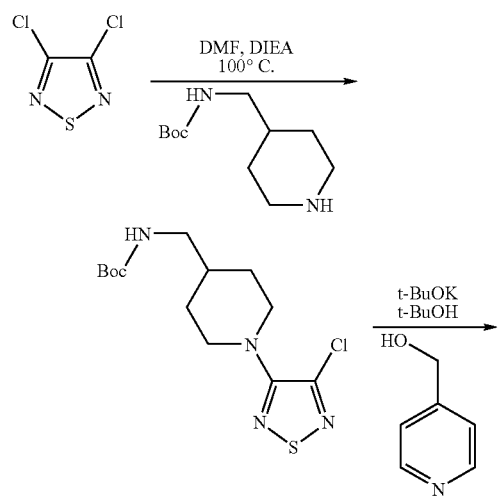

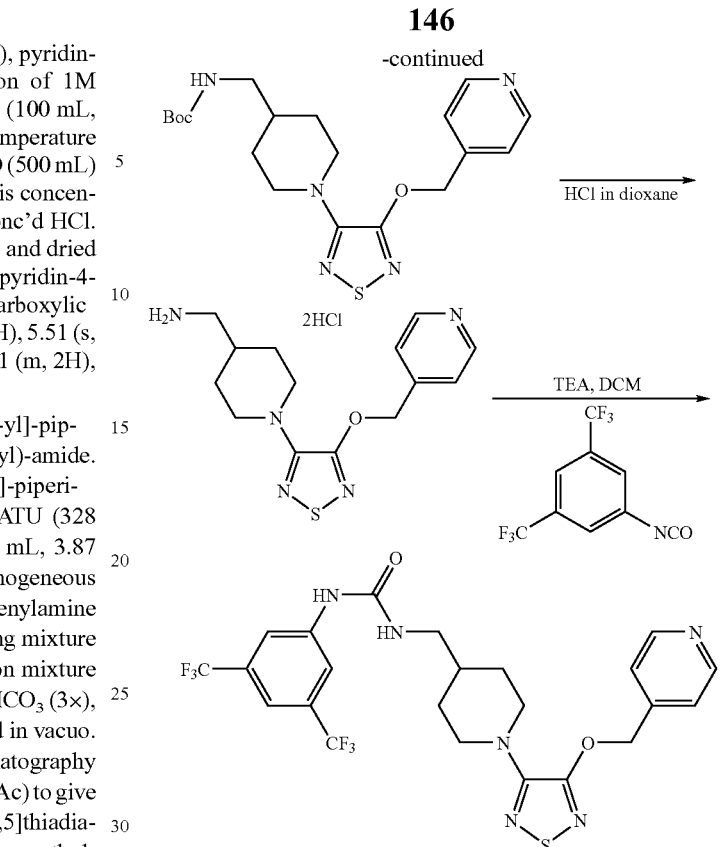

[1-(4-Chloro-[1,2,5]thiadiazol-3-yl)-piperidin-4-ylmethyl]-carbamic acid tert-butyl ester. 4-(tert-Butoxycarbonylaminomethyl)piperidine (3.96 g, 18.4 mmol) was dissolved in DMF (3.5 ml) and heated to 100° C. 3,4-Dichloro-1,2,5-thiadiazole (0.85 mL, 9.0 mmol) was added and the mixture stirred at 100° C. overnight. DIEA (2.0 ml, 11.5 mmol) was added and heating at 100° C. continued until the reaction was complete (~3 h). The reaction mixture was diluted with 1N HCl and extracted with EtOAc (3×). The combined EtOAc extractions were washed with H2O (1×), sat'd NaCl (1×), dried (MgSO4), and concentrated in vacuo to give 2.39 g (80%) of [1-(4-chloro-[1,2,5]thiadiazol-3-yl)-piperidin-4-ylmethyl]-carbamic acid tert-butyl ester as a tan solid. $^1$H NMR (DMSO-d6) 6.91 (t, 1H), 3.87 (m, 2H), 2.84 (m, 4H), 1.69 (m, 2H), 1.56 (m, 1H), 1.36 (s, 9H), 1.24 (m, 2H) ppm. LC-MS (MH+)=333.

{1-[4-(Pyridin-4-ylmethoxy)-[1,2,5]thiadiazol-3-yl]-piperidin-4-ylmethyl}-carbamic acid tert-butyl ester. A mixture of the product from step 1 (0.47 mmol, 155 mg), 1M potassium t-butoxide in t-butanol (1.5 ml), and 4-pyridyl carbinol (1.33 mmol, 0.145 g) was stirred at room temperature overnight. The mixture was quenched with ice/water and extracted with ethyl acetate (2×). The combined organic layer was washed with water (3×) and Sat. NaCl, dried over sodium sulfate and concentrated. The crude product was purified on silica column using 75% ethyl acetate/hexanes, affording 70 mg of product.

C-{1-[4-(Pyridin-4-ylmethoxy)-[1,2,5]thiadiazol-3-yl]-piperidin-4-yl}-methylamine dihydrochloride. The product (70 mg) obtained in step 2 was dissolved in 4M HCl in 1,4-dioxane (30 ml), and stirred for 2 hours. The mixture was concentrated. The residue was diluted with EtOAc and the solids filtered, washed with EtOAc, and dried under high vacuum to give 50 mg of the amine product as the HCl salt.

N-[3,5-bis(trifluoromethyl)phenyl]-N'-[(1-{4-[(pyridin-4-ylmethyl)oxy]-1,2,5-thiadiazol-3-yl}piperidin-4-yl)methyl]urea. A mixture of the product in step 3 (0.12 mmol, 50 mg), DCM (10 ml), TEA (0.42 mmol, 59 ul), and 3,5-bis(trifluoromethyl)-phenyl isocyanate (0.13 mmol, 23 ul) was stirred at room temperature overnight. After removal of solvent, the residue was diluted with EtOAc, stirred and filtered. The filtrate was concentrated and then purified on silica column using 75% ethyl acetate/hexanes to yield 22 mg of the title compound. $^1$H NMR (DMSO-d6) 9.207 (s, 1H), 8.607-8.593 (d, 2H), 8.083, (s, 2H), 7.55 (s, 1H), 7.438-7.423 (d, 2H), 6.621-6.592 (t, 1H), 5.520 (s, 2H), 4.163-4.131 (d, 2H), 3.302-3.031 (t, 2H), 2.909-2.850 (t, 2H), 1.743-1.713 (m, 3H), 1.274-1.243 (m, 2H) ppm.

Example 9

N-[3,5-bis(trifluoromethyl)phenyl]-4-{4-[(pyridin-4-ylmethyl)oxy]-1,2,5-thiadiazol-3-yl}-1,4-diazepane-1-carboxamide

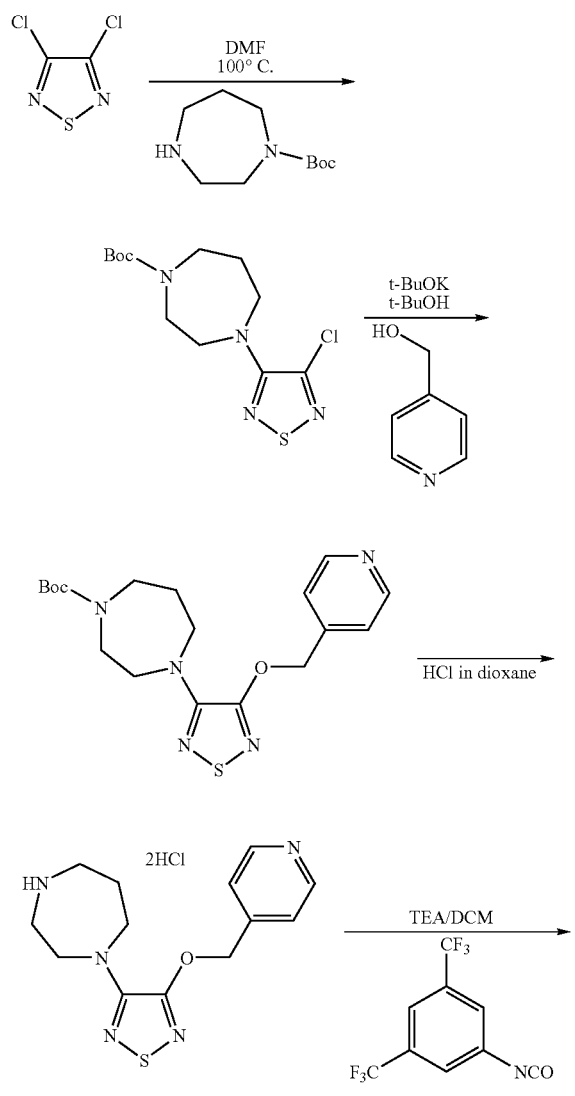

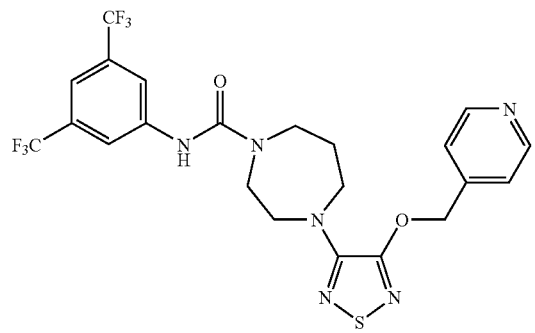

4-(4-Chloro-[1,2,5]thiadiazol-3-yl)-[1,4]diazepane-1-carboxylic acid tert-butyl ester. A mixture of t-butyl 1-homopiperazine carboxylate (45 mmol, 9 g) and DMF (50 ml) was heated to 100° C. 3,4-dichloro-1,2,5-thiadiazole (23 mmol, 2.2 ml) was added to the mixture and stirred at 100° C. for 2 days. The mixture was quenched with ice/water and extracted with ethyl acetate (3×). The combined organic layer was washed with water (2×) and brine, dried over sodium sulfate, filtered and concentrated. The crude was purified on silica column using 20% ethyl acetate/hexanes to give 5.8 g of product.

4-[4-(Pyridin-4-ylmethoxy)-[1,2,5]thiadiazol-3-yl]-[1,4]diazepane-1-carboxylic acid tert-butyl ester. The product obtained in the paragraph above was mixed with 1M potassium t-butoxide in t-butanol (40 ml) and 4-pyridylcarbinol (36.6 mmol, 4 g), and stirred at room temperature overnight. The mixture was quenched with ice/water and extracted with ethyl acetate (2×). The combined organic layer was washed with water (3×) and Sat. NaCl, dried over sodium sulfate and concentrated. The crude product was column purified on silica using 75% ethyl acetate/hexanes to give 3.68 g of the title compound.

1-[4-(Pyridin-4-ylmethoxy)-[1,2,5]thiadiazol-3-yl]-[1,4]diazepane dihydrochloride. The product (3.68 g) obtained as described in the paragraph above was dissolved in 4M HCl in 1,4-dioxane (100 ml), and stirred for 4 hours. The mixture was concentrated. The residue was diluted with EtOAc and the solids filtered, washed with EtOAc, and dried under high vacuum to give 3.3 g of the amine product as the HCl salt.

N-[3,5-bis(trifluoromethyl)phenyl]-4-{4-[(pyridin-4-ylmethyl)oxy]-1,2,5-thiadiazol-3-yl}-1,4-diazepane-1-carboxamide. A mixture of the product obtained as described in the paragraph above (0.41 mmol, 0.15 g), DCM (10 ml), TEA (1 mmol, 140 ul), and 3,5-bis(trifluoromethyl)-phenyl isocyanate (0.5 mmol, 86 ul) was stirred at room temperature overnight. After removal of solvent, the residue was diluted with EtOAc, stirred and filtered. The filtrate was concentrated and then purified on silica column using 75% ethyl acetate/hexanes to yield 150 mg of the title compound. $^1$H NMR (CDCl3) 9.52 (s, 2H), 7.838 (s, 2H), 7.508 (s, 1H), 7.321-7.307 (d, 2H), 6.769 (br. s, 1H), 5.464 (s, 2H), 3.925-3.851 (m, 4H), 3.820-3.790 (t, 2H), 3.612-3.582 (t, 2H), 1.987-1.959 (m, 2H) ppm.

Example 10

N-[3,5-bis(trifluoromethyl)phenyl]-4-[4-({[3-(dimethylamino)phenyl]methyl}oxy)-1,2,5-thiadiazol-3-yl]piperazine-1-carboxamide

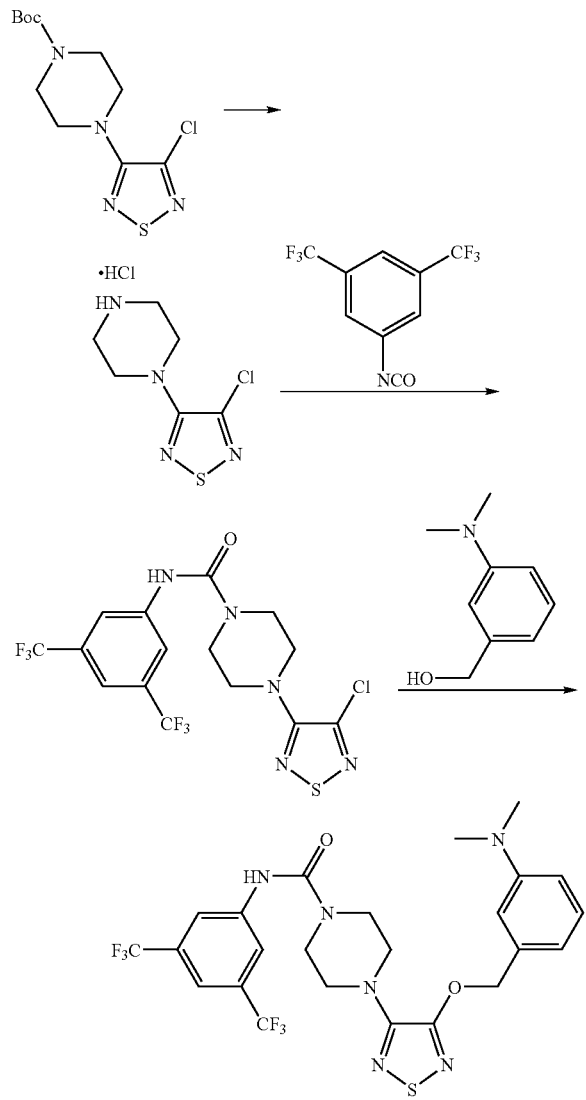

4-(4-Chloro-[1,2,5]thiadiazol-3-yl)-piperazine hydrochloride. To a round bottom flask equipped with a magnetic stir bar was added 4-(4-Chloro-[1,2,5]thiadiazol-3-yl)-piperazine-1-carboxylic acid tert-butyl ester (10 g, 32 mmol, 1.0 eq, prepared as Example 1a) and 4M HCl/Dioxane. The reaction was allowed to stir at room temperature for 2 hour. The resulting precipitate was filtered, washed with EtOAc three times, dried in vacuo to give 4-(4-Chloro-[1,2,5]thiadiazol-3-yl)-piperazine hydrochloride (7.8 g) as a white solid.

1-(4-Chloro-[1,2,5]thiadiazol-3-yl)piperazine hydrochloride. 4-(4-Chloro-[1,2,5]thiadiazol-3-yl)piperazine-1-carboxylic acid tert-butyl ester (1.0 g, 3.28 mmol) was suspended in 10 mL of 4 M HCl in dioxane. The suspension was stirred overnight and the solid material was removed by filtration. The solid was washed three times with 15 mL ethyl acetate and dried under vacuum. 756 mg of white powder was obtained.

4-(4-Chloro-[1,2,5]thiadiazol-3-yl)-piperazine-1-carboxylic acid (3,5-bis-trifluoromethyl-phenyl)-amide. To a round bottom flask equipped with a magnetic stir bar was added 4-(4-chloro-[1,2,5]thiadiazol-3-yl)-piperazine (7.8 g, 32.6 mmol, 1.0 eq.), dry $CH_2Cl_2$ (130 mL), triethyl amine (11.66 g, 16 mL, 115.2 mmol, 3.5 eq). To this mixture cooled in an ice bath was added 1-isocyanato-3,5-bis-trifluoromethyl-benzene (11.6 g, 7.9 ml, 45 mmol, 1.4 eq.) dissolved in dry $CH_2Cl_2$ (20 mL) dropwise. The resulting mixture was allowed to warm up to room temperature with stirring. After stirring for 3 hour, the reaction mixture was diluted with EtOAc. This solution was then washed with aqNaHCO$_3$, and brine. The organic layer was dried with $Na_2SO_4$, concentrated. The residue was purified by column chromatography using acetate/hexane (1:1 to 3:1), affording 4-(4-Chloro-[1,2,5]thiadiazol-3-yl)-piperazine-1-carboxylic acid (3,5-bis-trifluoromethyl-phenyl)-amide (11.8 g, 79% yield) as a solid.

4-[4-(3-Dimethylamino-benzyloxy)-[1,2,5]thiadiazol-3-yl]-piperazine-1-carboxylic acid (3,5-bis-trifluoromethyl-phenyl)-amide. To a round bottom flask equipped with a magnetic stir bar was added 4-(4-Chloro-[1,2,5]thiadiazol-3-yl)-piperazine-1-carboxylic acid (3,5-bis-trifluoromethyl-phenyl)-amide (0.1 g, 0.21 mmol, 1.0 eq.), (3-Dimethylamino-phenyl)-methanol (0.065 g, 0.062 mL, 0.43 mmol, 2.0 eq) and 1M potassium tert-butyl butoxide in t-butanol (0.65 ml, 0.65 mmol, 3.0 eq). The mixture was stirred at room temperature overnight. After removal of solvent in vacuo, the crude mixture was purified on preparative HPLC, affording the title compound N-[3,5-bis(trifluoromethyl)phenyl]-4-[4-({[3-(dimethylamino)phenyl]methyl}oxy)-1,2,5-thiadiazol-3-yl]piperazine-1-carboxamide as a white solid (0.06 g, 55% yield). $^1$H NMR (DMSO-d6) 9.23 (s, 1H), 8.18 (s, 2H), 7.59 (s, 1H), 7.22 (m, 1H), 6.89 (s, 1H), 6.78 (m, 2H), 5.39 (m, 4H), 3.61 (m, 4H), 3.53 (m, 4H), 2.92 (s, 6H) ppm.

The following compounds were prepared using the procedure as in Example 10 from 4-(4-Chloro-[1,2,5]thiadiazol-3-yl)-piperazine-1-carboxylic acid (3,5-bis-trifluoro-methyl-phenyl)-amide:

N-[3,5-bis(trifluoromethyl)phenyl]-4-{4-[(3-thienylmethyl)oxy]-1,2,5-thiadiazol-3-yl}piperazine-1-carboxamide. $^1$H NMR (CDCl3) 7.88 (s, 2H), 7.53 (s, 1H), 7.40-7.39 (m, 1H), 7.36 (dd, 1H), 7.17 (dd, 1H), 6.67 (s, 1H), 5.48 (s, 2H), 3.64-3.61 (m, 8H) ppm.

N-[3,5-bis(trifluoromethyl)phenyl]-4-[4-(1H-indol-5-yloxy)-1,2,5-thiadiazol-3-yl]piperazine-1-carboxamide. To a round bottom flask equipped with a magnetic stir bar was added 4-(4-chloro-[1,2,5]thiadiazol-3-yl)-piperazine-1-carboxylic acid (3,5-bis-trifluoromethyl-phenyl)-amide (0.1 g, 0.21 mmol, 1.0 eq.), H-Indol-5-ol (0.0579 g, 0.43 mmol, 2.0 eq) and 1M potassium tert-butyl butoxide in t-butanol (0.65 ml, 0.65 mmol, 3.0 eq). The reaction mixture was stirred at 70° C. for 2 hours. After removal of solvent in vacuo, the crude mixture was purified on preparative HPLC, affording the title compound N-[3,5-bis(trifluoromethyl)phenyl]-4-[4-(1H-indol-5-yloxy)-1,2,5-thiadiazol-3-yl]piperazine-1-carboxamide as a white solid (0.04 g, 33% yield). $^1$H NMR (DMSO-d6) 9.17 (s, 1H), 9.09 (s, 1H), 8.15 (s, 2H), 7.81 (d, 1H), 7.53 (m, 2H), 6.96 (d, 1H), 6.75 (d, 1H), 6.63 (d, 1H), 3.53 (m, 4H), 3.02 (m, 4H) ppm.

N-[3,5-bis(trifluoromethyl)phenyl]-4-{1,1-dioxido-4-[(pyridin-4-ylmethyl)oxy]-1,2,5-thiadiazol-3-yl}piperazine-1-carboxamide. To a round bottom flask equipped with a magnetic stir bar was added 4-[4-(Pyridin-4-ylmethoxy)-[1,2,5]thiadiazol-3-yl]-piperazine-1-carboxylic acid(3,5-bis-trifluoromethyl-phenyl)-amide (0.1 g, 0.19 mmol, 1.0 eq.) and dry $CH_2Cl_2$ (20 mL). The reaction was then cooled in using an ice bath followed by the addition of MCPBA (0.039 g, 0.23 mmol, 1.2 eq). The reaction was then allowed to slowly return to room temperature at which point the solvent was removed. The white solid was dissolved in DMSO (2 mL) and purified by preparative HPLC. The fraction containing the desired product was dried by lyophylization to give a white solid (1.5 mg, 1.5% yield). $^1$H NMR (DMSO-d6) 9.25 (s, 1H), 8.29 (d, 2H), 8.21 (s, 2H), 7.62 (s, 1H), 7.56 (d, 2H), 5.46 (d, 2H), 3.65 (m, 8H) ppm.

Example 11

N-[3,5-bis(trifluoromethyl)phenyl]-4-{5,6-dicyano-3-[(pyridin-4-ylmethyl)oxy]pyrazin-2-yl}piperazine-1-carboxamide

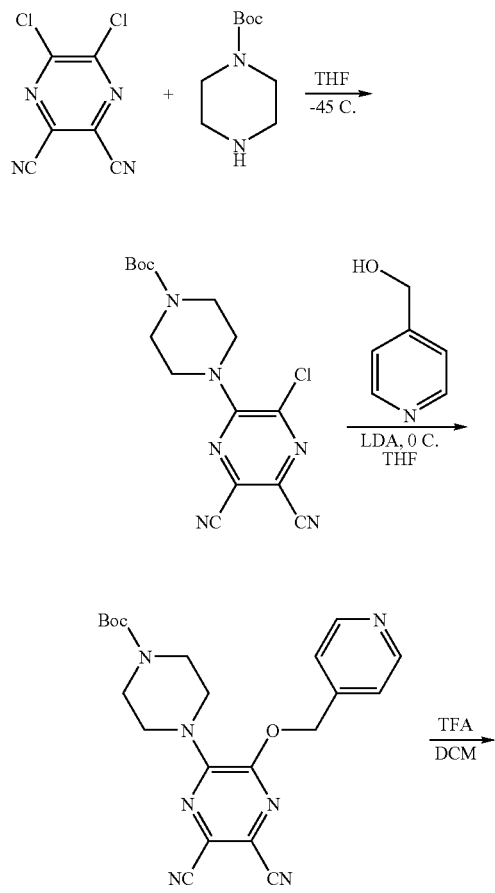

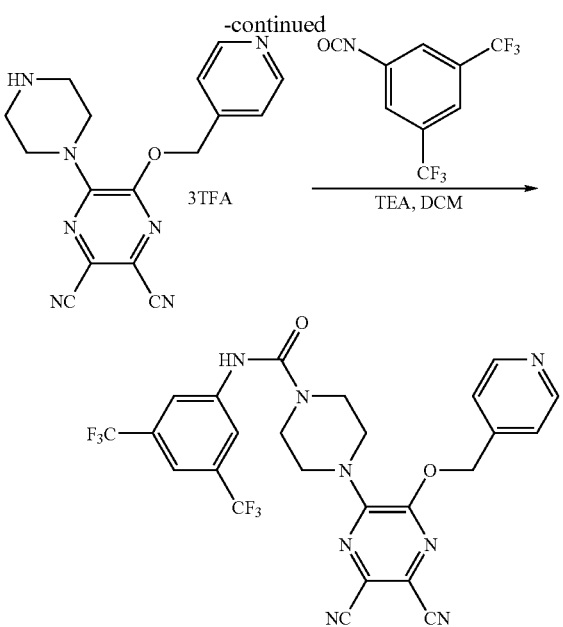

3'-Chloro-5',6'-dicyano-2,3,5,6-tetrahydro-[1,2']bipyrazinyl-4-carboxylic acid tert-butyl ester. To a solution of 1-Boc-piperazine (8 mmol, 1.5 g) and anhydrous tetrahydrofuran cooled at −45° C. was added 5,6-dichloro-2,3-dicyanopyrazine (4 mmol, 800 mg). The mixture was stirred at −45° C. for 1.5 hours. Reaction mixture was concentrated and stirred in EtOAc, filtered and concentrated. The crude material was purified on silica column using 30% EtOAc/hexanes to yield 3'-Chloro-5',6'-dicyano-2,3,5,6-tetrahydro-[1,2']bipyrazinyl-4-carboxylic acid tert-butyl ester (640 mg).

5',6'-Dicyano-3'-(pyridin-4-ylmethoxy)-2,3,5,6-tetrahydro-[1,2']bipyrazinyl-4-carboxylic acid tert-butyl ester. To a solution of 4-pyridylcarbinol (0.44 mmol, 45 mg) and anhydrous tetrahydrofuran (3 ml) cooled at 0° C. was added LDA (2M, 0.6 mmol, 300 ul). The mixture was stirred at 0° C. for 15 minutes. A solution of 3'-Chloro-5',6'-dicyano-2,3,5,6-tetrahydro-[1,2']bipyrazinyl-4-carboxylic acid tert-butyl ester (0.29 mmol, 100 mg) in THF (2 ml) was then added to the cold mixture and stirred at 0° C. for 1 hour. Reaction mixture was poured onto 0.5M acetic acid and extracted with ethyl acetate. The crude product was purified by column chromatograph on silica using 70% EtOAc/hexanes to yield product 5',6'-Dicyano-3'-(pyridin-4-ylmethoxy)-2,3,5,6-tetrahydro-[1,2']bipyrazinyl-4-carboxylic acid tert-butyl ester (100 mg).

N-[3,5-bis(trifluoromethyl)phenyl]-4-{5,6-dicyano-3-[(pyridin-4-ylmethyl)oxy]-pyrazin-2-yl}piperazine-1-carboxamide. A mixture of 5',6'-Dicyano-3'-(pyridin-4-ylmethoxy)-2,3,5,6-tetrahydro-[1,2']bipyrazinyl-4-carboxylic acid tert-butyl ester (100 mg) and 30% TFA in DCM (11 ml) was stirred for 2 hours. The mixture was concentrated in vacuo to dryness. To the residue was added DCM (5 ml), TEA (0.31 mmol, 51 ul), and 3,5-bis(trifluoromethyl)phenyl isocyanate (0.15 mmol, 26 ul). The resulting mixture was stirred at room temperature for 3 hours. After concentrated in vacuo, the crude product was purified by column on silica using 70% EtOAc/Hexanes to give the product N-[3,5-bis(trifluoromethyl)phenyl]-4-{5,6-dicyano-3-[(pyridin-4-ylmethyl)oxy]pyrazin-2-yl}piperazine-1-carboxamide. $^1$H NMR (CD3OD) 8.594 (s, 2H), 8.073 (s, 2H), 7.555-7.534 (m, 3H), 5.584 (s, 2H), 4.043-4.029 (m, 4H), 3.739-3.713 (m, 4H) ppm.

Example 12

N-[3,5-bis(trifluoromethyl)phenyl]-4-{2-[(pyridin-4-ylmethyl)oxy]phenyl}piperazine-1-carboxamide

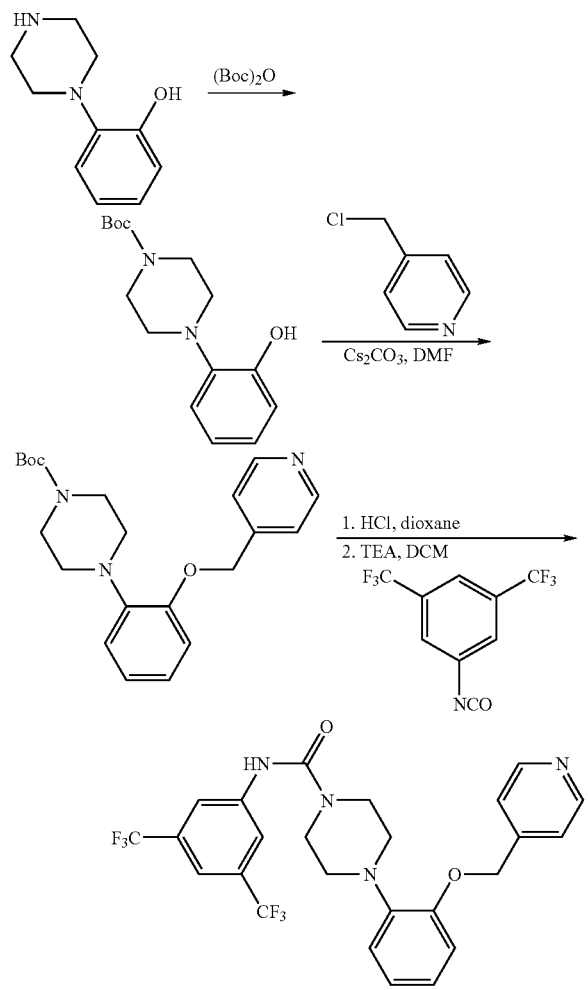

4-(2-Hydroxy-phenyl)-piperazine-1-carboxylic acid tert-butyl ester. To a solution of 2-(1-piperizine)phenol (56 mmol, 10 g) and 1,4-dioxane (120 ml) was added water (120 ml), sodium bicarbonate (56 mmol, 4.7 g), and di-t-butyl dicarbonate (56 mmol, 12.2 g). The mixture was stirred at room temperature overnight. The resulting precipitate from the mixture was filtered and washed with water, and then dissolved in ethyl acetate and washed with brine. The organic layer was concentrated in vacuo to give 4-(2-Hydroxy-phenyl)-piperazine-1-carboxylic acid tert-butyl ester (15.5 g).

4-[2-(Pyridin-4-ylmethoxy)-phenyl]-piperazine-1-carboxylic acid tert-butyl ester. A mixture of 4-(2-Hydroxy-phenyl)-piperazine-1-carboxylic acid tert-butyl ester (18 mmol, 5 g), DMF (40 ml) and cesium carbonate (40 mmol, 13 g) was stirred at room temperature for 15 minutes, followed by addition of 4-picolyl chloride hydrochloride (18 mmol, 2.953 g). The resulting mixture was stirred at room temperature overnight. The reaction mixture was poured onto ice/water and extracted with ethyl acetate (3×). The combined organic layer was washed with Sat. NaCl. The crude product was purified on silica column using 75% EtOAc/hexanes to give 4-[2-(Pyridin-4-ylmethoxy)-phenyl]-piperazine-1-carboxylic acid tert-butyl ester (4.5 g).

1-[2-(Pyridin-4-ylmethoxy)-phenyl]-piperazine dihydrochloride. The above product (4.5 g) was dissolved in 1,4-dioxane (25 ml) followed by addition of 4M HCl in dioxane (75 ml), and stirred for 3 hours. The resulting precipitate was filtered, washed with ethyl acetate and dried in vacuo to give 1-[2-(Pyridin-4-ylmethoxy)-phenyl]-piperazine dihydrochloride.

N-[3,5-bis(trifluoromethyl)phenyl]-4-{2-[(pyridin-4-ylmethyl)oxy]phenyl}-piperazine-1-carboxamide. A mixture of 1-[2-(Pyridin-4-ylmethoxy)-phenyl]-piperazine dihydrochloride (0.3 mmol, 100 mg), DCM (5 ml), TEA (1 mmol, 139 ul), and 3,5-bis(trifluoromethyl)phenyl isocyanate (0.6 mmol, 104 ul) was stirred at room temperature overnight. The mixture was concentrated in vacuo and purified on silica column using 80% EtOAc/hexanes to give N-[3,5-bis(trifluoromethyl)phenyl]-4-{2-[(pyridin-4-ylmethyl)oxy]phenyl}piperazine-1-carboxamide. $^1$H NMR (CDCl3) 8.599-8.586 (d, 2H), 7.855 (s, 2H), 7.559-7.452 (d, 2H), 7.390-7.377 (d, 2H), 7.021-6.888 (m, 4H), 5.146 (s, 2H), 3.728-3.704 (m, 4H), 3.149-3.125 (m, 4H) ppm.

Example 13

N-[3,5-bis(trifluoromethyl)phenyl]-4-(3-{[(2-fluoropyridin-4-yl)methyl]oxy}pyrazin-2-yl)piperazine-1-carboxamide

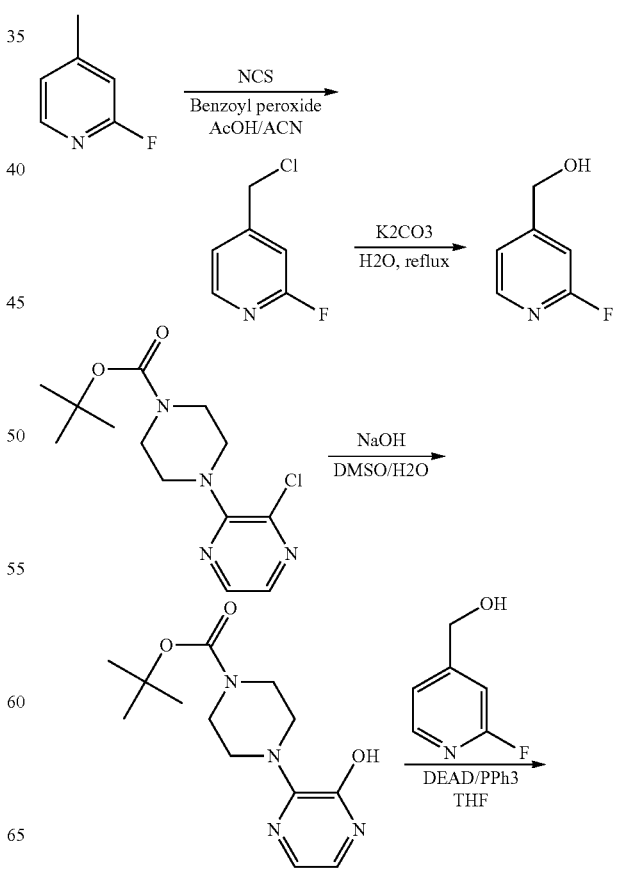

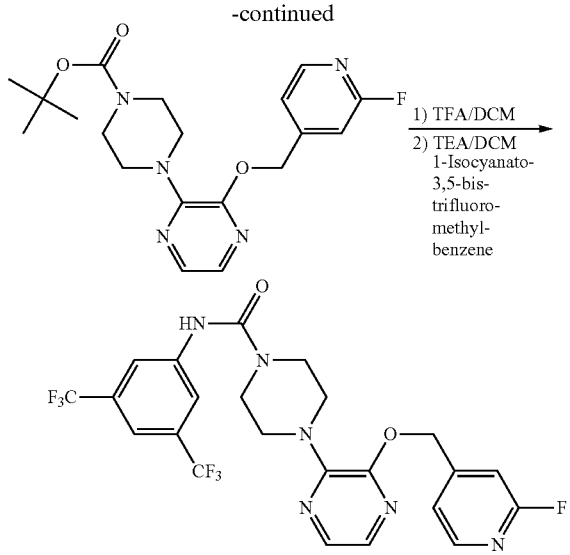

2-Fluoro-4-pyridinemethanol. This compound was prepared according to Pesti's procedure (J. Org. Chem. 2000, 65, 7718-7722). A mixture of 2-Fluoro-4-methyl-pyridine (1.99 g, 17.9 mmol), N-Chlorosuccinimide (3.59 g, 26.9 mmol), benzoyl peroxide (99.0 mg, 0.409 mmol), and acetic acid (60 µL, 1.05 mmol) in acetonitrile (10 mL) was heated at reflux for 90 min. The mixture was allowed to cool to room temperature, then poured into water (8 mL) and extracted with EtOAc. The organic phase was washed with brine, dried over MgSO$_4$, and concentrated in vacuo at 35° C. A red oil was obtained (2.6 g). $^1$H NMR revealed a 1.7:1 molar ratio of 4-chloromethyl-2-fluoro-pyridine to 2-fluoro-4-methyl-pyridine. The crude material was carried to the hydrolysis step without further purification. The crude material obtained (2.6 g, 12.1 mmol), and potassium carbonate (2.4 g, 17.4 mmol) were suspended in water (30 mL) and heated at reflux for 2 h. The mixture was allowed to cool to room temperature and the phases were separated. The oily phase was further extracted with water. The combined aqueous phases were washed with hexanes and extracted with EtOAc. The combined organic phases were dried over MgSO$_4$ and concentrated in vacuo to yield 2-fluoro-4-pyridinemethanol (514 mg, 22.5% over 2 steps, 95 LC area %) as an off white solid.

3'-Hydroxy-2,3,5,6-tetrahydro-[1,2']bipyrazinyl-4-carboxylic acid tert-butyl ester. To a solution of 3'-chloro-2,3,5,6-tetrahydro-[1,2']bipyrazinyl-4-carboxylic acid tert-butyl ester (1.85 g, 6.19 mmol, prepared in Example 5a) in DMSO (6 mL) was added a 2.5M aqueous solution of NaOH (30 mL). The resulting suspension was heated to reflux for 12 h before allowing to cool to room temperature. The suspension was then diluted with water (20 mL), acidified to pH=5 with 6M HCl, and extracted with EtOAc. The organic phase was concentrated in vacuo and the resulting solids were purified by flash chromatography (silica gel, 5.5:1 EtOAc:Hexanes). Product 3'-Hydroxy-2,3,5,6-tetrahydro-[1,2']bipyrazinyl-4-carboxylic acid tert-butyl ester was obtained as white solids (538 mg, 31.0%).

3'-(2-Fluoro-pyridin-4-ylmethoxy)-2,3,5,6-tetrahydro-[1,2']bipyrazinyl-4-carboxylic acid tert-butyl ester. To a suspension of 3'-hydroxy-2,3,5,6-tetrahydro-[1,2']bipyrazinyl-4-carboxylic acid tert-butyl ester (304 mg, 1.08 mmol), 2-Fluoro-4-pyridinemethanol (138 mg, 1.08 mmol), and triphenylphosphine (286 mg, 1.09 mmol) in THF (5 mL) was added diethyl azidocarboxylate (210 mg, 1.21 mmol) dropwise. The resulting clear brown solution was stirred at room temperature for 16 h, then concentrated in vacuo. The crude solids were purified by flash chromatography (silica gel, 1:2 EtOAc:Hexanes). Product 3'-(2-fluoro-pyridin-4-ylmethoxy)-2,3,5,6-tetrahydro-[1,2']bipyrazinyl-4-carboxylic acid tert-butyl ester was obtained as white solid (113 mg, 26.9% yield).

N-[3,5-bis(trifluoromethyl)phenyl]-4-(3-{[(2-fluoropyridin-4-yl)methyl]oxy}pyrazin-2-yl)piperazine-1-carboxamide. A 20% solution of TFA in dichloromethane was added to 3'-(2-fluoro-pyridin-4-ylmethoxy)-2,3,5,6-tetrahydro-[1,2']bipyrazinyl-4-carboxylic acid tert-butyl ester (113 mg, 0.290 mmol). The solution was stirred at room temperature for 1 h until complete de-protection was evident by LCMS, then concentrated in vacuo. The resulting solid was diluted with dichloromethane (3 mL). Triethylamine (193 mg, 1.91 mmol) was added and assured bacisity with pH paper. The solution was cooled to –5° C. and 1-isocyanato-3,5-bis-trifluoromethyl-benzene (88.6 mg, 0.347 mmol) was added dropwise. After the addition was complete, the solution was stirred at –5° C. for 5 min, then allowed to warm up to room temperature and stirred for an additional 3 h. The solution was then diluted with EtOAc (20 mL), washed with satd. NaHCO$_{3(aq)}$ and brine, dried over MgSO$_4$ and concentrated in vacuo. The crude solids were dissolved in MeOH and purified by preparative HPLC (50 mM NH$_4$OAc$_{(aq)}$, acetonitrile solvent system). The product was isolated by lyophilization of pure fractions yielding N-[3,5-bis(trifluoromethyl)phenyl]-4-(3-{[(2-fluoropyridin-4-yl)methyl]oxy}pyrazin-2-yl)piperazine-1-carboxamide (50.5 mg, 32.0% yield). $^1$H NMR (CDCl3) 8.24 (d, 1H), 7.91 (s, 2H), 7.82 (d, 1H), 7.61 (d, 1H), 7.54 (s, 1H), 7.22 (d, 1H), 6.98 (s, 1H), 6.73 (d, 1H), 5.51 (s, 2H), 3.70-3.65 (m, 8H) ppm.

Example 14

N-[3,5-bis(trifluoromethyl)phenyl]-4-(3-{[(2-chloro-pyridin-4-yl)methyl]oxy}pyrazin-2-yl)piperazine-1-carboxamide

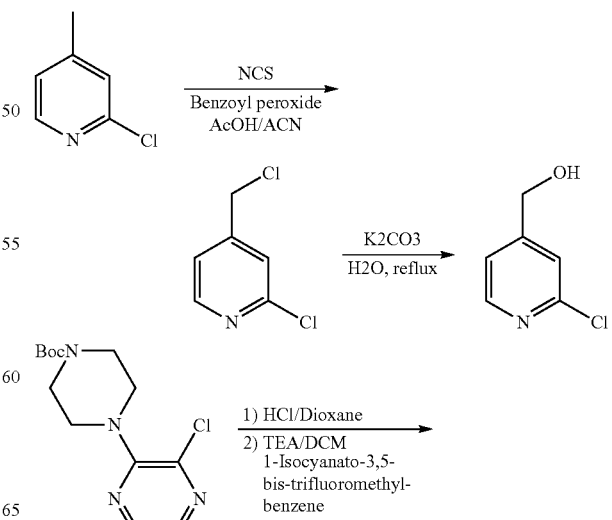

-continued

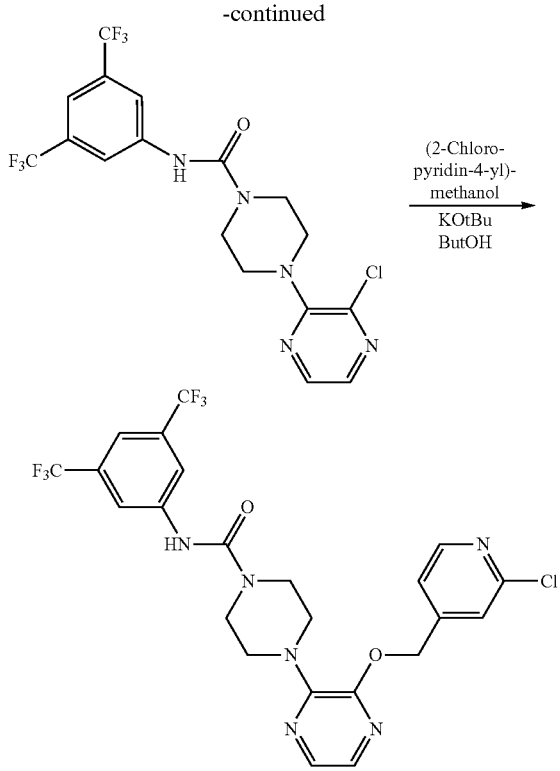

4-(Chloromethyl)-2-chloropyridine. A mixture of 2-chloro-4-methyl-pyridine (7.28 g, 57.1 mmol), N-Chlorosuccinimide (11.4 g, 85.3 mmol), benzoyl peroxide (276 mg, 1.13 mmol), and acetic acid (200 μL, 3.5 mmol) in acetonitrile (30 mL) was heated at reflux for 2.5 h. The mixture was allowed to cool to room temperature, then poured into water (10 mL) and extracted with EtOAc. The organic phase was washed with brine, dried over MgSO$_4$, and concentrated in vacuo at 35° C., yielding the crude product of 4-(chloromethyl)-2-chloropyridine (9.25 g) as an oil. The crude oil was carried on to the hydrolysis step without further purification.

2-Chloro-4-pyridinemethanol. The crude product of 4-(chloromethyl)-2-chloropyridine (9.25 g), and potassium carbonate (9.5 g, 68.7 mmol) were suspended in water (100 mL) and heated at reflux for 2.5 h. The mixture was allowed to cool to room temperature and the phases were separated. The oily phase was further extracted with water. The combined aqueous phases were washed with hexanes and extracted with EtOAc. The combined EtOAc phases were dried over MgSO$_4$ and concentrated in vacuo to yield 2-Chloro-4-pyridinemethanol as an off white solid (762 mg, 9.3% yield over 2 steps).

3'-Chloro-2,3,5,6-tetrahydro-[1,2']bipyrazinyl-4-carboxylic acid (3,5-bis-trifluoromethyl-phenyl)-amide. To a solution of 3'-chloro-2,3,5,6-tetrahydro-[1,2']bipyrazinyl-4-carboxylic acid tert-butyl ester (3.7 g, 12.4 mmol, prepared in Example 5a) and dichloromethane (20 mL) was added anhydrous 4M HCl/Dioxane (20 mL). The solution was stirred for 1 h until complete de-protection was evident by LCMS. The solution was concentrated in vacuo, which was then re-dissolved in dichloromethane (50 mL). Triethylamine (3.78 g, 37.4 mmol) was added and the solution was cooled to 0° C. before dropwise addition of 1-isocyanato-3,5-bis-trifluoromethyl-benzene (3.70 g, 14.5 mmol) with stirring. After completion of addition the solution was allowed to warm up to room temperature and stirred for 1 h. The reaction mixture was diluted with EtOAc (150 mL), then washed with saturated sodium bicarbonate, and brine. The organic phase was dried over MgSO$_4$ and concentrated in vacuo to yield 3'-chloro-2,3,5,6-tetrahydro-[1,2']bipyrazinyl-4-carboxylic acid (3,5-bis-trifluoromethyl-phenyl)-amide (5.6 g, 100%) as a white solid.

N-[3,5-bis(trifluoromethyl)phenyl]-4-(3-{[(2-chloropyridin-4-yl)methyl]oxy}pyrazin-2-yl)piperazine-1-carboxamide. To a solution of 3'-chloro-2,3,5,6-tetrahydro-[1,2']bipyrazinyl-4-carboxylic acid (3,5-bis-trifluoromethyl-phenyl)-amide (115 mg, 0.254 mmol) and 1M solution of potassium tert-butoxide in tert-butanol (0.80 mL, 0.80 mmol) was added 2-Chloro-4-pyridinemethanol (81.8 mg, 0.568 mmol). The resulting suspension was stirred at room temperature for 15 h. The crude reaction mixture was diluted with methanol and purified by preparative HPLC (50 mM NH$_4$OAc$_{(aq)}$, Acetonitrile system). The product was isolated by lyophilization of pure fractions yielding N-[3,5-bis(trifluoromethyl)phenyl]-4-(3-{[(2-chloropyridin-4-yl)methyl]oxy}pyrazin-2-yl)piperazine-1-carboxamide (29.9 mg, 21% yield). $^1$H NMR (CDCl3) 8.41 (d, 1H), 7.91 (s, 2H), 7.82 (d, 1H), 7.61 (d, 1H), 7.54 (s, 1H), 7.39 (s, 1H), 6.70 (s, 1H), 5.47 (s, 2H), 3.70-3.65 (m, 8H) ppm.

Example 15

4-[4-(2-Fluoro-pyridin-4-ylmethoxy)-[1,2,5]thiadiazol-3-yl]-piperazine-1-carboxylic acid (3,5-bis-trifluoromethyl-phenyl)-amide

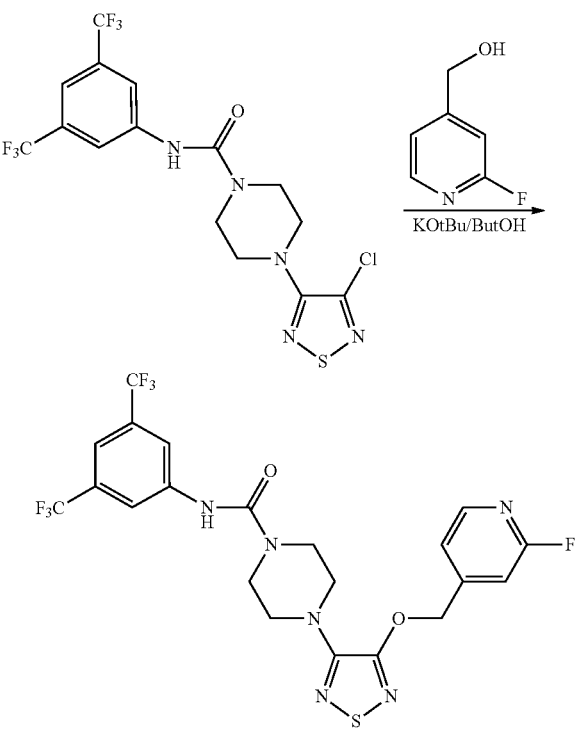

To a solution of 4-(4-chloro-[1,2,5]thiadiazol-3-yl)-piperazine-1-carboxylic acid (3,5-bis-trifluoromethyl-phenyl)-amide (117.7 mg, 0.265 mmol, prepared in Example 10b) and 1M solution of potassium tert-butoxide in tert-butanol (0.75 mL, 0.75 mmol) was added 2-Fluoro-4-pyridinemethanol (65.6 mg, 0.516 mmol, prepared in Example 15a). The resulting suspension was stirred at room temperature for 2 h. The crude reaction mixture was diluted with methanol and purified by preparative HPLC (50 mM NH$_4$OAc$_{(aq)}$, Acetonitrile system). The pure fractions were combined and the acetonitrile was removed in vacuo. The remaining aqueous solution was made basic with NaHCO$_3$ and the free based product was extracted into EtOAc. The organic phase was concentrated in vacuo, and the solids were re-dissolved in acetonitrile/water and lyophilized to obtain pure product 4-[4-(2-Fluoro-pyridin-4-ylmethoxy)-[1,2,5]thiadiazol-3-yl]-piperazine-1-carboxylic acid (3,5-bis-trifluoromethyl-phenyl)-amide. (19.0 mg, 13.5% yield). $^1$H NMR (CDCl3) 8.26 (d, 1H), 7.88 (s, 2H), 7.53 (s, 1H), 7.22 (d, 1H), 6.98 (s, 1H), 6.88 (s, 1H), 5.53 (s, 2H), 3.73-3.50 (m, 8H) ppm.

Example 16

N-[3,5-Bis(trifluoromethyl)phenyl]-4-(4-{[(2-chloropyridin-4-yl)methyl]oxy}-1,2,5-thiadiazol-3-yl)piperazine-1-carboxamide

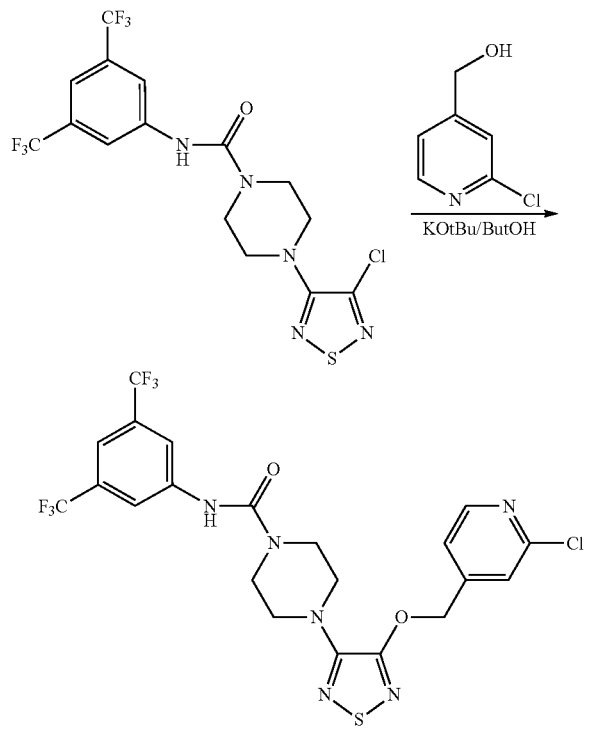

To a solution of 4-(4-chloro-[1,2,5]thiadiazol-3-yl)-piperazine-1-carboxylic acid (3,5-bis-trifluoromethyl-phenyl)-amide (103.7 mg, 0.226 mmol, prepared in Example 10b) and 1M solution of potassium tert-butoxide in tert-butanol (0.70 mL, 0.70 mmol) was added 2-chloro-4-pyridinemethanol (64.5 mg, 0.448 mmol, prepared in Example 16a). The resulting suspension was stirred at room temperature for 2 h. The crude reaction mixture was diluted with methanol and purified by preparative HPLC (0.1% TFA in water, 0.1% TFA in acetonitrile). The pure fractions were combined and the acetonitrile/TFA was removed in vacuo. The remaining aqueous solution was made basic with NaHCO$_3$ and the free based product was extracted into EtOAc. The organic phase was concentrated in vacuo yielding pure product N-[3,5-bis(trifluoromethyl)phenyl]-4-(4-{[(2-chloropyridin-4-yl)methyl]oxy}-1,2,5-thiadiazol-3-yl)piperazine-1-carboxamide (33.4 mg, 26.1% yield). $^1$H NMR (CDCl3) 8.43 (d, 1H), 7.90 (s, 2H), 7.55 (s, 1H), 7.38 (s, 1H), 6.68 (s, 1H), 5.49 (s, 2H), 3.66 (d, 8H) ppm.

Example 17

N-[3,5-bis(trifluoromethyl)phenyl]-4-(4-{[(2-bromopyridin-4-yl)methyl]oxy}-1,2,5-thiadiazol-3-yl) piperazine-1-carboxamide

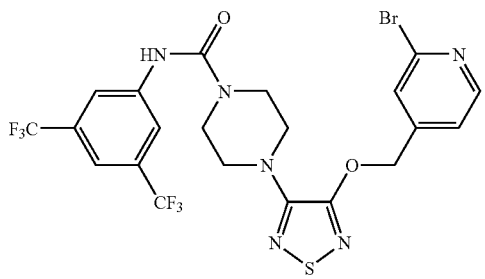

To a solution of potassium t-butoxide (0.070 g, 0.63 mmol) and t-butanol (0.5 mL) was added dropwise with stirring (2-bromo-pyridin-4-yl)-methanol (0.078 g, 0.42 mmol, prepared in the similar fashion as Example 16a from 2-Bromo-4-methyl-pyridine), followed by 4-(4-chloro-[1,2,5]thiadiazol-3-yl)-piperazine-1-carboxylic acid (3,5-bis-trifluoromethyl-phenyl)-amide (0.100 g, 0.21 mmol; prepared in Example 10b). The mixture was stirred at room temperature overnight. LC/MS analysis indicated formation of the desired product. The mixture was concentrated in vacuo, and the crude product was purified on preparative HPLC to afford N-[3,5-bis(trifluoromethyl)phenyl]-4-(4-{[(2-bromopyridin-4-yl)methyl]oxy}-1,2,5-thiadiazol-3-yl) piperazine-1-carboxamide (13 mg, 10% yield). $^1$H NMR (CDCl3) 8.40 (s, 1H), 7.95 (s, 2H), 7.45 (s, 2H), 7.25 (m, 1H), 6.6 (s, 1H), 5.45 (m, 2H), 3.6 (m, 4H), 1.6 (m, 4H) ppm.

Example 18

N-[3,5-bis(trifluoromethyl)phenyl]-4-(3-{[(2-bromopyridin-4-yl)methyl]-oxy}pyrazin-2-yl)piperazine-1-carboxamide

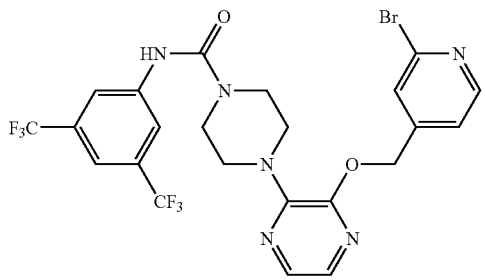

To a solution of potassium t-butoxide (0.073 g, 0.66 mmol) and t-butanol (0.5 mL) was added dropwise with stirring (2-bromo-pyridin-4-yl)-methanol (0.082 g, 0.44 mmol, prepared in the similar fashion as Example 16a from 2-Bromo-4-methyl-pyridine), followed by 3'-chloro-2,3,5,6-tetrahydro-[1,2'|bipyrazinyl-4-carboxylic acid (3,5-bis-trifluoromethyl-phenyl)-amide (0.100 g, 0.22 mmol; prepared in Example 16b). The mixture was stirred at room temperature overnight. LC/MS analysis indicated formation of the desired product. The mixture was concentrated in vacuo, and the crude product was purified on preparative HPLC to afford N-[3,5-bis(trifluoromethyl)phenyl]-4-(3-{[(2-bromopyridin-4-yl)methyl]-oxy}pyrazin-2-yl)piperazine-1-carboxamide (5 mg). ¹H NMR (CDCl3) 8.40 (s, 1H), 7.95 (s, 2H), 7.8 (s, 1H), 7.6 (s, 1H), 7.58 (m, 2H), 7.24 (m, 1H), 6.62 (s, 1H), 5.4 (s, 2H), 3.6 (m, 4H), 1.6 (m, 4H) ppm.

Example 19

N-(1-{3-[(pyridin-4-ylmethyl)oxy]pyrazin-2-yl}pyrrolidin-3-yl)-N'-[3-(trifluoromethyl)phenyl] urea

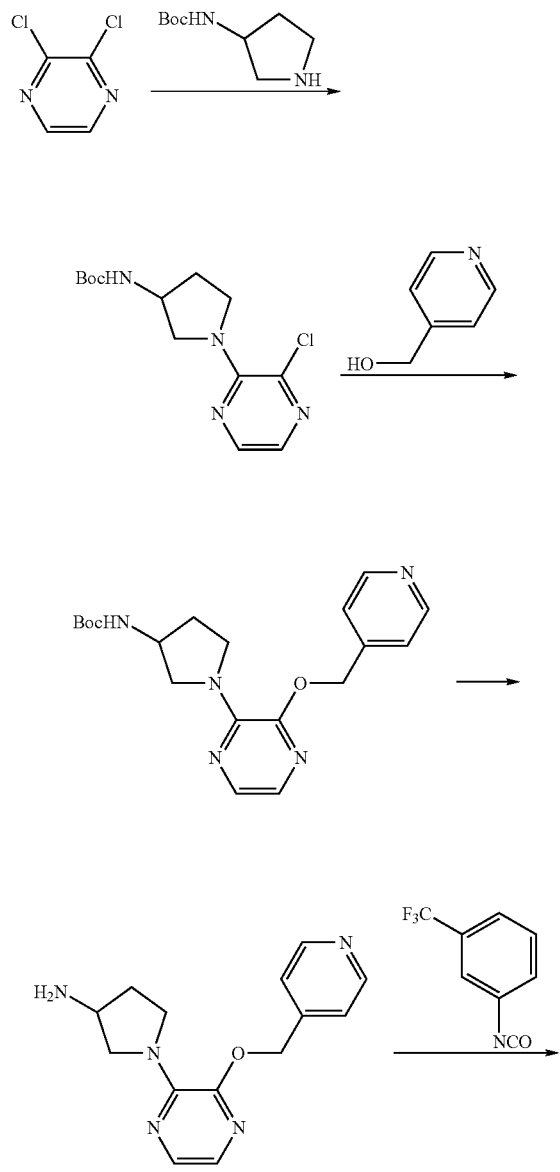

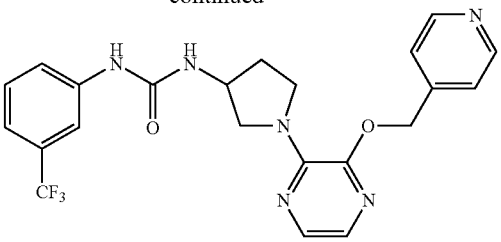

[1-(3-Chloro-pyrazin-2-yl)-pyrrolidin-3-yl]-carbamic acid tert-butyl ester. To a round bottom flask equipped with a magnetic stir bar was added 2,3-Dichloro-pyrazine (3 g, 20.2 mmol) and dry DMF (50 mL). 3-Boc-aminopyrrolidine (8.2 g, 44.5 mmol) was dissolved in dry DMF (50 mL) and added to the round bottom flask. The reaction mixture was allowed to continue to stir overnight at 100° C. LC/MS analysis indicated the desired product as the main component. The reaction mixture was cooled to room temperature and poured on ice. The mixture was extracted with EtOAc and the EtOAc layer was washed with water and brine and dried on sodium sulfate. After removal of solvent in vacuo the desired product [1-(3-Chloro-pyrazin-2-yl)-pyrrolidin-3-yl]-carbamic acid tert-butyl ester (6.8 g, 99% yield) was obtained.

{1-[3-(Pyridin-4-ylmethoxy)-pyrazin-2-yl]-pyrrolidin-3-yl}-carbamic acid tert-butyl ester. To a round-bottom flask purged with $N_2$ was charged with Potassium t-butoxide (7.6 g, 68.4 mmol) and t-butanol (140 mL). The mixture was flushed with $N_2$ for approximately 5 min., while stirring. To this mixture was added pyridylcarbinol (7.4 g, 68.4 mmol), followed by [1-(3-chloro-pyrazin-2-yl)-pyrrolidin-3-yl]-carbamic acid tert-butyl ester (6.8 g, 22.8 mmol). The mixture was stirred at room temperature overnight. The mixture was concentrated in vacuo, and then diluted with water and extracted with EtOAc three times. The organic layer was washed with water and brine, dried over sodium sulfate, and then concentrated in vacuo. Purification of the crude by column chromatography afforded {1-[3-(pyridin-4-ylmethoxy)-pyrazin-2-yl]-pyrrolidin-3-yl}-carbamic acid tert-butyl ester (1 g, 12% yield).

1-[3-(Pyridin-4-ylmethoxy)-pyrazin-2-yl]-pyrrolidin-3-ylamine. To compound {1-[3-(pyridin-4-ylmethoxy)-pyrazin-2-yl]-pyrrolidin-3-yl}-carbamic acid tert-butyl ester (1 g, 2.6 mmole) was added 50% TFA/DCM. The mixture was stirred for 1 hour, and concentrated in vacuo to give 1-[3-(Pyridin-4-ylmethoxy)-pyrazin-2-yl]-pyrrolidin-3-ylamine (1.2 g, 100% yield).

N-(1-{3-[(pyridin-4-ylmethyl)oxy]pyrazin-2-yl}pyrrolidin-3-yl)-N'-[3-(trifluoro-methyl)phenyl]urea. To a solution of 1-[3-(pyridin-4-ylmethoxy)-pyrazin-2-yl]-pyrrolidin-3-ylamine (50 mg, 0.18 mmole), triethylamine (excess eq.) in dichloromethane was added 1-isocyanato-3-trifluoromethyl-benzene (37 mg, 0.198 mmole). The mixture was stirred at room temperature for 1 hour. The mixture was then concentrated in vacuo, and purified by preparative HPLC to give N-(1-{3-[(pyridin-4-ylmethyl)oxy]pyrazin-2-yl}pyrrolidin-3-yl)-N'-[3-(trifluoro-methyl)phenyl]urea (13.2 mg, 12.5% yield). ¹H NMR (DMSO-d6) 8.80 (m, 3H), 7.97 (s, 1H), 7.90 (d, 2H), 7.68 (d, 1H), 7.4 (m, 2H), 7.3 (d, 1H), 7.2 (m, 1H), 6.8 (d, 1H), 5.3 (s, 2H), 4.25 (m, H), 3.9 (m, 1H), 3.75 (m, 2H), 3.6 (m, 1H), 2.40 (m, 1H), 1.85 (m, 1H) ppm.

Example 20

2-[2,5-bis(trifluoromethyl)phenyl]-N-(1-{4-[(pyridin-4-ylmethyl)oxy]-1,2,5-thiadiazol-3-yl}pyrrolidin-3-yl)acetamide

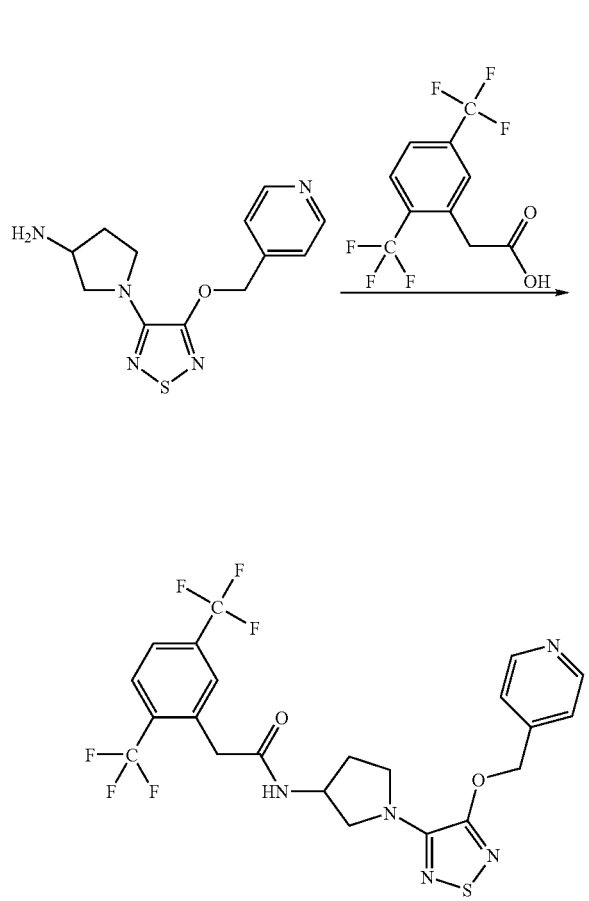

To a mixture of 1-[3-(pyridin-4-ylmethoxy)-pyrazin-2-yl]-pyrrolidin-3-ylamine dihydrochloride (100 mg, 0.29 mmol, 1.0 eq.), triethyl amine (0.119 ml, 0.858 mmol, 3.0 eq.), anhydrous DCM (1 mL), 2,5 Bis(triflouoromethyl)phenyl acetic acid (116.7 mg, 0.429 mmol, 1.5 eq.), was added 1-Ethyl-3-(3-dimethylaminopropyl)-carbodiimide hydrochloride (109.3 mg, 0.572 mmol, 2.0 eq.), followed by anhydrous 1-Hydroxybenzotriazole (HOBT) (57.91 mg, 0.429 mmol, 1.5 eq.). The reaction mixture was allowed to stir at room temperature overnight. After removal of solvent in vacuo, the mixture was purified on preparative HPLC to give 2-[2,5-bis(trifluoromethyl)phenyl]-N-(1-{4-[(pyridin-4-ylmethyl)oxy]-1,2,5-thiadiazol-3-yl}pyrrolidin-3-yl)acetamide (92.2 mg, 61% yield) as a white solid. $^1$H NMR (CDCl$_3$) 8.58 (d, 2H), 7.78-7.75 (s, 2H), 7.64 (d, 1H), 7.28-7.24 (m, 2H), 5.95 (d, 1H), 5.42 (s, 2H), 4.58-4.54 (m, 1H), 3.90-3.87 (m, 1H), 3.79-3.67 (m, 4H), 3.61-3.58 (m, 1H), 2.30-2.21 (m, 1H), 1.97-1.89 (m, 1H) ppm.

Example 21

N-[3,5-bis(trifluoromethyl)phenyl]-4-{4-[(pyridin-4-ylmethyl)amino]-1,2,5-thiadiazol-3-yl}piperazine-1-carboxamide

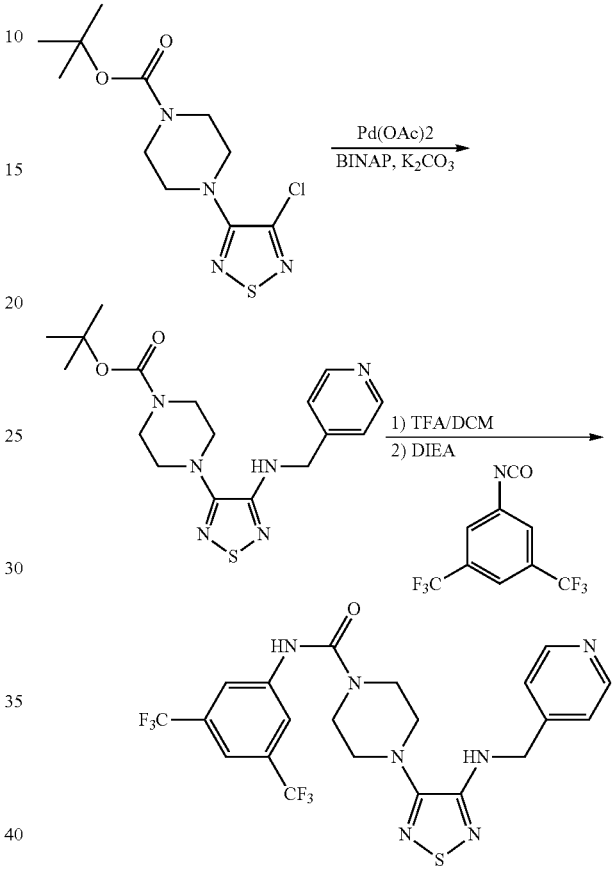

4-{4-[(Pyridin-4-ylmethyl)-amino]-[1,2,5]thiadiazol-3-yl}-piperazine-1-carboxylic acid tert-butyl ester. To a round-bottom flask purged with N$_2$ was charged with Pd (OAc)$_2$ (13.4 mg, 0.06 mmol, 2%), BINAP (37 mg, 0.02 mmol, 2%), and dry toluene (15 mL), followed by addition of 4-(4-Chloro-[1,2,5]thiadiazol-3-yl)-piperazine-1-carboxylic acid tert-butyl ester (912 mg, 3 mmol, prepared in Example 10b), picolylamine (388 mg, 3.6 mmol) and K2CO3 (2 g, 15 mmole). The mixture was refluxed with vigorous stirring under N2 atmosphere until the desired product was observed (LC/MS analysis). The reaction mixture was cooled down to room temperature, filtered through a plug of celite. After removal of solvent in vacuo, the crude reaction mixture was purified on preparative HPLC to obtain 4-{4-[(pyridin-4-ylmethyl)-amino]-[1,2,5]thiadiazol-3-yl}-piperazine-1-carboxylic acid tert-butyl ester (25 mg).

N-[3,5-bis(trifluoromethyl)phenyl]-4-{4-[(pyridin-4-ylmethyl)amino]-1,2,5-thiadiazol-3-yl}piperazine-1-carboxamide. To 4-{4-[(pyridin-4-ylmethyl)-amino]-[1,2,5]thiadiazol-3-yl}-piperazine-1-carboxylic acid tert-butyl ester (25 mg) was added 50% TFA/DCM. After stirring at room temperature for 1 hour, the mixture was concentrated in vacuo to a dryness, giving the de-protected amine (33 mg). To this de-protected amine (26 mg, 0.103 mmol) was added dichloromethane and triethylamine (excess eq.) with stirring, followed bis-trifluoromethylisocyanate (26.2 mg, 0.103 mmole). The mixture was stirred at room temperature for 1 hour. LC/MS analysis indicated the formation of desired product. The mixture was concentrated in vacuo and the crude product was purified on preparative HPLC to give N-[3,5-bis (trifluoromethyl)phenyl]-4-{4-[(pyridin-4-ylmethyl) amino]-1,2,5-thiadiazol-3-yl}piperazine-1-carboxamide (14 mg). ¹H NMR (DMSO-d6) 9.41 (s, 1H), 8.65 (br, s, 2H), 8.2 (s, 2H), 7.75 (d, 1H), 7.6 (s, 2H), 7.45 (t, 1H), 4.65 (d, 2H), 3.65 (m, 4H), 3.22 (m, 4H) ppm.

Example 22

N-[3,5-bis(trifluoromethyl)phenyl]-4-{4-[(piperidin-4-ylmethyl)oxy]-1,2,5-thiadiazol-3-yl}piperazine-1-carboxamide

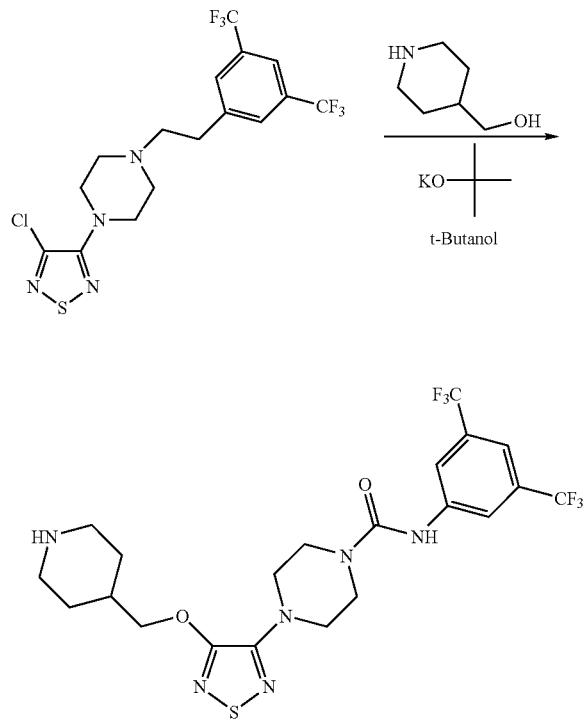

4-(4-Chloro-[1,2,5]thiadiazol-3-yl)-piperazine-1-carboxylic acid (3,5-bis-trifluoromethyl-phenyl)amide (50 mg, 0.11 mmol, prepared in Example 10b) was dissolved in 330 µL of t-butanol along with 4-piperadine methanol (38 mg, 0.33 mmol). Then, 330 µL of 1.0 M potassium t-butoxide in t-butanol was added. The reaction mixture was heated to 50° C. overnight. The reaction was quenched with the addition of a few drops of trifluoroacetic acid and the solution was diluted to 2 mL in volume with methanol. The reaction mixture was purified by reverse phase HPLC to give 9 mg of the product as a white solid. ¹H NMR DMSO-d₆) δ 9.37 (s, 1H), 8.25 (s, 2H), 7.62 (s, 1H), 4.28 (d, 2H), 3.63 (m, 4H), 3.54 (m, 4H), 3.08 (d, 2H), 2.59 (t, 2H), 1.93 (m, 1H), 1.71 (d, 2H), 1.29 (qd, 2H) ppm.

Example 23

1-phenyl-4-{4-[(pyridin-4-ylmethyl)oxy]-1,2,5-thiadiazol-3-yl}piperazine

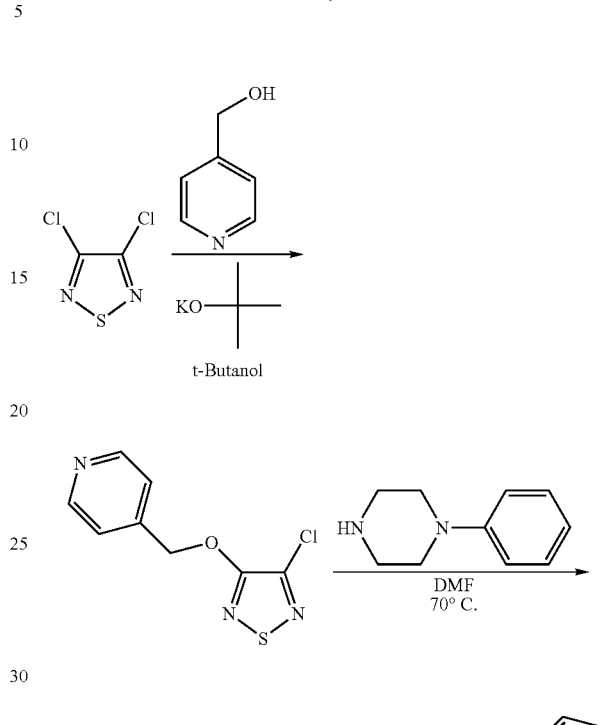

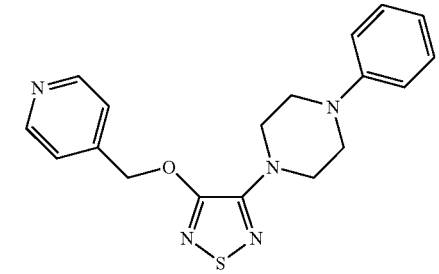

4-(4-Chloro-[1,2,5]thiadiazol-3-yloxymethyl)-pyridine. 3,4-Dichloro-1,2,5-thiadiazole (2.00 mL, 21.3 mmol) was dissolved in 70 mL of t-butanol along with 4-pyridine methanol (1.05 g, 9.62 mmol). 30 mL of 1.0 M potassium t-butoxide (30 mmol) was added and the reaction was stirred at room temperature overnight. The reaction was diluted with 100 mL of water and neutralized with 1.0 M HCl. The product was extracted 3 times with 100 mL portions of ethyl acetate. The combined organic fractions were dried with magnesium sulfate and concentrated under vacuum. The residue was purified by flash chromatography with a 2:1 solution of hexanes in ethyl acetate, affording 4-(4-chloro-[1,2,5]thiadiazol-3-yloxymethyl)-pyridine (821 mg) as an off-white solid.

1-phenyl-4-{4-[(pyridin-4-ylmethyl)oxy]-1,2,5-thiadiazol-3-yl}piperazine. 4-(4-chloro-[1,2,5]thiadiazol-3-yloxymethyl)-pyridine (50 mg, 0.22 mmol) was dissolved in 200 µL of DMF along with 1-phenylpiperazine (75 µL, 0.49 mmol). The reaction was heated to 70° C. overnight. The reaction mixture was diluted with methanol to a volume of 2 mL and the reaction mixture was purified by reverse phase chromatography, affording 1-phenyl-4-{4-[(pyridin-4-ylmethyl)oxy]-1,2,5-thiadiazol-3-yl}piperazine (7 mg). ¹H NMR (DMSO-d$_6$) δ 8.62 (d, 2H), 7.46 (d, 2H), 7.23 (t, 2H), 7.01 (d, 2H), 6.82 (t, 1H), 5.58 (s, 2H), 3.64 (m, 4H), 3.23 (m, 4H) ppm.

The following compounds were prepared in the similar fashion as Example 23 from 4-(4-chloro-[1,2,5]thiadiazol-3-yloxymethyl)-pyridine: 1-[(4-methylphenyl)methyl]-4-{4-[(pyridin-4-ylmethyl)oxy]-1,2,5-thiadiazol-3-yl}piperazine. $^1$H NMR (DMSO-d$_6$) δ 8.57 (d, 2H), 7.41 (d, 2H), 7.19 (d, 2H), 7.11 (d, 2H), 5.48 (s, 2H), 3.49 (m, 4H), 3.47 (s, 2H), 2.44 (m, 4H), 2.23 (s, 3H) ppm. 2-(4-{4-[(pyridin-4-ylmethyl)oxy]-1,2,5-thiadiazol-3-yl}piperazin-1-yl)pyrimidine. $^1$H NMR (DMSO-d6) 8.52 (s, 2H), 8.36 (s, 2H), 7.37 (s, 2H), 6.58 (s, 1H), 5.47 (s, 2H), 3.80 (t, 4H), 3.51 (t, 4H) ppm. 1-[2-nitro-4-(trifluoromethyl)phenyl]-4-{4-[(pyridin-4-ylmethyl)oxy]-1,2,5-thiadiazol-3-yl}piperazine. $^1$H NMR (DMSO-d6) 8.57 (s, 2H), 8.17 (s, 1H), 7.86 (d, 1H), 7.53 (d, 1H), 7.47-7.42 (m, 2H), 5.52 (s, 2H), 3.65-3.63 (t, 4H), 3.49-3.17 (t, 4H) ppm. 1-[4-(4-{4-[(pyridin-4-ylmethyl)oxy]-1,2,5-thiadiazol-3-yl}piperazin-1-yl)phenyl]ethanone. $^1$H NMR (DMSO-d6) 8.87-8.57 (m, 2H), 7.90 (d, 2H), 7.79 (d, 2H), 6.96 (d, 2H), 5.70 (s, 2H), 3.65-3.63 (m, 4H), 3.46-3.44 (m, 4H), 2.49 (s, 3H) ppm.

Example 24

N-[3,5-bis(trifluoromethyl)phenyl]-4-(2-{[(2,3,5,6-tetrafluoropyridin-4-yl)amino]methyl}phenyl)piperazine-1-carboxamide

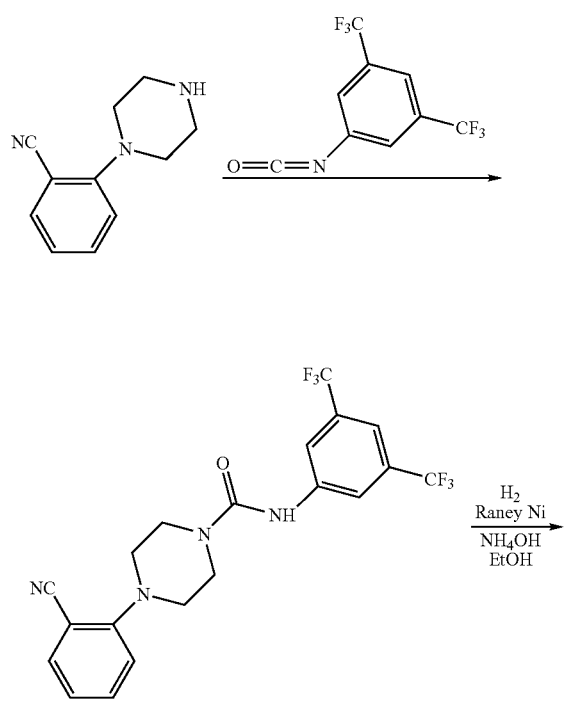

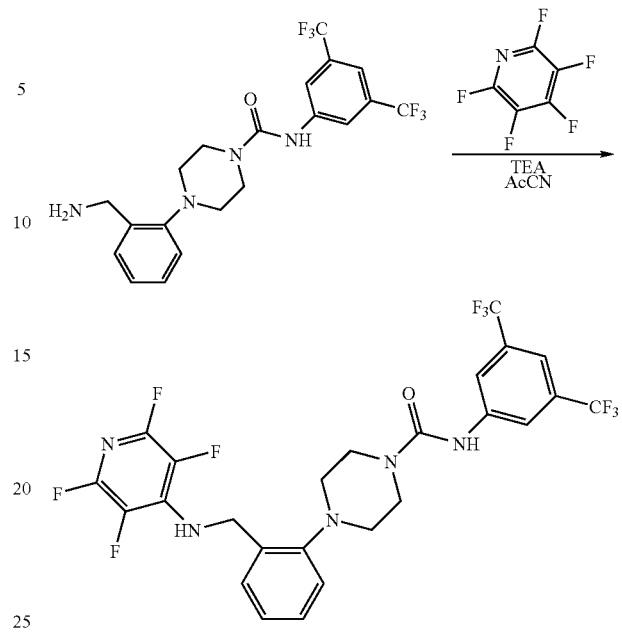

4-(2-Cyanophenyl)piperazine-1-carboxylic acid (3,5-bis-trifluoromethyl-phenyl)-amide. 1-(2-Cyanophenyl)piperazine (1.0 g, 5.34 mmol) was dissolved in 25 mL of dichloromethane. Then, triethylamine (820 μL, 5.88 mmol) was added, followed by 3,5-bis(trifluoromethyl)phenyl isocyanate (1020 μL, 5.87 mmol). The reaction stirred at room temperature overnight. The reaction mixture was diluted with 50 mL of water and extracted three times with 25 mL portions of ethyl acetate. The combined organic fractions were washed twice with 25 mL of 0.1 M HCl, once with 25 mL of water, and once with 25 mL of saturated sodium bicarbonate. The organic fraction was dried with magnesium sulfate and concentrated under vacuum. The crude product was used without further purification.

4-(2-Aminomethylphenyl)piperazine-1-carboxylic acid (3,5-bis-trifluoromethyl-phenyl)amide. 4-(2-Cyanophenyl)piperazine-1-carboxylic acid (3,5-bis-trifluoromethyl-phenyl)-amide (~5.3 mmol) was dissolved in 50 mL of ethanol. 5 mL of aqueous NH$_4$OH was added along with 500 mg of 50% Raney nickel in water. The reaction mixture was hydrogenated in a Parr shaker at 45 psi overnight. The reaction mixture was filtered through a plug of Celite and concentrated under vacuum. 2.5 g of crude product was obtained, and used without further purification.

N-[3,5-bis(trifluoromethyl)phenyl]-4-(2-{[(2,3,5,6-tetrafluoropyridin-4-yl)amino]methyl}phenyl)piperazine-1-carboxamide. 4-(2-Aminomethyl-phenyl)piperazine-1-carboxylic acid (3,5-bis-trifluoromethyl-phenyl)amide (50 mg, 0.11 mmol) was dissolved in 500 mL of acetonitrile. Then, triethylamine (20 L, 0.14 mmol) was added, followed by pentafluoropyridine (16 μL, 0.15 mmol). The reaction was stirred at room temperature overnight. The reaction mixture was diluted to 2 mL in volume with methanol and the mixture was purified by reverse phase HPLC to give 44 mg of the product as a white solid. $^1$H NMR (CDCl$_3$) δ 7.87 (s, 2H), 7.51 (s, 1H), 7.29-7.36 (m, 2H), 7.16-7.21 (m, 2H), 6.78 (s, 1H), 5.90 (br s, 1H), 4.79 (d, 2H), 3.71 (m, 4H), 3.02 (t, 4H) ppm.

Example 25

N-[3,5-bis(trifluoromethyl)phenyl]-4-(2-{[(3-chloro-2,5,6-trifluoropyridin-4-yl)amino]methyl}phenyl)piperazine-1-carboxamide

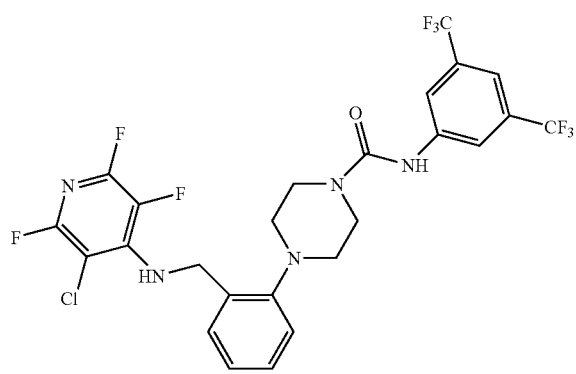

4-(2-Aminomethyl-phenyl)piperazine-1-carboxylic acid (3,5-bis-trifluoromethyl-phenyl)amide (50 mg, 0.11 mmol, prepared in Example 26b) was dissolved in 500 µL of acetonitrile. Then, triethylamine (20 µL, 0.14 mmol) was added, followed by 3-chloro-2,4,5,6-tetrafluoropyridine (17 µL, 0.15 mmol). The reaction was stirred at room temperature overnight. The reaction mixture was diluted to 2 mL in volume with methanol and the mixture was purified by reverse phase HPLC to give 15 mg of the product as a white solid. $^1$H NMR (CDCl$_3$) δ 7.88 (s, 2H), 7.52 (s, 1H), 7.31-7.38 (m, 2H), 7.15-7.22 (m, 2H), 6.70 (s, 1H), 5.88 (br t, 1H), 4.85 (dd, 2H), 3.71 (m, 4H), 3.02 (t, 4H) ppm.

Example 26

N-[3,5-bis(trifluoromethyl)phenyl]-4-{3-[(pyridin-4-ylmethyl)oxy]pyridin-2-yl}piperazine-1-carboxamide

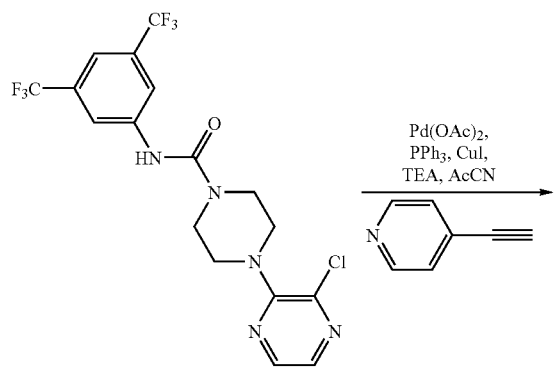

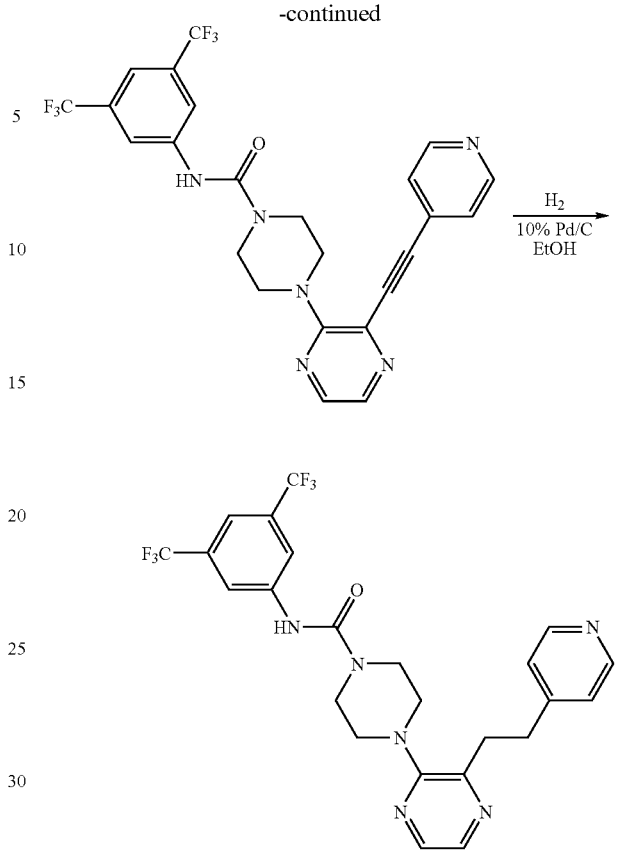

3'-Pyridin-4-ylethynyl-2,3,5,6-tetrahydro-[1,2']bipyrazinyl-4-carboxylic acid (3,5-bis-trifluoromethylphenyl)amide. 3'-Chloro-2,3,5,6-tetrahydro-[1,2']bipyrazinyl-4-carboxylic acid (3,5-bis-trifluoromethylphenyl)amide (200 mg, 0.441 mmol, prepared in Example 16b) was dissolved in 1.8 mL of acetonitrile. Another mixture was prepared containing 4-ethynylpyridine hydrochloride (125 mg, 0.896 mmol), palladium(II) acetate (12 mg, 0.053 mmol), copper(I) iodide (5 mg, 0.026 mmol), triphenylphosphine (28 mg, 0.107 mmol) and triethylamine (600 µL) in 600 µL of acetonitrile. The two mixtures were combined and stirred at 80° C. for 1 hr under a nitrogen atmosphere. The reaction mixture was filtered through Celite and concentrated under vacuum. The material was used without further purification.

N-[3,5-bis(trifluoromethyl)phenyl]-4-{3-[(pyridin-4-ylmethyl)oxy]pyridin-2-yl}piperazine-1-carboxamide. 3'-Pyridin-4-ylethynyl-2,3,5,6-tetrahydro-[1,2']bipyrazinyl-4-carboxylic acid (3,5-bis-trifluoromethylphenyl)amide (~0.4 mmol) was dissolved in 5 mL ethanol. Then, 50 mg of 10% palladium on carbon was added. The reaction flask was flushed with hydrogen and the reaction was stirred at room temperature for 5 hr under 1 atmosphere of hydrogen. The reaction mixture was filtered through Celite and concentrated under vacuum. The residue was purified by reverse phase HPLC to give N-[3,5-bis(trifluoromethyl)phenyl]-4-{3-[(pyridin-4-ylmethyl)oxy]pyridin-2-yl}piperazine-1-carboxamide (80 mg) as a yellow solid. $^1$H NMR (DMSO-d$_6$) δ 9.34 (s, 1H), 8.48 (d, 2H), 8.23 (s, 1H), 8.20 (d, 1H), 8.14 (d, 2H), 7.58 (s, 1H), 7.39 (d, 2H), 3.66 (m, 4H), 3.13-3.43 (m, 8H) ppm.

Example 27

N-[3,5-Bis(trifluoromethyl)phenyl]-4-{3-[(pyridin-4-ylmethyl)oxy]pyridin-2-yl}piperazine-1-carboxamide

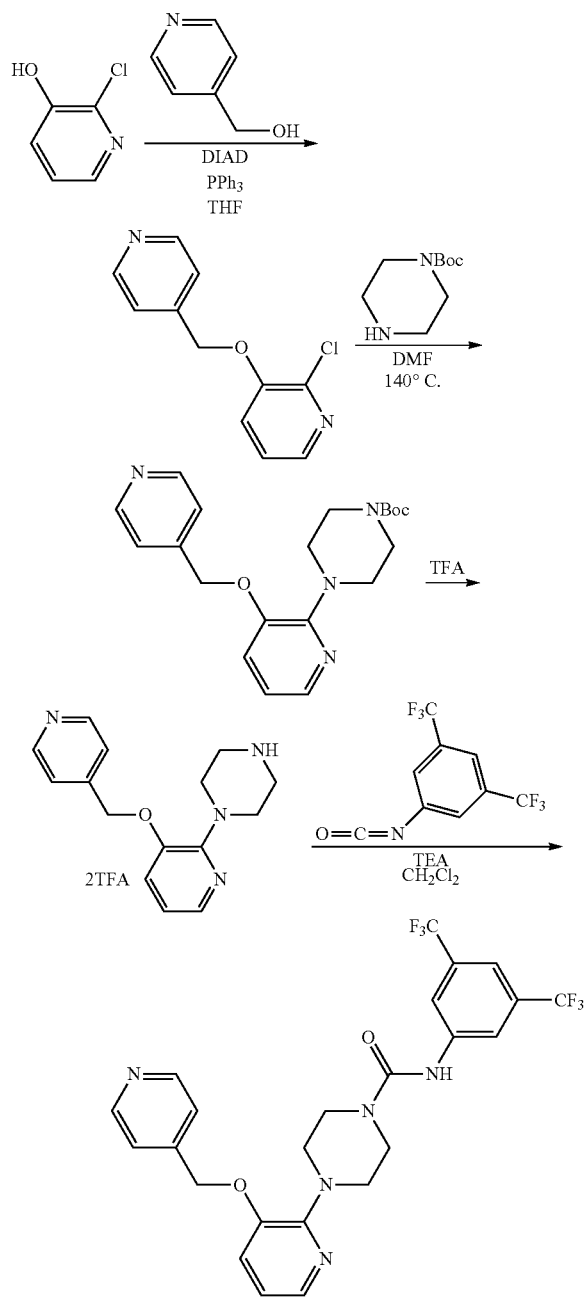

2-Chloro-3-(pyridin-4-ylmethoxy)pyridine. 2-Chloro-3-pyridinol (500 mg, 3.86 mmol) was dissolved in 20 mL of tetrahydrofuran along with 4-pyridyl methanol (465 mg, 4.26 mmol) and triphenylphosphine (1.15 g, 4.38 mmol). To this solution was added diisopropylazodicarboxylate (840 μL, 4.27 mmol). The reaction was stirred at room temperature overnight under a nitrogen atmosphere. The solvent was removed under vacuum and the residue was dissolved in 50 mL of ethyl acetate. The reaction mixture was washed 4 times with 25 mL portions of water. Then, the product was extracted by washing 3 times with 25 mL portions of 0.5 M HCl. The acidic washes were neutralized with 1.0 M NaOH and the product was extracted back into ethyl acetate with 3 washes of 25 mL. The combined organic fractions were dried with magnesium sulfate and concentrated under vacuum to give 620 mg of 2-chloro-3-(pyridin-4-ylmethoxy)pyridine as a yellow solid.

4-[3-(Pyridin-4-ylmethoxy)pyridin-2-yl]piperazine-1-carboxylic acid tert-butyl ester. 2-Chloro-3-(pyridin-4-ylmethoxy)pyridine (620 mg, 2.81 mmol) was dissolved in 3 mL DMF along with Boc-piperazine (2.5 g, 13.4 mmol). The reaction mixture was stirred at 140° C. for 48 hr. The reaction mixture solidified upon cooling and the product was extracted from the solid material by washing with a solution of ethyl acetate in hexanes (1:2). The organic washes were concentrated to give about 500 mg of the amine adduct in 50% purity, which was used for the next reaction without purification.

1-[3-(Pyridin-4-ylmethoxy)pyridin-2-yl]-piperazine trifluoroacetic acid salt. The crude 4-[3-(Pyridin-4-ylmethoxy)pyridin-2-yl]piperazine-1-carboxylic acid tert-butyl ester (~500 mg) was dissolved in 10 mL of 30% trifluoroacetic acid in dichloromethane. The reaction mixture was stirred for 3 hr and then the solvent was removed under vacuum. The impure material was used without purification.

N-[3,5-Bis(trifluoromethyl)phenyl]-4-{3-[(pyridin-4-ylmethyl)oxy]pyridin-2-yl}piperazine-1-carboxamide. The crude 1-[3-(Pyridin-4-ylmethoxy)pyridin-2-yl]-piperazine trifluoroacetic acid salt (~500 mg) was dissolved in 25 mL of tetrahydrofuran along with 2 g of trisamine resin. The suspension was stirred for 1 hr and the resin was removed by filtration. The filtrate was concentrated under vacuum. The free-based material was dissolved in 5 mL of dichloromethane. To this solution was added triethylamine (150 μL, 1.08 mmol) and 3,5-bis(trifluoromethyl)phenyl isocyanate (150 μL, 0.864 mmol). The reaction was stirred at room temperature for 1 hr. The reaction mixture was concentrated under vacuum and re-dissolved in 25 mL ethyl acetate. The reaction mixture was washed 3 times each with 25 mL portions of water, 0.05 M HCl and saturated aqueous sodium chloride. The organic fraction was dried with magnesium sulfate and concentrated under vacuum. The residue was purified by flash chromatography with a gradient of 0% to 10% methanol in ethyl acetate with 5% triethylamine, giving N-[3,5-bis(trifluoromethyl)phenyl]-4-{3-[(pyridin-4-ylmethyl)oxy]pyridin-2-yl}piperazine-1-carboxamide (14 mg). $^1$H NMR (DMSO-d$_6$) δ 9.24 (s, 1H), 8.60 (d, 2H), 8.22 (s, 2H), 7.84 (d, 1H), 7.58 (s, 1H), 7.46 (d, 2H), 7.33 (d, 1H), 6.92 (dd, 1H), 5.23 (s, 2H), 3.62-3.68 (m, 4H) 3.37-3.41 (m, 4H) ppm.

Example 28

N-[3,5-bis(trifluoromethyl)phenyl]-4-{2-[(pyridin-4-yloxy)methyl]phenyl}piperazine-1-carboxamide

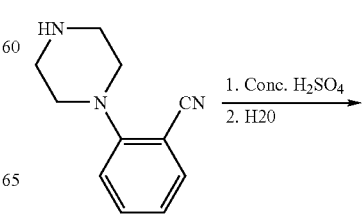

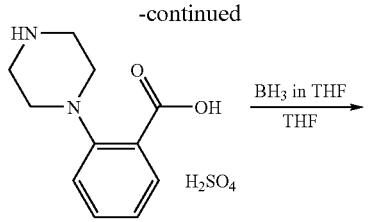

2-piperazin-1-yl-benzoic acid sulfuric acid salt. 1-(2-Cyanophenyl)piperazine (2.00 g, 10.68 mmol) was suspended in 10 mL of concentrated sulfuric acid. The piperazine slowly dissolved as the reaction mixture was heated to 100° C. After heating the reaction for 2 hr, the reaction was cooled to room temperature. 10 mL of water was added and the reaction was heated to 100° C. for another 4 hr. After cooling to room temperature, the reaction mixture was poured into 200 mL of ice water. The aqueous mixture was neutralized with ammonium hydroxide and the mixture was concentrated under vacuum. The product was extracted from the inorganic salts by washing with 25% methanol in tetrahydrofuran. The crude material was used in the next step without purification.

(2-piperazin-1-yl-phenyl)-methanol. 2-piperazin-1-yl-benzoic acid sulfuric acid salt (~10 mmol) was suspended in 50 mL of tetrahydrofuran. Then 100 mL of 1.0 M borane in tetrahydrofuran (100 mmol) was added and the reaction was stirred at room temperature overnight with a bubbler attached to release pressure in the flask. The reaction mixture was diluted with 50 mL of methanol. The reduced product (470 mg) crystallized out of the mixture during evaporation.

1-[2-(Pyridin-4-yloxymethyl)phenyl]piperazine. (2-piperazin-1-yl-phenyl)-methanol (200 mg, 1.04 mmol) was added to a suspension of 4-chloropyridine hydrochloride (225 mg, 1.50 mmol), tris[2-(2-methoxy)ethyl]amine (32 µL, 0.10 mmol), powdered potassium hydroxide (225 mg, 4.01 mmol) and potassium carbonate (275 mg, 1.99 mmol) in 10 mL of toluene. The reaction mixture was heated to 120° C. overnight. The reaction mixture was concentrated and the residue was purified by reverse phase HPLC. The material was still less than 50% pure, but was used in the next step without further purification.

N-[3,5-bis(trifluoromethyl)phenyl]-4-{2-[(pyridin-4-yloxy)methyl]phenyl}-piperazine-1-carboxamide. The impure 1-[2-(Pyridin-4-yloxymethyl)phenyl]piperazine (~50 mg) was dissolved in 5 mL of dichloromethane along with triethylamine (50 µL, 0.36 mmol). 3,5-Bis(trifluoromethyl)phenyl isocyanate (50 µL, 0.29 mmol) was added and the reaction was stirred at room temperature overnight. The solvent was removed under vacuum and the residue was dissolved in 2 mL methanol. The reaction mixture was purified by reverse phase HPLC to give 10 mg of product as a white solid. $^1$H NMR (DMSO-$d_6$) δ 10.58 (s, 1H), 8.28 (d, 2H), 8.17 (s, 2H), 7.73 (s, 1H), 7.49 (d, 1H), 7.38 (t, 1H), 7.18-7.25 (m, 4H), 5.39 (s, 2H), 3.80-3.85 (m, 4H) 3.00-3.04 (m, 4H).

Example 29

(4-{4-[4-(3,5-Bis-trifluoromethyl-phenylcarbamoyl)-piperazin-1-yl]-[1,2,5]thiadiazol-3-yloxymethyl-pyridin-2-yl)-carbamic acid tert-butyl ester

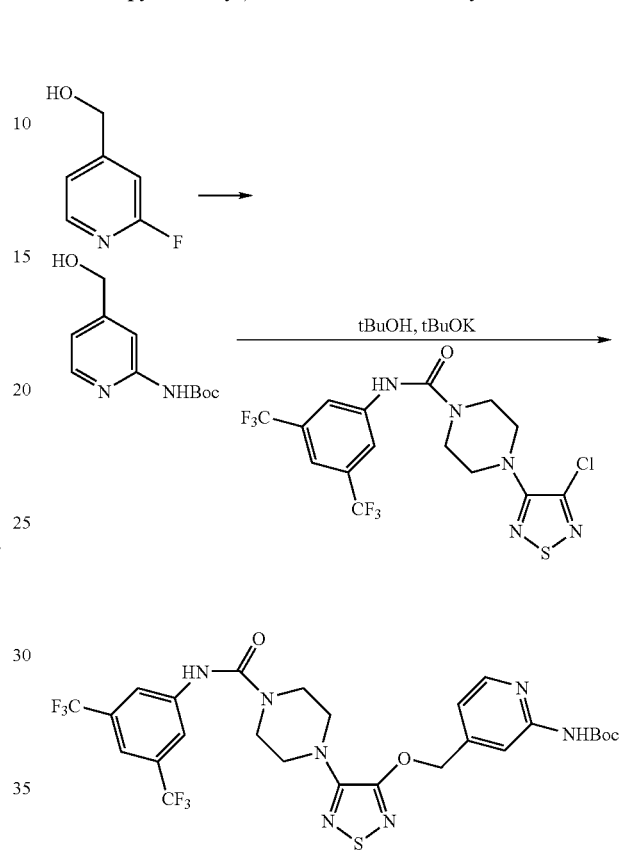

(4-Hydroxymethyl-pyridin-2-yl)-carbamic acid tert-butyl ester. A solution of (2-fluoro-pyridin-4-yl)-methanol (450 mg, 3.54 mmol) in 28% aqueous ammonia (5 mL) was heated in a sealed pressure tube at 150° C. for 17 h and at 175° C. for 21 h. The cooled solution was evaporated to a residue, which was partitioned between 1M $K_2CO_3$ and ethyl acetate. The aqueous phase was saturated with NaCl and extracted with several portions of ethyl acetate. The combined organic extracts were dried ($Na_2SO_4$), filtered and evaporated. The crude residue was dissolved in t-BuOH (5 mL) and was treated with di-tert-butyl dicarbonate (405 mg, 1.85 mmol) and stirred at room temperature for 15 h. The solvent was evaporated, and the crude residue was chromatographed on silica gel (1/1-$CH_2Cl_2$/ethyl acetate) to afford (4-hydroxymethyl-pyridin-2-yl)-carbamic acid tert-butyl ester (196 mg, 25%) as a solid: $^1$H NMR (400 MHz, $CDCl_3$) δ 1.53 (s, 9H), 2.27 (br s, 1H), 4.72 (s, 2H), 6.98 (m, 1H), 7.93 (s, 1H), 8.24 (d, 1H, J=5.2), 8.65 (s, 1H).

4-[4-(2-Amino-pyridin-4-ylmethoxy)-[1,2,5]thiadiazol-3-yl]-piperazine-1-carboxylic acid (3,5-bis-trifluoromethyl-phenyl)-amide. To a solution of (4-hydroxymethyl-pyridin-2-yl)-carbamic acid tert-butyl ester (100 mg, 0.45 mmol) and 4-(4-chloro-[1,2,5]thiadiazol-3-yl)-piperazine-1-carboxylic acid (3,5-bis-trifluoromethyl-phenyl)-amide (207 mg, 0.45 mmol) in t-BuOH (5 mL) was added solid potassium tert-butoxide (200 mg, 1.8 mmol) in one portion. The reaction solution was stirred at room temperature for 2 h and then at 40° C. for 1.75 h. Excess base was quenched with several drops of acetic acid and the volatiles were evaporated. The residue was partitioned between ethyl acetate and saturated NaHCO$_3$. The organic phase was washed with saturated NaCl, dried (MgSO$_4$), filtered and evaporated. Chromatography on silica gel (2/1-hexane/ethyl acetate) afforded a solid material that was recrystallized (hexane/ethyl acetate) to give (4-{4-[4-(3,5-bis-trifluoromethyl-phenylcarbamoyl)-piperazin-1-yl]-[1,2,5]thiadiazol-3-yloxymethyl-pyridin-2-yl)-carbamic acid tert-butyl ester (89 mg, 30%) as a crystalline adduct (1.3:1) with ethyl acetate: $^1$H NMR (400 MHz, CDCl$_3$) δ 1.52 (s, 9H), 3.71 (m, 8H), 5.49 (s, 2H), 6.77 (s, 1H), 6.96 (m, 1H), 7.53 (s, 1H), 7.89 (s, 2H), 7.93 (s, 1H), 8.12 (s, 1H), 8.27 (d, 1H, J=4.8); MS: 648 (M+1).

Example 30

4-[4-(2-Amino-pyridin-4-ylmethoxy)-[1,2,5]thiadiazol-3-yl]-piperazine-1-carboxylic acid (3,5-bis-trifluoromethyl-phenyl)-amide trifluoroacetate

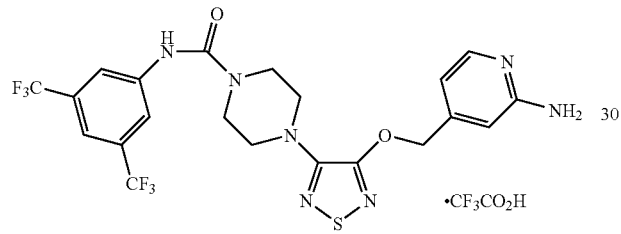

A solution of (4-{4-[4-(3,5-bis-trifluoromethyl-phenylcarbamoyl)-piperazin-1-yl]-[1,2,5]thiadiazol-3-yloxymethyl-pyridin-2-yl)-carbamic acid tert-butyl ester (40 mg, 0.062 mmol) in CH$_2$Cl$_2$ (1.5 mL) was treated with trifluoroacetic acid (1.5 mL), stirred at room temperature for 2.5 h and then was evaporated. The residue was dissolved in acetonitrile/water, filtered and lyophilized to afford 4-[4-(2-Amino-pyridin-4-ylmethoxy)-[1,2,5]thiadiazol-3-yl]-piperazine-1-carboxylic acid (3,5-bis-trifluoromethyl-phenyl)-amide trifluoroacetate (38 mg, 93%) as a white solid: $^1$H NMR (400 MHz, CD$_3$OD) δ 3.64 (m, 4H), 3.71 (m, 4H), 5.58 (s, 2H), 6.92 (dd, 1H, J=2, 6.4), 7.54 (s, 1H), 7.84 (dd, 1H, J=0.8, 6.8), 8.08 (s, 1H); MS: 548 (M+1).

Example 31

(4-{4-[4-(3,5-Bis-trifluoromethyl-phenylcarbamoyl)-piperazin-1-yl]-[1,2,5]thiadiazol-3-yloxymethyl}-pyridin-2-yl)-carbamic acid methyl ester

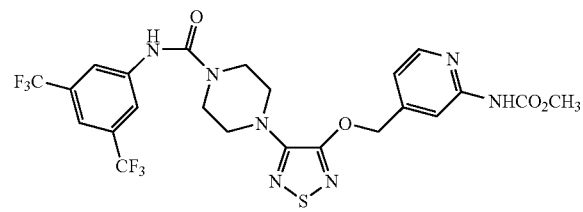

A solution of (4-{4-[4-(3,5-bis-trifluoromethyl-phenylcarbamoyl)-piperazin-1-yl]-[1,2,5]thiadiazol-3-yloxymethyl-pyridin-2-yl)-carbamic acid tert-butyl ester (45 mg, 0.070 mmol) in CH$_2$Cl$_2$ (3 mL) was treated with trifluoroacetic acid (3 mL), stirred at rt for 1 h and then was evaporated. The residue was dissolved in CH$_2$Cl$_2$ (3 mL) and was treated with iPr$_2$NEt (36 µL, 0.31 mmol) and methyl chloroformate (6 µL, 0.08 mmol). After stirring for 1 h at room temperature, a second portion of methyl chloroformate (3 µL) was added and the reaction was stirred for 1 h more. The solvent was evaporated, and the residue was partitioned between ethyl acetate and saturated NaHCO$_3$. The organic phase was washed with saturated NaCl, dried (MgSO$_4$), filtered and evaporated. Chromatography on silica gel (5/1-CH$_2$Cl$_2$/ethyl acetate) afforded a solid, which was dissolved in ethyl acetate and precipitated with hexane. The supernatant was removed and the solid was dissolved in dioxane, filtered and lyophilized to afford (4-{4-[4-(3,5-Bis-trifluoromethyl-phenylcarbamoyl)-piperazin-1-yl]-[1,2,5]thiadiazol-3-yloxymethyl}-pyridin-2-yl)-carbamic acid methyl ester (6.5 mg, 15%) as a white solid: $^1$H NMR (400 M&, DMSO-d$_6$) δ 3.58-3.67 (m overlapping s, 11H), 5.54 (s, 2H), 7.10 (d, 1H, J=5.2), 7.62 (s, 1H), 7.98 (s, 1H), 8.22 (s, 2H), 8.28 (d, 1H, J=5.2), 9.30 (s, 1H), 10.31 (s, 1H); MS: 606 (M+1).

EXEMPLARY EMBODIMENTS

The following compounds listed in Table 2 are examples in accordance with formula I. Generally, the compounds listed in Table 2 were identified by LC-MS, isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.).

Compounds were identified according to either their observed mass [M+1] ion (positive mode) or [M−1] ion (negative mode). Three LC-MS conditions, and methods used, are as follows: Method A: Agilent, method 3.3_1 ml; Column: C18, 30×3 mm, 5 micron; (BP Series 1100 MSD); Solvent: A 0.05 M NH4OAc/Water. B Acetonitrile; Flow rate: 1 ml/min; Gradient: 0-0.25 min, 20% B, 0.25-1.25 min, 20-90% B, 1.25-2 min, 90% B; Total run time: 3 min; UV: 220 and 254 nm. Method B: Agilent, method 3×3ACCN; Column: C18, 30×4.6 mm, 3.5 micron; (Agilent 1100 Series LC/MSD); Flow rate: 2 ml/min; UV: 254 nm; Solvent and Gradient are the same as for method A. Method C: Waters, method 220POS: Column: Waters Xterra C18, 15×2.0 mm; (Waters 8-Channel MUX System); Solvent: A=0.01% TFA in H2O; B=0.01% TFA in MeOH; Flow rate: 3.5 mL/min; Gradient: 0-0.20 min, 5% B; 0.20-2.75 min, 5-100% B; 2.75-3.25 min, 100% B; 3.25-3.30 min, 100-5% B; 3.30-3.50 min, 5% B; Total run time: 3.5 min; UV: 220 nm.

$^1$H-NMR data for compounds was taken with a Varian AS400 Spectrometer (400 MHz, available from Varian GmbH, Darmstadt, Germany).

TABLE 2

| # | Name | Calculated Parent MW | Observed Mass | Retention Time (min) | Method | $^1$H-NMR |
|---|------|------|------|------|------|------|
| 1 | N-[(1R,2S)-2-phenylcyclopropyl]-4-{4-[(pyridin-4-ylmethyl)oxy]-1,2,5-thiadiazol-3-yl}piperazine-1-carboxamide | 436.54 | 437.2 | 1.71 | B | (CD$_3$OD) 8.69(d, 2H), 7.87(d, 2H), 7.13(m, 2H), 7.03(m, 3H), 5.68(s, 2H), 3.45(m, 8H), 2.66(m, 1H), 1.91(m, 1H), 1.07(m, 2H) ppm |
| 2 | N-[3,5-bis(trifluoromethyl)phenyl]-4-{4-[(pyridin-4-ylmethyl)oxy]-1,2,5-thiadiazol-3-yl}piperazine-1-carboxamide | 532.47 | 533.1 | 1.89 | B | (CDCl3) 8.62(d, 2H), 7.84(s, 2H), 7.50(s, 1H), 7.31(d, 2H), 7.06(s, 1H), 5.49(s, 2H), 3.68-3.60(m, 8H) ppm |
| 3 | N-[3,5-bis(trifluoromethyl)phenyl]-4-{4-[(pyridin-4-ylmethyl)oxy]-1,2,5-thiadiazol-3-yl}piperazine-1-carboxamide | 532.47 | 533 | 1.83 | A | (DMSO-d6) 9.29(s, 1H), 8.62(d, 2H), 8.23(s, 2H), 7.65(s, 1H), 7.45(d, 2H), 5.68(s, 2H), 3.69(m, 4H), 3.58(m, 4H) ppm |
| 4 | N-[4-(1-methylethyl)phenyl]-4-{4-[(pyridin-4-ylmethyl)oxy]-1,2,5-thiadiazol-3-yl}piperazine-1-carboxamide | 438.55 | 439 | 1.82 | B | (CDCl3) 8.638-8.622(d, 2H), 7.311-7.296(d, 2H), 7.248-7.227(d, 2H), 7.152-7.131(d, 2H), 6.284(br. s, 1H), 5.480(s, 2H), 3.615(s, 8H), 2.89-2.82(m, 1H), 1.231-1.214(d, 6H) ppm |
| 5 | N-(3-bromophenyl)-4-{4-[(pyridin-4-ylmethyl)oxy]-1,2,5-thiadiazol-3-yl}piperazine-1-carboxamide | 475.37 | 476 | 2.11 | C | |
| 6 | N-[3-(methylthio)phenyl]-4-{4-[(pyridin-4-ylmethyl)oxy]-1,2,5-thiadiazol-3-yl}piperazine-1-carboxamide | 442.57 | 443.0 | 1.65 | B | (CDCl$_3$) 8.63(d, 2H), 7.32(m, 3H), 7.18(m, 1H), 7.07(m, 1H), 6.98(m, 1H), 6.48(br. s, 1H), 5.48(s, 2H), 3.62(m, 8H), 2.47(s, 3H) ppm |
| 7 | N-(3-ethylphenyl)-4-{4-[(pyridin-4-ylmethyl)oxy]-1,2,5-thiadiazol-3-yl}piperazine-1-carboxamide | 424.53 | 425.1 | 1.66 | B | (CDCl$_3$) 8.68(br. s, 2H), 7.50(d, 2H), 7.16(m, 2H), 6.87(d, 1H), 6.57(s, 1H), 5.55(s, 2H), 3.63(m, 8H), 2.61(q, 2H), 1.22(t, 3H) ppm |
| 8 | N-(3,5-dimethylphenyl)-4-{4-[(pyridin-4-ylmethyl)oxy]-1,2,5-thiadiazol-3-yl}piperazine-1-carboxamide | 424.53 | 425 | 1.95 | C | |
| 9 | 4-{4-[(pyridin-4-ylmethyl)oxy]-1,2,5-thiadiazol-3-yl}-N-[3-(trifluoromethyl)phenyl]piperazine-1-carboxamide | 464.47 | 465.1 | 1.74 | B | (CDCl$_3$) 8.63(d, 2H), 7.63(s, 1H), 7.55(d, 1H), 7.38(m, 1H), 7.32(m, 3H), 6.60(s, 1H), 5.48(s, 2H), 3.63(m, 8H) ppm |
| 10 | N-[3,5-bis(trifluoromethyl)phenyl]-4-(4-{[(2-methylquinolin-4-yl)methyl]oxy}-1,2,5-thiadiazol-3-yl)piperazine-1-carboxamide | 596.55 | 597.1 | 2.05 | A | (DMSO-d6) 9.31(s, 1H), 8.33(d, 1H), 8.21(s, 2H), 8.14(d, 1H), 8.01(t, 1H), 7.85(t, 1H), 7.80(s, 1H), 7.61(s, 1H), 6.14(s, 2H), 3.61(m, 4H), 3.56(m, 4H), 2.85(s, 3H) ppm |
| 11 | N-[3,5-bis(trifluoromethyl)phenyl]-4-[4-({[3-(dimethylamino)phenyl]methyl}oxy)-1,2,5-thiadiazol-3-yl]piperazine-1-carboxamide | 574.55 | 573.1 | 2.21 | A | (DMSO-d6) 9.23(s, 1H), 8.18(s, 2H), 7.59(s, 1H), 7.22(m, 1H), 6.89(d, 1H), 6.78(m, 2H), 5.39(m, 4H), 3.61(m, 4H), 3.53(m, 4H), 2.92(s, 6H) ppm |
| 12 | N-[3,5-bis(trifluoromethyl)phenyl]-4-[4-(1H-indol-5-yloxy)-1,2,5-thiadiazol-3-yl]piperazine-1-carboxamide | 556.49 | 555.1 | 1.95 | A | (DMSO-d6) 9.17(s, 1H), 9.09(s, 1H), 8.15(s, 2H), 7.81(d, 1H), 7.53(m, 2H), 6.96(d, 1H), 6.75(d, 1H), 6.63(d, 1H), 3.53(m, 4H), 3.02(m, 4H) ppm |
| 13 | N-[3,5-bis(trifluoromethyl)phenyl]-4-{4-[(3-thienylmethyl)oxy]-1,2,5-thiadiazol-3-yl}piperazine-1-carboxamide | 537.51 | 536.1 | 2.08 | A | (CDCl3) 7.88(s, 2H), 7.53(s, 1H), 7.40-7.39(m, 1H), 7.36(dd, 1H), 7.17(dd, 1H), 6.67(s, 1H), 5.48(s, 2H), 3.64-3.61(m, 8H) ppm |

TABLE 2-continued

| # | Name | Calculated Parent MW | Observed Mass | Retention Time (min) | Method | ¹H-NMR |
|---|---|---|---|---|---|---|
| 14 | N-[3,5-bis(trifluoromethyl)phenyl]-4-{4-[(2-morpholin-4-ylethyl)oxy]-1,2,5-thiadiazol-3-yl}piperazine-1-carboxamide | 554.51 | 553.1 | 1.87 | A | (DMSO-d6) 9.36(s, 1H), 8.22(s, 2H), 7.62(s, 1H), 4.74(m, 2H), 4.00(bs, 2H), 3.58(m, 15H), 3.23(bs, 2H) ppm |
| 15 | N-[3,5-bis(trifluoromethyl)phenyl]-4-(4-{[2-(1H-imidazol-1-yl)ethyl]oxy}-1,2,5-thiadiazol-3-yl)piperazine-1-carboxamide | 535.47 | 534.1 | 1.81 | A | (DMSO-d6) 9.32(s, 1H), 8.22(s, 2H), 7.71(d, 1H), 7.62(d, 1H), 7.27(s, 1H), 6.93(s, 1H), 4.65(m, 2H), 4.44(m, 2H), 3.56(m, 4H), 3.39(m, 4H) ppm |
| 16 | N-[3,5-bis(trifluoromethyl)phenyl]-4-{4-[(1-methylpiperidin-4-yl)oxy]-1,2,5-thiadiazol-3-yl}piperazine-1-carboxamide | 538.52 | 537.2 | 1.68 | A | (DMSO-d6) 9.31(s, 1H), 8.23(s, 2H), 7.63(s, 1H), 3.63(m, 4H), 3.58(m, 4H), 3.34(m, 8H), 2.80(m, 3H) ppm |
| 17 | N-[3,5-bis(trifluoromethyl)phenyl]-4-[4-({[4-(methyloxy)phenyl]methyl}oxy)-1,2,5-thiadiazol-3-yl]piperazine-1-carboxamide | 561.51 | 560.1 | 2.1 | B | (DMSO-d6) 9.22(s, 1H), 8.17(s, 2H), 7.59(s, 1H), 7.42(d, 2H), 6.95(d, 2H), 5.37(s, 2H), 3.75(s, 3H), 3.56(t, 4H), 3.48(t, 4H) ppm |
| 18 | 4-[4-({[3,4-bis(methyloxy)phenyl]methyl}oxy)-1,2,5-thiadiazol-3-yl]-N-[3,5-bis(trifluoromethyl)phenyl]piperazine-1-carboxamide | 591.53 | 590.1 | 2.05 | B | (DMSO-d6) 9.24(s, 1H), 8.20(s, 2H), 7.61(s, 1H), 7.12(s, 1H), 7.04(d, 1H), 7.00(d, 1H), 5.38(s, 2H), 3.80-3.76(m, 8H), 3.59-3.51(m, 6H) ppm |
| 19 | 4-{4-[(1,3-benzodioxol-5-ylmethyl)oxy]-1,2,5-thiadiazol-3-yl}-N-[3,5-bis(trifluoromethyl)phenyl]piperazine-1-carboxamide | 575.49 | 574.1 | 2.08 | B | (DMSO-d6) 9.24(s, 1H), 8.21(s, 2H), 7.61(s, 1H), 7.10(s, 1H), 7.01(d, 1H), 6.96(d, 1H), 6.04(s, 2H), 5.35(s, 2H), 3.59(t, 4H), 3.51(t, 4H) ppm |
| 20 | N-[3,5-bis(trifluoromethyl)phenyl]-4-{4-[(furan-3-ylmethyl)oxy]-1,2,5-thiadiazol-3-yl}piperazine-1-carboxamide | 521.44 | 520.1 | 2.04 | B | (DMSO-d6) 9.28(s, 1H), 8.23(s, 2H), 7.89(s, 1H), 7.72(s, 1H), 7.65(d, 1H), 6.67(d, 1H), 5.36(s, 2H), 3.65(t, 4H), 3.56(t, 4H) ppm |
| 21 | N-[3,5-bis(trifluoromethyl)phenyl]-4-{4-[(tetrahydrofuran-3-ylmethyl)oxy]-1,2,5-thiadiazol-3-yl}piperazine-1-carboxamide | 525.47 | 524.1 | 1.98 | B | (DMSO-d6) 9.26(s, 1H), 8.20(s, 2H), 7.59(s, 1H), 4.37-4.27(m, 2H), 3.79-3.73(m, 2H), 3.67-3.50(m, 10H), 2.72-2.69(m, 1H), 2.03-2.00(m, 1H), 1.68-1.64(m, 1H) ppm |
| 22 | N-[3,5-bis(trifluoromethyl)phenyl]-2-methyl-4-{4-[(pyridin-4-ylmethyl)oxy]-1,2,5-thiadiazol-3-yl}piperazine-1-carboxamide | 546.49 | 547.1 | 1.96 | B | (CDCl3) 8.80(br., d, 2H), 7.93(s, 2H), 7.66(d, 2H), 7.53(s, 1H), 6.90(s, 1H), 5.64(d, 2H), 4.43(br., m, 1H), 4.17(d, 1H), 4.07(d, 1H), 3.98(d, 1H), 3.46(td, 1H), 3.20(dd, 1H), 3.11(td, 1H) 1.39(d, 3H) ppm |
| 23 | N-[3,5-bis(trifluoromethyl)phenyl]-4-{4-[(pyridin-4-ylmethyl)oxy]-1,2,5-thiadiazol-3-yl}-1,4-diazepane-1-carboxamide | 546.49 | 547 | 1.84 | B | (CDCl3) 9.52(s, 2H), 7.838(s, 2H), 7.508(s, 1H), 7.321-7.307(d, 2H), 6.769(br. s, 1H), 5.464(s, 2H), 3.925-3.851(m, 4H), 3.820-3.790(t, 2H), 3.612-3.582(t, 2H), 1.987-1.959(m, 2H) ppm |
| 24 | 1-({[(1S,2R,5S)-5-methyl-2-(1-methylethyl)cyclohexyl]oxy}acetyl)-4-{4-[(pyridin-4-ylmethyl)oxy]-1,2,5-thiadiazol-3-yl}piperazine | 473.64 | 474.2 | 2.14 | B | (CD3OD) 8.83(d, 2H), 8.04(d, 2H), 5.81(s, 2H), 4.33(d, 1H), 4.16(d, 1H), 3.75-3.56(m, 8H), 3.23(m, 1H), 2.19(m, 2H), 1.66(m, 2H), 1.37(m, 1H), 1.26(m, 1H), 1.05(m, 1H), 1.02-0.82(m, 8H), 0.79(d, 3H) ppm |
| 25 | 5-phenyl-N-(1-{4-[(pyridin-4-ylmethyl)oxy]-1,2,5-thiadiazol-3-yl}pyrrolidin-3-yl)-1,3-oxazole-4-carboxamide | 448.51 | 449 | 1.76 | B | (CDCl3) 8.629-8.614(d, 2H), 8.304-8.279(m, 2H), 7.842(s, 1H), 7.506-7.395(m, 4H), 7.333-7.318(d, 2H), 5.460(s, 2H), 4.739(m, 1H), 4.062-4.019(m, 1H), 3.899-3.755(m, 3H), 2.40-2.31(m, 1H), 2.13-2.08(m, 1H) ppm |

TABLE 2-continued

| # | Name | Calculated Parent MW | Observed Mass | Retention Time (min) | Method | ¹H-NMR |
|---|---|---|---|---|---|---|
| 26 | 1-{4-[(pyridin-4-ylmethyl)oxy]-1,2,5-thiadiazol-3-yl}-4-{[3-(trifluoromethyl)phenyl]acetyl}piperazine | 463.48 | 464.1 | 1.81 | B | (CD$_3$OD) 8.83(d, 2H), 8.05(d, 2H), 7.60-7.54(m, 4H), 5.81(s, 2H), 3.94(s, 2H), 3.74(m, 4H), 3.57(m, 2H), 3.52(m, 2H) ppm |
| 27 | N-[3,5-bis(trifluoromethyl)phenyl]-4-{4-[(piperidin-4-ylmethyl)oxy]-1,2,5-thiadiazol-3-yl}piperazine-1-carboxamide | 538.52 | 539.2 | 1.69 | B | (DMSO-d$_6$) δ 9.37(s, 1H), 8.25(s, 2H), 7.62(s, 1H), 4.28(d, 2H), 3.63(m, 4H), 3.54(m, 4H), 3.08(d, 2H), 2.59(t, 2H), 1.93(m, 1H), 1.71(d, 2H), 1.29(qd, 2H) |
| 28 | N-[3,5-bis(trifluoromethyl)phenyl]-N'-[(1-{4-[(pyridin-4-ylmethyl)oxy]-1,2,5-thiadiazol-3-yl}piperidin-4-yl)methyl]urea | 561.51 | 561 | 1.85 | B | (DMSO-d6) 9.207(s, 1H), 8.607-8.593(d, 2H), 8.083,(s, 2H), 7.55(s, 1H), 7.438-7.423(d, 2H), 6.621-6.592(t, 1H), 5.520(s, 2H), 4.163-4.131(d, 2H), 3.302-3.031(t, 2H), 2.909-2.850(t, 2H), 1.743-1.713(m, 3H), 1.274-1.243(m, 2H) ppm |
| 29 | N-[3,5-bis(trifluoromethyl)phenyl]-4-{4-[(3-pyridin-3-ylpropyl)oxy]-1,2,5-thiadiazol-3-yl}piperazine-1-carboxamide | 560.52 | 561.1 | 1.98 | B | (DMSO-d6) 9.30(s, 1H), 8.70(s, 2H), 8.23-8.19(m, 3H), 7.79-7.75(m, 1H), 7.59(s, 1H), 4.44-4.40(m, 2H), 3.61(t, 4H), 3.48(t, 4H), 2.91-2.87(m, 2H), 2.18-2.14(m, 2H) ppm |
| 30 | N-[3,5-bis(trifluoromethyl)phenyl]-4-{1,1-dioxido-4-[(pyridin-4-ylmethyl)oxy]-1,2,5-thiadiazol-3-yl}piperazine-1-carboxamide | 564.47 | 563 | 1.55 | A | (DMSO-d6) 9.25(s, 1H), 8.29(d, 2H), 8.21(s, 2H), 7.62(s, 1H), 7.56(d, 2H), 5.46(d, 2H), 3.65(m, 8H) ppm |
| 31 | 4-[4-(1-azabicyclo[2.2.2]oct-3-yloxy)-1,2,5-thiadiazol-3-yl]-N-[3,5-bis(trifluoromethyl)phenyl]piperazine-1-carboxamide | 550.53 | 549 | 1.52 | A | (DMSO-d6) 9.81(s, 1H), 9.31(s, 1H), 8.21(s, 2H), 7.60(s, 1H), 5.20(m, 1H), 3.80-3.21(m, 15H), 2.00-1.75(m, 4H) ppm |
| 32 | 4-[({4-[4-({[3,5-bis(trifluoromethyl)phenyl]amino}carbonyl)piperazin-1-yl]-1,2,5-thiadiazol-3-yl}oxy)methyl]benzoic acid | 575.49 | 574 | 1.62 | A | (DMSO-d6) 9.24(s, 1H), 8.19(s, 2H), 7.96(d, 2H), 7.59(s, 2H), 7.57(s, 1H), 5.54(s, 2H), 3.62-3.52(m, 8H) ppm |
| 33 | N-[3,5-bis(trifluoromethyl)phenyl]-4-{4-[(piperidin-3-ylmethyl)oxy]-1,2,5-thiadiazol-3-yl}piperazine-1-carboxamide | 538.52 | 537 | 1.5 | A | (DMSO-d6) 9.30(s, 1H), 8.20(s, 2H), 7.60(s, 1H), 4.32(m, 2H), 3.63-3.51(m, 8H), 1.99(m, 7H), 1.82(m, 2H) ppm |
| 34 | N-[3,5-bis(trifluoromethyl)phenyl]-4-{4-[(2-pyrrolidin-1-ylethyl)oxy]-1,2,5-thiadiazol-3-yl}piperazine-1-carboxamide | 538.52 | 537 | 1.54 | A | (DMSO-d6) 9.90(br., s, 1H), 9.33(s, 1H), 8.20(s, 2H), 7.60(s, 1H), 4.70(t, 2H), 3.70-3.34(br., m, 12H), 3.13(br., m, 2H), 2.07-1.87(br., m, 4H) ppm |
| 35 | 4-{4-[(2-amino-2-methylpropyl)oxy]-1,2,5-thiadiazol-3-yl}-N-[3,5-bis(trifluoromethyl)phenyl]piperazine-1-carboxamide | 512.48 | 511 | 1.48 | A | (DMSO-d6) 9.29(s, 1H), 8.21(d, 2H), 8.10(br., s, 2H), 7.60(s, 1H), 4.42(s, 2H), 3.65-3.53(m, 8H), 1.37(s, 6H) ppm |
| 36 | N-[3,5-bis(trifluoromethyl)phenyl]-1-{4-[(pyridin-4-ylmethyl)oxy]-1,2,5-thiadiazol-3-yl}piperidine-4-carboxamide | 531.48 | 532.0 | 1.95 | B | (CD$_3$OD) 8.55(d, 2H), 8.22(s, 2H), 7.63(s, 1H), 7.50(d, 2H), 5.58(s, 2H), 4.32(m, 2H), 3.02(m, 2H), 2.64(m, 1H), 1.99-1.91(m, 4H) ppm |
| 37 | 1-{4-[(pyridin-4-ylmethyl)oxy]-1,2,5-thiadiazol-3-yl}-N-[3-(trifluoromethyl)phenyl]piperidine-4-carboxamide | 463.48 | 464.0 | 1.82 | B | (CD$_3$OD) 8.54(d, 2H), 8.02(s, 1H), 7.74(d, 1H), 7.51-7.46(m, 3H), 7.36(d, 1H), 5.57(s, 2H), 4.32(m, 2H), 3.00(m, 2H), 2.64(m, 1H), 1.96-1.90(m, 4H) ppm |

TABLE 2-continued

| # | Name | Calculated Parent MW | Observed Mass | Retention Time (min) | Method | $^1$H-NMR |
|---|------|----------------------|---------------|----------------------|--------|-----------|
| 38 | N-[3,5-bis(trifluoromethyl)phenyl]-4-{3-[(pyridin-4-ylmethyl)oxy]pyrazin-2-yl}piperazine-1-carboxamide | 526.44 | 525.1 | 1.78 | A | (CDCl3) 8.63(d, 2H), 7.90(s, 2H), 7.81(d, 1H), 7.62(d, 1H), 7.54(s, 1H), 7.34(d, 2H), 7.26(s, 2H), 6.78(s, 1H), 5.48(s, 2H), 3.67(m, 8H) ppm |
| 39 | N-[3,5-bis(trifluoromethyl)phenyl]-4-{3-[(pyridin-4-ylmethyl)oxy]pyrazin-2-yl}piperazine-1-carboxamide | 526.44 | 525.1 | 2.29 | A | (CDCl3) 8.62(d, 2H), 7.89(s, 2H), 7.79(d, 2H), 7.61(d, 1H), 7.34(dd, 2H), 6.93(s, 1H), 5.47(s, 2H), 3.67(m, 8H) ppm |
| 40 | 4-{3-[(pyridin-4-ylmethyl)oxy]pyrazin-2-yl}-N-[3-(trifluoromethyl)phenyl]piperazine-1-carboxamide | 458.44 | 459.1 | 1.71 | A | (CDCl3) 8.96(s, 1H), 8.81(bs, 2H), 7.94(s, 1H), 7.87(d, 1H), 7.84(bs, 1H), 7.75(d, 1H), 7.63(d, 1H), 7.48(t, 1H), 7.29(d, 1H), 5.64(s, 2H), 3.64(m, 4H), 3.57(m, 4H) ppm |
| 41 | N-[3,5-bis(trifluoromethyl)phenyl]-4-{4-[(2-piperidin-4-ylethyl)oxy]-1,2,5-thiadiazol-3-yl}piperazine-1-carboxamide | 552.54 | 551.2 | 1.69 | B | (DMSO-d6) 9.29(s, 1H), 8.46(s, 1H), 8.20(s, 2H), 7.60(s, 1H), 4.50-4.42(m, 2H), 3.60(t, 4H), 3.50(t, 4H), 3.41-3.24(m, 2H), 2.86-2.81(m, 2H), 1.85(d, 2H), 1.76-1.75(m, 3H), 1.38-1.33(m, 2H) ppm |
| 42 | 2-methyl-4-{4-[(pyridin-4-ylmethyl)oxy]-1,2,5-thiadiazol-3-yl}-N-[3-(trifluoromethyl)phenyl]piperazine-1-carboxamide | 478.5 | 477.1 | 1.79 | B | (DMSO-d6) 8.83(s, 1H), 8.59(s, 2H), 7.92(s, 1H), 7.75(m, 1H), 7.43(m, 3H), 7.24(m, 1H), 5.52(s, 2H), 4.47(s, 1H), 4.04(m, 2H), 3.36(s, 1H), 3.25(t, 1H), 3.08(d, 1H), 2.97(t, 1H), 1.20(m, 3H) ppm |
| 43 | 1-phenyl-4-{4-[(pyridin-4-ylmethyl)oxy]-1,2,5-thiadiazol-3-yl}piperazine | 353.45 | 354.1 | 1.78 | B | (DMSO-d$_6$) δ 8.62(d, 2H), 7.46(d, 2H), 7.23(t, 2H), 7.01(d, 2H), 6.82(t, 1H), 5.58(s, 2H), 3.64(m, 4H), 3.23(m, 4H) |
| 44 | 1-[(4-methylphenyl)methyl]-4-{4-[(pyridin-4-ylmethyl)oxy]-1,2,5-thiadiazol-3-yl}piperazine | 381.5 | 382.1 | 1.76 | B | (DMSO-d$_6$) δ 8.57(d, 2H), 7.41(d, 2H), 7.19(d, 2H), 7.11(d, 2H), 5.48(s, 2H), 3.49(m, 4H), 3.47(s, 2H), 2.44(m, 4H), 2.23(s, 3H) |
| 45 | N-[3,5-bis(trifluoromethyl)phenyl]-4-{4-[(pyridin-4-ylmethyl)amino]-1,2,5-thiadiazol-3-yl}piperazine-1-carboxamide | 531.48 | 532 | 1.9 | B | (DMSO-d6) 9.41(s, 1H), 8.65(br, s, 2H), 8.2(s, 2H), 7.75(d, 1H), 7.6(s, 2H), 7.45(t, 1H), 4.65(d, 2H), 3.65(m, 4H), 3.22(m, 4H) |
| 46 | 4-{4-[(pyridin-4-ylmethyl)oxy]-1,2,5-thiadiazol-3-yl}-N-[3-(trifluoromethyl)phenyl]-1,4-diazepane-1-carboxamide | 478.5 | 479 | 1.65 | B | (CDCl3) 8.639(s, 2H), 7.639(s, 1H), 7.529-7.507(d, 1H), 7.408-7.368(t, 1H), 7.319-7.305(d, 2H), 7.286(s, 1H), 6.552(s, 1H), 5.464(s, 2H), 3.904-3.859(t, 2H), 3.844-3.829(t, 2H), 3.795-3.781(t, 2H), 3.587-3.556(t, 2H), 1.997(m, 2H) ppm |
| 47 | 2-methyl-1-{[2-(methyloxy)phenyl]carbonyl}-4-{4-[(pyridin-4-ylmethyl)oxy]-1,2,5-thiadiazol-3-yl}piperazine | 425.51 | 426 | 2.05 | A | (CDCl3) 8.639(m, 2H), 7.389-7.227(m, 4H), 7.026-6.920(m, 2H), 5.494(m, 2H), 5.077[br. s, 1/2H(DS)], 4.714-4.708[d, 1/2H(DS)], 4.209-3.937(br. m, 2H), 3.895-3.765(m, 4H), 3.412-2.991(m, 3H), 1.403-1.26(m, 3H) ppm |
| 48 | N-[5-chloro-2-(methyloxy)phenyl]-N'-(1-{4-[(pyridin-4-ylmethyl)oxy]-1,2,5-thiadiazol-3-yl}pyrrolidin-3-yl)urea | 460.94 | 461.1 | 2.12 | B | (CDCl$_3$) 8.58(d, 2H), 8.17(s, 1H), 7.27(d, 1H), 7.24(s, 1H), 7.00(s, 1H), 6.87(d, 1H), 6.69(d, 1H), 5.41(s, 2H), 5.30(d, 1H), 4.52-4.50(m, 1H), 3.93-3.89(m, 1H), 3.79-3.67(m, 3H), 2.28-2.24(m, 1H), 2.00-1.70(m, 1H), 1.70(s, 3H) ppm |

TABLE 2-continued

| # | Name | Calculated Parent MW | Observed Mass | Retention Time (min) | Method | ¹H-NMR |
|---|---|---|---|---|---|---|
| 49 | N-[5-methyl-2-(methyloxy)phenyl]-N'-(1-{4-[(pyridin-4-ylmethyl)oxy]-1,2,5-thiadiazol-3-yl}pyrrolidin-3-yl)urea | 440.53 | 441.2 | 1.7 | B | (CDCl$_3$) 8.55(s, 2H), 7.88(s, 1H), 7.24(d, 2H), 7.16(s, 1H), 6.71-6.36(m, 2H), 5.88(d, 1H), 5.36(s, 2H), 4.50-4.48(m, 1H), 3.91-3.87(m, 1H), 3.75-3.64(m, 5H), 2.23-2.19(m, 4H), 1.98-1.95(m, 2H) ppm |
| 50 | N-(1-{4-[(pyridin-4-ylmethyl)oxy]-1,2,5-thiadiazol-3-yl}pyrrolidin-3-yl)-N'-[3-(trifluoromethyl)phenyl]urea | 464.47 | 465.1 | 2.14 | B | (DMSO-d6) 8.57(d, 2H), 8.42(s, 1H), 7.87(s, 1H), 7.77(s, 1H), 7.42-7.29(m, 3H), 7.13(d, 1H), 6.45(d, 1H), 5.47(s, 2H), 4.40(m, 1H), 3.93-3.89(m, 1H), 3.84-3.73(m, 2H), 3.67-3.64(m, 1H), 2.28-2.20(m, 1H), 2.02-1.96(s, 1H) ppm |
| 51 | 2-methyl-N-[4-(1-methylethyl)phenyl]-4-{4-[(pyridin-4-ylmethyl)oxy]-1,2,5-thiadiazol-3-yl}piperazine-1-carboxamide | 452.58 | 453 | 2.23 | A | (CDCl3) 8.651-8.590(br. m, 2H), 7.332-7.259(m, 4H), 7.147-7.127(d, 2H), 6.69(s, 1H), 5.491-5478(dd, 2H), 4.361(br. s, 1H), 4.116-4.027(m, 2H), 3.941-3.909(d, 1H), 3.392-3.354(t, 1H), 3.134-3.095(d, 1H), 3.029-2.9(t, 1H), 2.868-2.834(m, 1H), 1.326-1.309(d, 3H), 1.218-1.201(d, 6H) ppm |
| 52 | 2-methyl-N-[3-(methylthio)phenyl]-4-{4-[(pyridin-4-ylmethyl)oxy]-1,2,5-thiadiazol-3-yl}piperazine-1-carboxamide | 456.59 | 457 | 2.15 | A | (CDCl3) 8.654-8.640(d, 2H), 7.359-7.321(m, 3H), 7.197-7.157(t, 1H), 7.110-7.087(d, 1H), 6.929-6.908(d, 1H), 6.726(s, 1H), 5.528-5.447(m, 2H), 4.366(br. s, 1H), 4.127-4.035(m, 2H), 3.944-3.912(d, 1H), 3.400-3.370(m, 1H), 3.138-3.098(m, 1H), 3.035-2.96(m, 1H), 2.451(s, 3H), 1.337-1.321(d, 3H) ppm |
| 53 | (2R)-N-[3,5-bis(trifluoromethyl)phenyl]-2-methyl-4-{4-[(pyridin-4-ylmethyl)oxy]-1,2,5-thiadiazol-3-yl}piperazine-1-carboxamide | 546.49 | 547 | 2.04 | B | (CDCl3) 8.81(d, 2H), 7.92(s, 2H), 7.69(d, 2H), 7.54(s, 1H), 6.77(s, 1H), 5.65(d, 2H), 4.42(br., m, 1H), 4.18-3.95(m, 3H), 3.34(br., m, 3H) 1.39(d, 3H) ppm |
| 54 | (2R)-2-methyl-4-{4-[(pyridin-4-ylmethyl)oxy]-1,2,5-thiadiazol-3-yl}-N-[3-(trifluoromethyl)phenyl]piperazine-1-carboxamide | 478.5 | 479 | 1.84 | B | (CDCl3) 8.83(d, 2H), 7.71(d, 2H), 7.68(s, 1H), 7.58(d, 1H), 7.42(t, 1H), 7.31(d, 1H), 6.56(s, 1H), 5.66(d, 2H), 4.41(m, 1H), 4.17-3.94(m, 3H) 3.47-3.05(m, 3H) ppm |
| 55 | 1-[4-(4-{4-[(pyridin-4-ylmethyl)oxy]-1,2,5-thiadiazol-3-yl}piperazin-1-yl)phenyl]ethanone | 395.49 | 361.1 | 2.1 | B | (DMSO-d6) 8.87-8.57(m, 2H), 7.90(d, 2H), 7.79(d, 2H), 6.96(d, 2H), 5.70(s, 2H), 3.65-3.63(m, 4H), 3.46-3.44(m, 4H), 2.49(s, 3H) ppm |
| 56 | 2-(4-{4-[(pyridin-4-ylmethyl)oxy]-1,2,5-thiadiazol-3-yl}piperazin-1-yl)pyrimidine | 355.42 | 356.1 | 2.06 | B | (DMSO-d6) 8.52(s, 2H), 8.36(s, 2H), 7.37(s, 2H), 6.58(s, 1H), 5.47(s, 2H), 3.80(t, 4H), 3.51(t, 4H) ppm |
| 57 | 1-[2-nitro-4-(trifluoromethyl)phenyl]-4-{4-[(pyridin-4-ylmethyl)oxy]-1,2,5-thiadiazol-3-yl}piperazine | 466.44 | 467.1 | 2.2 | B | (DMSO-d6) 8.57(s, 2H), 8.17(s, 1H), 7.86(s, 1H), 7.53(d, 1H), 7.47-7.42(m, 2H), 5.52(s, 2H), 3.65-3.63(t, 4H), 3.49-3.17(t, 4H) ppm |
| 58 | (2S)-N-[3,5-bis(trifluoromethyl)phenyl]-2-methyl-4-{4-[(pyridin-4-ylmethyl)oxy]-1,2,5-thiadiazol-3-yl}piperazine-1-carboxamide | 546.49 | 547.1 | 2.23 | A | (CDCl3) 8.81(s, 2H), 7.94(s, 2H), 7.73(d, 2H), 7.48(s, 1H), 7.43(s, 1H), 5.66(d, 2H), 4.47(m, 1H), 4.15(d, 1H), 4.05(d, 2H), 3.46(m, 1H), 3.16(d, 1H), 3.05(m, 2H) ppm |
| 59 | (2S)-2-methyl-4-{4-[(pyridin-4-ylmethyl)oxy]-1,2,5-thiadiazol-3-yl}-N-[3-(trifluoromethyl)phenyl]piperazine-1-carboxamide | 478.5 | 479.1 | 2.14 | A | (DMSO-d6) 8.81(d, 2H), 7.74(d, 2H), 7.68(s, 1H), 7.60(d, 1H), 7.41(t, 2H), 7.27(m, 2H), 6.8(s, 1H), 5.66(d, 2H), 4.42(m, 1H), 4.15(d, 1H), 4.05(d, 1H), 3.96(d, 1H), 3.42(m, 1H), 3.21(m, 1H), 3.01(m, 1H) ppm |

TABLE 2-continued

| # | Name | Calculated Parent MW | Observed Mass | Retention Time (min) | Method | $^1$H-NMR |
|---|---|---|---|---|---|---|
| 60 | N-[3,5-bis(trifluoromethyl)phenyl]-4-(3-hydroxypyrazin-2-yl)piperazine-1-carboxamide | 435.33 | 434.1 | 2.04 | A | (DMSO-d6) 9.27(d, 1H), 8.86(d, 1H), 8.23(d, 2H), 7.92(d, 1H), 7.63(d, 1H), 6.90(d, 1H), 3.76(m, 4H), 4.67(d, 4H) ppm |
| 61 | 2-[2,5-bis(trifluoromethyl)phenyl]-N-(1-{4-[(pyridin-4-ylmethyl)oxy]-1,2,5-thiadiazol-3-yl}pyrrolidin-3-yl)acetamide | 531.48 | 532.1 | 2.2 | B | (CDCl$_3$) 8.58(d, 2H), 7.78-7.75(s, 2H), 7.64(d, 1H), 7.28-7.24(m, 2H), 5.95(d, 1H), 5.42(s, 2H), 4.58-4.54(m, 1H), 3.90-3.87(m, 1H), 3.79-3.67(m, 4H), 3.61-3.58(m, 1H), 2.30-2.21(m, 1H), 1.97-1.89(m, 1H) ppm |
| 62 | 1-{[2,5-bis(trifluoromethyl)phenyl]acetyl}-2-methyl-4-{4-[(pyridin-4-ylmethyl)oxy]-1,2,5-thiadiazol-3-yl}piperazine | 545.51 | 546 | 2.3 | A | (CDCl3) 8.645(br. s, 2H), 7.793-7.772(d, 1H), 7.648-7.626(m, 2H), 7.318-7.305(s, 2H), 5.512-5.430(m, 2H), 4.876[br. s, 1/2H (DS)], 4.543-4.511(d, 1/2H(DS)), 4.163-3.871[m, 4.5H(DS)], 3.700-3.574(m, 1H), 3.168-2.877[m, 2.5H(DS)], 1.418-1.257(m, 3H) ppm |
| 63 | N-[3,5-bis(trifluoromethyl)phenyl]-2-methyl-4-{3-[(pyridin-4-ylmethyl)oxy]pyrazin-2-yl}piperazine-1-carboxamide | 540.47 | 539.1 | 2.32 | A | (CDCl3) 8.86(d, 2H), 7.93(s, 2H), 7.83(m, 3H), 7.52(d, 2H), 5.69(d, 2H), 4.45(m, 1H), 4.24(d, 1H), 4.13(d, 1H), 3.97(d, 1H), 3.46(m, 1H), 3.24(dd, 1H), 3.06(m, 1H) ppm |
| 64 | 2-methyl-4-{3-[(pyridin-4-ylmethyl)oxy]pyrazin-2-yl}-N-[3-(trifluoromethyl)phenyl]piperazine-1-carboxamide | 472.47 | 471.1 | 2.16 | A | (CDCl3) 8.84(d, 2H), 7.85(s, 2H), 7.83(d, 2H), 7.67(s, 1H), 7.59(d, 1H), 7.59(d, 1H), 7.40(t, 1H), 7.36(d, 2H), 7.00(s, 1H), 5.69(d, 2H), 4.44(m, 1H), 4.22(d, 1H), 4.12(d, 1H), 3.97(d, 1H), 3.46(m, 1H), 3.22(dd, 1H), 3.06(m, 1H) ppm |
| 65 | N-[3,5-bis(trifluoromethyl)phenyl]-2,6-dimethyl-4-{3-[(pyridin-4-ylmethyl)oxy]pyrazin-2-yl}piperazine-1-carboxamide | 554.49 | 553.1 | 2.39 | A | (CDCl3) 8.87(d, 2H), 7.92(s, 2H), 7.83(m, 4H), 7.51(d, 2H), 5.69(s, 2H), 4.37(m, 2H), 4.17(d, 2H), 3.15(m, 2H), 1.48(d, 5H)ppm |
| 66 | 2,6-dimethyl-4-{3-[(pyridin-4-ylmethyl)oxy]pyrazin-2-yl}-N-[3-(trifluoromethyl)phenyl]piperazine-1-carboxamide | 486.5 | 485.2 | 1.89 | A | (CDCl3) 8.76(s, 1H), 7.81(d, 1H), 7.70(m, 3H), 7.61(d, 2H), 7.54(d, 2H), 5.62(s, 2H), 4.35(m, 2H), 4.17(d, 2H), 3.12(m, 3H), 1.37(d, 3H), 1.29(m, 3H) ppm |
| 67 | N-(1-{3-[(pyridin-4-ylmethyl)oxy]pyrazin-2-yl}pyrrolidin-3-yl)-N'-[3-(trifluoromethyl)phenyl]urea | 458.44 | 459 | 1.7 | B | (DMSO-d6) 8.80(m, 3H), 7.97(s, 1H), 7.90(d, 2H), 7.68(d, 1H), 7.4(m, 2H), 7.3(d, 1H), 7.2(m, 1H), 6.8(d, 1H), 5.3(s, 2H), 4.25(m, H), 3.9(m, 1H), 3.75(m, 2H), 3.6(m, 1H), 2.40(m, 1H), 1.85(m, 1H) |
| 68 | N-[3,5-bis(trifluoromethyl)phenyl]-N'-(1-{3-[(pyridin-4-ylmethyl)oxy]pyrazin-2-yl}pyrrolidin-3-yl)urea | 526.44 | 527 | 1.85 | B | (DMSO-d6) 9.20(s, 1H), 8.75(d, 2H), 8.05(s, 2H), 7.85(d, 2H), 7.68(m, 1H), 7.55(s, 1H), 7.3(m, 1H), 7.0(d, 1H), 5.3(s, 2H), 4.25(m, H), 3.9(m, 1H), 3.75(m, 2H), 3.6(m, 1H), 2.40(m, 1H), 1.85(m, 1H) |
| 69 | N-[3,5-bis(trifluoromethyl)phenyl]-2,6-dimethyl-4-{4-[(pyridin-4-ylmethyl)oxy]-1,2,5-thiadiazol-3-yl}piperazine-1-carboxamide | 560.52 | 561.1 | 2.47 | A | (CDCl$_3$) 8.67(d, 2H), 7.91(s, 2H), 7.53(s, 1H), 7.36(d, 2H), 6.74(s, 1H), 5.51(s, 2H), 4.31(m, 2H), 4.10(d, 2H), 3.11(dd, 2H), 1.47(d, 6H) ppm |
| 70 | 2,6-dimethyl-4-{4-[(pyridin-4-ylmethyl)oxy]-1,2,5-thiadiazol-3-yl}-N-[3-(trifluoromethyl)phenyl]piperazine-1-carboxamide | 492.52 | 493.1 | 2.27 | A | (CDCl3) 8.65(d, 2H), 7.69(s, 1H), 7.59(d, 1H), 7.41(t, 1H), 7.35(d, 2H), 7.30(d, 1H), 6.54(s, 1H), 5.50(s, 2H), 4.30(m, 2H), 4.10(d, 2H), 3.10(dd, 2H), 1.45(d, 6H) ppm |

TABLE 2-continued

| # | Name | Calculated Parent MW | Observed Mass | Retention Time (min) | Method | ¹H-NMR |
|---|------|----------------------|---------------|----------------------|--------|--------|
| 71 | N-[3,5-bis(trifluoromethyl)phenyl]-3-methyl-4-{3-[(pyridin-4-ylmethyl)oxy]pyrazin-2-yl}piperazine-1-carboxamide | 540.47 | 541.1 | 2.33 | A | (CDCl$_3$) 8.77(d, 2H), 7.94(s, 2H), 7.82(d, 1H), 7.71(d, 2H), 7.52(d, 1H), 7.49(s, 1H), 7.23(s, 1H), 5.62(s, 2H), 4.60(m, 1H), 4.01(m, 1H), 3.97-3.86(m, 2H), 3.52-3.45(m, 2H), 3.34(m, 1H), 1.26(d, 3H) ppm |
| 72 | 3-methyl-4-{3-[(pyridin-4-ylmethyl)oxy]pyrazin-2-yl}-N-[3-(trifluoromethyl)phenyl]piperazine-1-carboxamide | 472.47 | 473.2 | 2.16 | A | (CDCl$_3$) 8.76(d, 2H), 7.81(d, 1H), 7.69(m, 3H), 7.60(d, 1H), 7.52(d, 1H), 7.39(t, 1H), 7.27(d, 1H), 6.94(s, 1H), 5.61(s, 2H), 4.59(m, 1H), 4.05(m, 1H), 3.95(m, 1H), 3.85(m, 1H), 3.48(m, 2H), 3.33(m, 1H), 1.27(d, 3H) ppm |
| 73 | N-[3,5-bis(trifluoromethyl)phenyl]-4-{2-[(pyridin-4-ylmethyl)oxy]phenyl}piperazine-1-carboxamide | 524.46 | 525 | 1.98 | B | (CDCl3) 8.599-8.586(d, 2H), 7.855(s, 2H), 7.559-7.452(d, 2H), 7.390-7.377(d, 2H), 7.021-6.888(m, 4H), 5.146(s, 2H), 3.728-3.704(m, 4H), 3.149-3.125(m, 4H) ppm |
| 74 | 4-{2-[(pyridin-4-ylmethyl)oxy]phenyl}-N-[3-(trifluoromethyl)phenyl]piperazine-1-carboxamide | 456.47 | 457 | 1.82 | B | (CDCl3) 8.615-8.601(d, 2H), 7.634(s, 1H), 7.579-7.557(d, 1H), 7.378-7.364(d, 3H), 7.262-7.242(d, 1H), 7.017-6.869(m, 5H), 5.144(s, 2H), 3.695-3.670(m, 4H), 3.154-3.129(m, 4H) ppm |
| 75 | N-[3,5-bis(trifluoromethyl)phenyl]-2-methyl-4-{3-[(pyridin-4-ylmethyl)oxy]quinoxalin-2-yl}piperazine-1-carboxamide | 590.53 | 591.1 | 2.18 | B | (CDCl3) 8.63(d, 2H), 7.91(s, 2H), 7.88(m, 2H), 7.65(m, 4H), 6.85(s, 1H), 5.63(s, 2H), 4.40(m, 3H), 4.01(d, 1H), 3.48(m, 1H), 3.31(dd, 1H), 3.08(m, 1H), 1.38(d, 3H) ppm |
| 76 | N-[3,5-bis(trifluoromethyl)phenyl]-4-{3-[(pyridin-4-ylmethyl)oxy]pyrazin-2-yl}-1,4-diazepane-1-carboxamide | 540.47 | 541 | 1.95 | B | (CDCl3) 8.616-8.603(d, 2H), 7.821(s, 2H), 7.692-7.684(d, 1H), 7.482(s, 1H), 7.427-7.420(d, 1H), 7.326-7.312(d, 2H), 6.962(s, 1H), 5.416(s, 2H), 3.969-3.912(m, 4H), 3.798-3.784(t, 2H), 3.584-3.555(t, 2H), 1.951-1.924(t, 2H) ppm |
| 77 | 2-methyl-4-{3-[(pyridin-4-ylmethyl)oxy]quinoxalin-2-yl}-N-[3-(trifluoromethyl)phenyl]piperazine-1-carboxamide | 522.53 | 523.1 | 1.97 | B | (CDCl3) 8.65(d, 1H), 7.69(m, 7H), 7.49(m, 3H), 7.32(d, 1H), 5.61(s, 2H), 4.39(m, 2H), 3.96(d, 1H), 3.49(m, 1H), 3.29(dd, 1H), 3.08(m, 1H), 1.31(d, 3H) ppm |
| 78 | 4-{3-[(pyridin-4-ylmethyl)oxy]pyrazin-2-yl}-N-[3-(trifluoromethyl)phenyl]-1,4-diazepane-1-carboxamide | 472.47 | 473 | 1.75 | B | (CDCl3) 8.583-8.570(d, 2H), 7.677-7.671(d, 1H), 7.590(s, 1H), 7.502-7.482(d, 1H), 7.397-7.390(d, 1H), 7.358-7.318(t, 1H), 7.301-7.287(d, 2H), 7.238-7.219(d, 1H), 6.731(s, 1H), 5.394(s, 2H), 3.941-3.873(m, 4H), 3.764-3.737(t, 2H), 3.544-3.514(t, 2H), 1.939(t, 2H) ppm |
| 79 | N-[3,5-bis(trifluoromethyl)phenyl]-2,5-dimethyl-4-{3-[(pyridin-4-ylmethyl)oxy]pyrazin-2-yl}piperazine-1-carboxamide | 554.49 | 555.1 | 2.08 | B | (CDCl$_3$) 8.79(d, 2H), 7.94-7.80(s, 2H), 7.80(d, 1H), 7.76(s, 2H), 7.49-7.46(m, 2H), 7.08(s, 1H), 5.64(s, 2H), 4.68(m, 2H), 3.92(d, 1H), 3.80(d, 1H), 3.63-3.57(m, 2H), 1.34(d, 3H), 1.26(d, 3H) ppm |
| 80 | 2,5-dimethyl-4-{3-[(pyridin-4-ylmethyl)oxy]pyrazin-2-yl}-N-[3-(trifluoromethyl)phenyl]piperazine-1-carboxamide | 486.5 | 487.1 | 1.9 | B | (CDCl$_3$) 8.81(m, 2H), 7.80(d, 1H), 7.76(m, 1H), 7.69(s, 1H), 7.58(d, 1H), 7.45(d, 1H), 7.38(t, 1H), 7.27(d, 1H), 6.74(s, 1H), 5.64(s, 2H), 4.68(s, 1H), 4.41(s, 1H), 3.92(d, 1H), 3.76(d, 1H), 3.60(d, 2H), 1.33(d, 3H), 1.27(d, 3H) ppm |
| 81 | (2S)-N-[3,5-bis(trifluoromethyl)phenyl]-2-methyl-4-{3-[(pyridin-4-ylmethyl)oxy]pyrazin-2-yl}piperazine-1-carboxamide | 540.47 | 541.2 | 2.34 | A | (CDCl3) 8.62(d, 2H), 7.88(s, 2H), 7.77(d, 1H), 7.57(d, 1H), 7.51(s, 1H), 7.33(d, 2H), 6.64(s, 1H), 5.44(s, 2H), 4.32(m, 1H), 4.21(m, 2H), 3.95(d, 1H), 3.46(m, 1H), 3.15(dd, 1H), 3.03(m, 1H), 1.32(m, 3H) ppm |

TABLE 2-continued

| # | Name | Calculated Parent MW | Observed Mass | Retention Time (min) | Method | $^1$H-NMR |
|---|------|---------------------|---------------|---------------------|--------|-----------|
| 82 | (2S)-2-methyl-4-{3-[(pyridin-4-ylmethyl)oxy]pyrazin-2-yl}-N-[3-(trifluoromethyl)phenyl]piperazine-1-carboxamide | 472.47 | 473.2 | 1.79 | B | (CDCl3) 8.62(d, 2H), 7.88(s, 2H), 7.77(d, 1H), 7.57(d, 1H), 7.51(s, 1H), 7.33(d, 2H), 6.64(s, 1H), 5.44(s, 2H), 4.32(m, 1H), 4.18(m, 2H), 3.91(d, 1H), 3.43(m, 1H), 3.12(dd, 1H), 3.03(m, 1H), 1.27(m, 3H) ppm |
| 83 | N-[3,5-bis(trifluoromethyl)phenyl]-4-(4-{[(2-fluoropyridin-4-yl)methyl]oxy}-1,2,5-thiadiazol-3-yl)piperazine-1-carboxamide | 550.46 | 551 | 2.08 | B | (CDCl3) 8.26(d, 1H), 7.88(s, 2H), 7.53(s, 1H), 7.22(d, 1H), 6.98(s, 1H), 6.88(s, 1H), 5.53(s, 2H), 3.73-3.50(m, 8H) ppm |
| 84 | N-[3,5-bis(trifluoromethyl)phenyl]-4-(4-{[(2-chloropyridin-4-yl)methyl]oxy}-1,2,5-thiadiazol-3-yl)piperazine-1-carboxamide | 566.91 | 567 | 2.12 | B | (CDCl3) 8.43(d, 1H), 7.90(s, 2H), 7.55(s, 1H), 7.38(s, 1H), 6.68(s, 1H), 5.49(s, 2H), 3.66(d, 8H) ppm |
| 85 | N-[3,5-bis(trifluoromethyl)phenyl]-4-(3-{[(2-chloropyridin-4-yl)methyl]oxy}pyrazin-2-yl)piperazine-1-carboxamide | 560.88 | 561 | 2.08 | B | (CDCl3) 8.41(d, 1H), 7.91(s, 2H), 7.82(d, 1H), 7.61(d, 1H), 7.54(s, 1H), 7.39(s, 1H), 6.70(s, 1H), 5.47(s, 2H), 3.70-3.65(m, 8H) ppm |
| 86 | N-[3,5-bis(trifluoromethyl)phenyl]-4-(2-{[(2,3,5,6-tetrafluoropyridin-4-yl)amino]methyl}phenyl)piperazine-1-carboxamide | 595.44 | 596.1 | 2.21 | B | (CDCl$_3$) δ 7.87(s, 2H), 7.51(s, 1H), 7.29-7.36(m, 2H), 7.16-7.21(m, 2H), 6.78(s, 1H), 5.90(br s, 1H), 4.79(d, 2H), 3.71(m, 4H), 3.02(t, 4H) |
| 87 | N-[3,5-bis(trifluoromethyl)phenyl]-4-(2-{[(3-chloro-2,5,6-trifluoropyridin-4-yl)amino]methyl}phenyl)piperazine-1-carboxamide | 611.89 | 612.1 | 2.27 | B | (CDCl$_3$) δ 7.88(s, 2H), 7.52(s, 1H), 7.31-7.38(m, 2H), 7.15-7.22(m, 2H), 6.70(s, 1H), 5.88(br t, 1H), 4.85(dd, 2H), 3.71(m, 4H), 3.02(t, 4H) |
| 88 | N-[3,5-bis(trifluoromethyl)phenyl]-4-(4-{[(2-bromopyridin-4-yl)methyl]oxy}-1,2,5-thiadiazol-3-yl)piperazine-1-carboxamide | 611.36 | 613 | 2.55 | B | (CDCl3) 8.40(s, 1H), 7.95(s, 2H), 7.45(s, 2H), 7.25(m, 1H), 6.6(s, 1H), 5.45(m, 2H), 3.6(m, 4H), 1.6(m, 4H) |
| 89 | N-[3,5-bis(trifluoromethyl)phenyl]-4-(3-{[(2-bromopyridin-4-yl)methyl]oxy}pyrazin-2-yl)piperazine-1-carboxamide | 605.34 | 607 | 2.1 | B | (CDCl3) 8.40(s, 1H), 7.95(s, 2H), 7.8(s, 1H), 7.6(s, 1H), 7.58(m, 2H), 7.24(m, 1H), 6.62(s, 1H), 5.4(s, 2H), 3.6(m, 4H), 1.6(m, 4H) |
| 90 | N-[3,5-bis(trifluoromethyl)phenyl]-4-(3-{[(2-fluoropyridin-4-yl)methyl]oxy}pyrazin-2-yl)piperazine-1-carboxamide | 544.43 | 545.1 | 2.04 | B | (CDCl3) 8.24(d, 1H), 7.91(s, 2H), 7.82(d, 1H), 7.61(d, 1H), 7.54(s, 1H), 7.22(d, 1H), 6.98(s, 1H), 6.73(d, 1H), 5.51(s, 2H), 3.70-3.65(m, 8H) ppm |
| 91 | N-[3,5-bis(trifluoromethyl)phenyl]-4-{5,6-dicyano-3-[(pyridin-4-ylmethyl)oxy]pyrazin-2-yl}piperazine-1-carboxamide | 576.46 | 577 | 1.95 | B | (CD3OD) 8.594(s, 2H), 8.073(s, 2H), 7.555-7.534(m, 3H), 5.584(s, 2H), 4.043-4.029(m, 4H), 3.739-3.713(m, 4H) ppm |
| 92 | 4-{5,6-dicyano-3-[(pyridin-4-ylmethyl)oxy]pyrazin-2-yl}-N-[3-(trifluoromethyl)phenyl]piperazine-1-carboxamide | 508.46 | 509 | 1.81 | B | (CDCl3) 8.673(s, 2H), 7.653(s, 1H), 7.582-7.560(d, 1H), 7.420-7.380(t, 1H), 7.336-7.284(m, 3H), 6.965(s, 1H), 5.493(s, 2H), 4.025-3.999(m, 4H), 3.693-3.667(m, 4H) ppm |
| 93 | N-(3-ethylphenyl)-4-{3-[(pyridin-4-ylmethyl)oxy]pyrazin-2-yl}piperazine-1-carboxamide | 418.5 | 419 | 1.97 | C | |
| 94 | N-(3-ethylphenyl)-2,6-dimethyl-4-{3-[(pyridin-4-ylmethyl)oxy]pyrazin-2- | 446.55 | 447 | 2.00 | C | |

TABLE 2-continued

| # | Name | Calculated Parent MW | Observed Mass | Retention Time (min) | Method | $^1$H-NMR |
|---|------|---------------------|---------------|---------------------|--------|-----------|
| 95 | yl}piperazine-1-carboxamide<br>N-(3-ethylphenyl)-2-methyl-4-{3-[(pyridin-4-ylmethyl)oxy]quinoxalin-2-yl}piperazine-1-carboxamide | 482.59 | 483 | 1.95 | C | |
| 96 | N-[3,5-bis(trifluoromethyl)phenyl]-4-[3-(2-pyridin-4-ylethyl)pyrazin-2-yl]piperazine-1-carboxamide | 524.47 | 525.2 | 2.22 | B | (DMSO-d$_6$) δ 9.34(s, 1H), 8.48(d, 2H), 8.23(s, 1H), 8.20(d, 1H), 8.14(d, 2H), 7.58(s, 1H), 7.39(d, 2H), 3.66(m, 4H), 3.13-3.43(m, 8H) |
| 97 | N-[3,5-bis(trifluoromethyl)phenyl]-4-{3-[(pyridin-4-ylmethyl)oxy]pyridin-2-yl}piperazine-1-carboxamide | 525.45 | 526.1 | 2.21 | B | (DMSO-d$_6$) δ 9.24(s, 1H), 8.60(d, 2H), 8.22(s, 2H), 7.84(d, 1H), 7.58(s, 1H), 7.46(d, 2H), 7.33(d, 1H), 6.92(dd, 1H), 5.23(s, 2H), 3.62-3.68(m, 4H) 3.37-3.41(m, 4H) |
| 98 | N-[3,5-bis(trifluoromethyl)phenyl]-4-{2-[(pyridin-4-yloxy)methyl]phenyl}piperazine-1-carboxamide | 524.46 | 525.2 | 1.78 | B | (DMSO-d$_6$) δ 10.58(s, 1H), 8.28(d, 2H), 8.17(s, 2H), 7.73(s, 1H), 7.49(d, 1H), 7.38(t, 1H), 7.18-7.25(m, 4H), 5.39(s, 2H), 3.80-3.85(m, 4H) 3.00-3.04(m, 4H) |
| 99 | 4-[4-(2-Amino-pyridin-4-ylmethoxy)-[1,2,5]thiadiazol-3-yl]-piperazine-1-carboxylic acid (3,5-bis-trifluoromethyl-phenyl)-amide | 547.49 | | | | (CD$_3$OD) δ 3.64(m, 4H), 3.71(m, 4H), 5.58(s, 2H), 6.92(dd, 1H, J=2, 6.4), 7.54(s, 1H), 7.84(dd, 1H, J=0.8, 6.8), 8.08(s, 1H) |
| 100 | (4-{4-[4-(3,5-Bis-trifluoromethyl-phenylcarbamoyl)-piperazin-1-yl]-[1,2,5]thiadiazol-3-yloxymethyl-pyridin-2-yl)-carbamic acid tert-butyl ester | 647.6 | | | | (CDCl$_3$) δ 1.52(s, 9H), 3.71(m, 8H), 5.49(s, 2H), 6.77(s, 1H), 6.96(m, 1H), 7.53(s, 1H), 7.89(s, 2H), 7.93(s, 1H), 8.12(s, 1H), 8.27(d, 1H, J=4.8) |
| 101 | (4-{4-[4-(3,5-Bis-trifluoromethyl-phenylcarbamoyl)-piperazin-1-yl]-[1,2,5]thiadiazol-3-yloxymethyl}-pyridin-2-yl)-carbamic acid methyl ester | 605.52 | | | | (DMSO-d$_6$) δ 3.58-3.67(m overlapping s, 11H), 5.54(s, 2H), 7.10(d, 1H, J=5.2), 7.62(s, 1H), 7.98(s, 1H), 8.22(s, 2H), 8.28(d, 1H, J=5.2), 9.30(s, 1H), 10.31(s, 1H) |

Assays

For assay of activity, generally Tie-2, or a compound according to the invention is non-diffusably bound to an insoluble support having isolated sample-receiving areas (e.g., a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Exemplary methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

One measure of inhibition is $K_i$. For compounds with IC$_{50}$'s less than 1 μM, the $K_i$ or $K_d$ is defined as the dissociation rate constant for the interaction of the agent with a Tie-2. Exemplary compositions have $K_i$'s of, for example, less than about 100 μM, less than about 10 μM, less than about 1 μM, and further for example having $K_i$'s of less than about 100 nM, and still further, for example, less than about 10 nM. The $K_i$ for a compound is determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate data (i.e. compound concentration) are fitted to the equation:

$$V = V_{max}E_0 \left[ 1 - \frac{(E_0 + I_0 + K_d) - \sqrt{(E_0 + I_0 + K_d)^2 - 4E_0 I_0}}{2E_0} \right]$$

where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Exemplary compounds have $GI_{50}$'s of, for example, less than about 1 mM, less than about 10 µM, less than about 1 µM, and further, for example, having $GI_{50}$'s of less than about 100 nM, still further having $GI_{50}$'s of less than about 10 nM. Measurement of $GI_{50}$ is done using a cell proliferation assay.

Tyrosine kinase activity is determined by 1) measurement of kinase-dependent ATP consumption by in the presence of a generic substrate such as polyglutamine, tyrosine (pEY), by luciferase/luciferin-mediated chemiluminescence or; 2) incorporation of radioactive phosphate derived from $^{33}$P-ATP into a generic substrate which has been adsorbed onto the well surface of polystyrene microtiter plates. Phosphorylated substrate products are quantified by scintillation spectrometry.

Structure Activity Relationships

Table 3 shows structure activity relationship data for selected compounds of the invention. Inhibition is indicated as $IC_{50}$ with following key: A=$IC_{50}$ less than 50 nM, B=$IC_{50}$ greater than 50 nM, but less than or equal to 1000 nM, C=$IC_{50}$ greater than 1000 nM, but less than 10,000 nM, D=$IC_{50}$ 10,000 nM or greater, and "-"=no data available. The abbreviation for human enzyme, Tie-2, is defined as tyrosine kinase with immunoglobulin and EGF repeats.

TABLE 3

| Number | Name | $IC_{50}$ Tie-2 |
|---|---|---|
| 1 | N-[(1R,2S)-2-phenylcyclopropyl]-4-{4-[(pyridin-4-ylmethyl)oxy]-1,2,5-thiadiazol-3-yl}piperazine-1-carboxamide | C |
| 2 | N-[3,5-bis(trifluoromethyl)phenyl]-4-{4-[(pyridin-4-ylmethyl)oxy]-1,2,5-thiadiazol-3-yl}piperazine-1-carboxamide | A |
| 3 | N-[4-chloro-3-(trifluoromethyl)phenyl]-4-{4-[(pyridin-4-ylmethyl)oxy]-1,2,5-thiadiazol-3-yl}piperazine-1-carboxamide | — |
| 4 | N-[4-(1-methylethyl)phenyl]-4-{4-[(pyridin-4-ylmethyl)oxy]-1,2,5-thiadiazol-3-yl}piperazine-1-carboxamide | C |
| 5 | N-(3-bromophenyl)-4-{4-[(pyridin-4-ylmethyl)oxy]-1,2,5-thiadiazol-3-yl}piperazine-1-carboxamide | C |
| 6 | N-[3-(methylthio)phenyl]-4-{4-[(pyridin-4-ylmethyl)oxy]-1,2,5-thiadiazol-3-yl}piperazine-1-carboxamide | C |
| 7 | N-(3-ethylphenyl)-4-{4-[(pyridin-4-ylmethyl)oxy]-1,2,5-thiadiazol-3-yl}piperazine-1-carboxamide | B |
| 8 | N-(3,5-dimethylphenyl)-4-{4-[(pyridin-4-ylmethyl)oxy]-1,2,5-thiadiazol-3-yl}piperazine-1-carboxamide | B |
| 9 | 4-{4-[(pyridin-4-ylmethyl)oxy]-1,2,5-thiadiazol-3-yl}-N-[3-(trifluoromethyl)phenyl]piperazine-1-carboxamide | B |
| 10 | N-[3,5-bis(trifluoromethyl)phenyl]-4-(4-{[(2-methylquinolin-4-yl)methyl]oxy}-1,2,5-thiadiazol-3-yl)piperazine-1-carboxamide | D |
| 11 | N-[3,5-bis(trifluoromethyl)phenyl]-4-[4-({[3-(dimethylamino)phenyl]methyl}oxy)-1,2,5-thiadiazol-3-yl]piperazine-1-carboxamide | D |
| 12 | N-[3,5-bis(trifluoromethyl)phenyl]-4-[4-(1H-indol-5-yloxy)-1,2,5-thiadiazol-3-yl]piperazine-1-carboxamide | B |
| 13 | N-[3,5-bis(trifluoromethyl)phenyl]-4-{4-[(3-thienylmethyl)oxy]-1,2,5-thiadiazol-3-yl}piperazine-1-carboxamide | D |
| 14 | N-[3,5-bis(trifluoromethyl)phenyl]-4-{4-[(2-morpholin-4-ylethyl)oxy]-1,2,5-thiadiazol-3-yl}piperazine-1-carboxamide | D |
| 15 | N-[3,5-bis(trifluoromethyl)phenyl]-4-(4-{[2-(1H-imidazol-1-yl)ethyl]oxy}-1,2,5-thiadiazol-3-yl)piperazine-1-carboxamide | — |
| 16 | N-[3,5-bis(trifluoromethyl)phenyl]-4-{4-[(1-methylpiperidin-4-yl)oxy]-1,2,5-thiadiazol-3-yl}piperazine-1-carboxamide | — |
| 17 | N-[3,5-bis(trifluoromethyl)phenyl]-4-[4-({[4-(methyloxy)phenyl]methyl}oxy)-1,2,5-thiadiazol-3-yl]piperazine-1-carboxamide | D |
| 18 | 4-[4-({[3,4-bis(methyloxy)phenyl]methyl}oxy)-1,2,5-thiadiazol-3-yl]-N-[3,5-bis(trifluoromethyl)phenyl]piperazine-1-carboxamide | D |
| 19 | 4-{4-[(1,3-benzodioxol-5-ylmethyl)oxy]-1,2,5-thiadiazol-3-yl}-N-[3,5-bis(trifluoromethyl)phenyl]piperazine-1-carboxamide | D |
| 20 | N-[3,5-bis(trifluoromethyl)phenyl]-4-{4-[(furan-3-ylmethyl)oxy]-1,2,5-thiadiazol-3-yl}piperazine-1-carboxamide | D |
| 21 | N-[3,5-bis(trifluoromethyl)phenyl]-4-{4-[(tetrahydrofuran-3-ylmethyl)oxy]-1,2,5-thiadiazol-3-yl}piperazine-1-carboxamide | — |
| 22 | N-[3,5-bis(trifluoromethyl)phenyl]-2-methyl-4-{4-[(pyridin-4-ylmethyl)oxy]-1,2,5-thiadiazol-3-yl}piperazine-1-carboxamide | B |
| 23 | N-[3,5-bis(trifluoromethyl)phenyl]-4-{4-[(pyridin-4-ylmethyl)oxy]-1,2,5-thiadiazol-3-yl}-1,4-diazepane-1-carboxamide | B |
| 24 | 1-({[[(1S,2R,5S)-5-methyl-2-(1-methylethyl)cyclohexyl]oxy}acetyl)-4-{4-[(pyridin-4-ylmethyl)oxy]-1,2,5-thiadiazol-3-yl}piperazine | C |
| 25 | 5-phenyl-N-(1-{4-[(pyridin-4-ylmethyl)oxy]-1,2,5-thiadiazol-3-yl}pyrrolidin-3-yl)-1,3-oxazole-4-carboxamide | C |

TABLE 3-continued

| Number | Name | IC$_{50}$ Tie-2 |
|---|---|---|
| 26 | 1-{4-[(pyridin-4-ylmethyl)oxy]-1,2,5-thiadiazol-3-yl}-4-{[3-(trifluoromethyl)phenyl]acetyl}piperazine | — |
| 27 | N-[3,5-bis(trifluoromethyl)phenyl]-4-{4-[(piperidin-4-ylmethyl)oxy]-1,2,5-thiadiazol-3-yl}piperazine-1-carboxamide | D |
| 28 | N-[3,5-bis(trifluoromethyl)phenyl]-N'-[(4-{4-[(pyridin-4-ylmethyl)oxy]-1,2,5-thiadiazol-3-yl}piperazin-1-yl)methyl]urea | B |
| 29 | N-[3,5-bis(trifluoromethyl)phenyl]-4-{4-[(3-pyridin-3-ylpropyl)oxy]-1,2,5-thiadiazol-3-yl}piperazine-1-carboxamide | C |
| 30 | N-[3,5-bis(trifluoromethyl)phenyl]-4-{1,1-dioxido-4-[(pyridin-4-ylmethyl)oxy]-1,2,5-thiadiazol-3-yl}piperazine-1-carboxamide | — |
| 31 | 4-[4-(1-azabicyclo[2.2.2]oct-3-yloxy)-1,2,5-thiadiazol-3-yl]-N-[3,5-bis(trifluoromethyl)phenyl]piperazine-1-carboxamide | — |
| 32 | 4-[({4-[4-({[3,5-bis(trifluoromethyl)phenyl]amino}carbonyl)piperazin-1-yl]-1,2,5-thiadiazol-3-yl}oxy)methyl]benzoic acid | C |
| 33 | N-[3,5-bis(trifluoromethyl)phenyl]-4-{4-[(piperidin-3-ylmethyl)oxy]-1,2,5-thiadiazol-3-yl}piperazine-1-carboxamide | — |
| 34 | N-[3,5-bis(trifluoromethyl)phenyl]-4-{4-[(2-pyrrolidin-1-ylethyl)oxy]-1,2,5-thiadiazol-3-yl}piperazine-1-carboxamide | — |
| 35 | 4-{4-[(2-amino-2-methylpropyl)oxy]-1,2,5-thiadiazol-3-yl}-N-[3,5-bis(trifluoromethyl)phenyl]piperazine-1-carboxamide | — |
| 36 | N-[3,5-bis(trifluoromethyl)phenyl]-1-{4-[(pyridin-4-ylmethyl)oxy]-1,2,5-thiadiazol-3-yl}piperidine-4-carboxamide | B |
| 37 | 1-{4-[(pyridin-4-ylmethyl)oxy]-1,2,5-thiadiazol-3-yl}-N-[3-(trifluoromethyl)phenyl]piperidine-4-carboxamide | B |
| 38 | N-[3,5-bis(trifluoromethyl)phenyl]-4-{3-[(pyridin-4-ylmethyl)oxy]pyrazin-2-yl}piperazine-1-carboxamide | A |
| 39 | 4-{3-[(pyridin-4-ylmethyl)oxy]pyrazin-2-yl}-N-[3-(trifluoromethyl)phenyl]piperazine-1-carboxamide | A |
| 40 | N-[3,5-bis(trifluoromethyl)phenyl]-4-{4-[(2-piperidin-4-ylethyl)oxy]-1,2,5-thiadiazol-3-yl}piperazine-1-carboxamide | — |
| 41 | 2-methyl-4-{4-[(pyridin-4-ylmethyl)oxy]-1,2,5-thiadiazol-3-yl}-N-[3-(trifluoromethyl)phenyl]piperazine-1-carboxamide | B |
| 42 | 1-phenyl-4-{4-[(pyridin-4-ylmethyl)oxy]-1,2,5-thiadiazol-3-yl}piperazine | — |
| 43 | 1-[(4-methylphenyl)methyl]-4-{4-[(pyridin-4-ylmethyl)oxy]-1,2,5-thiadiazol-3-yl}piperazine | — |
| 44 | N-[3,5-bis(trifluoromethyl)phenyl]-4-{4-[(pyridin-4-ylmethyl)amino]-1,2,5-thiadiazol-3-yl}piperazine-1-carboxamide | C |
| 45 | 4-{4-[(pyridin-4-ylmethyl)oxy]-1,2,5-thiadiazol-3-yl}-N-[3-(trifluoromethyl)phenyl]-1,4-diazepane-1-carboxamide | C |
| 46 | 2-methyl-1-{[2-(methyloxy)phenyl]carbonyl}-4-{4-[(pyridin-4-ylmethyl)oxy]-1,2,5-thiadiazol-3-yl}piperazine | — |
| 47 | N-[5-chloro-2-(methyloxy)phenyl]-N'-(1-{4-[(pyridin-4-ylmethyl)oxy]-1,2,5-thiadiazol-3-yl}pyrrolidin-3-yl)urea | — |
| 48 | N-[5-methyl-2-(methyloxy)phenyl]-N'-(1-{4-[(pyridin-4-ylmethyl)oxy]-1,2,5-thiadiazol-3-yl}pyrrolidin-3-yl)urea | — |
| 49 | N-(1-{4-[(pyridin-4-ylmethyl)oxy]-1,2,5-thiadiazol-3-yl}pyrrolidin-3-yl)-N'-[3-(trifluoromethyl)phenyl]urea | C |
| 50 | 2-methyl-N-[4-(1-methylethyl)phenyl]-4-{4-[(pyridin-4-ylmethyl)oxy]-1,2,5-thiadiazol-3-yl}piperazine-1-carboxamide | C |
| 51 | 2-methyl-N-[3-(methylthio)phenyl]-4-{4-[(pyridin-4-ylmethyl)oxy]-1,2,5-thiadiazol-3-yl}piperazine-1-carboxamide | B |
| 52 | (2R)-N-[3,5-bis(trifluoromethyl)phenyl]-2-methyl-4-{4-[(pyridin-4-ylmethyl)oxy]-1,2,5-thiadiazol-3-yl}piperazine-1-carboxamide | B |
| 53 | (2R)-2-methyl-4-{4-[(pyridin-4-ylmethyl)oxy]-1,2,5-thiadiazol-3-yl}-N-[3-(trifluoromethyl)phenyl]piperazine-1-carboxamide | B |
| 54 | 1-[4-(4-{4-[(pyridin-4-ylmethy)oxy]-1,2,5-thiadiazol-3-yl}piperazin-1-yl)phenyl]ethanone | — |
| 55 | 2-(4-{4-[(pyridin-4-ylmethyl)oxy]-1,2,5-thiadiazol-3-yl}piperazin-1-yl)pyrimidine | — |
| 56 | 1-[2-nitro-4-(trifluoromethyl)phenyl]-4-{4-[(pyridin-4-ylmethyl)oxy]-1,2,5-thiadiazol-3-yl}piperazine | — |
| 57 | (2S)-N-[3,5-bis(trifluoromethyl)phenyl]-2-methyl-4-{4-[(pyridin-4-ylmethyl)oxy]-1,2,5-thiadiazol-3-yl}piperazine-1-carboxamide | B |
| 58 | (2S)-2-methyl-4-{4-[(pyridin-4-ylmethyl)oxy]-1,2,5-thiadiazol-3-yl}-N-[3-(trifluoromethyl)phenyl]piperazine-1-carboxamide | B |
| 59 | N-[3,5-bis(trifluoromethyl)phenyl]-4-(3-hydroxypyrazin-2-yl)piperazine-1-carboxamide | — |
| 60 | 2-[2,5-bis(trifluoromethyl)phenyl]-N-(1-{4-[(pyridin-4-ylmethyl)oxy]-1,2,5-thiadiazol-3-yl}pyrrolidin-3-yl)acetamide | B |
| 61 | 1-{[2,5-bis(trifluoromethyl)phenyl]acetyl}-2-methyl-4-{4-[(pyridin-4-ylmethyl)oxy]-1,2,5-thiadiazol-3-yl}piperazine | B |

TABLE 3-continued

| Number | Name | IC$_{50}$ Tie-2 |
|---|---|---|
| 62 | N-[3,5-bis(trifluoromethyl)phenyl]-2-methyl-4-{3-[(pyridin-4-ylmethyl)oxy]pyrazin-2-yl}piperazine-1-carboxamide | A |
| 63 | 2-methyl-4-{3-[(pyridin-4-ylmethyl)oxy]pyrazin-2-yl}-N-[3-(trifluoromethyl)phenyl]piperazine-1-carboxamide | B |
| 64 | N-[3,5-bis(trifluoromethyl)phenyl]-2,6-dimethyl-4-{3-[(pyridin-4-ylmethyl)oxy]pyrazin-2-yl}piperazine-1-carboxamide | B |
| 65 | 2,6-dimethyl-4-{3-[(pyridin-4-ylmethyl)oxy]pyrazin-2-yl}-N-[3-(trifluoromethyl)phenyl]piperazine-1-carboxamide | B |
| 66 | N-(1-{3-[(pyridin-4-ylmethyl)oxy]pyrazin-2-yl}pyrrolidin-3-yl)-N'-[3-(trifluoromethyl)phenyl]urea | B |
| 67 | N-[3,5-bis(trifluoromethyl)phenyl]-N'-(1-{3-[(pyridin-4-ylmethyl)oxy]pyrazin-2-yl}pyrrolidin-3-yl)urea | B |
| 68 | N-[3,5-bis(trifluoromethyl)phenyl]-2,6-dimethyl-4-{4-[(pyridin-4-ylmethyl)oxy]-1,2,5-thiadiazol-3-yl}piperazine-1-carboxamide | B |
| 69 | 2,6-dimethyl-4-{4-[(pyridin-4-ylmethyl)oxy]-1,2,5-thiadiazol-3-yl}-N-[3-(trifluoromethyl)phenyl]piperazine-1-carboxamide | B |
| 70 | N-[3,5-bis(trifluoromethyl)phenyl]-3-methyl-4-{3-[(pyridin-4-ylmethyl)oxy]pyrazin-2-yl}piperazine-1-carboxamide | A |
| 71 | 3-methyl-4-{3-[(pyridin-4-ylmethyl)oxy]pyrazin-2-yl}-N-[3-(trifluoromethyl)phenyl]piperazine-1-carboxamide | B |
| 72 | N-[3,5-bis(trifluoromethyl)phenyl]-4-{2-[(pyridin-4-ylmethyl)oxy]phenyl}piperazine-1-carboxamide | A |
| 73 | 4-{2-[(pyridin-4-ylmethyl)oxy]phenyl}-N-[3-(trifluoromethyl)phenyl]piperazine-1-carboxamide | B |
| 74 | N-[3,5-bis(trifluoromethyl)phenyl]-2-methyl-4-{3-[(pyridin-4-ylmethyl)oxy]quinoxalin-2-yl}piperazine-1-carboxamide | B |
| 75 | N-[3,5-bis(trifluoromethyl)phenyl]-4-{3-[(pyridin-4-ylmethyl)oxy]pyrazin-2-yl}-1,4-diazepane-1-carboxamide | B |
| 76 | 2-methyl-4-{3-[(pyridin-4-ylmethyl)oxy]quinoxalin-2-yl}-N-[3-(trifluoromethyl)phenyl]piperazine-1-carboxamide | B |
| 77 | 4-{3-[(pyridin-4-ylmethyl)oxy]pyrazin-2-yl}-N-[3-(trifluoromethyl)phenyl]-1,4-diazepane-1-carboxamide | B |
| 78 | N-[3,5-bis(trifluoromethyl)phenyl]-2,5-dimethyl-4-{3-[(pyridin-4-ylmethyl)oxy]pyrazin-2-yl}piperazine-1-carboxamide | A |
| 79 | 2,5-dimethyl-4-{3-[(pyridin-4-ylmethyl)oxy]pyrazin-2-yl}-N-[3-(trifluoromethyl)phenyl]piperazine-1-carboxamide | B |
| 80 | (2S)-N-[3,5-bis(trifluoromethyl)phenyl]-2-methyl-4-{3-[(pyridin-4-ylmethyl)oxy]pyrazin-2-yl}piperazine-1-carboxamide | A |
| 81 | (2S)-2-methyl-4-{3-[(pyridin-4-ylmethyl)oxy]pyrazin-2-yl}-N-[3-(trifluoromethyl)phenyl]piperazine-1-carboxamide | A |
| 82 | N-[3,5-bis(trifluoromethyl)phenyl]-4-(4-{[(2-fluoropyridin-4-yl)methyl]oxy}-1,2,5-thiadiazol-3-yl)piperazine-1-carboxamide | C |
| 83 | N-[3,5-bis(trifluoromethyl)phenyl]-4-(4-{[(2-chloropyridin-4-yl)methyl]oxy}-1,2,5-thiadiazol-3-yl)piperazine-1-carboxamide | C |
| 84 | N-[3,5-bis(trifluoromethyl)phenyl]-4-(3-{[(2-chloropyridin-4-yl)methyl]oxy}pyrazin-2-yl)piperazine-1-carboxamide | B |
| 85 | N-[3,5-bis(trifluoromethyl)phenyl]-4-(2-{[(2,3,5,6-tetrafluoropyridin-4-yl)amino]methyl}phenyl)piperazine-1-carboxamide | — |
| 86 | N-[3,5-bis(trifluoromethyl)phenyl]-4-(2-{[(3-chloro-2,5,6-trifluoropyridin-4-yl)amino]methyl}phenyl)piperazine-1-carboxamide | — |
| 87 | N-[3,5-bis(trifluoromethyl)phenyl]-4-(4-{[(2-bromopyridin-4-yl)methyl]oxy}-1,2,5-thiadiazol-3-yl)piperazine-1-carboxamide | C |
| 88 | N-[3,5-bis(trifluoromethyl)phenyl]-4-(3-{[(2-bromopyridin-4-yl)methyl]oxy}pyrazin-2-yl)piperazine-1-carboxamide | B |
| 89 | N-[3,5-bis(trifluoromethyl)phenyl]-4-(3-{[(2-fluoropyridin-4-yl)methyl]oxy}pyrazin-2-yl)piperazine-1-carboxamide | B |
| 90 | N-[3,5-bis(trifluoromethyl)phenyl]-4-{5,6-dicyano-3-[(pyridin-4-ylmethyl)oxy]pyrazin-2-yl}piperazine-1-carboxamide | B |
| 91 | 4-{5,6-dicyano-3-[(pyridin-4-ylmethyl)oxy]pyrazin-2-yl}-N-[3-(trifluoromethyl)phenyl]piperazine-1-carboxamide | B |
| 92 | N-(3-ethylphenyl)-4-{3-[(pyridin-4-ylmethyl)oxy]pyrazin-2-yl}piperazine-1-carboxamide | A |
| 93 | N-(3-ethylphenyl)-2-methyl-4-{3-[(pyridin-4-ylmethyl)oxy]pyrazin-2-yl}piperazine-1-carboxamide | A |
| 94 | N-(3-ethylphenyl)-2,6-dimethyl-4-{3-[(pyridin-4-ylmethyl)oxy]pyrazin-2-yl}piperazine-1-carboxamide | B |
| 95 | N-(3-ethylphenyl)-2-methyl-4-{3-[(pyridin-4-ylmethyl)oxy]quinoxalin-2-yl}piperazine-1-carboxamide | B |
| 96 | N-[3,5-bis(trifluoromethyl)phenyl]-4-[3-(2-pyridin-4-ylethyl)pyrazin-2-yl]piperazine-1-carboxamide | B |
| 97 | N-[3,5-bis(trifluoromethyl)phenyl]-4-{3-[(pyridin-4-ylmethyl)oxy]pyridin-2-yl}piperazine-1-carboxamide | A |
| 98 | N-[3,5-bis(trifluoromethyl)phenyl]-4-{2-[(pyridin-4-yloxy)methyl]phenyl}piperazine-1-carboxamide | — |

TABLE 3-continued

| Number | Name | IC$_{50}$ Tie-2 |
|---|---|---|
| 99 | 4-(4-{[(2-aminopyridin-4-yl)methyl]oxy}-1,2,5-thiadiazol-3-yl)-N-[3,5-bis(trifluoromethyl)phenyl]piperazine-1-carboxamide | A |
| 100 | 1,1-dimethylethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 101 | methyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 102 | 4-{[(4-piperazin-1-yl-1,2,5-thiadiazol-3-yl)oxy]methyl}pyridin-2-amine | D |
| 103 | N-(4-chlorophenyl)-4-{3-[(pyridin-4-ylmethyl)oxy]pyridin-2-yl}piperazine-1-carboxamide | D |
| 104 | 4-(4-{[(2-aminopyrimidin-4-yl)methyl]oxy}-1,2,5-thiadiazol-3-yl)-N-[3,5-bis(trifluoromethyl)phenyl]piperazine-1-carboxamide | A |
| 105 | N-(3-chlorophenyl)-4-{3-[(pyridin-4-ylmethyl)oxy]pyridin-2-yl}piperazine-1-carboxamide | B |
| 106 | 4-{[(4-piperazin-1-yl-1,2,5-thiadiazol-3-yl)oxy]methyl}-N-propylpyridin-2-amine | D |
| 107 | N-[3,5-bis(trifluoromethyl)phenyl]-4-[4-({[2-(propylamino)pyridin-4-yl]methyl}oxy)-1,2,5-thiadiazol-3-yl]piperazine-1-carboxamide | B |
| 108 | N-[3,5-bis(trifluoromethyl)phenyl]-4-[4-({[2-(methylamino)pyrimidin-4-yl]methyl}oxy)-1,2,5-thiadiazol-3-yl]piperazine-1-carboxamide | A |
| 109 | N-methyl-4-{[(4-piperazin-1-yl-1,2,5-thiadiazol-3-yl)oxy]methyl}pyridin-2-amine | D |
| 110 | N-ethyl-4-{[(4-piperazin-1-yl-1,2,5-thiadiazol-3-yl)oxy]methyl}pyridin-2-amine | — |
| 111 | N-butyl-4-{[(4-piperazin-1-yl-1,2,5-thiadiazol-3-yl)oxy]methyl}pyridin-2-amine | D |
| 112 | N-[3,5-bis(trifluoromethyl)phenyl]-4-[4-({[2-(methylamino)pyridin-4-yl]methyl}oxy)-1,2,5-thiadiazol-3-yl]piperazine-1-carboxamide | A |
| 113 | N-[3,5-bis(trifluoromethyl)phenyl]-4-[4-({[2-(ethylamino)pyridin-4-yl]methyl}oxy)-1,2,5-thiadiazol-3-yl]piperazine-1-carboxamide | A |
| 114 | N-[3,5-bis(trifluoromethyl)phenyl]-4-[4-({[2-(butylamino)pyridin-4-yl]methyl}oxy)-1,2,5-thiadiazol-3-yl]piperazine-1-carboxamide | B |
| 115 | N-[3,5-bis(trifluoromethyl)phenyl]-4-{4-[({2-[(phenylmethyl)amino]pyridin-4-yl}methyl)oxy]-1,2,5-thiadiazol-3-yl}piperazine-1-carboxamide | B |
| 116 | N-[3,5-bis(trifluoromethyl)phenyl]-4-{4-[({2-[(1-methylethyl)amino]pyrimidin-4-yl}methyl)oxy]-1,2,5-thiadiazol-3-yl}piperazine-1-carboxamide | B |
| 117 | N-[3,5-bis(trifluoromethyl)phenyl]-4-{4-[({2-[(phenylmethyl)amino]pyrimidin-4-yl}methyl)oxy]-1,2,5-thiadiazol-3-yl}piperazine-1-carboxamide | B |
| 118 | N-[3,5-bis(trifluoromethyl)phenyl]-4-[4-({[2-(phenylamino)pyrimidin-4-yl]methyl}oxy)-1,2,5-thiadiazol-3-yl]piperazine-1-carboxamide | A |
| 119 | N-[3,5-bis(trifluoromethyl)phenyl]-4-(4-{[(2-{[2-(dimethylamino)ethyl]amino}pyrimidin-4-yl)methyl]oxy}-1,2,5-thiadiazol-3-yl)piperazine-1-carboxamide | B |
| 120 | N-[3,5-bis(trifluoromethyl)phenyl]-4-(4-{[(2-{[2-(dimethylamino)ethyl]amino}pyridin-4-yl)methyl]oxy}-1,2,5-thiadiazol-3-yl)piperazine-1-carboxamide | B |
| 121 | N-[3,5-bis(trifluoromethyl)phenyl]-4-[4-({[2-(ethylamino)pyrimidin-4-yl]methyl}oxy)-1,2,5-thiadiazol-3-yl]piperazine-1-carboxamide | A |
| 122 | N-[3,5-bis(trifluoromethyl)phenyl]-4-[4-({[2-(propylamino)pyrimidin-4-yl]methyl}oxy)-1,2,5-thiadiazol-3-yl]piperazine-1-carboxamide | B |
| 123 | N-[3,5-bis(trifluoromethyl)phenyl]-4-[4-({[2-(cyclopropylamino)pyrimidin-4-yl]methyl}oxy)-1,2,5-thiadiazol-3-yl]piperazine-1-carboxamide | A |
| 124 | 4-[4-({[2-(acetylamino)pyrimidin-4-yl]methyl}oxy)-1,2,5-thiadiazol-3-yl]-N-[3,5-bis(trifluoromethyl)phenyl]piperazine-1-carboxamide | A |
| 125 | N-[3,5-bis(trifluoromethyl)phenyl]-4-{4-[({2-[(phenylcarbonyl)amino]pyridin-4-yl}methyl)oxy]-1,2,5-thiadiazol-3-yl}piperazine-1-carboxamide | C |
| 126 | N-[3,5-bis(trifluoromethyl)phenyl]-4-{4-[({2-[(phenylcarbonyl)amino]pyrimidin-4-yl}methyl)oxy]-1,2,5-thiadiazol-3-yl}piperazine-1-carboxamide | B |
| 127 | 4-{4-[({2-[bis(phenylcarbonyl)amino]pyridin-4-yl}methyl)oxy]-1,2,5-thiadiazol-3-yl}-N-[3,5-bis(trifluoromethyl)phenyl]piperazine-1-carboxamide | — |

TABLE 3-continued

| Number | Name | IC$_{50}$ Tie-2 |
|---|---|---|
| 128 | N-[3,5-bis(trifluoromethyl)phenyl]-4-[4-({[2-(cyclopentylamino)pyrimidin-4-yl]methyl}oxy)-1,2,5-thiadiazol-3-yl]piperazine-1-carboxamide | B |
| 129 | 4-[4-({[2-(acetylamino)pyridin-4-yl]methyl}oxy)-1,2,5-thiadiazol-3-yl]-N-[3,5-bis(trifluoromethyl)phenyl]piperazine-1-carboxamide | A |
| 130 | N-[3,5-bis(trifluoromethyl)phenyl]-4-{4-[({2-[({[3,5-bis(trifluoromethyl)phenyl]amino}carbonyl)amino]pyridin-4-yl}methyl)oxy]-1,2,5-thiadiazol-3-yl}piperazine-1-carboxamide | C |
| 131 | methyl {4-[({4-[4-({[3,5-bis(trifluoromethyl)phenyl]amino}carbonyl)piperazin-1-yl]-1,2,5-thiadiazol-3-yl}oxy)methyl]pyrimidin-2-yl}carbamate | A |
| 132 | 4-(4-{[(2-aminopyridin-4-yl)methyl]oxy}-1,2,5-thiadiazol-3-yl)-N-(3-ethylphenyl)piperazine-1-carboxamide | B |
| 133 | methyl [4-({[4-(4-{[(3-ethylphenyl)amino]carbonyl}piperazin-1-yl)-1,2,5-thiadiazol-3-yl]oxy}methyl)pyridin-2-yl]carbamate | A |
| 134 | N-[3,5-bis(trifluoromethyl)phenyl]-4-(4-{[(2-cyanopyrimidin-4-yl)methyl]oxy}-1,2,5-thiadiazol-3-yl)piperazine-1-carboxamide | D |
| 135 | 4-(3-{[(2-aminopyrimidin-4-yl)methyl]oxy}pyrazin-2-yl)-N-[3,5-bis(trifluoromethyl)phenyl]piperazine-1-carboxamide | A |
| 136 | 4-[({4-[4-({[3,5-bis(trifluoromethyl)phenyl]amino}carbonyl)piperazin-1-yl]-1,2,5-thiadiazol-3-yl}oxy)methyl]pyrimidine-2-carboxamide | B |
| 137 | N-[3,5-bis(trifluoromethyl)phenyl]-4-[4-({[2-(butyloxy)pyrimidin-4-yl]methyl}oxy)-1,2,5-thiadiazol-3-yl]piperazine-1-carboxamide | D |
| 138 | N-[3,5-bis(trifluoromethyl)phenyl]-4-{4-[(pyrimidin-4-ylmethyl)oxy]-1,2,5-thiadiazol-3-yl}piperazine-1-carboxamide | B |
| 139 | 4-[({4-[4-({[3,5-bis(trifluoromethyl)phenyl]amino}carbonyl)piperazin-1-yl]-1,2,5-thiadiazol-3-yl}oxy)methyl]pyridine-2-carboxylic acid | D |
| 140 | 2-pyrrolidin-1-ylethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 141 | 2-morpholin-4-ylethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 142 | 4-(3-{[(2-aminopyrimidin-4-yl)methyl]oxy}pyridin-2-yl)-N-[3,5-bis(trifluoromethyl)phenyl]piperazine-1-carboxamide | A |
| 143 | N-[3,5-bis(trifluoromethyl)phenyl]-4-(4-{[(2-{[(1-methylpiperidin-3-yl)carbonyl]amino}pyridin-4-yl)methyl]oxy}-1,2,5-thiadiazol-3-yl)piperazine-1-carboxamide | A |
| 144 | 4-(3-{[(2-aminopyrimidin-4-yl)methyl]oxy}pyridin-2-yl)-N-(3-ethylphenyl)piperazine-1-carboxamide | A |
| 145 | 2-(4-methylpiperazin-1-yl)ethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 146 | N-[3,5-bis(trifluoromethyl)phenyl]-4-(4-{[(2-{[(1-ethylpiperidin-4-yl)carbonyl]amino}pyridin-4-yl)methyl]oxy}-1,2,5-thiadiazol-3-yl)piperazine-1-carboxamide | A |
| 147 | 4-(4-{[(2-aminopyridin-4-yl)methyl]oxy}-1,2,5-thiadiazol-3-yl)-N-{3-[(trifluoromethyl)thio]phenyl}piperazine-1-carboxamide | A |
| 148 | 4-({[4-(4-{[3,5-bis(trifluoromethyl)phenyl]sulfonyl}piperazin-1-yl)-1,2,5-thiadiazol-3-yl]oxy}methyl)pyridin-2-amine | D |
| 149 | 4-(4-{[(2-aminopyridin-4-yl)methyl]oxy}-1,2,5-thiadiazol-3-yl)-N-naphthalen-1-ylpiperazine-1-carboxamide | D |
| 150 | N-[3,5-bis(trifluoromethyl)phenyl]-4-{4-[({2-[(N,N-dimethylglycyl)amino]pyridin-4-yl}methyl)oxy]-1,2,5-thiadiazol-3-yl}piperazine-1-carboxamide | A |
| 151 | N-[3,5-bis(trifluoromethyl)phenyl]-4-{4-[({2-[(morpholin-4-ylacetyl)amino]pyridin-4-yl}methyl)oxy]-1,2,5-thiadiazol-3-yl}piperazine-1-carboxamide | A |
| 152 | N-[3,5-bis(trifluoromethyl)phenyl]-4-{4-[({2-[(piperidin-1-ylacetyl)amino]pyridin-4-yl}methyl)oxy]-1,2,5-thiadiazol-3-yl}piperazine-1-carboxamide | B |
| 153 | ethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 154 | N-[3,5-bis(trifluoromethyl)phenyl]-4-{4-[({2-[(pyrrolidin-1-ylacetyl)amino]pyridin-4-yl}methyl)oxy]-1,2,5-thiadiazol-3-yl}piperazine-1-carboxamide | A |
| 155 | N-[3,5-bis(trifluoromethyl)phenyl]-4-(4-{[(2-{[(4-methylpiperazin-1-yl)acetyl]amino}pyridin-4-yl)methyl]oxy}-1,2,5-thiadiazol-3-yl)piperazine-1-carboxamide | A |
| 156 | N-[3,5-bis(trifluoromethyl)phenyl]-4-{4-[({2-[(N,N-diethylglycyl)amino]pyridin-4-yl}methyl)oxy]-1,2,5-thiadiazol-3-yl}piperazine-1-carboxamide | B |

TABLE 3-continued

| Number | Name | IC$_{50}$ Tie-2 |
|---|---|---|
| 157 | 1-ethylpiperidin-4-yl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 158 | 4-(4-{[(2-aminopyrimidin-4-yl)methyl]oxy}-1,2,5-thiadiazol-3-yl)-N-(3-ethylphenyl)piperazine-1-carboxamide | B |
| 159 | N-[3,5-bis(trifluoromethyl)phenyl]-4-[4-({[2-(2-oxo-1,3-oxazolidin-3-yl)pyridin-4-yl]methyl}oxy)-1,2,5-thiadiazol-3-yl]piperazine-1-carboxamide | D |
| 160 | 2-(diethylamino)ethyl {4-[({4-[4-({[3,5-bis(trifluoromethyl)phenyl]amino}carbonyl)piperazin-1-yl]-1,2,5-thiadiazol-3-yl}oxy)methyl]pyridin-2-yl}carbamate | A |
| 161 | methyl [4-({[2-(4-{[(3-ethylphenyl)amino]carbonyl}piperazin-1-yl)pyridin-3-yl]oxy}methyl)pyridin-2-yl]carbamate | A |
| 162 | 2-pyrrolidin-1-ylethyl {4-[({4-[4-({[3,5-bis(trifluoromethyl)phenyl]amino}carbonyl)piperazin-1-yl]-1,2,5-thiadiazol-3-yl}oxy)methyl]pyrimidin-2-yl}carbamate | B |
| 163 | 2-piperidin-1-ylethyl {4-[({4-[4-({[3,5-bis(trifluoromethyl)phenyl]amino}carbonyl)piperazin-1-yl]-1,2,5-thiadiazol-3-yl}oxy)methyl]pyrimidin-2-yl}carbamate | B |
| 164 | methyl [4-({[2-(4-{[(3-bromophenyl)amino]carbonyl}piperazin-1-yl)pyridin-3-yl]oxy}methyl)pyridin-2-yl]carbamate | A |
| 165 | methyl {4-[({2-[4-({[3-(methyloxy)phenyl]amino}carbonyl)piperazin-1-yl]pyridin-3-yl}oxy)methyl]pyridin-2-yl}carbamate | B |
| 166 | 4-(3-{[(2-aminopyrimidin-4-yl)methyl]oxy}pyridin-2-yl)-N-[3-(methyloxy)phenyl]piperazine-1-carboxamide | B |
| 167 | 4-(3-{[(2-aminopyrimidin-4-yl)methyl]oxy}pyridin-2-yl)-N-[3-(1-methylethyl)phenyl]piperazine-1-carboxamide | A |
| 168 | 4-(3-{[(2-aminopyrimidin-4-yl)methyl]oxy}pyridin-2-yl)-N-{3-[(trifluoromethyl)oxy]phenyl}piperazine-1-carboxamide | A |
| 169 | 4-(3-{[(2-aminopyrimidin-4-yl)methyl]oxy}pyridin-2-yl)-N-[2-fluoro-5-(trifluoromethyl)phenyl]piperazine-1-carboxamide | A |
| 170 | N-(3-ethylphenyl)-4-[3-({[2-({[(3-ethylphenyl)amino]carbonyl}amino)pyridin-4-yl]methyl}oxy)pyridin-2-yl]piperazine-1-carboxamide | A |
| 171 | N-(3-ethylphenyl)-4-(3-{[(2-{[(4-methylpiperazin-1-yl)acetyl]amino}pyridin-4-yl)methyl]oxy}pyridin-2-yl)piperazine-1-carboxamide | A |
| 172 | N-(3-ethylphenyl)-4-(4-{[(2-{[(4-methylpiperazin-1-yl)acetyl]amino}pyridin-4-yl)methyl]oxy}-1,2,5-thiadiazol-3-yl)piperazine-1-carboxamide | A |
| 173 | N-[3,5-bis(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | A |
| 174 | 4-(3-{[(2-aminopyrimidin-4-yl)methyl]oxy}pyridin-2-yl)-N-[3-(trifluoromethyl)phenyl]piperazine-1-carboxamide | A |
| 175 | 4-[3-({[2-(acetylamino)pyridin-4-yl]methyl}oxy)pyridin-2-yl]-N-(3-ethylphenyl)piperazine-1-carboxamide | A |
| 176 | 4-(3-{[(2-aminopyrimidin-4-yl)methyl]oxy}pyridin-2-yl)-N-(3-ethyl-4-fluorophenyl)piperazine-1-carboxamide | A |
| 177 | 2-[4-(3-{[(2-aminopyrimidin-4-yl)methyl]oxy}pyridin-2-yl)piperazin-1-yl]-N-[3,5-bis(trifluoromethyl)phenyl]acetamide | C |
| 178 | 4-(3-{[(2-aminopyrimidin-4-yl)methyl]oxy}pyridin-2-yl)-N-phenylpiperazine-1-carboxamide | C |
| 179 | 4-(3-{[(2-aminopyrimidin-4-yl)methyl]oxy}pyridin-2-yl)-N-(3-chloro-5-ethylphenyl)piperazine-1-carboxamide | A |
| 180 | 4-(3-{[(2-aminopyrimidin-4-yl)methyl]oxy}pyridin-2-yl)-N-(5-ethyl-2-fluorophenyl)piperazine-1-carboxamide | A |
| 181 | 4-(3-{[(2-aminopyrimidin-4-yl)methyl]oxy}pyridin-2-yl)-N-(3-bromo-5-ethylphenyl)piperazine-1-carboxamide | A |
| 182 | 2-(4-methylpiperazin-1-yl)ethyl [4-({[2-(4-{[(3-ethylphenyl)amino]carbonyl}piperazin-1-yl)pyridin-3-yl]oxy}methyl)pyridin-2-yl]carbamate | A |
| 183 | 4-(3-{[(2-aminopyrimidin-4-yl)methyl]oxy}pyridin-2-yl)-N-(3-chlorophenyl)piperazine-1-carboxamide | B |
| 184 | 4-(3-{[(2-aminopyrimidin-4-yl)methyl]oxy}pyridin-2-yl)-N-(3-bromophenyl)piperazine-1-carboxamide | A |
| 185 | N-[4-({[2-(4-acetylpiperazin-1-yl)pyridin-3-yl]oxy}methyl)pyridin-2-yl]-2-(4-methylpiperazin-1-yl)acetamide | D |
| 186 | 4-(3-{[(2-aminopyrimidin-4-yl)methyl]oxy}pyridin-2-yl)-N-(3-fluorophenyl)piperazine-1-carboxamide | B |
| 187 | 4-(3-{[(2-aminopyrimidin-4-yl)methyl]oxy}pyridin-2-yl)-N-(4-fluorophenyl)piperazine-1-carboxamide | C |
| 188 | 4-(3-{[(2-aminopyrimidin-4-yl)methyl]oxy}pyridin-2-yl)-N-(2-fluorophenyl)piperazine-1-carboxamide | C |
| 189 | 4-(3-{[(2-aminopyrimidin-4-yl)methyl]oxy}pyridin-2-yl)-N-(3,5-diethylphenyl)piperazine-1-carboxamide | A |

TABLE 3-continued

| Number | Name | IC$_{50}$ Tie-2 |
|---|---|---|
| 190 | 4-(3-{[(2-aminopyrimidin-4-yl)methyl]oxy}-5-bromopyridin-2-yl)-N-(3-ethylphenyl)piperazine-1-carboxamide | A |
| 191 | N-methyl-4-(3-{[(2-{[(4-methylpiperazin-1-yl)acetyl]amino}pyridin-4-yl)methyl]oxy}pyridin-2-yl)piperazine-1-carboxamide | C |
| 192 | 4-(3-{[(2-aminopyrimidin-4-yl)methyl]oxy}pyridin-2-yl)-N-[2-chloro-5-(trifluoromethyl)phenyl]piperazine-1-carboxamide | A |
| 193 | 4-(3-{[(2-aminopyrimidin-4-yl)methyl]oxy}pyridin-2-yl)-N-(5-chloro-2-fluorophenyl)piperazine-1-carboxamide | B |
| 194 | 4-(3-{[(2-amino-5-bromopyrimidin-4-yl)methyl]oxy}-5-bromopyridin-2-yl)-N-(3-ethylphenyl)piperazine-1-carboxamide | A |
| 195 | 4-(3-{[(2-aminopyrimidin-4-yl)methyl]oxy}pyridin-2-yl)-N-[2-fluoro-3-(trifluoromethyl)phenyl]piperazine-1-carboxamide | B |
| 196 | 4-(3-{[(2-aminopyrimidin-4-yl)methyl]oxy}pyridin-2-yl)-N-[3-fluoro-5-(trifluoromethyl)phenyl]piperazine-1-carboxamide | A |
| 197 | 4-(3-{[(2-aminopyrimidin-4-yl)methyl]oxy}pyridin-2-yl)-N-(3,5-dichlorophenyl)piperazine-1-carboxamide | A |
| 198 | N-(3-chloro-5-ethylphenyl)-4-(3-{[(2-{[(4-methylpiperazin-1-yl)acetyl]amino}pyridin-4-yl)methyl]oxy}pyridin-2-yl)piperazine-1-carboxamide | A |
| 199 | N-(5-ethyl-2-fluorophenyl)-4-(3-{[(2-{[(4-methylpiperazin-1-yl)acetyl]amino}pyridin-4-yl)methyl]oxy}pyridin-2-yl)piperazine-1-carboxamide | A |
| 200 | 4-(3-{[(2-aminopyrimidin-4-yl)methyl]oxy}pyridin-2-yl)-N-[3-ethyl-5-(trifluoromethyl)phenyl]piperazine-1-carboxamide | A |
| 201 | 4-(3-{[(2-aminopyrimidin-4-yl)methyl]oxy}pyrazin-2-yl)-N-(3-ethylphenyl)piperazine-1-carboxamide | A |
| 202 | 4-(3-{[(2-aminopyrimidin-4-yl)methyl]oxy}pyrazin-2-yl)-N-(3-chloro-5-ethylphenyl)piperazine-1-carboxamide | A |
| 203 | 4-(3-{[(2-aminopyrimidin-4-yl)methyl]oxy}pyrazin-2-yl)-N-(5-ethyl-2-fluorophenyl)piperazine-1-carboxamide | A |
| 204 | 4-(3-{[(2-aminopyrimidin-4-yl)methyl]oxy}pyridin-2-yl)-N-methylpiperazine-1-carboxamide | D |
| 205 | 4-(3-{[(2-aminopyrimidin-4-yl)methyl]oxy}pyridin-2-yl)-N-ethylpiperazine-1-carboxamide | D |
| 206 | 4-(3-{[(2-aminopyrimidin-4-yl)methyl]oxy}pyridin-2-yl)-N-cyclohexylpiperazine-1-carboxamide | C |
| 207 | 4-({[2-(4-acetylpiperazin-1-yl)pyridin-3-yl]oxy}methyl)pyrimidin-2-amine | D |
| 208 | 4-({[2-(4-propanoylpiperazin-1-yl)pyridin-3-yl]oxy}methyl)pyrimidin-2-amine | D |
| 209 | N-(3-cyclopropylphenyl)-4-(3-{[(2-{[(4-methylpiperazin-1-yl)acetyl]amino}pyridin-4-yl)methyl]oxy}pyridin-2-yl)piperazine-1-carboxamide | A |
| 210 | 4-(3-{[(2-aminopyrimidin-4-yl)methyl]oxy}pyridin-2-yl)-N-(3-cyclopropylphenyl)piperazine-1-carboxamide | A |
| 211 | N-[2-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | B |
| 212 | N-[3-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | A |
| 213 | N-(3,5-dichlorophenyl)-4-(3-{[(2-{[(4-methylpiperazin-1-yl)acetyl]amino}pyridin-4-yl)methyl]oxy}pyridin-2-yl)piperazine-1-carboxamide | A |
| 214 | 4-(3-{[(2-{[(4-methylpiperazin-1-yl)acetyl]amino}pyridin-4-yl)methyl]oxy}pyridin-2-yl)-N-[3-(trifluoromethyl)phenyl]piperazine-1-carboxamide | A |
| 215 | 4-(3-{[(2-aminopyrimidin-4-yl)methyl]oxy}pyrazin-2-yl)-N-(3,5-diethylphenyl)piperazine-1-carboxamide | A |
| 216 | 4-(3-{[1-(2-aminopyrimidin-4-yl)ethyl]oxy}pyridin-2-yl)-N-[3,5-bis(trifluoromethyl)phenyl]piperazine-1-carboxamide | A |
| 217 | 4-(3-{[(2-aminopyrimidin-4-yl)methyl]oxy}pyrazin-2-yl)-N-(3,5-dichlorophenyl)piperazine-1-carboxamide | A |
| 218 | 4-(3-{[(2-aminopyrimidin-4-yl)methyl]oxy}pyrazin-2-yl)-N-[3-fluoro-5-(trifluoromethyl)phenyl]piperazine-1-carboxamide | A |
| 219 | 4-[({2-[4-(3,4-dihydroquinolin-1(2H)-ylcarbonyl)piperazin-1-yl]pyridin-3-yl}oxy)methyl]pyrimidin-2-amine | D |
| 220 | 4-(3-{[(2-aminopyrimidin-4-yl)methyl]oxy}pyridin-2-yl)-N-(2-methylpropyl)piperazine-1-carboxamide | D |
| 221 | 4-(4-{[(2-aminopyrimidin-4-yl)methyl]oxy}-1,2,5-thiadiazol-3-yl)-N-(3-chloro-5-ethylphenyl)piperazine-1-carboxamide | A |
| 222 | 4-(4-{[(2-aminopyrimidin-4-yl)methyl]oxy}-1,2,5-thiadiazol-3-yl)-N-(5-ethyl-2-fluorophenyl)piperazine-1-carboxamide | B |
| 223 | 4-(4-{[(2-aminopyrimidin-4-yl)methyl]oxy}-1,2,5-thiadiazol-3-yl)-N-(3,5-dichlorophenyl)piperazine-1-carboxamide | B |
| 224 | 4-(3-{[(2-aminopyrimidin-4-yl)methyl]oxy}pyrazin-2-yl)-N-phenylpiperazine-1-carboxamide | B |

TABLE 3-continued

| Number | Name | IC$_{50}$ Tie-2 |
|---|---|---|
| 225 | 4-(3-{[(2-aminopyrimidin-4-yl)methyl]oxy}pyrazin-2-yl)-N-[2-fluoro-5-(trifluoromethyl)phenyl]piperazine-1-carboxamide | A |
| 226 | N-(3,5-diethylphenyl)-4-(3-{[(2-{[(4-methylpiperazin-1-yl)acetyl]amino}pyridin-4-yl)oxy]methyl}pyridin-2-yl)piperazine-1-carboxamide | A |
| 227 | 4-(3-{[(2-aminopyrimidin-4-yl)methyl]oxy}-6-methylpyridin-2-yl)-N-(3-ethylphenyl)piperazine-1-carboxamide | A |
| 228 | 4-(3-{[(2-aminopyrimidin-4-yl)methyl]oxy}-6-methylpyridin-2-yl)-N-[3,5-bis(trifluoromethyl)phenyl]piperazine-1-carboxamide | A |
| 229 | 4-(3-{[(2-aminopyrimidin-4-yl)methyl]oxy}pyrazin-2-yl)-N-[3-(trifluoromethyl)phenyl]piperazine-1-carboxamide | A |
| 230 | 4-(4-{[(2-aminopyrimidin-4-yl)methyl]oxy}-1,2,5-thiadiazol-3-yl)-N-phenylpiperazine-1-carboxamide | D |
| 231 | 4-(4-{[(2-aminopyrimidin-4-yl)methyl]oxy}-1,2,5-thiadiazol-3-yl)-N-[3-(trifluoromethyl)phenyl]piperazine-1-carboxamide | A |
| 232 | 4-(4-{[(2-aminopyrimidin-4-yl)methyl]oxy}-1,2,5-thiadiazol-3-yl)-N-[2-fluoro-5-(trifluoromethyl)phenyl]piperazine-1-carboxamide | B |
| 233 | N-[3-chloro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | A |
| 234 | 4-(3-{[(2-aminopyrimidin-4-yl)methyl]oxy}pyrazin-2-yl)-N-[3-chloro-5-(trifluoromethyl)phenyl]piperazine-1-carboxamide | A |
| 235 | 4-(3-{[(2-aminopyrimidin-4-yl)methyl]oxy}pyridin-2-yl)-N-[3-chloro-5-(trifluoromethyl)phenyl]piperazine-1-carboxamide | A |
| 236 | 4-(3-{[(2-aminopyrimidin-4-yl)methyl]oxy}pyrazin-2-yl)-N-(3-bromo-5-ethylphenyl)piperazine-1-carboxamide | A |
| 237 | 4-(3-{[(2-aminopyrimidin-4-yl)methyl]oxy}-6-chloropyridin-2-yl)-N-(3-ethylphenyl)piperazine-1-carboxamide | A |
| 238 | 4-(4-{[(2-aminopyrimidin-4-yl)methyl]oxy}-1,2,5-thiadiazol-3-yl)-N-(3-bromo-5-ethylphenyl)piperazine-1-carboxamide | A |
| 239 | 4-(4-{[(2-aminopyrimidin-4-yl)methyl]oxy}-1,2,5-thiadiazol-3-yl)-N-[3-fluoro-5-(trifluoromethyl)phenyl]piperazine-1-carboxamide | A |
| 240 | 4-(4-{[(2-aminopyrimidin-4-yl)methyl]oxy}-1,2,5-thiadiazol-3-yl)-N-[3-chloro-5-(trifluoromethyl)phenyl]piperazine-1-carboxamide | A |
| 241 | 4-(3-{[(2-aminopyrimidin-4-yl)methyl]oxy}pyrazin-2-yl)-N-(3-ethyl-4-fluorophenyl)piperazine-1-carboxamide | A |
| 242 | 4-(4-{[(2-aminopyrimidin-4-yl)methyl]oxy}-1,2,5-thiadiazol-3-yl)-N-(3,5-diethylphenyl)piperazine-1-carboxamide | A |
| 243 | N-[3-chloro-2-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | A |
| 244 | 4-(3-{[(2-aminopyrimidin-4-yl)methyl]oxy}-6-chloropyridin-2-yl)-N-[3,5-bis(trifluoromethyl)phenyl]piperazine-1-carboxamide | A |
| 245 | 4-(3-{[1-(2-aminopyrimidin-4-yl)ethyl]oxy}pyridin-2-yl)-N-(3-ethylphenyl)piperazine-1-carboxamide | A |
| 246 | 4-(3-{[(2-aminopyrimidin-4-yl)methyl]oxy}-6-chloropyridin-2-yl)-N-(5-ethyl-2-fluorophenyl)piperazine-1-carboxamide | A |
| 247 | 4-(3-{[(2-aminopyrimidin-4-yl)methyl]oxy}pyridin-2-yl)-N-(3-ethyl-5-fluorophenyl)piperazine-1-carboxamide | A |
| 248 | 4-(4-{[(2-aminopyrimidin-4-yl)methyl]oxy}-1,2,5-thiadiazol-3-yl)-N-[3-chloro-2-fluoro-5-(trifluoromethyl)phenyl]piperazine-1-carboxamide | A |
| 249 | 4-(3-{[(2-aminopyrimidin-4-yl)methyl]oxy}pyridin-2-yl)-N-[3-chloro-2-fluoro-5-(trifluoromethyl)phenyl]piperazine-1-carboxamide | A |
| 250 | 4-(3-{[(2-aminopyrimidin-4-yl)methyl]oxy}pyridin-2-yl)-N-[3,5-bis(trifluoromethyl)phenyl]-N-methylpiperazine-1-carboxamide | A |
| 251 | 4-(3-{[(2-aminopyrimidin-4-yl)methyl]oxy}pyrazin-2-yl)-N-[3-(1-methylethyl)phenyl]piperazine-1-carboxamide | A |
| 252 | 4-(4-{[(2-aminopyrimidin-4-yl)methyl]oxy}-1,2,5-thiadiazol-3-yl)-N-(3-ethyl-4-fluorophenyl)piperazine-1-carboxamide | B |
| 253 | 4-(4-{[(2-aminopyrimidin-4-yl)methyl]oxy}-1,2,5-thiadiazol-3-yl)-N-(3-chloro-4-fluorophenyl)piperazine-1-carboxamide | C |
| 254 | 4-(4-{[(2-aminopyrimidin-4-yl)methyl]oxy}-1,2,5-thiadiazol-3-yl)-N-[2,5-bis(methyloxy)phenyl]piperazine-1-carboxamide | C |
| 255 | 4-(2-{[(2-aminopyrimidin-4-yl)methyl]oxy}phenyl)-N-[3,5-bis(trifluoromethyl)phenyl]piperazine-1-carboxamide | A |
| 256 | 4-(2-{[(2-aminopyrimidin-4-yl)methyl]oxy}phenyl)-N-(3-ethylphenyl)piperazine-1-carboxamide | A |
| 257 | 4-(4-{[(2-aminopyrimidin-4-yl)methyl]oxy}-1,2,5-thiadiazol-3-yl)-N-(5-chloro-2-fluorophenyl)piperazine-1-carboxamide | C |
| 258 | 4-(4-{[(2-aminopyrimidin-4-yl)methyl]oxy}-1,2,5-thiadiazol-3-yl)-N-{3-[(trifluoromethyl)oxy]phenyl}piperazine-1-carboxamide | A |

TABLE 3-continued

| Number | Name | IC$_{50}$ Tie-2 |
|---|---|---|
| 259 | 4-(4-{[(2-aminopyrimidin-4-yl)methyl]oxy}-1,2,5-thiadiazol-3-yl)-N-[3-(methyloxy)phenyl]piperazine-1-carboxamide | B |
| 260 | 4-(4-{[(2-aminopyrimidin-4-yl)methyl]oxy}-1,2,5-thiadiazol-3-yl)-N-[3-ethyl-5-(trifluoromethyl)phenyl]piperazine-1-carboxamide | A |
| 261 | 4-(4-{[(2-aminopyrimidin-4-yl)methyl]oxy}-1,2,5-thiadiazol-3-yl)-N-[3-(1-methylethyl)phenyl]piperazine-1-carboxamide | A |
| 262 | 4-(4-{[(2-aminopyrimidin-4-yl)methyl]oxy}-1,2,5-thiadiazol-3-yl)-N-[2-chloro-5-(trifluoromethyl)phenyl]piperazine-1-carboxamide | B |
| 263 | 4-(4-{[(2-aminopyrimidin-4-yl)methyl]oxy}-1,2,5-thiadiazol-3-yl)-N-(3-fluorophenyl)piperazine-1-carboxamide | C |
| 264 | 4-(4-{[(2-aminopyrimidin-4-yl)methyl]oxy}-1,2,5-thiadiazol-3-yl)-N-[2-(ethyloxy)phenyl]piperazine-1-carboxamide | D |
| 265 | 4-(4-{[(2-aminopyrimidin-4-yl)methyl]oxy}-1,2,5-thiadiazol-3-yl)-N-(3,4-difluorophenyl)piperazine-1-carboxamide | D |
| 266 | 4-(4-{[(2-aminopyrimidin-4-yl)methyl]oxy}-1,2,5-thiadiazol-3-yl)-N-[3-(methylthio)phenyl]piperazine-1-carboxamide | B |
| 267 | N-(3-acetylphenyl)-4-(4-{[(2-aminopyrimidin-4-yl)methyl]oxy}-1,2,5-thiadiazol-3-yl)piperazine-1-carboxamide | C |
| 268 | 4-(2-{[(2-aminopyrimidin-4-yl)methyl]oxy}phenyl)-N-[2-fluoro-5-(trifluoromethyl)phenyl]piperazine-1-carboxamide | A |
| 269 | 4-(2-{[(2-aminopyrimidin-4-yl)methyl]oxy}phenyl)-N-(3-fluorophenyl)piperazine-1-carboxamide | C |
| 270 | 4-(2-{[(2-aminopyrimidin-4-yl)methyl]oxy}phenyl)-N-phenylpiperazine-1-carboxamide | C |
| 271 | 4-(2-{[(2-aminopyrimidin-4-yl)methyl]oxy}phenyl)-N-(3,5-dichlorophenyl)piperazine-1-carboxamide | A |
| 272 | 4-(2-{[(2-aminopyrimidin-4-yl)methyl]oxy}phenyl)-N-[3-fluoro-5-(trifluoromethyl)phenyl]piperazine-1-carboxamide | A |
| 273 | 4-[4-({[6,7-bis(methyloxy)quinolin-4-yl]methyl}oxy)-1,2,5-thiadiazol-3-yl]-N-[3,5-bis(trifluoromethyl)phenyl]piperazine-1-carboxamide | A |
| 274 | 4-({[4-(4-{[3,5-bis(trifluoromethyl)phenyl]acetyl}piperazin-1-yl)-1,2,5-thiadiazol-3-yl]oxy}methyl)pyrimidin-2-amine | B |
| 275 | 5-{[(2-aminopyrimidin-4-yl)methyl]oxy}-6-[4-({[3,5-bis(trifluoromethyl)phenyl]amino}carbonyl)piperazin-1-yl]pyrazine-2-carboxamide | A |
| 276 | 4-(4-{[6,7-bis(methyloxy)quinolin-4-yl]oxy}-1,2,5-thiadiazol-3-yl)-N-[3,5-bis(trifluoromethyl)phenyl]piperazine-1-carboxamide | A |
| 277 | 4-(2-{[(2-aminopyrimidin-4-yl)methyl]oxy}phenyl)-N-[3-ethyl-5-(trifluoromethyl)phenyl]piperazine-1-carboxamide | A |
| 278 | 4-(2-{[(2-aminopyrimidin-4-yl)methyl]oxy}phenyl)-N-(5-ethyl-2-fluorophenyl)piperazine-1-carboxamide | A |
| 279 | 4-(2-{[(2-aminopyrimidin-4-yl)methyl]oxy}phenyl)-N-(3,5-diethylphenyl)piperazine-1-carboxamide | A |
| 280 | 4-[({4-[4-(naphthalen-2-ylacetyl)piperazin-1-yl]-1,2,5-thiadiazol-3-yl}oxy)methyl]pyrimidin-2-amine | D |
| 281 | 4-(2-{[(2-aminopyrimidin-4-yl)methyl]oxy}phenyl)-N-(3-chloro-5-ethylphenyl)piperazine-1-carboxamide | A |

What is claimed is:

1. A compound of Formula I,

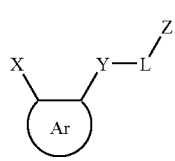

I or a pharmaceutically acceptable salt thereof, wherein,
Ar is selected from the following formulae

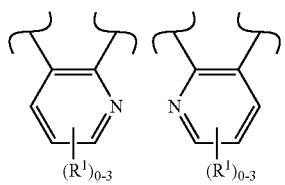

wherein Ar is substituted with —X and —Y-L-Z, in an ortho relationship to each other, and said Ar is optionally substituted with up to four $R^1$;

each $R^1$ is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, —OC(O)R$^3$, optionally substituted lower alkyl, optionally substituted aryl, optionally substituted lower arylalkyl, optionally substituted heterocyclyl, and optionally substituted lower heterocyclylalkyl;

X is selected from the following formulae

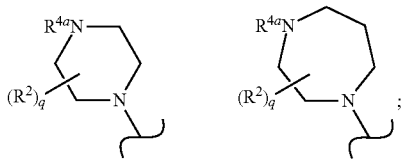

wherein R$^{4a}$ is —C(O)N(R$^3$)R$^3$;
n=1 or 2;
p=0 or 1;
q is 1 to 3;
M is –OR$^3$ or —N(R$^3$)R$^4$;
each R$^2$ is independently selected from —H, haloalkyl, —C$_{1-6}$alkyl-N(R$^3$)R$^3$, —C$_{1-6}$alkyl-OR$^3$, —C$_{1-6}$alkyl-CO$_2$R$^3$, and —C$_{1-6}$alkyl-C(O)N(R$^3$)R$^3$;
each R$^3$ is independently selected from —H, optionally substituted lower alkyl, optionally substituted aryl, optionally substituted lower arylalkyl, optionally substituted heterocyclyl, and optionally substituted lower heterocyclylalkyl; or
two of R$^3$, when taken together with a common nitrogen to which they are attached, form an optionally substituted five- to seven-membered heterocyclyl ring, said optionally substituted five- to seven-membered heterocyclyl ring optionally containing at least one additional heteroatom selected from N, O, S, and P;
each R$^4$ is independently selected from R$^3$, —SO$_2$R$^3$, —SO$_2$N(R$^3$)R$^3$, —CO$_2$R$^3$, —C(O)N(R$^3$)R$^3$, and —C(O)R$^3$;
Y-L-Z is selected from the following formulae,

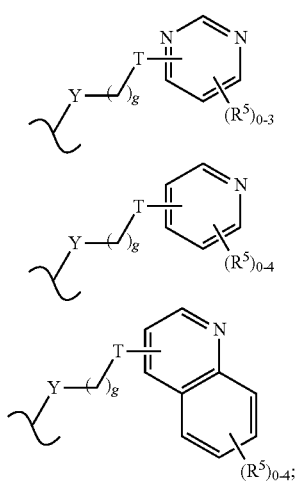

wherein g is zero to two; T is selected from absent, —N(R$^3$)—, —S— and —O—; and each methylene between Y and T is optionally substituted; provided that when both Y and T are heteroatoms then g must be two; Y is —O— or optionally substituted —CH$_2$—;

R$^5$ is selected from —H, halogen, —CN, —NO$_2$, —OR$^3$, —N(R$^3$)R$^4$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, optionally substituted lower alkyl, optionally substituted aryl, optionally substituted lower arylalkyl, optionally substituted heterocyclyl, and optionally substituted lower heterocyclylalkyl; and optionally two of R$^5$, together with the atoms to which they are attached, form a second ring system fused with said five- to seven-membered ring system, said second ring system substituted with zero to four of R$^5$.

2. The compound according to claim 1, wherein g is one or two.

3. The compound according to claim 2, wherein each R$^5$ is independently selected from —H, halogen, —CN, —NH$_2$, —NO$_2$, —OR$^3$, —N(R$^3$)R$^4$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, and optionally substituted lower alkyl.

4. The compound according to claim 3, wherein —Y-L-Z is selected from the following formulae

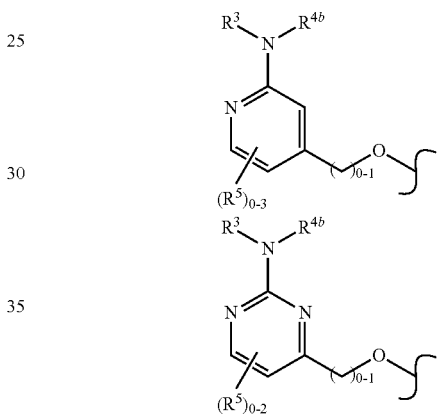

wherein R$^{4b}$ is selected from R$^3$, H, CO$_2$R$^3$, C(O)N(R$^3$)R$^3$, and C(O)R$^3$.

5. The compound according to claim 4, having formula III,

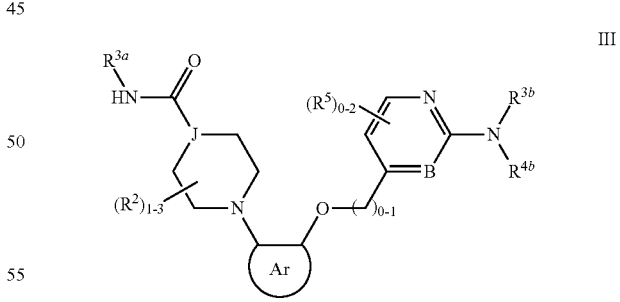

III wherein J is N, and B is =N— or =C(R$^5$)—. R$^{3a}$ is selected from optionally substituted aryl, optionally substituted lower arylalkyl, optionally substituted heterocyclyl, and optionally substituted lower heterocyclylalkyl;

R$^{3b}$ is H, and

R$^{4b}$ is R$^3$, —H, —CO$_2$R$^3$, —C(O)N(R$^3$)R$^4$, or —C(O)R$^3$.

6. The compound according to claim 5, wherein R$^{3a}$ is selected from optionally substituted aryl and optionally substituted heteroaryl.

7. The compound according to claim 6, wherein $R^{3a}$ is optionally substituted phenyl.

8. The compound according to claim 7, wherein said optionally substituted phenyl is substituted with at least one of halogen, —CN, —CF$_3$, —NH$_2$, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, optionally substituted lower alkyl, and optionally substituted aryl.

9. The compound according to claim 8, wherein said optionally substituted phenyl group is substituted with at least one trifluoromethyl group.

10. The compound according to claim 9, wherein said optionally substituted phenyl group is substituted with at least two trifluoromethyl groups.

11. The compound according to claim 8, wherein said optionally substituted phenyl group is substituted with at least one lower alkyl group.

12. The compound according to claim 8, wherein $R^{3b}$ is —H.

13. The compound according to claim 12, wherein $R^{4b}$ is selected from R$^3$, —H, —CO$_2$R$^3$, —C(O)N(R$^3$)R$^4$, and —C(O)R$^3$.

14. The compound according to claim 13, wherein Ar is according to the formula below

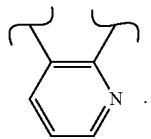

15. The compound according to claim 13, wherein Ar is according to the formula below

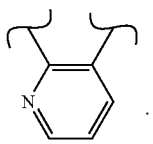

16. A compound of Formula IV,

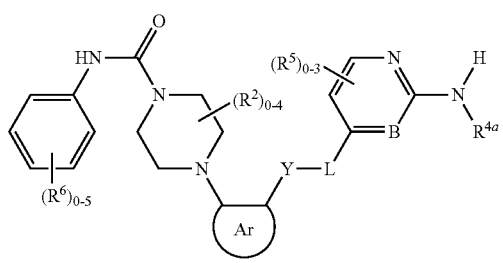

or a pharmaceutically acceptable salt thereof, wherein,
Ar is selected from the following formulae:

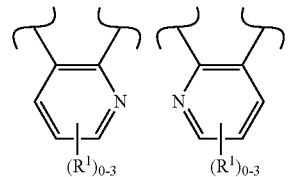

each R$^1$ is independently selected from —H, halogen, —CN, —NO$_2$, —OR$^3$, —N(R$^3$)R$^3$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —C(O)R$^3$, optionally substituted lower alkyl, optionally substituted aryl, optionally substituted lower arylalkyl, optionally substituted heterocyclyl, and optionally substituted lower heterocyclylalkyl;

optionally two of R$^1$, together with the atoms to which they are attached, form a first ring system fused with Ar, said first ring system substituted with zero to three additional of R$^1$;

each R$^2$ is independently selected from —H, halogen, oxo, —CN, —NH$_2$, —NO$_2$, —OR$^3$, —N(R$^3$)R$^3$, —N(R$^3$)R$^5$, —S(O)$_{0-2}$R$^3$, —SO$_2$N(R$^3$)R$^3$, —CO$_2$R$^3$, —C(O)N(R$^3$)R$^3$, —N(R$^3$)SO$_2$R$^3$, —N(R$^3$)C(O)R$^3$, —N(R$^3$)CO$_2$R$^3$, —N(R$^3$)C(O)N(R$^3$)R$^3$, —C(O)R$^3$, optionally substituted lower alkyl, optionally substituted aryl, optionally substituted lower arylalkyl, optionally substituted heterocyclyl, and optionally substituted lower heterocyclylalkyl;

two of R$^2$, together with the atoms to which they are attached, can form an optionally substituted three- to seven-membered ring system;

each R$^3$ is independently selected from —H, optionally substituted lower alkyl, optionally substituted aryl, optionally substituted lower arylalkyl, optionally substituted heterocyclyl, and optionally substituted lower heterocyclylalkyl; or two of R$^3$, when taken together with a common nitrogen to which they are attached, form an optionally substituted five- to seven-membered heterocyclyl ring, said optionally substituted five- to seven-membered heterocyclyl ring optionally containing at least one additional heteroatom selected from N, O, S, and P;

each R$^4$ is independently selected from R$^3$, —SO$_2$R$^3$, —SO$_2$N(R$^3$)R$^3$, —CO$_2$R$^3$, —C(O)N(R$^3$)R$^3$, and —C(O)R$^3$;

Y is selected from optionally substituted —CH$_2$—, —O—, —S—, and —N(R$^3$)—;

L is selected from optionally substituted —CH$_2$—, —O—, —S—, —N(R$^3$)— and absent;

provided that Y and L are not both heteroatoms;

B is =N— or =C(H)—;

at each instance, R$^5$ and R$^6$ are independently selected from —H, halogen, —CN, —NO$_2$, —OR$^3$, —N(R$^3$)R$^4$, —S(O)$_{0-2}$R$^3$, —SO$_2$N(R$^3$)R$^3$, —CO$_2$R$^3$, —C(O)N(R$^3$)R, —N(R$^3$)SO$_2$R$^3$, —N(R$^3$)C(O)R$^3$, —N(R$^3$)CO$_2$R$^3$, —C(O)R$^3$, optionally substituted lower alkyl, optionally substituted aryl, optionally substituted lower arylalkyl, optionally substituted heterocyclyl, and optionally substituted lower heterocyclylalkyl; and optionally two of R$^5$, together with the atoms to which they are attached, form a ring system fused with the ring containing B according to formula IV, said ring system substituted with zero to two additional of R⁵.

17. The compound according to claim 16, wherein Y is —O— and L is optionally substituted —CH₂—.

18. The compound according to claim 17, wherein at least one of R⁶ is optionally substituted lower alkyl.

19. The compound according to claim 18, wherein said at least one optionally substituted lower alkyl is meta- to the piperazine urea function as depicted in formula IV.

20. The compound according to claim 19, wherein $R^{4a}$ is selected from $R^3$, —H, —CO₂R³, —C(O)N(R³)R⁴, and —C(O)R³.

21. The compound according to claim 20, wherein $R^{4a}$ is selected from —H, —CO₂R³, —C(O)N(R³)R⁴, and —C(O)R³.

22. The compound according to claim 21, wherein —Y-L- is —OCH₂—.

23. The compound according to claim 22, wherein Ar is according to the formula below

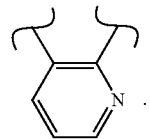

24. The compound according to claim 22, wherein Ar is according to the formula below

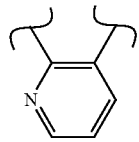

25. A compound selected from Table 4.

TABLE 4

| 97 | N-[3,5-bis(trifluoromethyl)phenyl]-4-{3-[(pyridin-4-ylmethyl)oxy]pyridin-2-yl}piperazine-1-carboxamide | 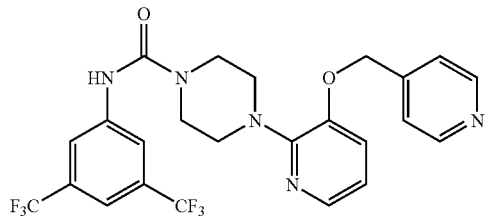 |
| --- | --- | --- |
| 103 | N-(4-chlorophenyl)-4-{3-[(pyridin-4-ylmethyl)oxy]yridin-2-yl}piperazine-1-carboxamide | 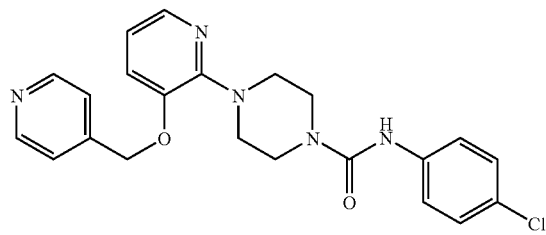 |
| 105 | N-(3-chlorophenyl)-4-{3-[(pyridin-4-ylmethyl)oxy]pyridin-2-yl}piperazine-1-carboxamide | 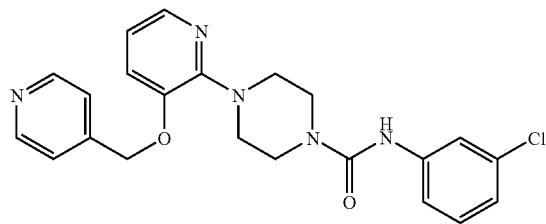 |
| 142 | 4-(3-{[(2-aminopyrimidin-4-yl)methyl]oxy}pyridin-2-yl)-N-[3,5-bis(trifluoromethyl)phenyl]piperazine-1-carboxamide | 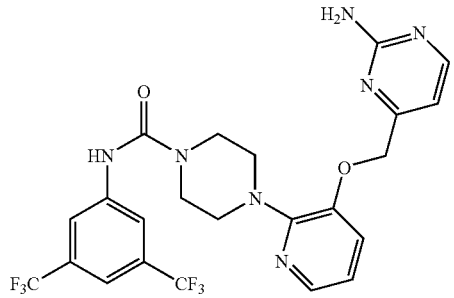 |

TABLE 4-continued

| | | |
|---|---|---|
| 144 | 4-(3-{[(2-aminopyrimidin-4-yl)methyl]oxy}pyridin-2-yl)-N-(3-ethylphenyl)piperazine-1-carboxamide | 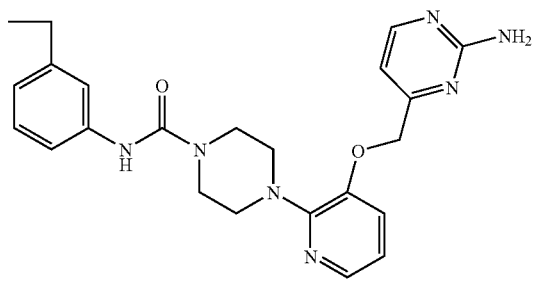 |
| 161 | methyl {4-({[2-(4-{[(3-methylphenyl)amino]carbonyl}piperazin-1-yl)pyridin-3-yl]oxy}methyl)pyridin-2-yl}carbamate | 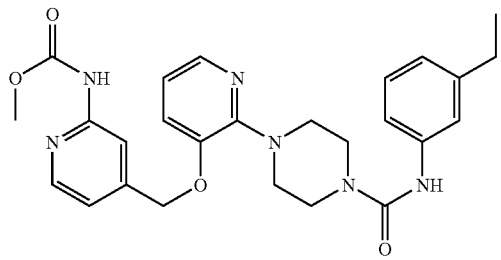 |
| 164 | methyl [4-({[2-(4-{[(3-bromophenyl)amino]carbonyl}piperazin-1-yl)pyridin-3-yl]oxy}methyl)pyridin-2-yl]carbamate | 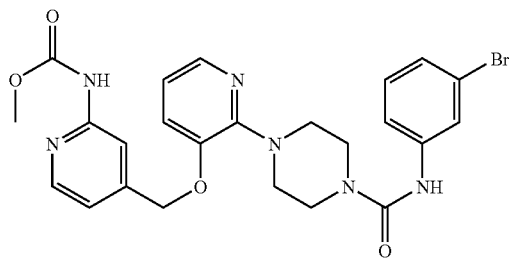 |
| 165 | methyl {4-[({2-[4-({[3-(methyloxy)phenyl]amino}carbonyl)piperazin-1-yl]pyridin-3-yl}oxy)methyl]pyridin-2-yl}carbamate | 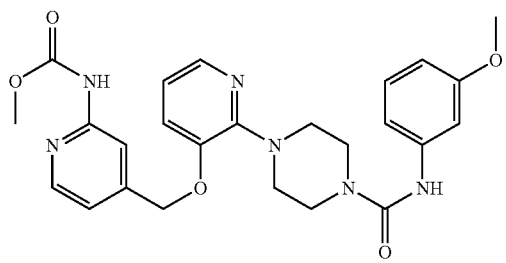 |
| 166 | 4-(3-{[(2-aminopyrimidin-4-yl)methyl]oxy}pyridin-2-yl)-N-[3-(methyloxy)phenyl]piperazine-1-carboxamide | 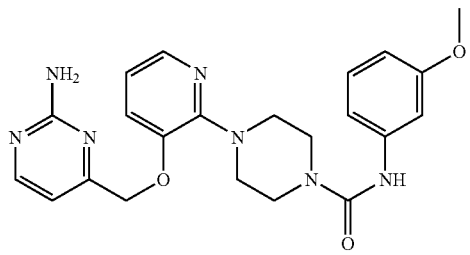 |
| 167 | 4-(3-{[(2-aminopyrimidin-4-yl)methyl]oxy}pyridin-2-yl)-N-[3-(1-methylethyl)phenyl]piperazine-1-carboxamide | 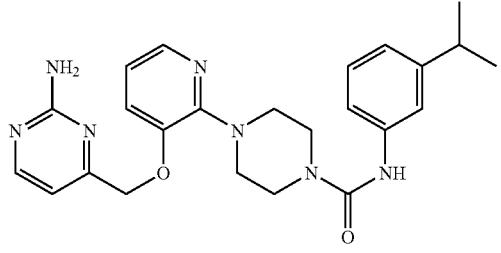 |

TABLE 4-continued

| 168 | 4-(3-{[(2-aminopyrimidin-4-yl)methyl]oxy}pyridin-2-yl)-N-{3-[(trifluoromethyl)oxy]phenyl}piperazine-1-carboxamide | 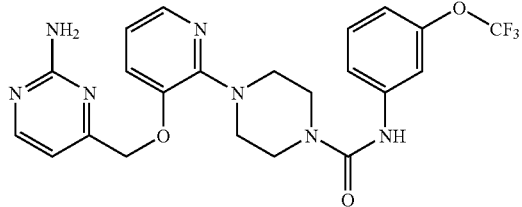 |
| 169 | 4-(3-{[(2-aminopyrimidin-4-yl)methyl]oxy}pyridin-2-yl)-N-[2-fluoro-5-(trifluoromethyl)phenyl]piperazine-1-carboxamide | 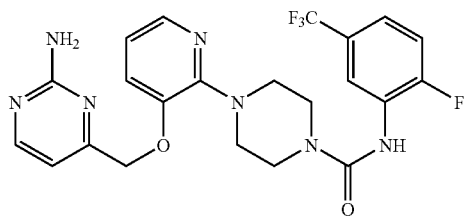 |
| 170 | N-(3-ethylphenyl)-4-[3-({[2-({[(3-ethylphenyl)amino]carbonyl}amino)pyridin-4-yl]methyl}oxy)pyridin-2-yl]piperazine-1-carboxamide | 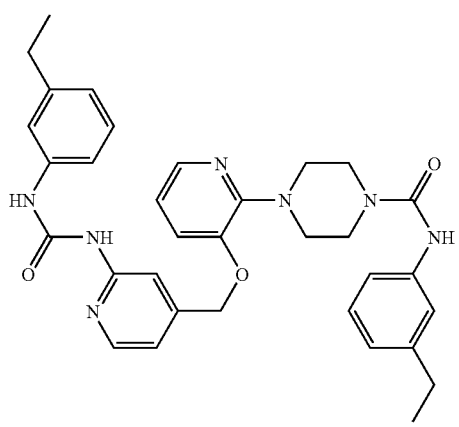 |
| 171 | N-(3-ethylphenyl)-4-(3-{[(2-{[(4-methylpiperazin-1-yl)acetyl]amino}pyridin-4-yl)methyl]oxy}pyridin-2-yl)piperazine-1-carboxamide | 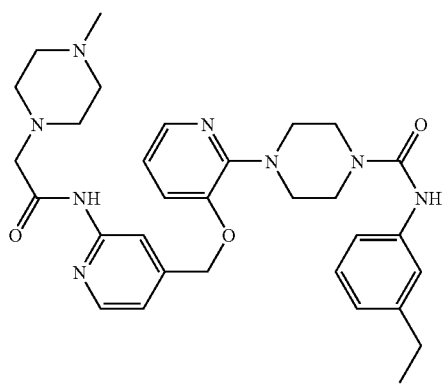 |
| 173 | N-[3,5-bis(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 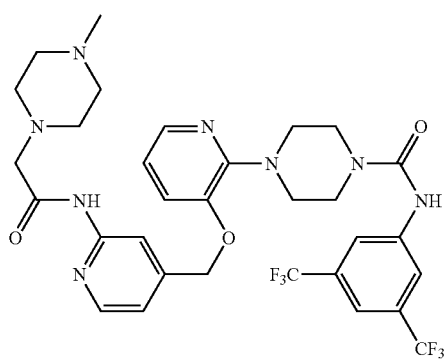 |

TABLE 4-continued

| 174 | 4-(3-{[(2-aminopyrimidin-4-yl)methyl]oxy}pyridin-2-yl)-N-[3-(trifluoromethyl)phenyl]piperazine-1-carboxamide | 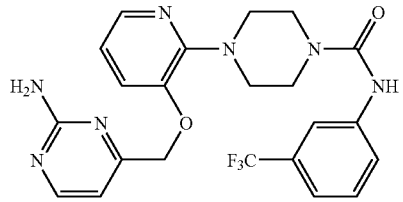 |
| 175 | 4-[3-({[2-(acetylamino)pyridin-4-yl]methyl}oxy)pyridin-2-yl]-N-(3-ethylphenyl)piperazine-1-carboxamide | 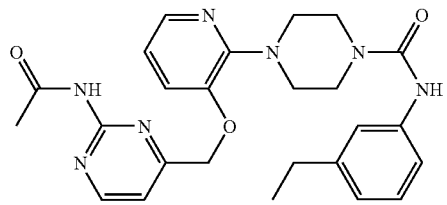 |
| 176 | 4-(3-{[(2-aminopyrimidin-4-yl)methyl]oxy}pyridin-2-yl)-N-(3-ethyl-4-fluorophenyl)piperazine-1-carboxamide | 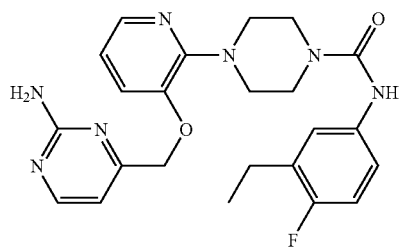 |
| 177 | 2-[4-(3-{[(2-aminopyrimidin-4-yl)methyl]oxy}pyridin-2-yl)piperazin-1-yl]-N-[3,5-bis(trifluoromethyl)phenyl]acetamide | 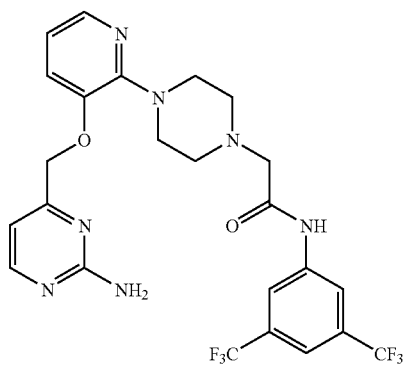 |
| 178 | 4-(3-{[(2-aminopyrimidin-4-yl)methyl]oxy}pyridin-2-yl)-N-phenylpiperazine-1-carboxamide | 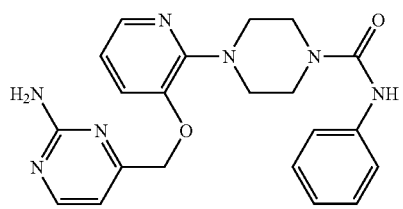 |
| 179 | 4-(3-{[(2-aminopyrimidin-4-yl)methyl]oxy}pyridin-2-yl)-N-(3-chloro-5-ethylphenyl)piperazine-1-carboxamide | 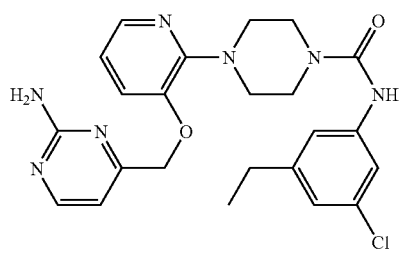 |

TABLE 4-continued

| 180 | 4-(3-{[(2-aminopyrimidin-4-yl)methyl]oxy}pyridin-2-yl)-N-(5-ethyl-2-fluorophenyl)piperazine-1-carboxamide | 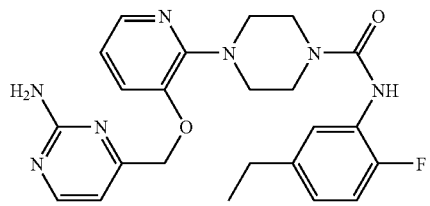 |
| 181 | 4-(3-{[(2-aminopyrimidin-4-yl)methyl]oxy}pyridin-2-yl)-N-(3-bromo-5-ethylphenyl)piperazine-1-carboxamide | 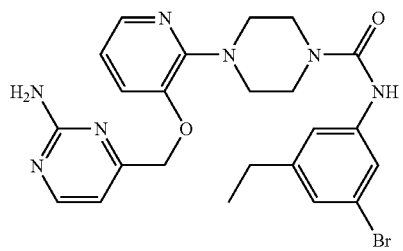 |
| 182 | 2-(4-methylpiperazin-1-yl)ethyl [4-({[2-(4-{[(3-ethylphenyl)amino]carbonyl}piperazin-1-yl)pyridin-3-yl]oxy}methyl)pyridin-2-yl]carbamate | 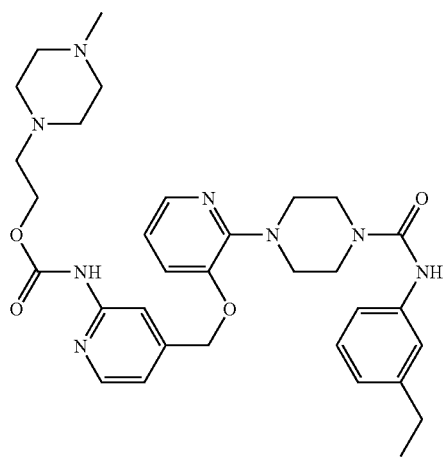 |
| 183 | 4-(3-{[(2-aminopyrimidin-4-yl)methyl]oxy}pyridin-2-yl)-N-(3-chlorophenyl)piperazine-1-carboxamide | 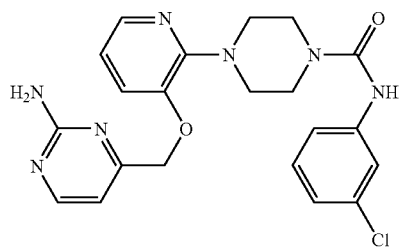 |
| 184 | 4-(3-{[(2-aminopyrimidin-4-yl)methyl]oxy}pyridin-2-yl)-N-(3-bromophenyl)piperazine-1-carboxamide | 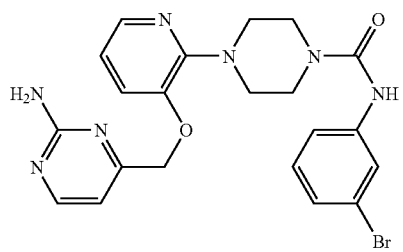 |
| 185 | N-[4-({[2-(4-acetylpiperazin-1-yl)pyridin-3-yl]oxy}methyl)pyridin-2-yl]-2-(4-methylpiperazin-1-yl)acetamide | 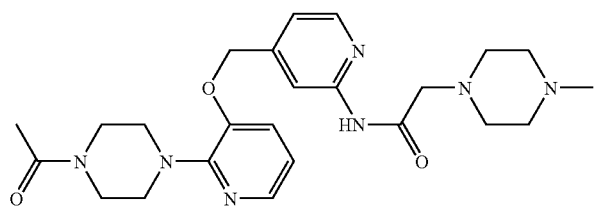 |

TABLE 4-continued

| 186 | 4-(3-{[(2-aminopyrimidin-4-yl)methyl]oxy}pyridin-2-yl)-N-(3-fluorophenyl)piperazine-1-carboxamide | 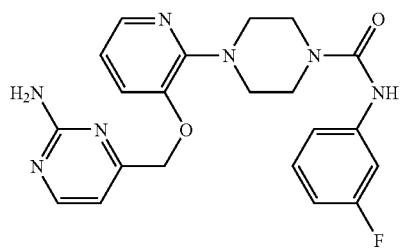 |
| 187 | 4-(3-{[(2-aminopyrimidin-4-yl)methyl]oxy}pyridin-2-yl)-N-(4-fluorophenyl)piperazine-1-carboxamide | 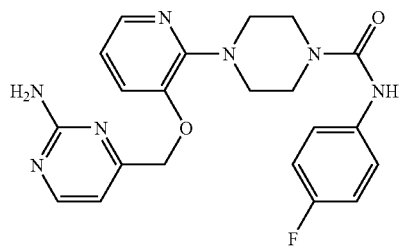 |
| 188 | 4-(3-{[(2-aminopyrimidin-4-yl)methyl]oxy}pyridin-2-yl)-N-(2-fluorophenyl)piperazine-1-carboxamide | 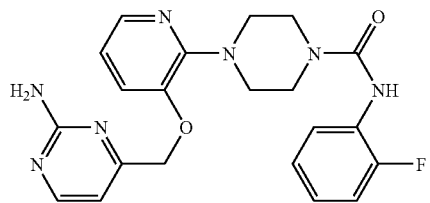 |
| 189 | 4-(3-{[(2-aminopyrimidin-4-yl)methyl]oxy}pyridin-2-yl)-N-(3,5-diethylphenyl)piperazine-1-carboxamide | 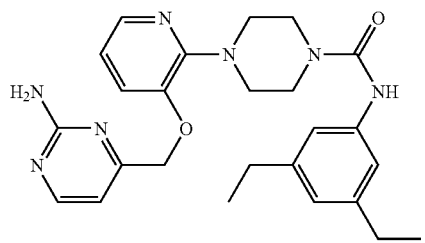 |
| 190 | 4-(3-{[(2-aminopyrimidin-4-yl)methyl]oxy}-5-bromopyridin-2-yl)-N-(3-ethylphenyl)piperazine-1-carboxamide | 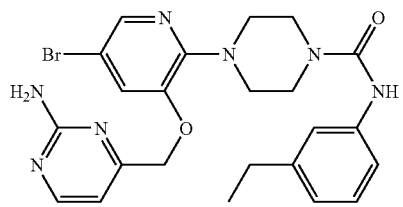 |
| 191 | N-methyl-4-(3-{[(2-{[(4-methylpiperazin-1-yl)acetyl]amino}pyridin-4-yl)methyl]oxy}pyridin-2-yl)piperazine-1-carboxamide | 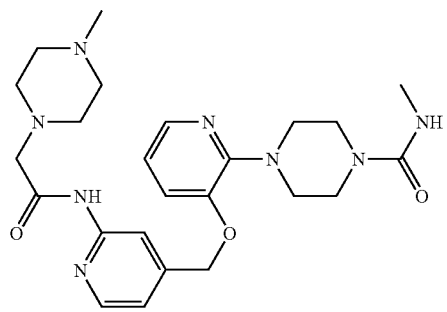 |

TABLE 4-continued

| 192 | 4-(3-{[(2-aminopyrimidin-4-yl)methyl]oxy}pyridin-2-yl)-N-[2-chloro-5-(trifluoromethyl)phenyl]piperazine-1-carboxamide | 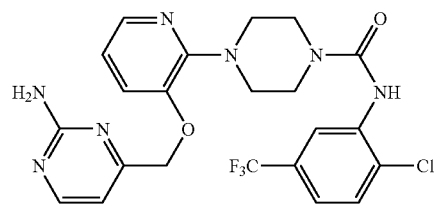 |
| 193 | 4-(3-{[(2-aminopyrimidin-4-yl)methyl]oxy}pyridin-2-yl)-N-(5-chloro-2-fluorophenyl)piperazine-1-carboxamide | 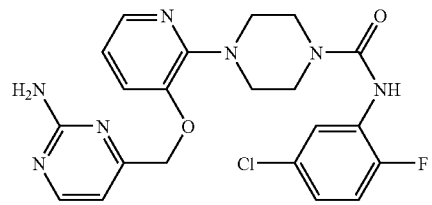 |
| 194 | 4-(3-{[(2-amino-5-bromopyrimidin-4-yl)methyl]oxy}-5-bromopyridin-2-yl)-N-(3-ethylphenyl)piperazine-1-carboxamide | 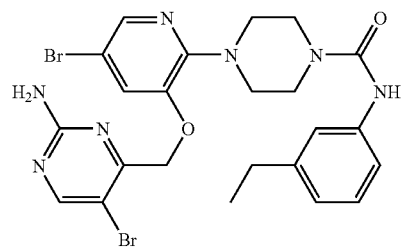 |
| 195 | 4-(3-{[(2-aminopyrimidin-4-yl)methyl]oxy}pyridin-2-yl)-N-[2-fluoro-3-(trifluoromethyl)phenyl]piperazine-1-carboxamide | 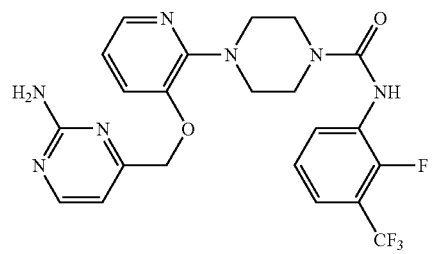 |
| 196 | 4-(3-{[(2-aminopyrimidin-4-yl)methyl]oxy}pyridin-2-yl)-N-[3-fluoro-5-(trifluoromethyl)phenyl]piperazine-1-carboxamide | 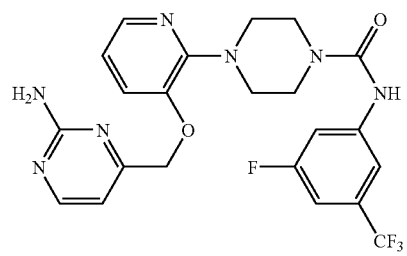 |
| 197 | 4-(3-{[(2-aminopyrimidin-4-yl)methyl]oxy}pyridin-2-yl)-N-(3,5-dichlorophenyl)piperazine-1-carboxamide | 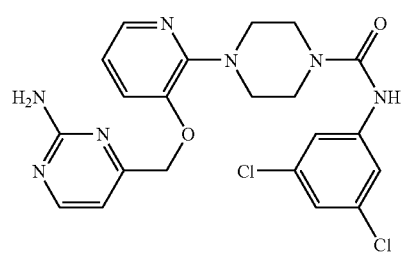 |

TABLE 4-continued

| | | |
|---|---|---|
| 198 | N-(3-chloro-5-ethylphenyl)-4-(3-{[(2-{[(4-methylpiperazin-1-yl)acetyl]amino}pyridin-4-yl)methyl]oxy}pyridin-2-yl)piperazine-1-carboxamide | 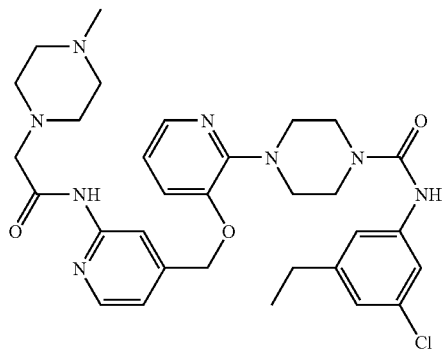 |
| 199 | N-(5-ethyl-2-fluorophenyl)-4-(3-{[(2-{[(4-methylpiperazin-1-yl)acetyl]amino}pyridin-4-yl)methyl]oxy}pyridin-2-yl)piperazine-1-carboxamide | 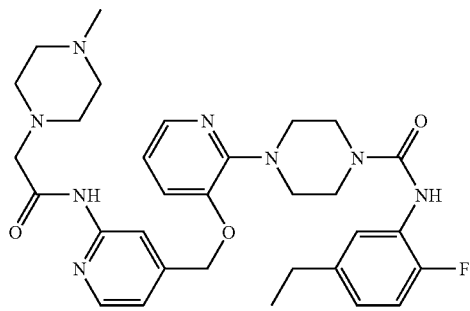 |
| 200 | 4-(3-{[(2-aminopyrimidin-4-yl)methyl]oxy}pyridin-2-yl)-N-[3-ethyl-5-(trifluoromethyl)phenyl]piperazine-1-carboxamide | 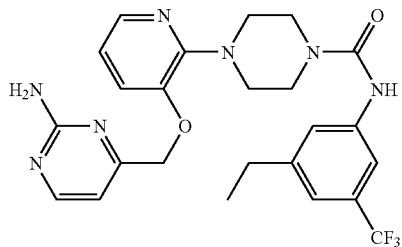 |
| 204 | 4-(3-{[(2-aminopyrimidin-4-yl)methyl]oxy}pyridin-2-yl)-N-methylpiperazine-1-carboxamide | 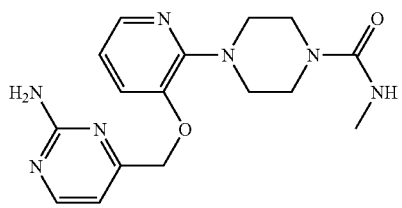 |
| 205 | 4-(3-{[(2-aminopyrimidin-4-yl)methyl]oxy}pyridin-2-yl)-N-ethylpiperazine-1-carboxamide | 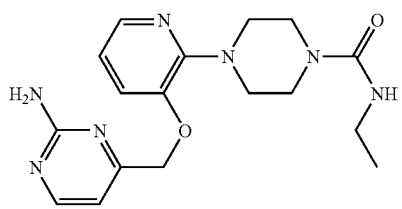 |
| 206 | 4-(3-{[(2-aminopyrimidin-4-yl)methyl]oxy}pyridin-2-yl)-N-cyclohexylpiperazine-1-carboxamide | 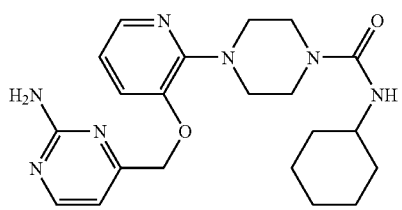 |

TABLE 4-continued

| # | Name |
|---|---|
| 207 | 4-({[2-(4-acetylpiperazin-1-yl)pyridin-3-yl]oxy}methyl)pyrimidin-2-amine |
| 208 | 4-({[2-(4-propanoylpiperazin-1-yl)pyridin-3-yl]oxy}methyl)pyrimidin-2-amine |
| 209 | N-(3-cyclopropylphenyl)-4-(3-{[(2-{[(4-methylpiperazin-1-yl)acetyl]amino}pyridin-4-yl)methyl]oxy}pyridin-2-yl)piperazine-1-carboxamide |
| 210 | 4-(3-{[(2-aminopyrimidin-4-yl)methyl]oxy}pyridin-2-yl)-N-(3-cyclopropylphenyl)piperazine-1-carboxamide |
| 211 | N-[2-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide |
| 212 | N-[3-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide |

TABLE 4-continued

| 213 | N-(3,5-dichlorophenyl)-4-(3-{[(2-{[(4-methylpiperazin-1-yl)acetyl]amino}pyridin-4-yl)methyl]oxy}pyridin-2-yl)piperazine-1-carboxamide | 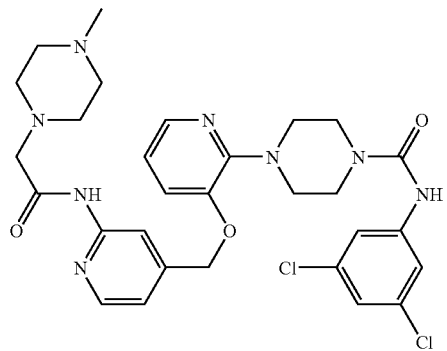 |
| 214 | 4-(3-{[(2-{[(4-methylpiperazin-1-yl)acetyl]amino}pyridin-4-yl)methyl]oxy}pyridin-2-yl)-N-[3-(trifluoromethyl)phenyl]piperazine-1-carboxamide | 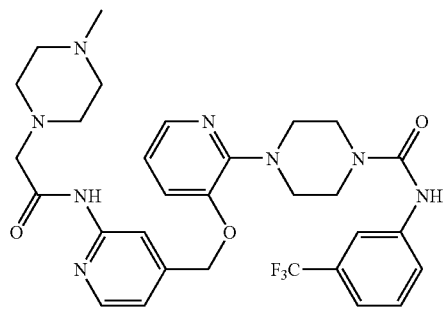 |
| 216 | 4-(3-{[1-(2-aminopyrimidin-4-yl)ethyl]oxy}pyridin-2-yl)-N-[3,5-bis(trifluoromethyl)phenyl]piperazine-1-carboxamide | 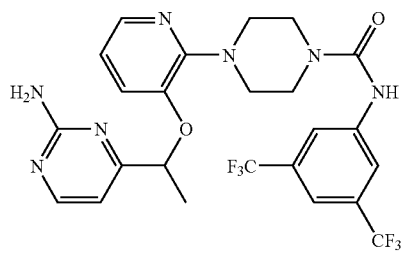 |
| 219 | 4-[({2-[4-(3,4-dihydroquinolin-1(2H)-ylcarbonyl)piperazin-1-yl]pyridin-3-yl}oxy)methyl]pyrimidin-2-amine | 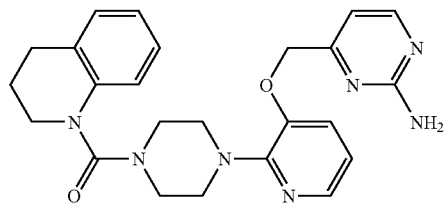 |
| 220 | 4-(3-{[(2-aminopyrimidin-4-yl)methyl]oxy}pyridin-2-yl)-N-(2-methylpropyl)piperazine-1-carboxamide | 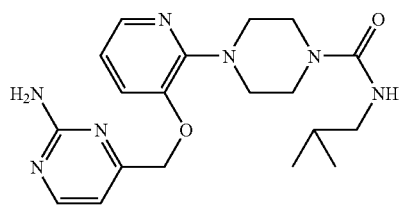 |

TABLE 4-continued

| 226 | N-(3,5-diethylphenyl)-4-(3-{[(2-{[(4-methylpiperazin-1-yl)acetyl]amino}pyridin-4-yl)oxy]methyl}pyridin-2-yl)piperazine-1-carboxamide | 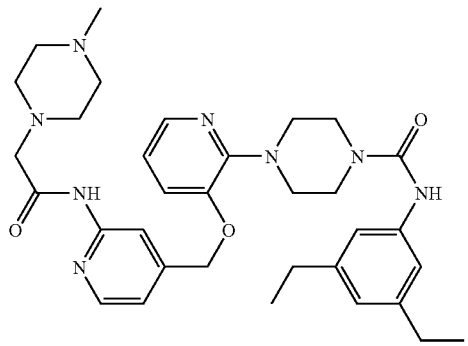 |
| --- | --- | --- |
| 227 | 4-(3-{[(2-aminopyrimidin-4-yl)methyl]oxy}-6-methylpyridin-2-yl)-N-(3-ethylphenyl)piperazine-1-carboxamide | 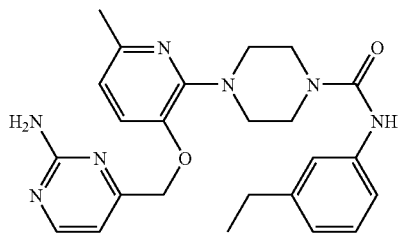 |
| 228 | 4-(3-{[(2-aminopyrimidin-4-yl)methyl]oxy}-6-methylpyridin-2-yl)-N-[3,5-bis(trifluoromethyl)phenyl]piperazine-1-carboxamide | 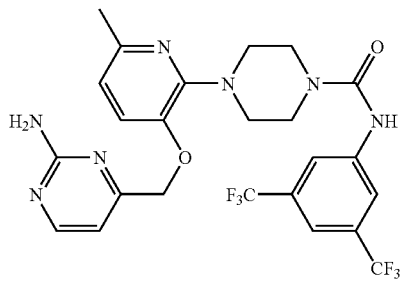 |
| 233 | N-[3-chloro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 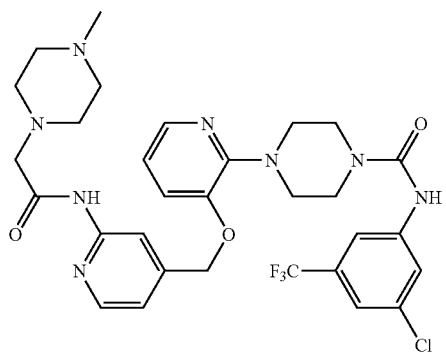 |
| 235 | 4-(3-{[(2-aminopyrimidin-4-yl)methyl]oxy}pyridin-2-yl)-N-[3-chloro-5-(trifluoromethyl)phenyl]piperazine-1-carboxamide | 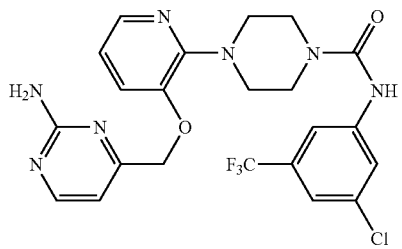 |

TABLE 4-continued

| 237 | 4-(3-{[(2-aminopyrimidin-4-yl)methyl]oxy}-6-chloropyridin-2-yl)-N-(3-ethylphenyl)piperazine-1-carboxamide | 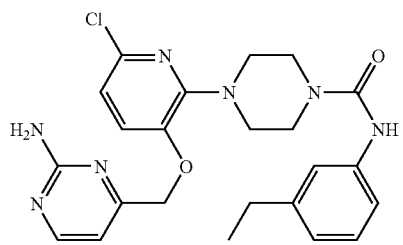 |
| 243 | N-[3-chloro-2-fluoro-5-(trifluoromethyl)phenyl]-4-(3-{[(2-{[(4-methylpiperazin-1-yl)acetyl]amino}pyridin-4-yl)methyl]oxy}pyridin-2-yl)piperazine-1-carboxamide | 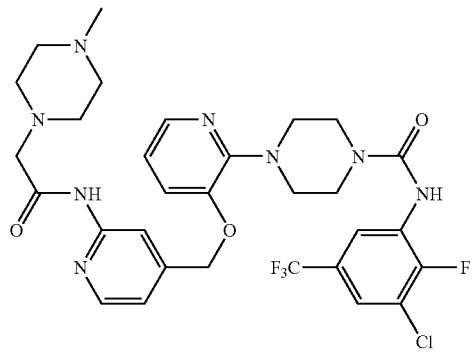 |
| 244 | 4-(3-{[(2-aminopyrimidin-4-yl)methyl]oxy}-6-chloropyridin-2-yl)-N-[3,5-bis(trifluoromethyl)phenyl]piperazine-1-carboxamide | 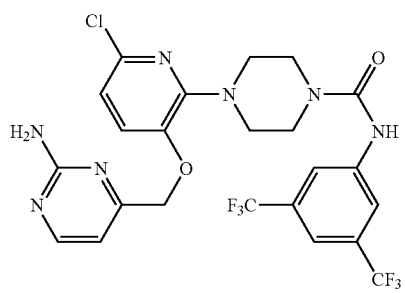 |
| 245 | 4-(3-{[1-(2-aminopyrimidin-4-yl)ethyl]oxy}pyridin-2-yl)-N-(3-ethylphenyl)piperazine-1-carboxamide | 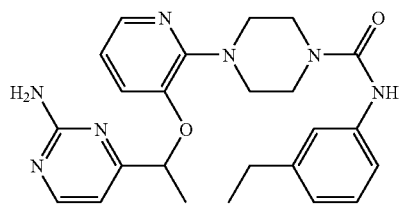 |
| 246 | 4-(3-{[(2-aminopyrimidin-4-yl)methyl]oxy}-6-chloropyridin-2-yl)-N-(5-ethyl-2-fluorophenyl)piperazine-1-carboxamide | 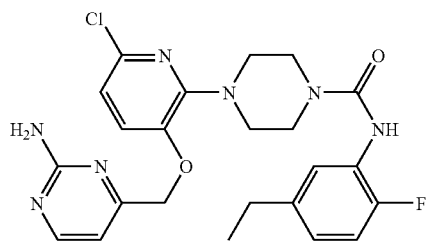 |
| 247 | 4-(3-{[(2-aminopyrimidin-4-yl)methyl]oxy}pyridin-2-yl)-N-(3-ethyl-5-fluorophenyl)piperazine-1-carboxamide | 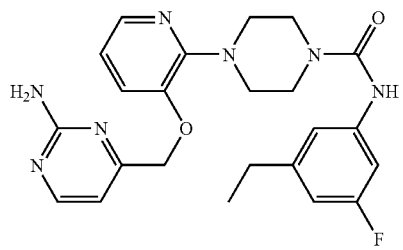 |

TABLE 4-continued
| 249 | 4-(3-{[(2-aminopyrimidin-4-yl)methyl]oxy}pyridin-2-yl)-N-[3-chloro-2-fluoro-5-(trifluoromethyl)phenyl]piperazine-1-carboxamide | 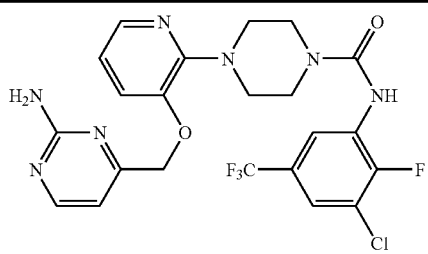 |
| --- | --- | --- |
| 250 | 4-(3-{[(2-aminopyrimidin-4-yl)methyl]oxy}pyridin-2-yl)-N-[3,5-bis(trifluoromethyl)phenyl]-N-methylpiperazine-1-carboxamide | 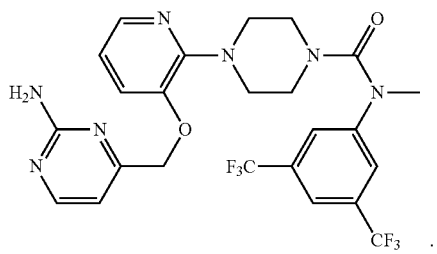 |
26. A pharmaceutical composition comprising the compound according to claim 1 and a pharmaceutically acceptable carrier.
* * * * *